US008871777B2

(12) United States Patent
Liu et al.

(10) Patent No.: US 8,871,777 B2

(45) Date of Patent: Oct. 28, 2014

(54) PHENYLPYRIMIDONE COMPOUNDS, THE PHARMACEUTICAL COMPOSITIONS, PREPARATION METHODS AND USES THEREOF

(75) Inventors: Zheng Liu, Shanghai (CN); Jianfeng Li, Shanghai (CN); Xiaojun Yang, Shanghai (CN); Zhen Wang, Shanghai (CN); Jinfeng Zhang, Shanghai (CN); Yi Zhu, Shandong (CN); Guanghui Tian, Shanghai (CN); Qing Jin, Shanghai (CN); Jingkang Shen, Shanghai (CN); Weiliang Zhu, Shanghai (CN); Hualiang Jiang, Shanghai (CN); Jingshan Shen, Shanghai (CN)

(73) Assignees: Topharman Shanghai Co., Ltd., Shanghai (CN); Shanghai Institute of Materia Medica, Chinese Academy of Sciences, Shanghai (CN); Topharman Shandong Co., Ltd., Shandong (CN)

( * ) Notice: Subject to any disclaimer, the term of this patent is extended or adjusted under 35 U.S.C. 154(b) by 212 days.

(21) Appl. No.: 13/139,156

(22) PCT Filed: Dec. 10, 2009

(86) PCT No.: PCT/CN2009/001418

§ 371 (c)(1), (2), (4) Date: Aug. 24, 2011

(87) PCT Pub. No.: WO2010/066111

PCT Pub. Date: Jun. 17, 2010

(65) Prior Publication Data

US 2011/0301109 A1 Dec. 8, 2011

(30) Foreign Application Priority Data

Dec. 10, 2008 (CN) .......................... 2008 1 0204368

(51) Int. Cl.

| | |
|---|---|
| ***A01N 43/54*** | (2006.01) |
| ***A61K 31/505*** | (2006.01) |
| ***C07D 239/02*** | (2006.01) |
| ***C07D 401/12*** | (2006.01) |
| ***C07D 417/12*** | (2006.01) |
| ***C07D 409/12*** | (2006.01) |
| ***C07D 239/36*** | (2006.01) |
| ***C07D 405/12*** | (2006.01) |
| ***C07D 403/12*** | (2006.01) |
| ***C07H 15/26*** | (2006.01) |

(52) U.S. Cl.

CPC ............ *A61K 31/505* (2013.01); *C07D 401/12* (2013.01); *C07D 417/12* (2013.01); *C07D 409/12* (2013.01); *C07D 239/36* (2013.01); *C07D 405/12* (2013.01); *C07D 403/12* (2013.01); *C07H 15/26* (2013.01)

USPC .......................................... 514/269; 544/319

(58) Field of Classification Search

None

See application file for complete search history.

(56) References Cited

U.S. PATENT DOCUMENTS 4,031,093 A * 6/1977 Juby et al. ..................... 544/319

FOREIGN PATENT DOCUMENTS

| | | | |
|---|---|---|---|
| CA | 2339677 | A1 | 9/2001 |
| CN | 1746171 | A | 3/2006 |
| EP | 1889843 | A1 | 2/2008 |
| EP | 2030974 | A1 | 3/2009 |
| GB | 1541351 | A | 2/1979 |
| WO | 9428902 | A1 | 12/1994 |
| WO | 9849166 | A1 | 11/1998 |
| WO | 9954333 | A1 | 10/1999 |
| WO | 0187888 | A1 | 11/2001 |
| WO | 03020724 | A1 | 3/2003 |
| WO | 2004096810 | A1 | 11/2004 |
| WO | 2004101567 | A1 | 11/2004 |
| WO | 2004108726 | A1 | 12/2004 |
| WO | 2005012303 | A1 | 2/2005 |
| WO | 2005089752 | A1 | 9/2005 |
| WO | 2006126081 | A2 | 11/2006 |
| WO | 2006126083 | A1 | 11/2006 |
| WO | 2007002125 | A1 | 1/2007 |
| WO | 2007020521 | A1 | 2/2007 |
| WO | 2007056955 | A1 | 5/2007 |

OTHER PUBLICATIONS

Bretscneider, et. al., Monatshefte fuer Chemie (1950), 81, 781-3.*

Hai-Jun Chen et al., "Rational Design and Synthesis of 2,2-Bisheterocycle Tandem Derivatives as Non-Nucleoside Hepatitis B Virus Inhibitors", ChemMedChem, Sep. 15, 2008, pp. 1316-1321, vol. 3, No. 9, Wiley-VCH Verlag GmbH & Co., KGaA, Weinheim, Published online on Jul. 28, 2008.

Supplementary European Search Report, Application No. 10838611 filed Oct. 31, 2012.

European Search Report of European Publication No. 2383262 (Application No. 09831388.5 filed Dec. 10, 2009).

* cited by examiner

*Primary Examiner* — Jeffrey H Murray

(74) *Attorney, Agent, or Firm* — Baker & Hostetler LLP

(57) ABSTRACT

The present invention relates to a class of phenylpyrimidone compounds, the pharmaceutical composition, the preparation method and the use thereof. More specifically, the present invention relates to a type of phenylpyrimidone compounds of the following formula I, the pharmaceutically acceptable salts or solvates thereof and to the pharmaceutical composition as well as the preparation method of the compounds. The compounds of formula I according to the present invention can effectively inhibit type V phosphodiesterase (PDE5), and thus can be used for the treatment of various vascular disorders, such as male erectile dysfunction, pulmonary hypertension and the like.

I

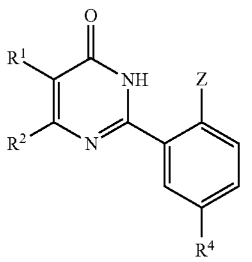

14 Claims, No Drawings

PHENYLPYRIMIDONE COMPOUNDS, THE PHARMACEUTICAL COMPOSITIONS, PREPARATION METHODS AND USES THEREOF

CROSS-REFERENCE TO RELATED APPLICATION

This application claims foreign priority to and is a National Stage Application of International Application No. PCT/CN2009/001418, entitled, "PHENYLPYRIMIDONE COMPOUNDS, THE PHARMACEUTICAL COMPOSITIONS, PREPARATION METHODS AND USES THEREOF," filed Dec. 10, 2009, which claims priority to Chinese Application No. 200810204368.4, entitled, "PHENYLPYRIMIDONE COMPOUNDS, THE PHARMACEUTICAL COMPOSITIONS, PREPARATION METHODS AND USES THEREOF," filed Dec. 10, 2008, which are both hereby incorporated by reference in their entirety.

FIELD OF THE INVENTION

The present invention relates to a class of phenylpyrimidone compounds, the pharmaceutically acceptable salts and solvates thereof. The present invention also relates to a pharmaceutical composition comprising the compound and a process for preparing the compound. The phenylpyrimidone compound according to the present invention can effectively inhibit type V phosphodiesterase (PDE5), and thus can be used for the treatment of various vascular disorders, such as male erectile dysfunction, pulmonary hypertension and the like.

BACKGROUND OF THE INVENTION

Sildenafil (WO94/28902) developed by Pfizer Inc. is an oral PED5 inhibitor for treating male erectile dysfunction. It increases the level of cGMP, an enzyme substrate of type V phosphodiesterase (PDE5), in smooth muscle cells to relax the smooth muscle and induce vasodilatation by inhibiting the type V phosphodiesterase, so as to increase the flow rate of blood in the smooth muscle to induce erection.

From then on, many big pharmas and research teams have developed a lot of PED5 inhibitors with other different chemical structures. WO98/49166, WO99/54333 and WO 01/87888 disclose another series of pyrazolo[4,3-d]pyrimidin-7-one derivatives; WO2004/096810 discloses a series of 5,7-diaminopyrazolo[4,3-d]pyrimidine compounds; WO2004/108726 discloses a series of dihydropyrrolo[2,3-d]pyrimidin-4-one compounds; WO2004/101567 discloses a series of imidazo[1,5-a]-1,3,5-triazin4(3H)-one compounds; WO2006/126081, WO2006/126083, WO2007/020521 and CA02339677 disclose a series of pyridinopyrazinone compounds; WO2005089752 discloses a series of tetracyclic carboline compounds; WO2005/012303 and WO2007/002125 disclose a series of xanthine derivatives; and WO03/020724 discloses a series of polycyclic guanidine xanthine compounds. All of these compounds also show strong inhibitory activities of PDE5.

The developing PDE5 inhibitors are also used for pulmonary hypertension, diabeticgrastrointestinal disorder, insulin resistance, hyperlipemia and the like.

Although sildenafil has achieved a good clinical effect, it shows some side effects, such as headache, facial flushing, upset stomach, nasal obstruction, blurred vision, sensitivity to light, bluish vision and the like in clinic, since it also has inhibition on other PDE isoenzymes to the different extent.

On the one hand, as the side effects are dose-dependent, there is a need for a PDE5 inhibitor having a stronger activity to decrease the dose and alleviate the side effects; on the other hand, since the vision disorders is caused by inhibition of type VI phosphodiesterases (PDE6) existing in retina, it is another object in finding out a new PDE5 inhibitor to increase the selectivity, especially against PDE6.

SUMMARY OF THE INVENTION

Thus, one object of the invention is to provide a type of phenylpyrimidone compounds of formula I, the pharmaceutically acceptable salts or solvates thereof.

Another object of the invention is to provide a pharmaceutical composition containing the said phenylpyrimidone compound of formula I, the pharmaceutically acceptable salts or solvates thereof.

Still another object of the invention is to provide a process for preparing the said phenylpyrimidone compound of formula I, the pharmaceutically acceptable salts or solvates thereof.

Still another object of the invention is to provide a use of the said phenylpyrimidone compound of formula I, the pharmaceutically acceptable salts or solvates thereof in preparing drugs for treating various vascular disorders, such as male erectile dysfunction, pulmonary hypertension, etc.

The inventors of the present invention designed and synthesized a type of novel phenylpyrimidone compounds of formula I, the pharmaceutically acceptable salts or solvates thereof:

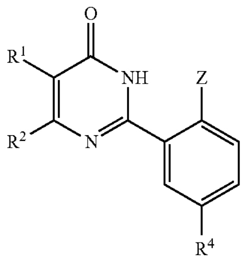

I wherein, $R^1$ and $R^2$ are each independently H, $C_1$-$C_{10}$ alkyl; $C_3$-$C_6$ alkenyl; $C_3$-$C_6$ cycloalkyl; halogen; $CF_3$; CN; $NO_2$; $OR^5$; $NR^6R^7$; $NHSO_2NR^6R^7$; $CNR^6R^7$; $CO_2R^8$; $NHCOR^8$; aryl; Het; $C_1$-$C_4$ alkyl optionally substituted with aryl, $OR^5$, $NR^6R^7$, CN, $CONR^6R^7$ or $CO_2R^8$; or $C_2$-$C_4$ alkenyl optionally substituted with CN, $CONR^6R^7$ or $CO_2R^8$; with the proviso that when $R^1$ is $CONR^6R^7$ or $CO_2R^8$, $R^2$ is not H;

Z is $OR^3$, $NR^3R^{10}$, $COR^{11}$, $NHCOR^{15}$ or $OCOR^{15}$;

$R^3$ is $C_1$-$C_6$ alkyl; $C_3$-$C_6$ cycloalkyl; $C_3$-$C_6$ alkenyl; $C_1$-$C_3$ haloalkyl; or $C_1$-$C_3$ alkyl substituted with $C_1$-$C_3$ alkoxy or $C_3$-$C_6$ cycloalkyl;

$R^4$ is $NO_2$; CN; $SO_2NR^6R^7$; $NR^9R^{10}$; $COR^{11}$; $OR^{12}$; $C_2$-$C_4$ alkyl optionally substituted with OH, CN, $C_1$-$C_4$ alkoxy, $NR^6R^7$, $CONR^6R^7$ or $CO_2R^8$; $C_2$-$C_4$ alkenyl optionally substituted with CN, $CONR^6R^7$ or $CO_2R^8$; or $R^4$ is a 5~7-member heterocyclyl optionally substituted with one or more substituents selected from OH, $COOR^8$, $CONH_2$, $C_1$-$C_6$ alkyl, $C_1$-$C_4$ alkoxy, $C_3$-$C_6$ cycloalkyl, aryl, Het, and $C_1$-$C_6$ alkyl substituted with halogen or alkoxy or hydroxyl; or $R^4$ is a 5- or 6-member monosaccharide group optionally substituted with one or more substituents selected from $C_1$-$C_6$ alkyl, trimethylsilyl, benzyl and acetyl;

$R^5$ is H; $C_1$-$C_6$ alkyl; $C_3$-$C_6$ alkenyl; $C_3$-$C_6$ cycloalkyl; $C_1$-$C_4$ alkyl optionally substituted with OH, $C_1$-$C_4$ alkoxy or $NR^6R^7$; aryl; or Het;

$R^6$ and $R^7$ are each independently H, OH, $C_1$-$C_6$ alkyl, $C_1$-$C_6$ alkoxy, $C_3$-$C_6$ alkenyl, $C_3$-$C_6$ cycloalkyl, adamantyl, $C_3$-$C_8$ lactamyl, aryl, Het, or $(CH_2CH_2O)_jH$ wherein j is 1~3; or $R^6$ and $R^7$ are each independently $C_1$-$C_6$ alkyl optionally substituted with OH, $C_1$-$C_4$ alkoxy, $SO_3H$, $SO_2NR^{13}R^{14}$, $SO_2R^{16}$, $PO(OH)_2$, $PO(OR^{16})_2$, $NR^{13}R^{14}$, aryl, Het or 4~8-member heterocyclyl; or $R^6$ and $R^7$ are each independently a 4~8-member heterocyclyl optionally substituted with one or more substituents selected from OH, $COOR^8$, $CONH_2$, $COR^{16}$, $SO_2R^{16}$, $C_1$-$C_6$ alkyl, $C_1$-$C_4$ alkoxy, $C_3$-$C_6$ cycloalkyl, aryl, Het and $C_1$-$C_6$ alkyl substituted with halogen or $C_1$-$C_4$ alkoxy or hydroxyl; or $R^6$ and $R^7$, together with the nitrogen atom to which they are attached, form a 4~8-member heterocyclyl optionally substituted with one or more substituents selected from OH, $COOR^8$, $CONH_2$, $COR^{16}$, $SO_2R^{16}$, $C_1$-$C_6$ alkyl, $(CH_2CH_2O)_jH$ wherein j is 1~3, $C_1$-$C_4$ alkoxy, $C_3$-$C_6$ cycloalkyl, aryl, Het, and $C_1$-$C_6$ alkyl substituted with halogen or $C_1$-$C_4$ alkoxy or hydroxyl; or $R^6$ and $R^7$, together with the nitrogen atom to which they are attached, form glucosylamino group, amino-acid residue, amino-acid ester residue or amino-amide residue, which are optionally substituted with one or more substituents selected from $C_1$-$C_6$ alkyl, $NR^{13}R^{14}$, $COR^{16}$, benzyl, benzyloxycarbonyl and t-butyloxycarbonyl;

$R^8$ is H, $C_1$-$C_6$ alkyl or aryl;

$R^9$ is H, $C_1$-$C_6$ alkyl or $SO_2R^{16}$;

$R^{10}$ is H; $C_1$-$C_6$ alkyl; $COR^{15}$; $SO_2NR^6R^7$; $SO_2R^{16}$;

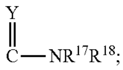 ; 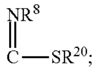 ;

a 5- or 6-member monosaccharide group optionally substituted with one or more substituents selected from $C_1$-$C_6$ alkyl, trimethylsilyl, benzyl and acetyl; or, $R^{10}$ is a 5-member heterocyclyl optionally substituted with one or more substituents; or, when $R^9$ is H, $R^{10}$ is an amino-acid residue optionally substituted with one or more substituents selected from OH, $C_1$-$C_6$ alkyl, $C_1$-$C_4$ alkoxy, $COR^{16}$, benzyl, benzyloxycarbonyl and t-butyloxycarbonyl;

$R^{11}$ is H; OH; $C_1$-$C_6$ alkyl; aryl; Het; $NH(CH_2)_kNH_2$, $NH(CH_2)_kNHSO_2R^{16}$, or $NH(CH_2)_kNHCOR^{16}$, wherein k is 0~4; $C_1$-$C_3$ alkyl substituted with halogen, OH or $C_1$-$C_6$ alkoxy; or $(CH_2)_mNR^6R^7$, wherein m is 0~2; or, $R^{11}$ is an amino-acid residue or an amino-amide residue optionally substituted with $C_1$-$C_6$ alkyl or $C_1$-$C_4$ alkoxy;

$R^{12}$ is H, $COR^{19}$, $SO_2R^{16}$, or a 5- or 6-member monosaccharide group optionally substituted with one or more substituents selected from $C_1$-$C_6$ alkyl, trimethylsilyl, benzyl and $COR^{16}$;

$R^{13}$ and $R^{14}$ are each independently H or $C_1$-$C_6$ alkyl; or, $R^{13}$ and $R^{14}$, together with the nitrogen atom to which they are attached, form a 4~8-member heterocyclyl optionally substituted with one or more substituents selected from OH, $C_1$-$C_6$ alkyl, $C_1$-$C_4$ alkoxy, $C_3$-$C_6$ cycloalkyl, aryl and Het;

$R^{15}$ is H; $CF_3$; $C_1$-$C_6$ alkyl optionally substituted with halogen, OH, $C_1$-$C_6$ alkoxycarbonylamino, $NR^{13}R^{14}$, $NHSO_2R^{16}$, $NHCOR^{16}$, $SO_3H$, $SO_2NR^{13}R^{14}$, $SO_2R^{16}$, $PO(OH)_2$, $PO(OR^{16})_2$, aryl or Het; $(CH_2)_nCOOR^8$; $(CH_2)_nCONHR^8$, wherein n is 0~6; $C_2$-$C_4$ alkenyl optionally substituted with $C_1$-$C_6$ alkyl, OH, $C_1$-$C_6$ alkoxy or $NR^{13}R^{14}$; $C_3$-$C_6$ cycloalkyl optionally substituted with $C_1$-$C_6$ alkyl or OH; $C_3$-$C_6$ cycloalkoxy optionally substituted with $C_1$-$C_6$ alkyl or OH; aryl; or Het;

$R^{16}$ is $C_1$-$C_6$ alkyl, aryl or Het;

$R^{17}$ and $R^{18}$ are each independently H; $C_1$-$C_6$ alkyl optionally substituted with OH, $SO_3H$, $SO_2NR^{13}R^{14}$, $SO_2R^{16}$, $PO(OH)_2$, $PO(OR^{16})_2$, $NR^{13}R^{14}$, aryl, Het or 4~8-member heterocyclyl; $C_3$-$C_6$ cycloalkyl; or aryl optionally substituted with OH; or, $R^{17}$ and $R^{18}$, together with the nitrogen atom to which they are attached, form a 4~8-member heterocyclyl optionally substituted with one or more substituents selected from OH, $C_1$-$C_6$ alkyl, $C_1$-$C_4$ alkoxy, $C_3$-$C_6$ cycloalkyl, aryl and Het;

$R^{19}$ is $C_1$-$C_6$ alkyl, aryl or $NHR^8$;

$R^{20}$ is $C_1$-$C_3$ alkyl;

halogen is F, Cl, Br or I;

Y is O, S or $NR^8$;

The said 'aryl' is phenyl unsubstituted or substituted with one or more substituents selected from halogen, $C_1$-$C_3$ alkyl, $C_1$-$C_3$ alkoxy, $CF_3$, CN and $NO_2$;

The said '5~7-member heterocyclyl', '4~8-member heterocyclyl' and '5-member heterocyclyl' denote saturated or unsaturated heterocyclyl comprising one or more heteroatoms selected from N, S and O;

The said 'Het' is a 5~6-member aromatic heterocyclyl comprising 1~4 heteroatoms selected from N, S and O, the said 5~6-member aromatic heterocyclyl being optionally substituted with one or more substituents selected from halogen, $C_1$-$C_3$ alkyl, $C_1$-$C_3$ alkoxy, $CF_3$, CN and $NO_2$.

In a preferred embodiment of the present invention, in formula I:

$R^1$ and $R^2$ are each independently H; $C_1$-$C_{10}$ alkyl; halogen; $CF_3$; CN; $OR^5$; $NR^6R^7$; $NHCOR^8$; aryl; or $C_1$-$C_4$ alkyl optionally substituted with aryl, $OR^5$, $NR^6R^7$, CN, $CONR^6R^7$ or $CO_2R^8$;

Z is $OR^3$, $NR^3R^{10}$, $COR^{11}$, $NHCOR^{15}$ or $OCOR^{15}$;

$R^3$ is $C_1$-$C_6$ alkyl or $C_1$-$C_3$ alkyl substituted with $C_1$-$C_3$ alkoxy;

$R^4$ is $NO_2$; CN; $SO_2NR^6R^7$; $NR^9R^{10}$; $COR^{11}$; $OR^{12}$; $C_2$-$C_4$ alkyl optionally substituted with OH, $C_1$-$C_4$ alkoxy or $NR^6R^7$; or, $R^4$ is a 5- or 6-member heterocyclyl optionally substituted with one or more substituents selected from OH, $COOR^8$, $CONH_2$, $C_1$-$C_6$ alkyl, $C_1$-$C_4$ alkoxy, $C_3$-$C_6$ cycloalkyl, aryl, Het and $C_1$-$C_6$ alkyl substituted with OH; or, $R^4$ is a 5- or 6-member monosaccharide group optionally substituted with one or more substituents selected from $C_1$-$C_6$ alkyl, trimethylsilyl, benzyl and acetyl;

$R^5$ is H; $C_1$-$C_6$ alkyl; $C_1$-$C_4$ alkyl optionally substituted with OH, $C_1$-$C_4$ alkoxy or $NR^6R^7$; or aryl;

$R^6$ and $R^7$ are each independently H, OH, $C_1$-$C_6$ alkyl, $C_1$-$C_6$ alkoxy, $C_3$-$C_6$ alkenyl, $C_3$-$C_6$ cycloalkyl, adamantyl, $C_3$-$C_8$ lactamyl, aryl, Het, or $(CH_2CH_2O)_jH$ wherein j is 1~3; or $R^6$ and $R^7$ are each independently $C_1$-$C_6$ alkyl optionally substituted with OH, $C_1$-$C_4$ alkoxy, $SO_3H$, $SO_2NR^{13}R^{14}$, $SO_2R^{16}$, $PO(OH)_2$, $PO(OR^{16})_2$, $NR^{13}R^{14}$, aryl, Het or 4~8-member heterocyclyl; or $R^6$ and $R^7$ are each independently a 4~8-member heterocyclyl, wherein the said 4~8-member heterocyclyl is furyl, thienyl, thiazolyl, imidazolyl, pyrazolyl, pyridyl, pyrimidinyl, pyrazinyl, morpholinyl, thiomorpholinyl, piperidyl, pyrrolidinyl or piperazinyl, and the said 4~8-member heterocyclyl is optionally substituted with one or more substituents selected from OH, $COOR^8$, $CONH_2$, $COR^{16}$, $SO_2R^{16}$, $C_1$-$C_6$ alkyl, $C_3$-$C_6$ cycloalkyl, aryl, Het and $C_1$-$C_6$ alkyl substituted with $C_1$-$C_4$ alkoxy or hydroxy; or $R^6$ and $R^7$, together with the nitrogen atom to which they are attached, form a 4~8-member heterocyclyl optionally substituted with one or more substituents selected from OH, $COOR^8$, $CONH_2$, $COR^{16}$, $SO_2R^{16}$, $C_1$-$C_6$ alkyl, $(CH_2CH_2O)_jH$ wherein j is 1~3, $C_3$-$C_6$ cycloalkyl, aryl, Het, and $C_1$-$C_6$ alkyl substituted with $C_1$-$C_4$ alkoxy or hydroxyl or aryl; or $R^6$ and $R^7$, together with the nitrogen atom to which they are attached, form glucosylamino group, amino-acid residue, amino-acid ester residue or amino amide residue, which are optionally substituted with one or more substituents selected from $C_1$-$C_6$ alkyl, $NR^{13}R^{14}$, $COR^{16}$, benzyl, benzyloxycarbonyl and t-butyloxycarbonyl;

$R^8$ is H, $C_1$-$C_6$ alkyl or aryl;

$R^9$ is H, $C_1$-$C_6$ alkyl or $SO_2R^{16}$;

$R^{10}$ is H; $C_1$-$C_6$ alkyl; $COR^{15}$; $SO_2R^{16}$;

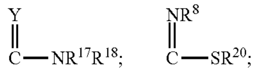

a 5- or 6-member monosaccharide group; or $R^{10}$ is a 5-member heterocyclyl optionally substituted with one or more substituents, wherein the heterocyclyl is dihydroimidazolyl substituted with hydroxyalkyl, or 1,2,4-triazolyl optionally substituted with $C_1$-$C_6$ alkyl, aryl or amino group; or when $R^9$ is H, $R^{10}$ is an amino-acid residue optionally substituted with one or more substituents selected from OH, $C_1$-$C_6$ alkyl, $C_1$-$C_4$ alkoxy, $COR^{16}$, benzyl, benzyloxycarbonyl and t-butyloxycarbonyl;

$R^{11}$ is H; OH; $C_1$-$C_6$ alkyl; aryl; Het; $NH(CH_2)_kNH_2$, $NH(CH_2)_kNHSO_2R^{16}$, or $NH(CH_2)_kNHCOR^{16}$, wherein k is 0~4; $C_1$-$C_3$ alkyl substituted with halogen, OH or $C_1$-$C_6$ alkoxy; or $(CH_2)_mNR^6R^7$, wherein m is 0~2; or, $R^{11}$ is an amino-acid residue or an aminoamide residue optionally substituted with $C_1$-$C_4$ alkoxy;

$R^{12}$ is H, $COR^{19}$, $SO_2R^{16}$ or a 5- or 6-member monosaccharide group;

$R^{13}$ and $R^{14}$ are each independently H or $C_1$-$C_6$ alkyl; or, $R^{13}$ and $R^{14}$, together with the nitrogen atom to which they are attached, form a 4~8-member heterocyclyl optionally substituted with one or more substituents selected from OH and $C_1$-$C_6$ alkyl;

$R^{15}$ is H; $CF_3$; $C_1$-$C_6$ alkyl optionally substituted with halogen, OH, $C_1$-$C_6$ alkoxycarbonylamino, $NR^{13}R^{14}$, $NHSO_2R^{16}$, $NHCOR^{16}$, $SO_3H$, $SO_2NR^{13}R^{14}$, $SO_2R^{16}$, $PO(OH)_2$, $PO(OR^{16})_2$, aryl or Het; $(CH_2)_nCOOR^8$, or $(CH_2)_nCONHR^8$, wherein n is 0~6; $C_2$-$C_4$ alkenyl optionally substituted with $C_1$-$C_6$ alkyl, OH, $C_1$-$C_6$ alkoxy or $NR^{13}R^{14}$; $C_3$-$C_6$ cycloalkyl optionally substituted with $C_1$-$C_6$ alkyl or OH; $C_3$-$C_6$ cycloalkoxy optionally substituted with $C_1$-$C_6$ alkyl or OH; aryl; or Het;

$R^{16}$ is $C_1$-$C_6$ alkyl or aryl;

$R^{17}$ and $R^{18}$ are each independently H; $C_1$-$C_6$ alkyl optionally substituted with OH, $SO_3H$, $SO_2NR^{13}R^{14}$, $SO_2R^{16}$, $PO(OH)_2$, $PO(OR^{16})_2$, $NR^{13}R^{14}$, aryl, Het or 4~8-member heterocyclyl; $C_3$-$C_6$ cycloalkyl; or aryl optionally substituted with OH; or, $R^{17}$ and $R^{18}$, together with the nitrogen atom to which they are attached, form a 4~8-member heterocyclyl optionally substituted with one or more substituents selected from OH and $C_1$-$C_6$ alkyl;

$R^{19}$ is $C_1$-$C_6$ alkyl, aryl or $NHR^8$;

$R^{20}$ is $C_1$-$C_3$ alkyl;

Halogen is F, Cl, Br or I;

Y is O, S or $NR^8$;

The said 'aryl' is phenyl unsubstituted or substituted with one or more substituents selected from halogen, $C_1$-$C_3$ alkyl, and $C_1$-$C_3$ alkoxy;

The said '5- or 6-member heterocyclyl', '4~8-member heterocyclyl', '5-member heterocyclyl' denote saturated or unsaturated heterocyclyl comprising one or more heteroatoms selected from N, S and O;

The said 'Het' is a 5~6-member aromatic heterocyclyl comprising 1~4 heteroatoms selected from N, S and O, the said 5~6-member aromatic heterocyclyl being optionally substituted with one or more substituents selected from halogen, $C_1$-$C_3$ alkyl, $C_1$-$C_3$ alkoxy, $CF_3$, CN and $NO_2$.

The said 'amino-acid' is glycine, alanine, phenylalanine, serine, tryptophane, valine, leucine, isoleucine, t-leucine, tyrosine, lysine, histidine, methionine, arginine, threonine, aspartate, cysteine, proline, glutamic acid, asparagine, glutamine, ornithine or citrulline;

The said '5- or 6-member monosaccharide' is ribose, deoxyribose, xylose, arabinose, glucose, mannose, galactose or fructose.

In a further preferred embodiment of the present invention, in formula I:

$R^1$ is H, F, Cl, Br, I, $NH_2$, OH, CN, methyl, ethyl, propyl, isopropyl or acetamido;

$R^2$ is $NH_2$, Br, $CF_3$, $OR^5$, ethyl, propyl, isopropyl, benzylamino, phenyl, benzyl, isobutyl, n-octyl or acetamido;

Z is $OR^3$;

$R^3$ is ethyl, propyl, n-butyl, n-hexyl or 3-methoxyl propyl;

$R^4$ is $NO_2$, $SO_2NR^6R^7$, $NR^9R^{10}$, $COR^{11}$, $OR^{12}$ or glucosyl; or $R^4$ is a 5- or 6-member heterocyclyl, wherein the said 5- or 6-member heterocyclyl is thienyl, thiazolyl, 1,2,4-triazolyl, imidazolyl, pyrrolyl, oxadiazolyl, pyrimidinyl, morpholinyl, thiomorpholinyl, piperidyl, pyrrolidinyl or piperazinyl, and the said 5- or 6-member heterocyclyl is optionally substituted with one or more substituents selected from OH, COOH, $CONH_2$, $C_1$-$C_6$ alkyl, $C_1$-$C_4$ alkoxy, $C_3$-$C_6$ cycloalkyl, aryl, Het and $C_1$-$C_6$ alkyl substituted with OH;

$R^5$ is H; $C_1$-$C_4$ alkyl optionally substituted with OH, $C_1$-$C_4$ alkoxy or $NR^6R^7$; or aryl;

$R^6$ and $R^7$ are each independently H, methyl, methoxyl, cyclopropyl, propenyl, isobutyl, t-butyl, adamantyl, cyclohexyl, caprolactamyl, 2-(1-methylpyrrol-2-yl)ethylamino, pyridylmethyl, thienylmethyl,

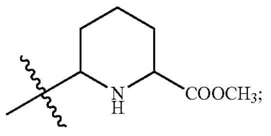 [SMILES: *C1CCCC(C(=O)OC)N1]

or $C_2$-$C_3$ alkyl optionally substituted with OH, $NR^{13}R^{14}$, $SO_3H$, $SO_2NR^{13}R^{14}$ or 5~6-member heterocyclyl, wherein the said 5~6-member heterocyclyl is morpholinyl, thiomorpholinyl, piperidyl, pyrrolidinyl or piperazinyl, and the said 5~6-member heterocyclyl is optionally substituted with one or more substituents selected from OH, $COOR^8$, $CONH_2$, $COR^{16}$, $SO_2R^{16}$, $C_1$-$C_6$ alkyl and aryl; or $R^6$ and $R^7$, together with the nitrogen atom to which they are attached, form a 5~6-member heterocyclyl, wherein the said 5~6-member heterocyclyl is morpholinyl, thiomorpholinyl, piperidyl, pyrrolidinyl or piperazinyl, and the said 5~6-member heterocyclyl is optionally substituted with one or more substituents selected from OH, $COOR^8$, $CONH_2$, $COR^{16}$, $SO_2R^{16}$, $C_1$-$C_6$ alkyl, $(CH_2CH_2O)_jH$ wherein j is 1~2, dichlorophenyl, benzyl, pyridyl and aryl; or $NR^6R^7$ is glucosylamino group, amino-acid residue, amino-acid ester residue or amino-amide residue, which are optionally substituted with one or more substituents selected from $NR^{13}R^{14}$ and acetyl;

$R^8$ is H, methyl or ethyl;

$R^9$ is H, methyl or $SO_2R^{16}$;

$R^{10}$ is H, methyl, $COR^{15}$, $SO_2R^{16}$,

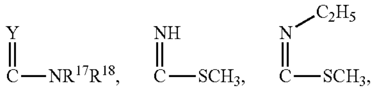

glucosyl or mannosyl; dihydroimidazolyl substituted with hydroxyethyl; or when $R^9$ is H, $R^{10}$ is an amino-acid residue optionally substituted with one or more selected from OH, t-butyloxycarbonyl, and acetyl;

$R^{11}$ is OH, pyrazolyl substituted with isopropyl; aminoamide residue; amino-ester residue; $NR^6R^7$; $CH_2Br$ or $CH_2NR^6R^7$;

$R^{12}$ is H, $COR^{19}$, $SO_2R^{16}$, mannosylorglucosyl;

$R^{13}$ and $R^{14}$ are each independently H or ethyl; or, $R^{13}$ and $R^{14}$, together with the nitrogen atom to which they are attached, form a 5~6-member heterocyclyl, wherein the said 5~6-member heterocyclyl is morpholinyl, piperidyl, pyrrolidinyl or piperazinyl, and the said 5~6-member heterocyclyl is optionally substituted with one or more substituents selected from OH and $C_1$-$C_6$ alkyl;

$R^{15}$ is H; methyl; ethyl; cyclohexyl; $CF_3$; $(CH_2)_nCOOR^8$, or $(CH_2)_nCONH_2$, wherein, n is 0 or 1; vinyl; propenyl; pyridyl; phenyl substituted with ethoxy; or thiazolyl substituted with isopropyl;

$R^{16}$ is methyl;

$R^{17}$ and $R^{18}$ are each independently H, ethyl or phenyl; or $R^{17}$ and $R^{18}$, together with the nitrogen atom to which they are attached, form a 4~8-member heterocyclyl, wherein the said 4~8-member heterocyclyl is morpholinyl, piperidyl, pyrrolidinyl or piperazinyl, and the said 4~8-member heterocyclyl is optionally substituted with one or more substituents selected from OH and $C_1$-$C_6$ alkyl; or when Y is NH, $R^{17}$ and C(Y)N form a dihydroimidazolyl;

$R^{19}$ is methyl or $NHC_2H_5$;

$R^{20}$ is methyl;

Halogen is F, Cl, Br or I;

Y is O, S, NH or $NC_2H_5$.

The said 'aryl' is phenyl unsubstituted or substituted with one or more substituents selected from halogen, $C_1$-$C_3$ alkyl, and $C_1$-$C_3$ alkoxy;

The said 'Het' is a 5~6-member aromatic heterocyclyl comprising 1~4 heteroatoms selected from N, S and O, the said 5~6-member aromatic heterocyclyl being optionally substituted with one or more substituents selected from halogen, $C_1$-$C_3$ alkyl, $C_1$-$C_3$ alkoxy, $CF_3$, CN and $NO_2$.

The said 'amino-acid' is glycine, alanine, phenylalanine, serine, tryptophane, valine, leucine, isoleucine, t-leucine, tyrosine, lysine, histidine, methionine, arginine, threonine, aspartate, cysteine, proline, glutamic acid, asparagine, glutamine, ornithine or citrulline;

The said '5- or 6-member monosaccharide' is glucose or mannose.

In another further preferred embodiment of the present invention, the phenylpyrimidone compound of formula I, pharmaceutically acceptable salts or solvates thereof are selected from the following compounds:

6-isopropyl-2-[2-n-propoxyl-5-(4-methyl-1-piperazinylsulfonyl)phenyl]pyrimid-4(3H)-one, 6-amino-2-[2-n-propoxyl-5-(4-methyl-1-piperazinylsulfonyl)phenyl]pyrimid-4(3H)-one, 6-hydroxy-2-[2-n-propoxyl-5-(4-methyl-1-piperazinylsulfonyl)phenyl]pyrimid-4(3H)-one, 5-acetamido-6-hydroxy-2-[2-n-propoxyl-5-(4-methyl-1-piperazinylsulfonyl)phenyl]pyrimid-4(3H)-one, 6-phenyl-2-[2-n-propoxyl-5-(4-methyl-1-piperazinylsulfonyl)phenyl]pyrimid-4(3H)-one, 6-ethyl-2-[2-n-propoxyl-5-(4-methyl-1-piperazinylsulfonyl)phenyl]pyrimid-4 (3H)-one, 5-acetamido-6-ethyl-2-[2-n-propoxyl-5-(4-methyl-1-piperazinylsulfonyl)phenyl]pyrimid-4(3H)-one, 5-acetamido-6-amino-2-[2-n-propoxyl-5-(4-methyl-1-piperazinylsulfonyl)phenyl]pyrimid-4(3H)-one, 6-acetamido-2-[2-n-propoxyl-5-(4-methyl-1-piperazinylsulfonyl)phenyl]pyrimid-4(3H)-one, 5-bromo-6-isopropyl-2-[2-n-propoxyl-5-(4-methyl-1-piperazinylsulfonyl)phenyl]pyrimid-4(3H)-one, 6-isopropyl-2-[2-ethoxyl-5-(4-methyl-1-piperazinylsulfonyl)phenyl]pyrimid-4(3H)-one, 5-bromo-6-isopropyl-2-[2-ethoxyl-5-(4-methyl-1-piperazinylsulfonyl)phenyl]pyrimid-4(3H)-one, 5-chloro-6-isopropyl-2-[2-ethoxyl-5-(4-methyl-1-piperazinylsulfonyl)phenyl]pyrimid-4(3H)-one, 5-acetamido-6-isopropyl-2-[2-ethoxyl-5-(4-methyl-1-piperazinylsulfonyl)phenyl]pyrimid-4(3H)-one, 5-bromo-6-isopropyl-2-[2-n-butoxy-5-(4-methyl-1-piperazinylsulfonyl)phenyl]pyrimid-4(3H)-one 5-bromo-6-n-octyl-2-[2-ethoxyl-5-(4-methyl-1-piperazinylsulfonyl)phenyl]pyrimid-4(3H)-one, 5-bromo-6-phenyl-2-[2-ethoxyl-5-(4-methyl-1-piperazinylsulfonyl)phenyl]pyrimid-4(3H)-one, 5-methyl-6-isopropyl-2-[2-n-propoxyl-5-(4-methyl-1-piperazinylsulfonyl)phenyl]pyrimid-4(3H)-one, 5-fluoro-6-ethyl-2-[2-n-propoxyl-5-(4-methyl-1-piperazinylsulfonyl)phenyl]pyrimid-4(3H)-one, 5-methyl-6-ethyl-2-[2-n-propoxyl-5-(4-methyl-1-piperazinylsulfonyl)phenyl]pyrimid-4(3H)-one, 5-hydroxy-6-isopropyl-2-[2-ethoxyl-5-(4-methyl-1-piperazinylsulfonyl)phenyl]pyrimid-4(3H)-one, 5-amino-6-isopropyl-2-[2-ethoxyl-5-(4-methyl-1-piperazinylsulfonyl)phenyl]pyrimid-4 (3H)-one, 5-bromo-6-isopropyl-2-[2-n-hexyloxy-5-(4-methyl-1-piperazinylsulfonyl)phenyl]pyrimid-4(3H)-one, 5-bromo-6-isobutyl-2-[2-ethoxyl-5-(4-methyl-1-piperazinylsulfonyl)phenyl]pyrimid-4(3H)-one, 5-bromo-6-isopropyl-2-{2-n-propoxyl-5-[N-methyl-N-(2-hydroxyethyl)aminosulfonyl]phenyl}pyrimid-4(3H)-one, 5-bromo-6-isopropyl-2-{2-n-propoxyl-5-[N-(2-morpholinoethyl)aminosulfonyl]phenyl}pyrimid-4(3H)-one, 5-bromo-6-isopropyl-2-{2-n-propoxyl-5-[N-(3-morpholinopropyl)aminosulfonyl]phenyl}pyrimid-4(3H)-one, 5-bromo-6-isopropyl-2-{2-n-propoxyl-5-[N—(N',N'-diethylamino)ethylaminosulfonyl]phenyl}pyrimid-4 (3H)-one, 5,6-diethyl-2-[2-n-propoxyl-5-(4-methyl-1-piperazinylsulfonyl)phenyl]pyrimid-4(3H)-one 5,6-diethyl-2-{2-n-propoxyl-5-[N-methyl-N-(hydroxyethyl)aminosulfonyl]phenyl}pyrimid-4(3H)-one, 5,6-diethyl-2-{2-n-propoxyl-5-[N-(2-ethylaminoethyl)aminosulfonyl]phenyl}pyrimid-4 (3H)-one, N-(3-(4,5-diethyl-1,6-dihydro-6-oxopyrimidin-2-yl)-4-n-propoxyphenylsulfonylproline, 2-(5-nitro-2-n-propoxyphenyl)-5-bromo-6-isopropylpyrimid-4(3H)-one, 2-(5-amino-2-n-propoxyphenyl)-5-bromo-6-isopropylpyrimid-4(3H)-one, 1-(3-(4-isopropyl-5-bromo-1,6-dihydro-6-oxopyrimidin-2-yl)-4-n-propoxyphenyl)-3-ethyl thiourea, 1-[3-(4-isopropyl-5-bromo-1,6-dihydro-6-oxopyrimidin-2-yl)-4-n-propoxyphenyl]-3-ethyl-2-methylisothiourea, N-[3-(4-isopropyl-5-bromo-1,6-dihydro-6-oxopyrimidin-2-yl)-4-n-propoxyphenyl]-N',N''-triethylguanidine, N-[3-(4-isopropyl-5-bromo-1,6-dihydro-6-oxopyrimidin-2-yl)-4-n-propoxyphenyl]-N'-ethyl-piperidyl-1-formamidine, N-[3-(4-isopropyl-5-bromo-1,6-dihydro-6-oxopyrimidin-2-yl)-4-n-propoxyphenyl]-N'-ethyl-pyrrolyl-1-formamidine, 2-{2-[3-(4-isopropyl-5-bromo-1,6-dihydro-6-oxopyrimidin-2-yl)-4-n-propoxyphenyl]amino-4,5-dihydro-imidazol-1-yl}-ethanol, 2-(5-nitro-2-n-propoxyphenyl)-5,6-diethylpyrimid-4(3H)-one, 2-(5-amino-2-n-propoxyphenyl)-5,6-diethylpyrimid-4(3H)-one, 1-(3-(4,5-diethyl-1,6-dihydro-6-oxopyrimidin-2-yl)-4-n-propoxyphenyl)-3-ethylthiourea, 1-[3-(4,5-diethyl-1,6-dihydro-6-oxopyrimidin-2-yl)-4-n-propoxyphenyl]-3-ethyl-2-methylisothiourea, N-[3-(4,5-diethyl-1,6-dihydro-6-oxopyrimidin-2-yl)-4-n-propoxyphenyl]-N'-ethyl-piperidyl-1-formamidine, N-[3-(4,5-diethyl-1,6-dihydro-6-oxopyrimidin-2-yl)-4-n-propoxyphenyl]-N',N''-triethyl guanidine, 2-{2-[3-(4,5-diethyl-1,6-dihydro-6-oxopyrimidin-2-yl)-4-n-propoxyphenyl]amino-4,5-dihydro-imidazol-1-yl}-ethanol, N-[3-(4,5-diethyl-1,6-dihydro-6-oxopyrimidin-2-yl)-4-n-propoxyphenyl]-N'-ethyl-pyrrolyl-1-formamide, N-[3-(4,5-diethyl-1,6-dihydro-6-oxopyrimidin-2-yl)-4-n-propoxyphenyl]-pyrrolyl-1-formamidine, 5-bromo-6-isopropyl-2-(2-n-propoxyl-5-mesylamidophenyl)pyrimid-4(3H)-one, 5,6-diethyl-2-(2-n-propoxyl-5-mesylamidophenyl)pyrimid-4(3H)-one, N-(3-(1,6-dihydro-4-isopropyl-5-bromo-6-oxopyrimidin-2-yl)-4-propoxyphenyl)acetamide, N-(3-(1,6-dihydro-4,5-diethyl-6-oxopyrimidin-2-yl)-4-propoxyphenyl)acetamide, N-(3-(1,6-dihydro-4,5-diethyl-6-oxopyrimidin-2-yl)-4-propoxyphenyl)propionamide, N-(3-(1,6-dihydro-4,5-diethyl-6-oxopyrimidin-2-yl)-4-propoxyphenyl)cyclohexamide, N-(3-(1,6-dihydro-4,5-diethyl-6-oxopyrimidin-2-yl)-4-propoxyphenyl)formamide, N-(3-(1,6-dihydro-4,5-diethyl-6-oxopyrimidin-2-yl)-4-propoxyphenyl)-1-t-butyloxycarbonyl-4-hydroxy-prolylamide, 4-n-propoxyl-3-(1,6-dihydro-4,5-diethyl-6-oxopyrimidin-2-yl)benzoic acid, (morpholin-1-yl)(3-(4,5-diethyl-1,6-dihydro-6-oxopyrimidin-2-yl)-4-n-propoxyl)benzophenone, (piperid-1-yl)(3-(4,5-diethyl-1,6-dihydro-6-oxopyrimidin-2-yl)-4-n-propoxyl)benzophenone, (2-aminoformylpyrrol-1-yl)(3-(4,5-diethyl-1,6-dihydro-6-oxopyrimidin-2-yl)-4-n-propoxyl)benzophenone, 4-n-propoxyl-3-(1,6-dihydro-4-isopropyl-6-oxopyrimidin-2-yl)benzoic acid, (morpholin-1-yl)(3-(4-isopropyl-5-bromo-1,6-dihydro-6-oxopyrimidin-2-yl)-4-n-propoxyl)benzophenone, (piperid-1-yl)(3-(4-isopropyl-5-bromo-1,6-dihydro-6-oxopyrimidin-2-yl)-4-n-propoxyl)benzophenone, (4-methyl-piperazin-1-yl)(3-(4-isopropyl-5-bromo-1,6-dihydro-6-oxopyrimidin-2-yl)-4-n-propoxyl)benzophenone, 2-(5-(N,N-dimethylamino-2-n-propoxyphenyl)-5,6-diethylpyrimid-4(3H)-one, 1-(3-(4,5-diethyl-1,6-dihydro-6-oxopyrimidin-2-yl)-4-n-propoxyphenyl)urea, 1-(3-(4,5-diethyl-1,6-dihydro-6-oxopyrimidin-2-yl)-4-n-propoxyphenyl)-3-ethylurea, 1-(3-(4-isopropyl-5-bromo-1,6-dihydro-6-oxopyrimidin-2-yl)-4-n-propoxyphenyl)-3-phen ylthiourea, 1-(3-(4,5-diethyl-1,6-dihydro-6-oxopyrimidin-2-yl)-4-n-propoxyphenyl)-guanidine, 5-bromo-6-isopropyl-2-(5-(2-bromoacetyl)-2-n-propoxyphenyl)pyrimid-4(3H)-one, 5-bromo-6-isopropyl-2-(5-(2-morpholinylacetyl)-2-n-propoxyphenyl)pyrimid-4(3H)-one, 5-bromo-6-isopropyl-2-(5-(2-(4-methyl-piperazin-1-yl)acetyl)-2-n-propoxyphenyl)pyrimid-4(3H)-one, 5,6-diethyl-2-(5-(2-bromoacetyl)-2-n-propoxyphenyl)pyrimid-4(3H)-one, 5,6-diethyl-2-(5-(2-(4-methyl-piperazin-1-yl)acetyl)-2-n-propoxyphenyl)pyrimid-4(3H)-one, 5,6-diethyl-2-(5-(2-morpholinylacetyl)-2-n-propoxyphenyl)pyrimid-4(3H)-one, 5-bromo-6-isopropyl-2-(2-n-propoxyl-5-(tetrahydro-3,4,5-trihydroxy-6-(hydroxymethyl)-2H-pyran-2-ylamino)phenyl)pyrimid-4(3H)-one, 5-bromo-6-isopropyl-2-(2-n-propoxyl-5-(tetrahydro-3,4-dihydroxy-5-(1,2-dihydroxyethyl)fur-2-ylamino)phenyl)pyrimid-4(3H)-one, 5,6-diethyl-2-(2-n-propoxyl-5-(tetrahydro-3,4-dihydroxy-5-(1,2-dihydroxyethyl)fur-2-ylamino)phenyl)pyrimid-4(3H)-one, 5,6-diethyl-2-(2-n-propoxyl-5-(tetrahydro-3,4,5-trihydroxy-6-(hydroxymethyl)-2H-pyran-2-ylamino)phenyl)pyrimid-4(3H)-one, 2-(5-hydroxy-2-n-propoxyphenyl)-5,6-diethylpyrimid-4(3H)-one, (3-(4,5-diethyl-1,6-dihydro-6-oxopyrimidin-2-yl)-4-n-propoxyphenyl)acetate, (3-(4,5-diethyl-1,6-dihydro-6-oxopyrimidin-2-yl)-4-n-propoxyphenyl)ethylaminoformate, 5,6-diethyl-2-(2-n-propoxyl-5-(tetrahydro-3,4,5-trihydroxy-6-(hydroxymethyl)-2H-pyran-2-yloxy)phenyl)pyrimid-4(3H)-one, (3-(4,5-diethyl-1,6-dihydro-6-oxopyrimidin-2-yl)-4-n-propoxyphenyl)mesylate, 2-(5-(2,5-dimethyl-1H-pyrrol-1-yl)-2-propoxyphenyl)-5,6-diethylpyrimid-4(3H)-one, 2,2'-(4-n-propoxyl-1,3-phenylene)bis(5,6-diethylpyrimid-4(3H)-one), 2-(5-(1,3,4-oxadiazol-2-yl)-2-propoxyphenyl)-5,6-diethylpyrimid-4(3H)-one, ethyl 2-(3-(4,5-diethyl-1,6-dihydro-6-oxopyrimidin-2-yl)-4-n-propoxybenzamido)acetate, 3-(4,5-diethyl-1,6-dihydro-6-oxopyrimidin-2-yl)-N-(2-morpholinylethyl)-4-n-propoxybenzamide, 3-(4,5-diethyl-1,6-dihydro-6-oxopyrimidin-2-yl)-N,N-di(2-hydroxyethyl)-4-n-propoxybenzamide, 3-(4,5-diethyl-1,6-dihydro-6-oxopyrimidin-2-yl)-N-(2-caprolactam-3-yl)-4-n-propoxybenzamide, (4-(2,3-dichlorophenyl)piperazin-1-yl)(3-(4,5-diethyl-1,6-dihydro-6-oxopyrimidin-2-yl)-4-n-propoxyl)benzophenone, (3-isopropylpyrazol-1-yl)(3-(4,5-diethyl-1,6-dihydro-6-oxopyrimidin-2-yl)-4-n-propoxyl)benzophenone, N-cyclohexyl-3-(4,5-diethyl-1,6-dihydro-6-oxopyrimidin-2-yl)-4-n-propoxybenzamide, N-((pyrid-2-yl)methyl)-3-(4,5-diethyl-1,6-dihydro-6-oxopyrimidin-2-yl)-4-n-propoxybenzamide, methyl 2-(3-(4,5-diethyl-1,6-dihydro-6-oxopyrimidin-2-yl)-4-n-propoxybenzamido)-3,3-dimethylbutyrate, N-(3-(4,5-diethyl-1,6-dihydro-6-oxopyrimidin-2-yl)-4-n-propoxyphenyl)-2,2,2-trifluoro acetamide, ethyl N-(3-(4,5-diethyl-1,6-dihydro-6-oxopyrimidin-2-yl)-4-n-propoxyphenyl)aminoformylformate, N-(3-(4,5-diethyl-1,6-dihydro-6-oxopyrimidin-2-yl)-4-n-propoxyphenyl)acrylamide, N-(3-(4,5-diethyl-1,6-dihydro-6-oxopyrimidin-2-yl)-4-n-propoxyphenyl)-2-crotonamide, ethyl N-(3-(4,5-diethyl-1,6-dihydro-6-oxopyrimidin-2-yl)-4-n-propoxyphenyl)aminoformylacetate, 2-ethoxyl-N-(3-(4,5-diethyl-1,6-dihydro-6-oxopyrimidin-2-yl)-4-n-propoxyphenyl)benzamide, N-(3-(4,5-diethyl-1,6-dihydro-6-oxopyrimidin-2-yl)-4-n-propoxyphenyl)nicotinamide, N-(3-(4,5-diethyl-1,6-dihydro-6-oxopyrimidin-2-yl)-4-n-propoxyphenyl)-5-isopropylthiazolyl-2-formamide, t-butyl 3-(N-(3-(4,5-diethyl-1,6-dihydro-6-oxopyrimidin-2-yl)-4-n-propoxyphenyl)aminoformyl)propylamino formate, 4-acetamido-N-(3-(4,5-diethyl-1,6-dihydro-6-oxopyrimidin-2-yl)-4-n-propoxyphenyl)butyramide, 1-acetyl-N-(3-(4,5-diethyl-1,6-dihydro-6-oxopyrimidin-2-yl)-4-n-propoxyphenyl)pyrrolidinyl-2-formamide, 2-acetamido-N-(3-(4,5-diethyl-1,6-dihydro-6-oxopyrimidin-2-yl)-4-n-propoxyphenyl)-3-methylbutyramide, 2-acetamido-N-(3-(4,5-diethyl-1,6-dihydro-6-oxopyrimidin-2-yl)-4-n-propoxyphenyl)-3-phenylpropionamide, 2-acetamido-N-(3-(4,5-diethyl-1,6-dihydro-6-oxopyrimidin-2-yl)-4-n-propoxyphenyl)propionamide, 2,6-diacetamido-N-(3-(4,5-diethyl-1,6-dihydro-6-oxopyrimidin-2-yl)-4-n-propoxyphenyl) hexanamide, $N^1$-(3-(4,5-diethyl-1,6-dihydro-6-oxopyrimidin-2-yl)-4-n-propoxyphenyl)propanediamide, $N^1$-(3-(4,5-diethyl-1,6-dihydro-6-oxopyrimidin-2-yl)-4-n-propoxyphenyl)oxalamide, N-(aminoformylmethyl)-3-(4,5-diethyl-1,6-dihydro-6-oxopyrimidin-2-yl)-4-n-propoxybenzamide, 5,6-diethyl-2-{2-n-propoxyl-5-[(2-(1-methylpyrrol-2-yl) ethyl)aminosulfonyl]phenyl}pyrimid-4(3H)-one, 3-(4,5-diethyl-1,6-dihydro-6-oxopyrimidin-2-yl)-N-(2-(1-methylpyrrol-2-yl)ethyl)-4-n-propoxylbenzamide, 2-(N-(3-(4,5-diethyl-1,6-dihydro-6-oxopyrimidin-2-yl)-4-n-propoxyphenyl)sulfonyl)amino-5-ureapentanoic acid, 2-(N-(3-(4,5-diethyl-1,6-dihydro-6-oxopyrimidin-2-yl)-4-n-propoxyphenyl)sulfonyl)amino-5-aminopentanoic acid, 2-(N-(3-(4,5-diethyl-1,6-dihydro-6-oxopyrimidin-2-yl)-4-n-propoxyphenyl)sulfonyl)amino-3-methylbutyric acid, 2-(N-(3-(4,5-diethyl-1,6-dihydro-6-oxopyrimidin-2-yl)-4-n-propoxyphenyl)sulfonyl)aminopropanoic acid, 2-(N-(3-(4,5-diethyl-1,6-dihydro-6-oxopyrimidin-2-yl)-4-n-propoxyphenyl)sulfonyl)amino-3-hydroxypropanoic acid, ethyl 2-(N-(3-(4,5-diethyl-1,6-dihydro-6-oxopyrimidin-2-yl)-4-n-propoxyphenyl)sulfonyl)aminopropionate, 3-(N-(3-(4,5-diethyl-1,6-dihydro-6-oxopyrimidin-2-yl)-4-n-propoxyphenyl)sulfonyl)aminopropylsulfonic acid, 2-(N-(3-(4,5-diethyl-1,6-dihydro-6-oxopyrimidin-2-yl)-4-n-propoxyphenyl)sulfonyl)aminoethylsulfonic acid, 2-(N-(3-(4,5-diethyl-1,6-dihydro-6-oxopyrimidin-2-yl)-4-n-propoxyphenyl)sulfonyl)amino-3-amino formylpropanoic acid, 2-(N-(3-(4,5-diethyl-1,6-dihydro-6-oxopyrimidin-2-yl)-4-n-propoxyphenyl)sulfonyl)amino-3-indolepropionic acid, 2-(N-(3-(4,5-diethyl-1,6-dihydro-6-oxopyrimidin-2-yl)-4-n-propoxyphenyl)sulfonyl)aminoacetic acid, 2-(N-(3-(4,5-diethyl-1,6-dihydro-6-oxopyrimidin-2-yl)-4-n-propoxyphenyl)sulfonyl)amino-3,3-dimethylbutyric acid, 2-(N-(3-(4,5-diethyl-1,6-dihydro-6-oxopyrimidin-2-yl)-4-n-propoxyphenyl)sulfonyl)amino-4-aminoformylbutyric acid, ethyl 2-(N-(3-(4,5-diethyl-1,6-dihydro-6-oxopyrimidin-2-yl)-4-n-propoxyphenyl)sulfonyl)amino-3-methylvalerate, methyl 2-(3-(4,5-diethyl-1,6-dihydro-6-oxopyrimidin-2-yl)-4-n-propoxyphenylsulfonamido)-6-acetamidocaproate, 5,6-diethyl-2-(2-n-propoxyl-5-(4-hydroxyethyl-1-piperazinylsulfonyl)phenyl]pyrimid-4 (3H)-one, 5,6-diethyl-2-(2-n-propoxyl-5-(3-hydroxypropylamino sulfonyl)phenyl]pyrimid-4 (3H)-one 5,6-diethyl-2-(2-n-propoxyl-5-(N-(2-morpholinylethyl)-N-(2-hydroxyethyl)aminosulfonyl)phenyl)pyrimid-4(3H)-one, 5,6-diethyl-2-(2-n-propoxyl-5-(N-methyl-N-(2-(pyrrolidin-1-yl)ethyl)aminosulfonyl)phenyl)pyrimid-4(3H)-one, 5,6-diethyl-2-(2-n-propoxyl-5-(2-(N,N-diethyl)amino ethylamino sulfonyl)phenyl]pyrimid-4(3H)-one maleate, 2-(3-(4,5-diethyl-1,6-dihydro-6-oxopyrimidin-2-yl)-4-n-propoxybenzamido)-3-phenylpropanoic acid, methyl N-(3-(4,5-diethyl-1,6-dihydro-6-oxopyrimidin-2-yl)-4-n-propoxylbenzoylprolinate, methyl 2-(3-(4,5-diethyl-1,6-dihydro-6-oxopyrimidin-2-yl)-4-n-propoxylbenzamido)-3-(4-hydroxyphenyl) propionate, ethyl 2-(3-(4,5-diethyl-1,6-dihydro-6-oxopyrimidin-2-yl)-4-n-propoxybenzamido)-3-(1H-indol-3-yl)propionate, methyl 2-(3-(4,5-diethyl-1,6-dihydro-6-oxopyrimidin-2-yl)-4-n-propoxylbenzamido)-3-methyl butyrate, methyl 2-(3-(4,5-diethyl-1,6-dihydro-6-oxopyrimi din-2-yl)-4-n-propoxylbenzamido)-3-(1H-imidazol-4-yl)propionate, ethyl 2-3-(4,5-diethyl-1,6-dihydro-6-oxopyrimidin-2-yl)-4-n-propoxybenzamido)-3-methylvalerate, 2-(3-(4,5-diethyl-1,6-dihydro-6-oxopyrimidin-2-yl)-4-n-propoxylbenzamido)propionic acid, 2-(3-(4,5-diethyl-1,6-dihydro-6-oxopyrimidin-2-yl)-4-n-propoxybenzamido)-3-aminoformylpropionic acid, 2-(3-(4,5-diethyl-1,6-dihydro-6-oxopyrimidin-2-yl)-4-n-propoxybenzamido)-4-aminoformylbutyric acid, 2-(3-(4,5-diethyl-1,6-dihydro-6-oxopyrimidin-2-yl)-4-n-propoxybenzamido)-3-hydroxypropionic acid, 2-(3-(4,5-diethyl-1,6-dihydro-6-oxopyrimidin-2-yl)-4-n-propoxybenzamido)-5-guanidinopentanoic acid, methyl 2-(3-(4,5-diethyl-1,6-dihydro-6-oxopyrimidin-2-yl)-4-n-propoxybenzamido)-3-phenylpropionate, methyl 2-(3-(4,5-diethyl-1,6-dihydro-6-oxopyrimidin-2-yl)-4-n-propoxybenzamido)propionate, methyl 2-(3-(4,5-diethyl-1,6-dihydro-6-oxopyrimidin-2-yl)-4-n-propoxybenzamido)-4-methylvalerate, ethyl 2-(3-(4,5-diethyl-1,6-dihydro-6-oxopyrimidin-2-yl)-4-n-propoxybenzamido)propionate, 3-(4,5-diethyl-1,6-dihydro-6-oxopyrimidin-2-yl)-N-(1-(4-methylpiperazin-1-yl)-1-oxopropan-2-yl)-4-n-propoxybenzamide, N-(1-aminoformylethyl)-3-(4,5-diethyl-1,6-dihydro-6-oxopyrimidin-2-yl)-4-n-propoxybenzamide, 3-(4,5-diethyl-1,6-dihydro-6-oxopyrimidin-2-yl)-4-n-propoxybenzamide, 3-(4,5-diethyl-1,6-dihydro-6-oxopyrimidin-2-yl)-4-n-propoxyl-N-(2-(thien-2-yl)ethyl)benzamide, 3-(4,5-diethyl-1,6-dihydro-6-oxopyrimidin-2-yl)-4-n-propoxyl-N-((fur-2-yl)methyl)benzamide, N-t-butyl-3-(4,5-diethyl-1,6-dihydro-6-oxopyrimidin-2-yl)-4-n-propoxybenzamide, 3-(4,5-diethyl-1,6-dihydro-6-oxopyrimidin-2-yl)-N-isobutyl-4-n-propoxylbenzamide,
3-(4,5-diethyl-1,6-dihydro-6-oxopyrimidin-2-yl)-N-allyl-4-n-propoxylbenzamide,
(4-(pyrid-2-yl)piperazin-1-yl)(3-(4,5-diethyl-1,6-dihydro-6-oxopyrimidin-2-yl)-4-n-propoxylbenzophenone,
(4-(hydroxyethyloxylethyl)piperazin-1-yl)(3-(4,5-diethyl-1,6-dihydro-6-oxopyrimidin-2-yl)-4-n-propoxylbenzophenone,
(4-(hydroxyethyl)piperazin-1-yl)(3-(4,5-diethyl-1,6-dihydro-6-oxopyrimidin-2-yl)-4-n-propoxylbenzophenone,
3-(4,5-diethyl-1,6-dihydro-6-oxopyrimidin-2-yl)-N-(3-hydroxypropyl)-4-n-propoxylbenzamide,
3-(4,5-diethyl-1,6-dihydro-6-oxopyrimidin-2-yl)-N-(1-hydroxy-2-propyl)-4-n-propoxybenzamide,
N-ethyl-3-(4,5-diethyl-1,6-dihydro-6-oxopyrimidin-2-yl)-N-(2-hydroxyethyl)-4-n-propoxylbenzamide,
3-(4,5-diethyl-1,6-dihydro-6-oxopyrimidin-2-yl)-N-(2-diethylaminoethyl)-4-n-propoxylbenzamide,
3-(3-(4,5-diethyl-1,6-dihydro-6-oxopyrimidin-2-yl)-4-n-propoxybenzamido)propyl-1-sulfonic acid,
2-(3-(4,5-diethyl-1,6-dihydro-6-oxopyrimidin-2-yl)-4-n-propoxybenzamido)ethylsulfonic acid,
3-(4,5-diethyl-1,6-dihydro-6-oxopyrimidin-2-yl)-N-(2-hydroxyethyl)-N-methyl-4-n-propoxylbenzamide,
(4-benzylpiperazin-1-yl)(3-(4,5-diethyl-1,6-dihydro-6-oxopyrimidin-2-yl)-4-n-propoxylbenzophenone,
3-(4,5-diethyl-1,6-dihydro-6-oxopyrimidin-2-yl)-N-methyl-N-(2-(pyrrolidin-1-yl)ethyl)-4-n-propoxybenzamide,
methyl 5-(3-(4,5-diethyl-1,6-dihydro-6-oxopyrimidin-2-yl)-4-n-propoxybenzamido)piperidyl-2-formate,
3-(4,5-diethyl-1,6-dihydro-6-oxopyrimidin-2-yl)-N-methoxyl-N-methyl-4-n-propoxybenzamide,
5,6-diethyl-2-[2-(3-methoxyln-propoxyl)-5-(4-methyl-1-piperazinylsulfonyl)phenyl]pyrimid-4(3H)-one,
2-chloro-N-3-(4,5-diethyl-1,6-dihydro-6-oxopyrimidin-2-yl)-4-n-propoxyphenyl)acetamide,
2-(dimethylamino)-N-3-(4,5-diethyl-1,6-dihydro-6-oxopyrimidin-2-yl)-4-n-propoxyphenyl)acetamide,
N-(3-(4,5-diethyl-1,6-dihydro-6-oxopyrimidin-2-yl)-4-n-propoxyphenyl)-2-(4-methylpiperazin-1-yl)acetamide,
N-(3-(4,5-diethyl-1,6-dihydro-6-oxopyrimidin-2-yl)-4-n-propoxyphenyl)-2-morpholinyl)acetamide,
N-(3-(4,5-diethyl-1,6-dihydro-6-oxopyrimidin-2-yl)-4-n-propoxyphenyl)-2-(piperid-1-yl)acetamide,
dimethyl (3-(4,5-diethyl-1,6-dihydro-6-oxopyrimidin-2-yl)-4-n-propoxyphenylaminoformyl)methylphosphate,
N-(3-(4,5-diethyl-1,6-dihydro-6-oxopyrimidin-2-yl)-4-n-propoxyphenyl)isobutyramide,
N-(3-(4,5-diethyl-1,6-dihydro-6-oxopyrimidin-2-yl)-4-n-propoxyphenyl)-3-methylbutyramide,
N-(3-(4,5-diethyl-1,6-dihydro-6-oxopyrimidin-2-yl)-4-n-propoxyphenyl)-2-phenylacetamide,
N-(3-(4,5-diethyl-1,6-dihydro-6-oxopyrimidin-2-yl)-4-n-propoxyphenyl)benzamide,
ethyl 3-(3-(4,5-diethyl-1,6-dihydro-6-oxopyrimidin-2-yl)-4-n-propoxyphenylaminoformyl)propionate,
N-(3-(4,5-diethyl-1,6-dihydro-6-oxopyrimidin-2-yl)-4-n-propoxyphenyl)-5-oxopyrrolidinyl-2-formamide,
2-acetamido-N-3-(4,5-diethyl-1,6-dihydro-6-oxopyrimidin-2-yl)-4-n-propoxyphenyl)-4-methylpentanamide,
N-(3-(4,5-diethyl-1,6-dihydro-6-oxopyrimidin-2-yl)-4-n-propoxyphenyl)-2-acetamido-3-(1H-indol-3-yl)propionamide,
2-acetamido-N-(3-(4,5-diethyl-1,6-dihydro-6-oxopyrimidin-2-yl)-4-n-propoxyphenyl)glutaramide,
2-acetamido-N-(3-(4,5-diethyl-1,6-dihydro-6-oxopyrimidin-2-yl)-4-n-propoxyphenyl)-3-hydroxybutyramide,
2-acetamido-N-(3-(4,5-diethyl-1,6-dihydro-6-oxopyrimidin-2-yl)-4-n-propoxyphenyl)-3-hydroxypropionamide,
-(2-(3-(4,5-diethyl-1,6-dihydro-6-oxopyrimidin-2-yl)-4-n-propoxyphenylaminoformyl)-2-acetamidoethyl)acetate,
5,6-diethyl-2-(5-(ethylamino)-2-n-propoxyphenyl)pyrimid-4(3H)-one,
N-ethyl-N-(3-(4,5-diethyl-1,6-dihydro-6-oxopyrimidin-2-yl)-4-n-propoxyphenyl)propionamide,
ethyl (N-ethyl-N-(3-(4,5-diethyl-1,6-dihydro-6-oxopyrimidin-2-yl)-4-n-propoxyphenyl)aminoformylformate,
1,3-diethyl-1-(3-(4,5-diethyl-1,6-dihydro-6-oxopyrimidin-2-yl)-4-n-propoxyphenyl)urea,
N-(3-(4,5-diethyl-1,6-dihydro-6-oxopyrimidin-2-yl)-4-n-propoxyphenyl)piperidyl-1-formamide,
N-(3-(4,5-diethyl-1,6-dihydro-6-oxopyrimidin-2-yl)-4-n-propoxyphenyl)-4-methylpiperazinyl-1-formamide,
1-(3-(4,5-diethyl-1,6-dihydro-6-oxopyrimidin-2-yl)-4-n-prop oxyphenyl)-3-propylurea,
1-cyclohexyl-3-(3-(4,5-diethyl-1,6-dihydro-6-oxopyrimidin-2-yl)-4-n-propoxyphenyl)urea
1,1-diethyl-3-(3-(4,5-diethyl-1,6-dihydro-6-oxopyrimidin-2-yl)-4-n-propoxyphenyl)urea,
1-(2-(diethylamino)ethyl)-3-(3-(4,5-diethyl-1,6-dihydro-6-oxopyrimidin-2-yl)-4-n-propoxyphenyl)urea maleate,
(4-methylpiperazin-1-yl)(3-(4,5-diethyl-1,6-dihydro-6-oxopyrimidin-2-yl)-4-n-propoxylbenzophenone,
5-iodo-6-isopropyl-2-[2-n-propoxyl-5-(4-methyl-1-piperazinylsulfonyl)phenyl]pyrimid-4 (3H)-one,
5-chloro-6-ethyl-2-[2-n-propoxyl-5-(4-methyl-1-piperazinylsulfonyl)phenyl]pyrimid-4 (3H)-one,
5,6-diethyl-2-(2-n-propoxyl-5-((tetrahydro-2,4,5-trihydroxy-6-(hydroxymethyl)-2H-pyran-3-ylamino)sulfonyl)phenyl]pyrimid-4 (3H)-one,
2-(3-(4,5-diethyl-1,6-dihydro-6-oxopyrimidin-2-yl)-4-n-propoxybenzamido)-5-urea pentanoic acid,
2-(3-(4,5-diethyl-1,6-dihydro-6-oxopyrimidin-2-yl)-4-n-propoxybenzamido)-5-aminopentanoic acid,
3-(3-(4,5-diethyl-1,6-dihydro-6-oxopyrimidin-2-yl)-N-(tetrahydro-2,4,5-trihydroxy-6-(hydroxymethyl)-2H-pyran-3-yl)-4-n-propoxybenzamide,
2-(3-(4,5-diethyl-1,6-dihydro-6-oxopyrimidin-2-yl)-4-n-propoxybenzamido)ethylsulfamide,
3-(4,5-diethyl-1,6-dihydro-6-oxopyrimidin-2-yl)-N-(4-methyl-piperazin-1-ylsulfonylethyl)-4-n-propoxybenzamide,
3-(4,5-diethyl-1,6-dihydro-6-oxopyrimidin-2-yl)-N—(N,N-diethylaminosulfonylethyl)-4-n-propoxybenzamide,
3-(3-(4,5-diethyl-1,6-dihydro-6-oxopyrimidin-2-yl)-4-n-propoxybenzamido)propylsulfamide,
3-(4,5-diethyl-1,6-dihydro-6-oxopyrimidin-2-yl)-N-(4-methyl-piperazin-1-ylsulfonylpropyl)-4-n-propoxybenzamide,
3-(4,5-diethyl-1,6-dihydro-6-oxopyrimidin-2-yl)-N—(N,N-diethylaminosulfonylpropyl)-4-n-propoxybenzamide,
5,6-diethyl-2-(5-(tetrahydro-3,4,5-trihydroxy-6-(hydroxymethyl)-2H-pyran-2-yl)-2-n-prop oxyphenyl)pyrimid-4 (3H)-one,
5-iodo-6-ethyl-2-[2-n-propoxyl-5-(4-methyl-1-piperazinylsulfonyl)phenyl]pyrimid-4(3H)-one,
5-bromo-6-ethyl-2-[2-n-propoxyl-5-(4-methyl-1-piperazinylsulfonyl)phenyl]pyrimid-4(3H)-one, and
5-chloro-6-isopropyl-2-[2-n-propoxyl-5-(4-methyl-1-piperazinylsulfonyl)phenyl]pyrimid-4(3H)-one.

In the best embodiment of the present invention, the said phenylpyrimidone compound of formula I, pharmaceutically acceptable salts or solvates thereof are selected from the following compounds:

5,6-diethyl-2-[2-n-propoxyl-5-(4-methyl-1-piperazinylsulfonyl)phenyl]pyrimid-4(3H)-one,
5,6-diethyl-2-{2-n-propoxyl-5-[N-(2-morpholinylethyl) aminosulfonyl)phenyl}pyrimid-4(3H)-one,
N-(3-(4,5-diethyl-1,6-dihydro-6-oxopyrimidin-2-yl)-4-n-propoxyphenylsulfonylproline,
1-(3-(4,5-diethyl-1,6-dihydro-6-oxopyrimidin-2-yl)-4-n-propoxyphenyl)-3-ethylthiourea,
N-[3-(4,5-diethyl-1,6-dihydro-6-oxopyrimidin-2-yl)-4-n-propoxyphenyl]-N',N"-triethylguanidine,
N-[3-(4,5-diethyl-1,6-dihydro-6-oxopyrimidin-2-yl)-4-n-propoxyphenyl]-pyrrolyl-1-formamide,
5-bromo-6-isopropyl-2-(2-n-propoxyl-5-mesylamidophenyl)pyrimid-4(3H)-one,
5,6-diethyl-2-(2-n-propoxyl-5-mesylamidophenyl)pyrimid-4(3H)-one,
N-(3-(1,6-dihydro-4-isopropyl-5-bromo-6-oxopyrimidin-2-yl)-4-propoxyphenyl)acetamide,
N-(3-(1,6-dihydro-4,5-diethyl-6-oxopyrimidin-2-yl)-4-propoxyphenyl)acetamide,
N-(3-(1,6-dihydro-4,5-diethyl-6-oxopyrimidin-2-yl)-4-propoxyphenyl)propionamide,
N-(3-(1,6-dihydro-4,5-diethyl-6-oxopyrimidin-2-yl)-4-propoxyphenyl)cyclohexamide,
N-(3-(1,6-dihydro-4,5-diethyl-6-oxopyrimidin-2-yl)-4-propoxyphenyl)-1-t-butyloxycarbonyl-4-hydroxy-prolylamide,
(morpholin-1-yl)(3-(4,5-diethyl-1,6-dihydro-6-oxopyrimidin-2-yl)-4-n-propoxyl)benzophenone,
(piperid-1-yl)(3-(4,5-diethyl-1,6-dihydro-6-oxopyrimidin-2-yl)-4-n-propoxyl)benzophenone,
(2-aminoformylpyrrol-1-yl)(3-(4,5-diethyl-1,6-dihydro-6-oxopyrimidin-2-yl)-4-n-propoxyl)benzophenone,
(morpholin-1-yl) (3-(4-isopropyl-5-bromo-1,6-dihydro-6-oxopyrimidin-2-yl)-4-n-propoxyl)benzophenone,
1-(3-(4,5-diethyl-1,6-dihydro-6-oxopyrimidin-2-yl)-4-n-propoxyphenyl)urea,
1-(3-(4,5-diethyl-1,6-dihydro-6-oxopyrimidin-2-yl)-4-n-propoxyphenyl)-3-ethylurea,
5,6-diethyl-2-(5-(2-morpholinylacetyl)-2-n-propoxyphenyl) pyrimid-4(3H)-one,
2,2'-(4-n-propoxyl-1,3-phenylenyl)bis(5,6-diethylpyrimid-4(3H)-one),
ethyl 2-(3-(4,5-diethyl-1,6-dihydro-6-oxopyrimidin-2-yl)-4-n-propoxybenzamido)acetate,
N-(3-(4,5-diethyl-1,6-dihydro-6-oxopyrimidin-2-yl)-4-n-propoxyphenyl)-2,2,2-trifluoroacetamide,
ethyl N-(3-(4,5-diethyl-1,6-dihydro-6-oxopyrimidin-2-yl)-4-n-propoxyphenyl)aminoformylacetate,
4-acetamido-N-(3-(4,5-diethyl-1,6-dihydro-6-oxopyrimidin-2-yl)-4-n-propoxyphenyl)buty ramide,
1-acetyl-N-(3-(4,5-diethyl-1,6-dihydro-6-oxopyrimidin-2-yl)-4-n-propoxyphenyl)pyrrolidinyl-2-formamide,
2-acetamido-N-(3-(4,5-diethyl-1,6-dihydro-6-oxopyrimidin-2-yl)-4-n-propoxyphenyl)-3-phenylpropionamide,
$N^1$-(3-(4,5-diethyl-1,6-dihydro-6-oxopyrimidin-2-yl)-4-n-propoxyphenyl) oxalamide,
5,6-diethyl-2-{2-n-propoxyl-5-[(2-(1-methylpyrrol-2-yl) ethyl)aminosulfonyl]phenyl}pyrimid-4(3H)-one,
3-(4,5-diethyl-1,6-dihydro-6-oxopyrimidin-2-yl)-N-(2-(1-methylpyrrol-2-yl)ethyl)-4-n-propoxylbenzamide,
2-(N-(3-(4,5-diethyl-1,6-dihydro-6-oxopyrimidin-2-yl)-4-n-propoxyphenyl)sulfonyl)amino-5-urea pentanoic acid,
2-(N-(3-(4,5-diethyl-1,6-dihydro-6-oxopyrimidin-2-yl)-4-n-propoxyphenyl)sulfonyl)amino-5-aminopentanoic acid,
ethyl 2-(N-(3-(4,5-diethyl-1,6-dihydro-6-oxopyrimidin-2-yl)-4-n-propoxyphenyl)sulfonyl)aminopropionate,
3-(N-(3-(4,5-diethyl-1,6-dihydro-6-oxopyrimidin-2-yl)-4-n-propoxyphenyl)sulfonyl)aminopropylsulfonic acid,
2-(N-(3-(4,5-diethyl-1,6-dihydro-6-oxopyrimidin-2-yl)-4-n-propoxyphenyl)sulfonyl)amino ethylsulfonic acid,
2-(N-(3-(4,5-diethyl-1,6-dihydro-6-oxopyrimidin-2-yl)-4-n-propoxyphenyl)sulfonyl)amino-3-aminoformylpropanoic acid,
5,6-diethyl-2-(2-n-propoxyl-5-(4-hydroxyethyl-1-piperazinylsulfonyl)phenyl]pyrimid-4(3H)-one,
5,6-diethyl-2-(2-n-propoxyl-5-(N-(2-morpholinylethyl)-N-(2-hydroxyethyl)aminosulfonyl)phenyl)pyrimid-4(3H)-one,
2-(3-(4,5-diethyl-1,6-dihydro-6-oxopyrimidin-2-yl)-4-n-propoxybenzamido)-3-phenylpropanoic acid,
methyl N-(3-(4,5-diethyl-1,6-dihydro-6-oxopyrimidin-2-yl)-4-n-propoxylbenzoylprolinate,
methyl 2-(3-(4,5-diethyl-1,6-dihydro-6-oxopyrimidin-2-yl)-4-n-propoxylbenzamido)-3-(4-hydroxyphenyl)propionate,
2-(3-(4,5-diethyl-1,6-dihydro-6-oxopyrimidin-2-yl)-4-n-propoxylbenzamido)propanoic acid,
2-(3-(4,5-diethyl-1,6-dihydro-6-oxopyrimidin-2-yl)-4-n-propoxybenzamido)-3-aminoformylpropanoic acid,
2-(3-(4,5-diethyl-1,6-dihydro-6-oxopyrimidin-2-yl)-4-n-propoxybenzamido)-5-guanidinopentanoic acid,
methyl 2-(3-(4,5-diethyl-1,6-dihydro-6-oxopyrimidin-2-yl)-4-n-propoxybenzamido)-3-phenylpropanoic acid,
methyl 2-(3-(4,5-diethyl-1,6-dihydro-6-oxopyrimidin-2-yl)-4-n-propoxybenzamido)propanoic acid,
3-(4,5-diethyl-1,6-dihydro-6-oxopyrimidin-2-yl)-N-(1-(4-methylpiperazin-1-yl)-1-oxopropan-2-yl)-4-n-propoxybenzamide,
N-(1-aminoformylethyl)-3-(4,5-diethyl-1,6-dihydro-6-oxopyrimidin-2-yl)-4-n-propoxybenzamide,
(4-(hydroxyethyoxylethyl)piperazin-1-yl)(3-(4,5-diethyl-1,6-dihydro-6-oxopyrimidin-2-yl)-4-n-propoxylbenzophenone,
(4-(hydroxyethyl)piperazin-1-yl)(3-(4,5-diethyl-1,6-dihydro-6-oxopyrimidin-2-yl)-4-n-propoxylbenzophenone,
3-(4,5-diethyl-1,6-dihydro-6-oxopyrimidin-2-yl)-N-(1-hydroxy-2-propyl)-4-n-propoxybenzamide,
3-(3-(4,5-diethyl-1,6-dihydro-6-oxopyrimidin-2-yl)-4-n-propoxybenzamido)propyl-1-sulfonic acid,
methyl 5-(3-(4,5-diethyl-1,6-dihydro-6-oxopyrimidin-2-yl)-4-n-propoxybenzamido)piperidinyl-2-formate,
N-(3-(4,5-diethyl-1,6-dihydro-6-oxopyrimidin-2-yl)-4-n-propoxyphenyl)-2-(4-methylpiperazin-1-yl)acetamide,
N-(3-(4,5-diethyl-1,6-dihydro-6-oxopyrimidin-2-yl)-4-n-propoxyphenyl)benzamide,
1-(2-(diethylamino)ethyl)-3-(3-(4,5-diethyl-1,6-dihydro-6-oxopyrimidin-2-yl)-4-n-propoxyphenyl)urea maleate,
(4-methylpiperazin-1-yl)(3-(4,5-diethyl-1,6-dihydro-6-oxopyrimidin-2-yl)-4-n-propoxylbenzophenone,
5,6-diethyl-2-(2-n-propoxyl-5-((tetrahydro-2,4,5-trihydroxy-6-(hydroxymethyl)-2H-pyran-3-ylamino)sulfonyl) phenyl]pyrimid-4(3H)-one,
2-(3-(4,5-diethyl-1,6-dihydro-6-oxopyrimidin-2-yl)-4-n-propoxybenzamido)-5-urea pentanoic acid,
2-(3-(4,5-diethyl-1,6-dihydro-6-oxopyrimidin-2-yl)-4-n-propoxybenzamido)-5-aminopentanoic acid,
3-(3-(4,5-diethyl-1,6-dihydro-6-oxopyrimidin-2-yl)-N-(tetrahydro-2,4,5-trihydroxy-6-(hydroxymethyl)-2H-pyran-3-yl)-4-n-propoxybenzamide, 2-(3-(4,5-diethyl-1,6-dihydro-6-oxopyrimidin-2-yl)-4-n-propoxybenzamido)ethylsulfamide, 3-(4,5-diethyl-1,6-dihydro-6-oxopyrimidin-2-yl)-N-(4-methyl-piperazin-1-ylsulfonylethyl)-4-n-propoxybenzamide, 3-(4,5-diethyl-1,6-dihydro-6-oxopyrimidin-2-yl)-N—(N,N-diethylaminosulfonylethyl)-4-n-propoxybenzamide, 3-(3-(4,5-diethyl-1,6-dihydro-6-oxopyrimidin-2-yl)-4-n-propoxybenzamido)propylsulfamide, 3-(4,5-diethyl-1,6-dihydro-6-oxopyrimidin-2-yl)-N-(4-methyl-piperazin-1-ylsulfonylpropyl)-4-n-propoxybenzamide, 3-(4,5-diethyl-1,6-dihydro-6-oxopyrimidin-2-yl)-N—(N,N-diethylaminosulfonylpropyl)-4-n-propoxybenzamide, and 5,6-diethyl-2-(5-(tetrahydro-3,4,5-trihydroxy-6-(hydroxymethyl)-2H-pyran-2-yl)-2-n-prop oxyphenyl)pyrimid-4(3H)-one.

In the above definitions, unless indicated specifically, alkyl or alkoxy with 3 or more carbon atoms can be straight or branched.

The compound of formula I can have one or more chiral sites, so it can have stereoisomers, i.e. enantiomers, diastereoisomers or the mixture thereof. If the compound of formula I contains an alkenyl or an alkenylene, it can further exist cis(E)-trans(Z) isomerism. Accordingly, the compound of formula I according to the present invention can be a single isomer or the mixture of various isomers.

The separation of diastereoisomers or cis- and trans-isomers can be achieved by using the common technologies, for example, the fractional crystallization, chromatography or HPLC of the stereoisomeric mixture of the compound of formula I, the acceptable salts or derivatives of thereof. The compound of formula I can also be prepared from the corresponding optically pure intermediates; or by the resolution of the corresponding racemoids using a suitable chiral vector, for example, by separating the diastereoisomeric salts generated by reacting the corresponding racemoid with a suitable optically active acid or base through HPLC or fractional crystallization.

The compound of formula I can have tautomers, and the present invention also includes a single tautomer or the mixture thereof.

The present invention includes the radiolabelled derivatives of the compound of formula I, which are suitable for bioresearch.

The present invention provides the pharmaceutically acceptable salts of the compound of formula I having an alkaline center, for example, a nontoxic acid addition salt formed with an inorganic acid such as hydrochloric acid, hydrobromic acid, hydroiodic acid, sulphuric acid and phosphoric acid, or with an organic carboxylic acid or an organic sulfonic acid. The compound of formula I can also react with a base to produce a pharmaceutically acceptable metal salts, especially a nontoxic alkali metal salt such as sodium salt and potassium salt. Preferred are methanesulphonate and hydrochlorate.

The present invention includes any prodrug of the compound of formula I.

The present invention also includes the pharmaceutically acceptable solvates of the compound of formula I, such as hydrate (here are the solvates of formula I).

The present invention still includes the pharmaceutically acceptable oxides of the compound of formula I, and pharmaceutically acceptable salts and solvates thereof (here are the salts and solvates of the pharmaceutically acceptable oxide).

The present invention still includes various crystal forms of the compound of formula I and the salts thereof.

The present invention also provides a process for preparing the phenylpyrimidone compound of formula I, pharmaceutically acceptable salts or solvates thereof, wherein the process comprises:

(A) when Z is $OR^3$, the compound of formula I can be prepared by the following methods:

(1) when $R^4$ is OH, $SO_2NR^6R^7$, $COR^{11}$, unsubstituted or substituted $C_2$-$C_4$ alkyl, unsubstituted or substituted $C_2$-$C_4$ alkenyl, or unsubstituted or substituted 5~7-member heterocyclyl, the compound of formula I can be obtained by cyclization of the compound of formula II with the compound of formula III in the presence of a base, wherein $R^1$, $R^2$, $R^3$, $R^6$, $R^7$, $R^{11}$ and the said 5~7-member heterocyclyl are defined the same as the above. The reaction is commonly performed at a temperature within the range of 50° C. to 120° C. The solvent is preferably selected from the group consisting of chloroform, methanol, ethanol, ethylene glycol monomethyl ether, N,N-dimethylformamide and dioxane. The reaction time is with in the range of 0.5-10 h, and the said base is preferably $K_2CO_3$ or $NaOC_2H_5$;

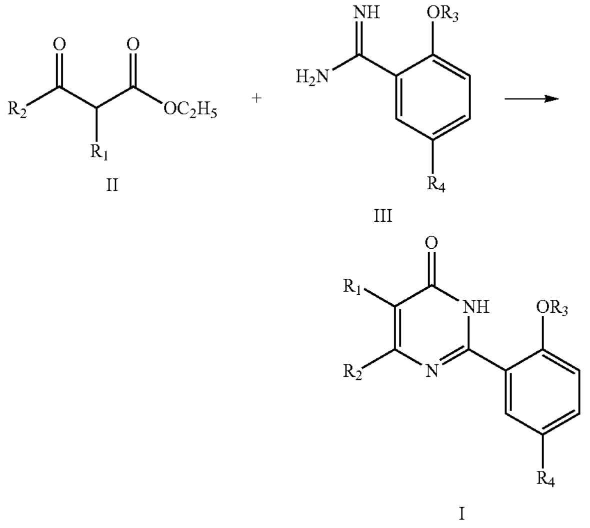

II

III

I or, (2) the compound of formula I can be obtained by conversion of the compound of formula Ia, the compound of formula Ie or other compounds of formula I, wherein $R^1$, $R^2$, $R^3$, $R^5$, $R^6$, $R^7$, $R^8$, $R^9$, $R^{10}$, $R^{12}$, $R^{15}$, $R^{16}$, $R^{17}$, $R^{18}$, $R^{19}$ and $R^{20}$ are defined the same as the above, wherein the method of preparing the compound of formula Ia refers to the above said Method (1), and the compound of formula Ie (which is a known compound) can be obtained by bromination of the compound of formula Ia, wherein, 1) when $R^4$ is $SO_2NR^6R^7$, the compound of formula Ib can be prepared from the compound of formula Ia through chlorosulfonating followed by reacting with $R^6R^7NH$ in the presence of an organic base, such as pyridine or triethylamine in a suitable organic solvent, such as tetrahydrofuran, dichlormethane or the like;

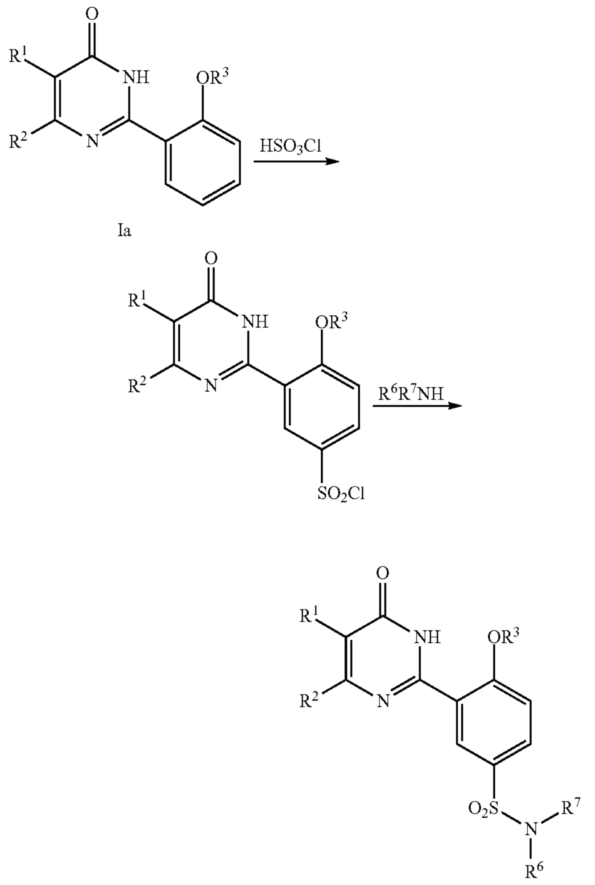

Ia

Ib or, 2) when $R^4$ is $NO_2$, the compound of formula Ic can be prepared by nitrating the compound of formula Ia, wherein the nitrating reagent can be a mixture of concentrated nitric acid and concentrated sulfuric acid;

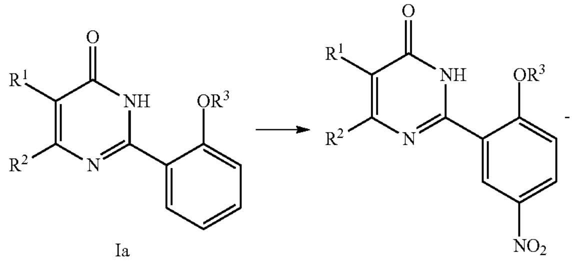

Ia Ic or, 3) when $R^4$ is $NH_2$, the compound of formula Id can be prepared by reduction of the compound of formula Ic, for example, by using a traditional catalytic hydrogen reduction wherein Raney-Ni or Pd/C is used as the catalyst, or by using reduced iron powder in an acid condition (e.g. concentrated hydrochloric acid is used as the solvent) at a suitable temperature (20-100° C.);

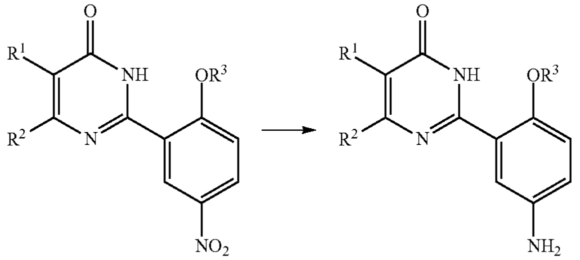

Ic Id or, 4) when $R^4$ is CN, the compound of formula If can be prepared from the compound of formula Ie by nucleophilic substitution with a cyanide such as CuCN in a suitable solvent (e.g. N,N-dimethylformamide) at a suitable temperature (e.g. 70-160° C.);

or,

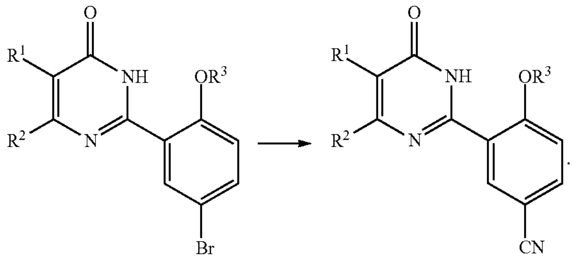

Ie If 5) when $R^4$ is COOH, the compound of formula Ig can be prepared from the compound of formula If by hydrolysis in the presence of a base (e.g. 2N NaOH in water);

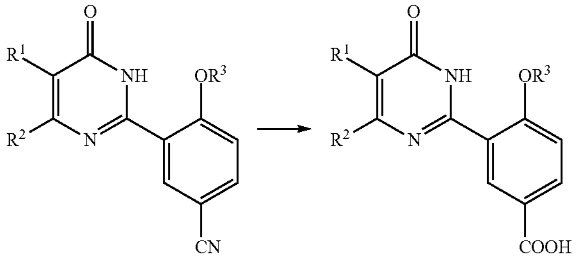

If Ig or, 6) when $R^4$ is $NR^9R^{10}$, the compound of formula I can be prepared from the compound of formula Id wherein $R^4$ is $NH_2$, wherein, 1> when $R^9$ and $R^{10}$ are simultaneously methyl, the compound of formula I can be prepared through N-methylation by using paraformaldehyde as a methylating agent with formic acid as a solvent at a suitable temperature (e.g. 80° C.);

2> when $R^9$ is H and $R^{10}$ is $SO_2R^{16}$, the compound of formula I can be prepared from the compound of formula Id through sulfonylation in the presence of an organic base (e.g. pyridine or triethylamine) in a suitable organic solvent (e.g. tetrahydrofuran, dichloromethane, etc.), wherein the sulfonylating agent is preferably a sulfonyl halide (e.g. methylsulfonyl chloride).

3> when $R^9$ is H and $R^{10}$ is $COR^{15}$, the compound of formula I can be prepared by firstly reacting an organic acid with oxalyl chloride or thionyl chloride to give an acyl chloride in a suitable organic solvent (e.g. tetrahydrofuran, dichloromethane, etc.), followed by reacting the resulting acyl chloride with the compound of formula Id; or by condensing the compound of formula Id with an organic acid (e.g. formic acid, cyclohexanecarboxylic acid, etc.) in the presence of a coupling agent (e.g. 1,3-dicyclohexylcarbodiimide (DCC) or 1-(3-dimethylaminopropyl)-3-ethylcarbodiimide (EDCI)) and an activator (e.g. 1-hydroxy-benzo-triazole (HOBT));

4> when $R^9$ is H, $R^{10}$ is $C(Y)NR^{17}R^{18}$, and Y is O or S, the compound of formula I can be prepared by the addition reaction of the compound of formula Id with a compound of formula $Y{=}C{=}NR^{17}R^{18}$ in a suitable solvent (e.g. ethanol) at a suitable temperature (e.g. 50-80° C.);

5> when $R^9$ is H, $R^{10}$ is a 5- or 6-member monosaccharide group, the compound of formula I can be prepared by reacting the compound of formula Id with a unprotected 5- or 6-member monosaccharide in the presence of a trace amount of an organic acid (e.g. glacial acetic acid) as a catalyst in a suitable solvent (e.g. ethanol, ethylene glycol monomethyl ether, N,N-dimethylformamide, n-butyl alcohol, etc.) at a suitable temperature (e.g. 50-150° C.);

6> when $R^9$ is H, $R^{10}$ is

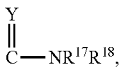

and Y is $NR^8$, the compound of formula I can be prepared by a nucleophilic substitution of the compound of formula Ih with a compound of formula $R^{17}NHR^{18}$ in a suitable solvent (e.g. ethanol, ethylene glycol monomethyl ether, N,N-dimethylformamide, n-butyl alcohol, etc.) at a suitable temperature (e.g. 50-150° C.), wherein the compound of formula Ih can be prepared by the addition reaction of the compound of formula Ii with iodomethane in a suitable solvent (e.g. methanol, ethanol, tetrahydrofuran, etc.) at a suitable temperature (e.g. 40-80° C.), and the compound of formula II can be prepared by the addition reaction of the compound of formula Id with $R^8SCN$ in a suitable solvent (e.g. methanol, ethanol, tetrahydrofuran, acetic acid and water, etc.) at a suitable temperature (e.g. 40-80° C.);

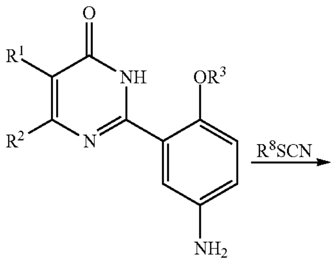

Id

-continued

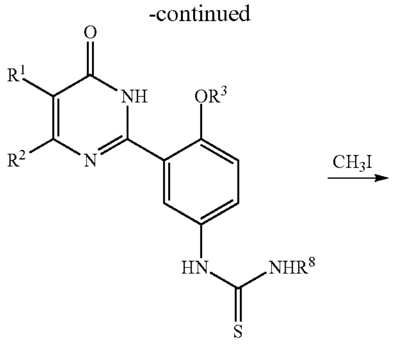

Ii

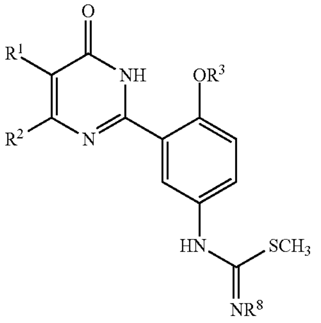

Ih

7> when $R^9$ is H and $R^{10}$ is an amino acid residue substituted with acetyl, the compound of formula I can be prepared by firstly condensing the compound of formula Id with a N-Boc protected amino acid in an organic solvent including tetrahydrofuran or dichloromethane in the presence of a coupling agent including 1,3-dicyclohexylcarbodiimide or 1-(3-dimethylaminopropyl)-3-ethylcarbodiimide and an activator such as 1-hydroxy-benzo-triazole to give an intermediate, then deprotecting Boc group in trifluoroacetic acid, and finally reacting with acetic anhydride in pyridine;

or, 7) when $R^4$ is $COR^{11}$ and $R^{11}$ is $NR^6R^7$, the compound of formula I can be prepared by condensing the compound of formula Ig with $R^6R^7NH$ with a coupling agent being preferably 1,3-dicyclohexylcarbodiimide (DCC) or 1-(3-dimethylamino propyl)-3-ethylcarbodiimide (EDCI); or by transforming the compound of formula Ig into an corresponding acyl chloride derivative, followed by reacting with $R^6R^7NH$;

or, 8) when $R^4$ is $COR^{11}$ and $R^{11}$ is $CH_2NR^6R^7$, the compound of formula I can be prepared by condensing the compound of formula Ij with $R^6R^7NH$ in the presence of an organic base, wherein the said organic base is preferably pyridine or triethylamine; the compound of formula Ij can be prepared by bromizing the compound of formula Ik, wherein the bromination reagent is preferably bromine or N-bromosuccinimide (NBS); the compound of formula Ik can be prepared by reacting the compound of formula Ia with vinyl n-butyl ether in the presence of an metal catalyst (e.g. palladium acetate), followed by hydrolysis in a diluted hydrochloric acid; or the compound of formula Ij can also be prepared by Friedel-Crafts reaction of the compound of formula Ia with bromoacetyl bromide using excess $AlCl_3$ as Lewis acid, wherein the reaction solvent is preferably dichloromethane;

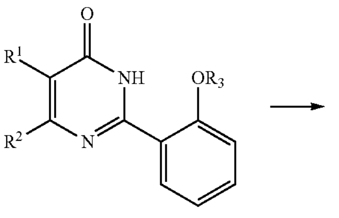

Ia

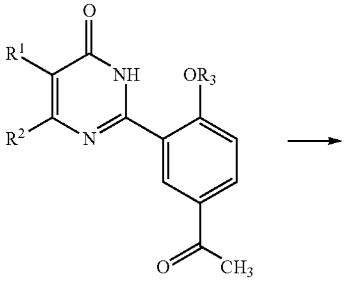

Ik

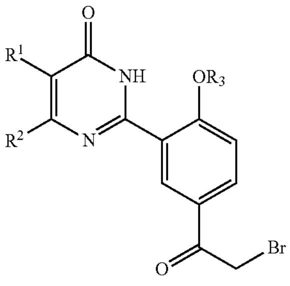

Ij or, 9) when $R^4$ is $OR^{12}$, the compound of formula I can be prepared from the compound of formula Il through a traditional chemosynthesis method, wherein, 1> when $R^{12}$ is $COR^{19}$ and $R^{19}$ is $C_1$-$C_6$ alkyl or aryl, the compound of formula I can be prepared by esterifying the compound of formula Il wherein $R^4$ is OH in a suitable solvent (e.g. tetrahydrofuran, dichloromethane, etc.) in the presence of an organic base (e.g. pyridine or triethylamine);

2> when $R^{12}$ is $COR^{19}$ and $R^{19}$ is $NHR^8$, the compound of formula I can be prepared by addition reaction of $R^8NCO$ with the compound of formula Il wherein $R^4$ is OH;

3> when $R^{12}$ is $SO_2R^{16}$, the compound of formula I can be prepared by sulfonylation of the compound of formula Il wherein $R^4$ is OH in the presence of an organic base (e.g. pyridine or triethylamine) in a suitable solvent (e.g. tetrahydrofuran, dichloromethane, etc.), and the sulfonylating reagent is preferably a sulfonyl halide (e.g. mesyl chloride);

4> when $R^{12}$ is a 5- or 6-member monosaccharide group, the compound of formula In can be prepared by firstly condensing the compound of formula Il with a 5- or 6-member monosaccharide activated with trichloroacetonitrile and protected at hydroxyl by a protecting group such as tetraacetyl, etc., under the catalysis of Lewis acid (e.g. boron trifluoride diethyl ether) according to the method of Schmidt et al. (*Angew. Chem.*, 1980, 92, 763-764) to give the compound of formula Im, followed by hydrolysis under an alkaline condition to remove the acetyl protective group;

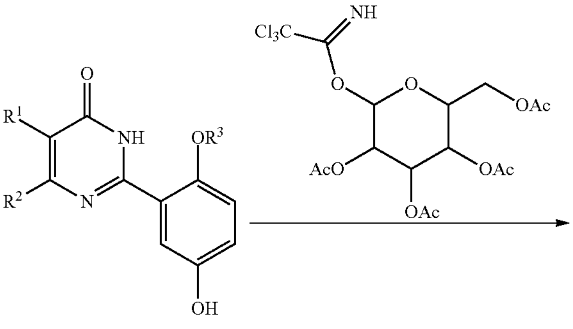

Il

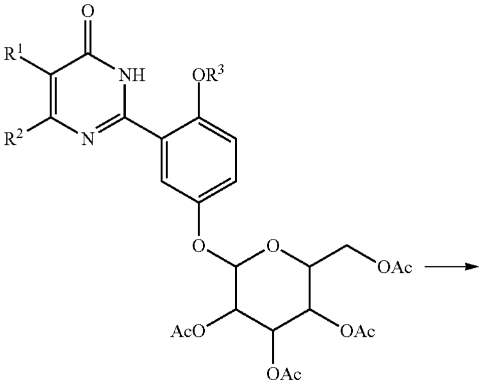

Im

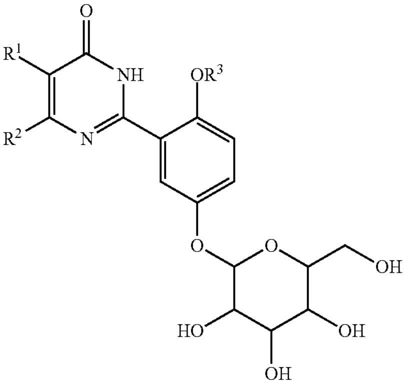

In or, 10) when $R^4$ is pyrrolyl, the compound of formula Io can be prepared by condensingation of 2,5-hexanedione with the compound of formula Id where $R^4$ is $NH_2$ in the presence of an organic acid, wherein the said organic acid is preferably acetic acid and typically the reaction solvent is preferably ethanol;

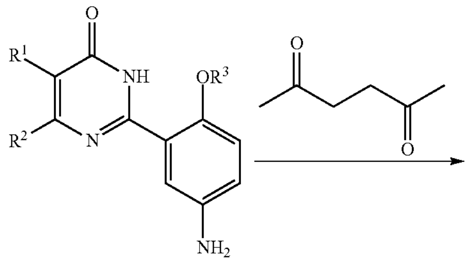

Id

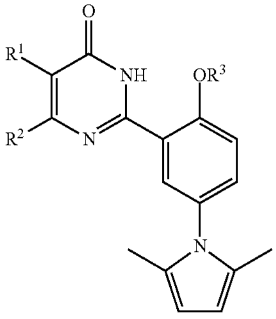

Io or, 11) when $R^4$ is a glycoside, the compound of formula I can be prepared by firstly reacting the compound of formula Ie where $R^4$ is Br with n-BuLi, then reacting with a glucolactone protected by a protective group (e.g. trimethylsilicane), followed by reduction by using a reducing agent (e.g. triethylsilicane).

or, (3) the compound of formula I can also be prepared by converting other compounds of formula I where $R^1$ is a different substituent, wherein $R^2$, $R^3$ and $R^4$ are defined the same as the above, wherein, 1) when $R^1$ is halogen, the compound of formula Iq can be prepared by halogenating the compound of formula Ip where $R^1$ is H in the presence of an organic base, wherein the said organic base is preferably pyridine, the halogenating agent is preferably elementary halogen, e.g. chlorine gas, liquid bromine etc., and the reaction solvent is preferably dichloromethane;

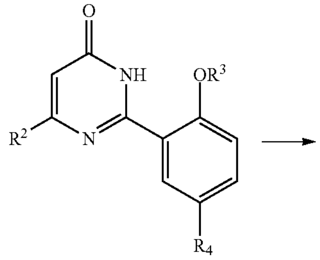

Ip

-continued

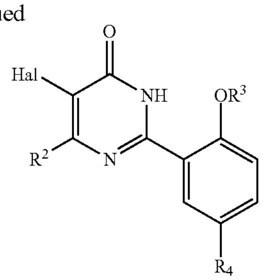

Iq or, 2) when $R^1$ is $NH_2$, the compound of formula Is can be prepared by hydrolyzing the compound of formula Ir wherein $R^1$ is acetamido under a strong acidic condition, wherein the reaction solvent is preferably concentrated hydrochloric acid, and the reaction temperature is typically 90~110° C.

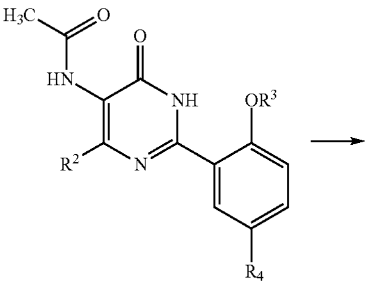

Ir

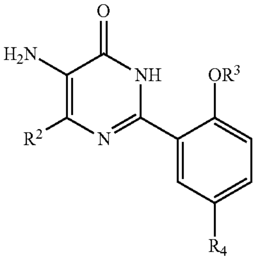

Is or, (B) when Z is $NR^3R^{10}$, the compound of formula I can be prepared by nitration, reduction and N-substitution, with reference to a similar method with that for preparing the above compound of formula I wherein $R^4$ is $NR^9R^{10}$;

or, (C) when Z is $COR^{11}$, $NHCOR^{15}$ or $OCOR^{15}$, the compound of formula I can be prepared, with reference to the method for preparing the above compound of formula I wherein $R^4$ is $COR^{11}$, $NHCOR^{15}$ or $OCOR^{15}$.

The present invention also includes the new intermediates during the preparation of the compound of formula I and the preparation process thereof, for example, the compounds of formulae III, V and Ia, and the preparation processes thereof

III

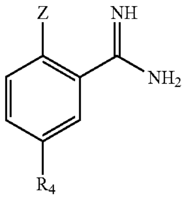

V

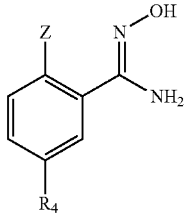

Ia

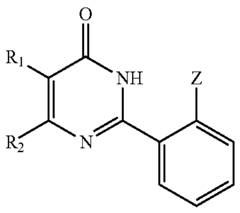

When Z is $OR_3$, the compound of formula III can be prepared by the following method:

The compound of formula III can be prepared from the compound of formula IV and lithium bis(trimethylsilyl)amide ($LiN(Si(CH_3)_3)_2$) in tetrahydrofuran (THF), according to the method of Schmidt et al. (*Angew. Chem.*, 1980, 92, 763-764).

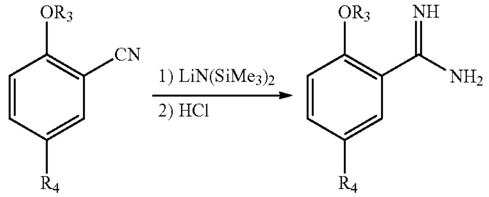

IV III

The compound of formula III can also be prepared by firstly reacting the compound of formula IV with hydroxylamine hydrochloride in a suitable solvent (e.g. a mixture of water and methanol) at a suitable temperature (e.g. 40-80° C.) according to the method of Juby et al. (U.S. Pat. No. 4,031,093), to give a compound of formula V, followed by hydrogenation in acetic acid solution at a suitable temperature (e.g. 60° C.) under a suitable hydrogen pressure (1~5 MPa), wherein Pd/C is used as the catalyst for the reduction.

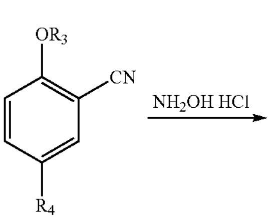

IV

-continued

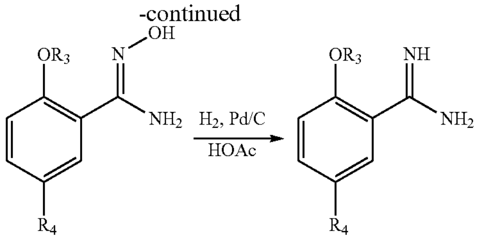

V III

The compounds of formulae II and IV are commercially available from Sinopharm Chemical Reagent Co. Ltd, and if unavailable, they can be prepared according to the methods in literatures.

In addition, the present invention also provides a pharmaceutical composition with inhibition activity for PDE5 containing a therapeutically effective dose of the compound of formula I, the pharmaceutically acceptable salts or solvates thereof.

The said pharmaceutical composition comprises a therapeutically effective dose of one or more compounds of formula I (or the pharmaceutically acceptable salts thereof, or their pharmaceutically acceptable solvates) and at least one pharmaceutically acceptable auxiliary. The said pharmaceutically acceptable auxiliary can be selected according to the administration route and action mechanism, and is commonly selected from filler, diluent, adhesive, wetting agent, disintegrating agent, lubricant, emulsifier, suspending agent, etc.

The pharmaceutical composition of the present invention can be administered orally, by injection (intravenously, intramuscularly, hypodermically and intracoronary), sublingually, buccally, rectally, urethrally, vaginally, intranasally, inhalationally or by local administration. Preferred are oral administration.

The above composition comprises 0.1%~99.9 wt %, preferably 1%~99 wt % of the compound of formula I, the pharmaceutically acceptable salts or solvates thereof, based on the total weight of the composition.

The present invention also provides a process for preparing the pharmaceutical composition comprising the compound of formula I, the pharmaceutically acceptable salts or solvates thereof. Typically, the compound of formula I, the pharmaceutically acceptable salts or solvates thereof are mixed with pharmaceutically acceptable auxiliaries and formulated into a dosage form (formulation) suitable for a certain administration route by a common formulating method. The said formulation includes tablet, capsule, granule, pill, solution, suspension, emulsion, paste, pellicle, cream, aerosol, injection, suppository, etc., preferably tablet and capsule.

The formula of the tablet and capsule can comprise a therapeutically effective dose of one or more compounds of formula I, the pharmaceutically acceptable salts, or solvates thereof, and one or more usually used auxiliaries, for example, a filler such as starch, sucrose, lactose, glucose, microcrystalline cellulose, mannose, etc.; an adhesive such as carboxymethylcellulose, gelatin, alginate and polyvinyl pyrrolidone, etc.; a wetting agent such as glycerine, etc.; a disintegrant such as agar, ethylcellulose, sodium carboxymethylstarch, calcium carbonate, etc.; a lubricant such as magnesium stearate, talc powder, polyglycol, etc.

The compound according to the present invention is typically administered in an amount of 1~500 mg, preferably 10~100 mg per day, in a single or multiple administration. However, if necessary, the above dose can be suitably deviated. A skilled person in the art can determine the optimum dose according to the professional knowledge and specific situations including the severity of the disease, the individual difference of a patient, the characteristics of a formulation and the administration route, etc.

Besides, the present invention further provides a use of the compound of formula I, the pharmaceutically acceptable salts or solvates thereof, or compositions thereof as a human drug.

The present invention further provides a use of the compound of formula I, the pharmaceutically acceptable salts or solvates thereof in preparing a human drug as a PDE5 inhibitor.

The present invention further provides a use of the compound of formula I, the pharmaceutically acceptable salts or solvates thereof, or compositions thereof in preparing a human drug for treating or preventing male erectile dysfunction, benign prostatic hyperplasia, female sexual dysfunction, premature delivery, menorrhalgia, bladder outlet obstruction, incontinence, instable and variant Prinzmetal angina pectoris, hypertension, pulmonary hypertension, congestive heart failure, renal failure, atherosclerosis, apoplexy, peripheral vascular diseases, Raynaud's diseases, inflammation diseases, bronchitis, chronicity asthma, allergic asthma, allergic coryza, glaucoma or diseases characterized by enterokinesia dysfunction (e.g. irritable bowel syndrome).

The present invention further provides a use of the compound of formula I, the pharmaceutically acceptable salts or solvates thereof, or compositions thereof in combination with other drugs in treating or preventing diseases such as male erectile dysfunction, benign prostatic hyperplasia, etc., for example, in combination with a selective 5-hydroxytryptamine (5-HTA) reuptake inhibitor for treating prospermia; in combination with an α-acceptor retarder for treating male erectile dysfunction (ED) combined with benign prostatic hyperplasia (BPH); in combination with an antihypertensive drug for treating ED combined with hypertension; in combination with propionyl-L-carnitine (Levocarnitine, PLC) for treating diabetic ED; in combination with testosterone undecanoate for treating the penile erection dysfunction of a patient suffering from ED combined diabetes; in combination with Tianeptine for effectively treating depression combined with sexual dysfunction, etc.

The compound of formula I, the pharmaceutically acceptable salts or solvates thereof have an inhibition activity for PDE5. It is more important that most of these compounds have a stronger inhibition activity for PDE5 than Sildenafil, and have a higher selectivity for PDE6 distributed in retinal. Accordingly, the compounds provided by the present invention can be expected to show better clinical safety and effectivity, and thus possess a broad prospect of clinical application.

BEST MODE FOR CARRYING OUT THE INVENTION

Preparation Examples and Examples

The following examples will further illustrate the process for preparing the compounds of the present invention and the intermediates thereof, but are not to be construed to limit the scope of the present invention. $^1$H NMR was completed on a Mercury-400 or Mercury-300 NMR spectrometer (Varian Company). Common abbreviations are as follow: s, singlet; d, doublet; t, triplet; q, quartet; m, multiplet; br, broad peak.

Preparation Example 1

2-n-Propoxy-5-(4-methylpiperazin-1-yl)sulfonylbenzonitrile

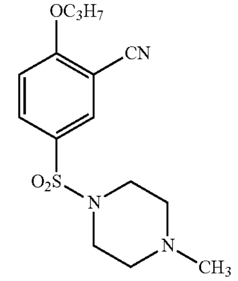

2-n-propoxybenzonitrile (32.2 g, 0.2 mol) was slowly added into chlorosulfonic acid (120 ml) under ice-bath. The ice bath was removed, and after stirred for 2 h at room temperature, the reaction mixture was added dropwise in brash ice carefully to generate a lot of precipitate. After filtered, the precipitate was washed with ice water, dissolved in $CH_2Cl_2$ (300 ml), and added dropwise into methylpiperazidine (19.8 g, 0.2 mol) dissolved in $CH_2Cl_2$ (250 ml) under ice-bath. After the addition, the stirring continued for 30 min. The resulting organic phase was washed with water (3×200 ml) and saturated brine (100 ml). After solvent was evaporated to dryness, the residue was recrystallized in ethyl acetate/petroleum ether to afford the title compound (48.5 g, total yield of the two steps: 75%). $^1$H NMR (DMSO-$d_6$) δ: 8.05 (1H, dd), 7.77 (1H, t), 7.36 (1H, d), 4.15 (2H, t), 2.87 (4H, t), 2.36 (4H, t), 2.13 (3H, s), 1.79 (2H, m), 0.99 (3H, t).

Preparation Example 2

5-Hydroxy-2-n-propoxybenzonitrile

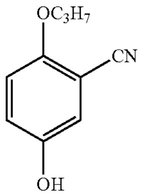

5-acetyl-2-n-propoxybenzonitrile (20.3 g, 0.10 mol) was dissolved in glacial acetic acid (100 ml), followed by addition of ammonium persulfate (60 g, 0.26 mol). After sulphuric acid solution ($H_2SO_4$ 10 ml/$H_2O$ 14 ml) was slowly added dropwise under ice-water bath, the reaction temperature was raised to 45° C. for 3 h. The reaction mixture was poured into ice water to generate precipitates, stirred for 0.5 h, filtered, and dried to give the title compound (13.0 g, yield: 73%). $^1$H NMR ($CDCl_3$) δ: 8.00 (1H, d), 7.04 (1H, dd), 6.90 (1H, d), 4.05 (2H, t), 1.78 (2H, m), 1.01 (3H, t).

Preparation Example 3

3-Cyano-4-n-propoxybenzoic acid

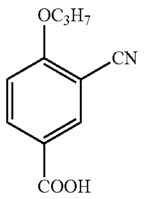

NaOH (5.52 g, 0.138 mol) was dissolved in water (35 ml) under ice-bath, followed by slow addition of liquid bromine (3.5 ml, 0.068 mol) under cooling. After a solution of 5-acetyl-2-n-propoxybenzonitrile (7 g, 0.034 mol) in dioxane (35 ml) was slowly added dropwise thereto, the reaction continued for 2 h. The reaction mixture was adjusted slowly to a pH of about 2 with a diluted hydrochloric acid to generate a large amount of light yellow solid. After filtered, the resultant solid was washed with ethyl acetate, and filtered to obtain the title compound (6.5 g, yield: 92%). $^1H$ NMR ($CDCl_3$) δ: 13.21 (1H, br), 8.18 (1H, d), 8.15 (1H, dd), 7.34 (1H, d), 4.18 (2H, t), 1.79 (2H, m), 1.00 (3H, t).

Preparation Example 4

4-n-Propoxy-m-benzene dinitrile

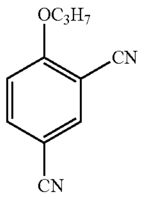

The compound (3 g, 14.6 mmol) of Preparation example 3 was suspended in dichloromethane (30 ml), followed by addition of thionyl chloride (2.12 ml, 29.2 mmol). After refluxed for 2 hours, the reaction mixture was concentrated to dryness to obtain an oil. The oil was dissolved in dried benzene (10 ml), and concentrated off the solvent. After the dissolution-concentration was repeated three times, the oil was dissolved in dried dichloromethane (10 ml), and then slowly added dropwise into a solution of ammonia in methanol (15 ml) cooled under ice bath, followed by reacting for 0.5 h. The reaction mixture was concentrated to dryness, and then dissolved in dichloromethane (20 ml). The organic layer was washed with water (30 ml×2) and saturated brine (40 ml), respectively. The resulting organic phase was dried with anhydrous $Na_2SO_4$ and concentrated under reduced pressure. The obtained solid was recrystallized from petroleum ether/ethyl acetate, and refluxed in phosphorus oxychloride (10 ml) for 1 h. The cooled reaction mixture was poured into ice water to generate precipitate, stirred for 0.5 h, filtered, washed with clear water, and dried to obtain the title compound (2.3 g, total yield of two steps: 83%). $^1H$ NMR ($CDCl_3$) δ: 7.85 (1H, d), 7.80 (1H, dd), 7.05 (1H, d), 4.12 (2H, t), 1.91 (2H, m), 1.09 (3H, t).

Preparation Example 5

3-Cyano-4-n-propoxybenzoylhydrazine

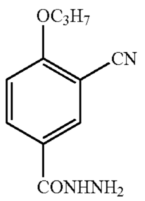

The compound (3 g, 14.6 mmol) of Preparation example 3 was suspended in dichloromethane (30 ml), followed by addition of thionyl chloride (2.12 ml, 29.2 mmol). The reaction mixture was refluxed for 2 hours, and then concentrated to dryness to obtain an oil. The oil was dissolved in dried benzene (10 ml), and concentrated off the solvent. After the dissolution-concentration was repeated three times. The obtained oil was dissolved in dried dichloromethane (10 ml), and then slowly added dropwise into a mixed solution of hydrazine hydrate (85%) (15 ml) and methanol (15 ml) cooled under ice bath, followed by reacting for 0.5 h. The reaction mixture was concentrated to dryness, and then dissolved in dichloromethane (20 ml). The resulting organic layer was washed with water (30 ml×2) and saturated brine (40 ml), respectively. The resulting organic phase was dried with anhydrous $Na_2SO_4$ and concentrated under reduced pressure. The obtained solid was recrystallized from petroleum ether/ethyl acetate to obtain the title compound (2.3 g, yield: 72%). $^1H$ NMR ($CDCl_3$) δ: 7.98 (1H, d), 7.94 (1H, dd), 7.59 (1H, br), 7.00 (1H, d), 4.09 (2H, t), 1.90 (2H, m), 1.09 (3H, t).

Preparation Example 6

5-(1,3,4-Qxadiazol-2-ly)-2-n-propoxybenzonitrile

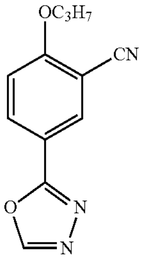

The compound (1.5 g, 6.8 mmol) of preparation example 5 was added in triethyl orthoformate (10 ml), and refluxed for 2 h. The reaction mixture was concentrated to dryness, and the resultant solid was recrystallized from ethyl acetate/petroleum ether to obtain the title compound (1.2 g, yield: 76%).

$^1H$ NMR ($CDCl_3$) δ: 8.47 (1H, d), 8.27 (1H, dd), 8.25 (1H, s), 7.11 (1H, d), 4.13 (2H, t), 1.91 (2H, m), 1.10 (3H, t).

Preparation Example 7

2-n-Propoxy-5-(4-methylpiperazin-1-yl)sulfonylbenzamidine

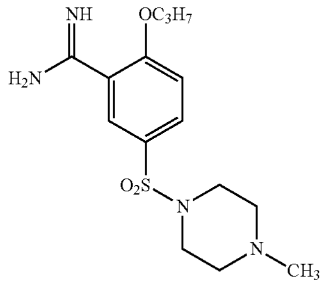

Under ice-bath, the compound (10 g, 31 mmol) of Preparation example 1 was added into a THF solution (150 ml) containing 20% $LiN(Si(CH_3)_3)_2$, and t stirred for 18 h at room temperature. After 4N HCl was added to adjust to a pH of 2-3, THF and most of water were distilled off and the remaining water phase was washed with EtOAc, adjusted to a pH of 12-13 with 4N NaOH, and extracted with $CH_2Cl_2$. The organic phase was washed with saturated saline and concentrated to dryness to give the title compound as a reddish brown oil, which was directly used in the subsequent step without purification.

Preparation Example 8

5-(1,3,4-Oxadiazol-2-yl)-2-n-propoxybenzamidine

The title compound was prepared from the compound (0.5 g, 2.2 mmol) of preparation example 6 as a starting material in the same manner as that of preparation example 7, to give the title compound as a reddish brown oil, which was directly used in the subsequent step without purification.

Preparation Example 9

$N^{1\prime}$,$N^{3\prime}$-dihydroxy-4-n-propoxy-isophthalamidine

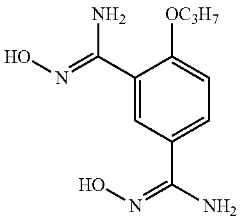

The compound (3.0 g, 16.0 mmol) of preparation example 4 was dissolved in a mixed solution of methanol (50 ml) and water (50 ml), and potassium carbonate (8.9 g, 65.2 mmol) and hydroxylamine hydrochloride (4.5 g, 65.2 mmol) were added respectively. The reaction mixture was refluxed overnight, and then concentrated off methanol, and cooled down slowly to separate a white solid. After filtered, the solid was washed with water (30 ml×3), and dried to give the title compound (2.0 g, yield: 49%). $^1H$ NMR ($CDCl_3$) δ: 9.45 (2H, br), 7.75 (1H, d), 7.63 (1H, dd), 7.05 (1H, d), 5.73 (2H, s), 5.60 (2H, s), 4.01 (2H, t), 1.75 (2H, m), 0.99 (3H, t).

Preparation Example 10

4-n-Propoxy-1,3-diamidinobenzene

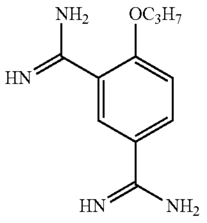

The compound (2.0 g, 7.8 mmol) of preparation example 9 was dissolved in glacial acetic acid (100 ml), added with 10% Pd/C (100 mg), and hydrogenized at 65° C. under a pressure of 3 MPa for 8 h. The reaction mixture was concentrated to dryness to give 1 g of the title compound as a reddish brown solid, which was directly used in the subsequent step without purification.

Preparation Example 11

5-Hydroxy-2-n-propoxybenzamidine

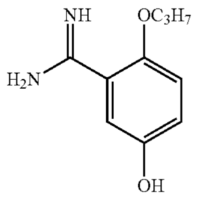

The title compound was prepared from the compound (2.0 g, 7.8 mmol) of preparation example 2 in the same manner as that of preparation examples 9 and 10, and directly used in the subsequent step without purification.

Preparation Example 12

3-Guanyl-4-n-propoxybenzoic acid

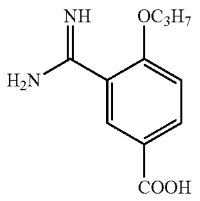

The title compound was prepared from the compound (6.1 g, 29.8 mmol) of preparation example 3 in the same manner as that of preparation examples 9 and 10, and directly used in the subsequent step without purification.

Preparation Example 13

2-Ethoxybenzamidine

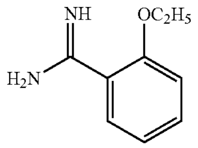

The title compound was prepared from 2-ethoxybenzonitrile (20.5 g, 127.3 mmol) in the same manner as that of preparation examples 9 and 10, and directly used in the subsequent step without purification.

Preparation Example 14

2-n-Propoxybenzamidine

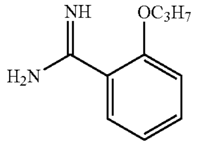

The title compound was prepared from 2-n-propoxybenzonitrile (20.5 g, 127.3 mmol) in the same manner as that of preparation examples 9 and 10, and directly used in the subsequent step without purification.

Preparation Example 15

2-n-Butoxybenzamidine

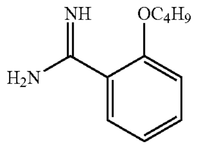

The title compound was prepared from 2-butoxybenzonitrile (2.0 g, 11.4 mmol) in the same manner as that of preparation examples 9 and 10, and directly used in the subsequent step without purification.

Preparation Example 16

2-n-Hexoxybenzamidine

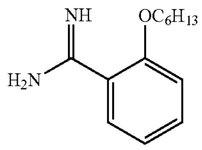

The title compound was prepared from 2-n-hexoxybenzonitrile (2.0 g, 9.8 mmol) in the same manner as that of preparation examples 9 and 10, and directly used in the subsequent step without purification.

Preparation Example 17

5-Bromo-2-n-propoxybenzamidine

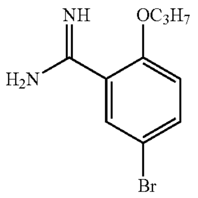

The title compound was prepared from 5-bromo-2-n-propoxybenzonitrile (5.0 g, 22.1 mmol) in the same manner as that of preparation examples 9 and 10, and directly used in the subsequent step without purification.

Preparation Example 18

2-(2-n-Butoxypropoxyphenyl)-6-isopropylpyrimid-4(3H)-one

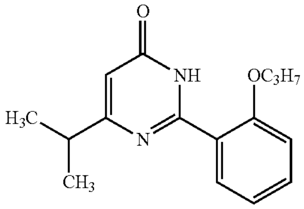

ru

The compound (10.0 g, 42 mmol) of preparation example 14 and $K_2CO_3$ (11.6 g, 84 mmol) were mixed and suspended in DMF (80 ml), and ethyl isobutyrylacetate (7.3 g, 46 mmol) was added thereto in one portion. The reaction mixture was stirred for 4 h at 100° C. under nitrogen protection, and then cooled down and poured into ice water. The generated solid was washed with water (1.5 L), and dried at 60° C. to give a light yellow solid crude, which was recrystallized from ethyl acetate to give the white title compound (8.4 g, yield: 73%). $^1$H NMR ($CDCl_3$) δ: 11.23 (1H, br), 8.51 (1H, dd), 7.48 (1H, t), 7.19 (1H, t), 7.03 (1H, d), 6.20 (1H, s), 4.18 (2H, t), 2.82 (1H, m), 1.99 (2H, m), 1.27 (6H, d), 1.13 (3H, t).

Preparation Example 19

2-(2-n-Propoxyphenyl)-5-bromo-6-isopropylpyrimid-4(3H)-one

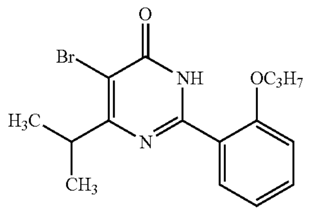

The compound (3.2 g, 12 mmol) of preparation example 18 was dissolved in $CH_2Cl_2$ (150 ml), and added with pyridine (1 ml), followed by dropwise addition of liquid bromine (1.9 g, 12 mmol) under ice-bath. After reacting for 10 min, the reaction mixture was washed with 1M $Na_2S_2O_3$ (50 ml), 1M HCl (40 ml) and saturated saline (50 ml) respectively. The organic phase was dried with anhydrous sodium sulfate, and concentrated to dryness under reduced pressure. The residue was recrystallized from acetonitrile-ethylether to give the title compound (3.9 g, yield: 95%). $^1$H NMR ($CDCl_3$) δ: 11.41 (1H, br), 8.53 (1H, d), 7.51 (1H, t), 7.13 (1H, t), 7.04 (1H, d), 4.20 (2H, t), 3.51 (1H, m), 2.00 (2H, m), 1.28 (6H, d), 1.14 (3H, t).

Preparation Example 20

2-(2-Ethoxyphenyl)-6-isopropylpyrimid-4(3H)-one

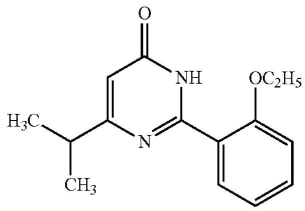

The title compound was prepared with the compound (4.0 g, 20 mmol, calculated on the base of acetate) of preparation example 13 and ethyl isobutyrylacetate (3.3 g, 21 mmol) as the raw materials in the same manner as that of preparation example 18. Yield: 85%. $^1$H NMR ($CDCl_3$) δ: 11.22 (1H, br), 8.52 (1H, dd), 7.48 (1H, t), 7.12 (1H, t), 7.03 (1H, d), 6.20 (1H, s), 4.29 (2H, t), 2.82 (1H, m), 1.59 (3H, t), 1.27 (6H, d).

Preparation Example 21

2-(2-Ethoxyphenyl)-5-bromo-6-isopropylpyrimid-4 (3H)-one

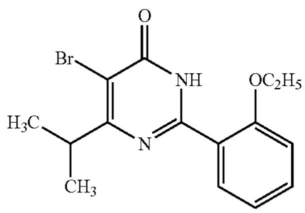

The title compound was prepared with the compound of preparation example 20 as a raw material in the same manner as that of preparation example 19. Yield: 95%. $^1$H NMR ($CDCl_3$) δ: 8.53 (1H, d), 7.51 (1H, t), 7.13 (1H, t), 7.04 (1H, d), 4.32 (2H, q), 3.51 (1H, m), 1.59 (3H, t), 1.27 (6H, d).

Preparation Example 22

2-(2-Ethoxyphenyl)-5-chloro-6-isopropylpyrimid-4 (3H)-one

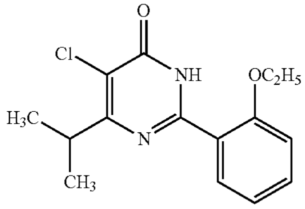

The compound (0.52 g, 2 mmol) of preparation example 20 was dissolved in $CH_2Cl_2$ (50 ml), and added with pyridine (0.5 ml), followed by feeding slowly chlorine gas (1.9 g, 12 mmol) for 3 minutes under ice-bath. The reaction mixture was washed with 1M $Na_2S_2O_3$ (20 ml), 1M HCl (20 ml) and saturated saline (40 ml) respectively. The organic phase was dried with anhydrous sodium sulfate, and concentrated to dryness under reduced pressure. The residue was recrystallized from acetonitrile-ethylether to give the title compound (0.57, yield: 98%). $^1$H NMR ($CDCl_3$) δ: 8.52 (1H, d), 7.50 (1H, t), 7.13 (1H, t), 7.04 (1H, d), 4.31 (2H, q), 3.49 (1H, m), 1.59 (3H, t), 1.27 (6H, d).

Preparation Example 23

2-(2-Ethoxyphenyl)-5-acetamido-6-isopropylpyrimid-4(3H)-one

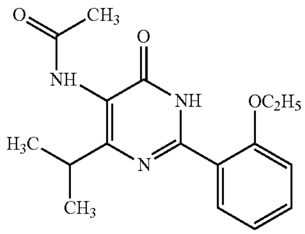 [SMILES: CCOc1ccccc1-c1nc(C(C)C)c(NC(C)=O)c(=O)[nH]1]

The title compound was prepared with the compound (1.2 g, 5.0 mmol) of preparation example 13 and ethyl 2-acetamidoisobutyrylacetate (1.1 g, 5.1 mmol) as raw materials in the same manner as that of preparation example 18. Yield: 65%. $^1$H NMR ($CDCl_3$) δ: 8.52 (1H, d), 7.50 (1H, t), 7.13 (1H, t), 7.04 (1H, d), 4.21 (2H, q), 3.00 (1H, m), 2.01 (3H, s), 1.10 (6H, d), 0.96 (3H, t).

Preparation Example 24

2-(2-n-Butoxyphenyl)-5-bromo-6-isopropylpyrimid-4(3H)-one

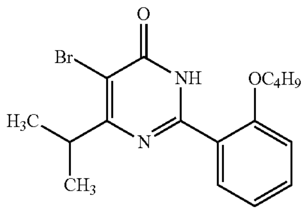

2-(2-n-butoxyphenyl)-6-isopropylpyrimid-4(3H)-one was prepared with the compound (1.3 g, 5.0 mmol) of preparation example 15 and ethyl isobutyrylacetate (0.8 g, 5.1 mmol) as raw materials in the same manner as that of preparation example 18, and then bromized in the same manner as that of preparation example 19 to give the title compound (total yield of two steps: 69%). $^1$H NMR (DMSO-$d_6$) δ: 7.89 (1H, d), 7.85 (1H, dd), 7.39 (1H, d), 4.14 (2H, t), 3.37 (1H, m), 1.71 (2H, m), 1.35 (2H, m), 1.23 (3H, t), 1.15 (6H, d), 0.81 (3H, t).

Preparation Example 25

2-(2-Ethoxyphenyl)-5-bromo-6-n-octylpyrimid-4(3H)-one

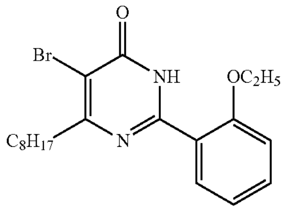

2-(2-ethoxyphenyl)-6-n-octylpyrimid-4(3H)-one was prepared with hydrochlorate (1.0 g, 5.0 mmol) of the compound obtained in preparation example 13 and ethyl nonanoylacetate (1.2 g, 5.1 mmol) as raw materials in the same manner as that of preparation example 18, and then bromized in the same manner as that of preparation example 19 to give the title compound (total yield of two steps: 78%). $^1$H NMR ($CDCl_3$) δ: 11.40 (1H, br), 8.47 (1H, d), 7.50 (1H, t), 7.12 (1H, t), 7.03 (1H, d), 4.31 (2H, q), 2.84 (2H, t), 1.76 (2H, m), 1.58 (3H, t), 1.51-1.19 (12H, m), 0.88 (3H, t).

Preparation Example 26

2-(2-Ethoxyphenyl)-5-bromo-6-phenylpyrimid-4(3H)-one

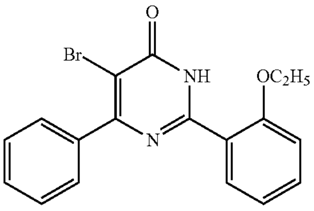 [SMILES: CCOc1ccccc1-c1nc(-c2ccccc2)c(Br)c(=O)[nH]1]

2-(2-ethoxyphenyl)-6-phenylpyrimid-4(3H)-one was prepared with hydrochlorate (1.0 g, 5.0 mmol) of 2-ethoxybenzamidine (the compound of preparation example 13) and ethyl benzoylacetate (1.0 g, 5.1 mmol) as raw materials in the same manner as that of preparation example 18, and then bromized in the same manner as that of preparation example 19 to give the title compound (total yield of two steps: 80%). $^1$H NMR ($CDCl_3$) δ: 8.52 (1H, d), 7.84 (2H, m), 7.49 (4H, m), 7.08 (2H, m), 4.35 (2H, q), 1.62 (3H, t).

Preparation Example 27

2-(2-n-Propoxyphenyl)-5-methyl-6-isopropylpyrimid-4(3H)-one

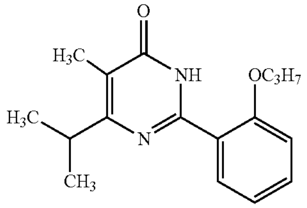

The title compound was prepared with the compound (1.2 g, 5.0 mmol) of preparation example 14 and ethyl 2-methyl-isobutyrylacetate (0.9 g, 5.1 mmol) as raw materials in the same manner as that of preparation example 18 (yield: 69%). $^1$H NMR ($CDCl_3$) δ: 8.52 (1H, d), 7.45 (1H, t), 7.11 (1H, t), 7.02 (1H, d), 4.17 (2H, t), 3.17 (1H, m), 2.12 (3H, s), 1.99 (2H, m), 1.25 (6H, d), 1.14 (3H, t).

Preparation Example 28

2-(2-n-Propoxyphenyl)-5-fluoro-6-ethylpyrimid-4(3H)-one

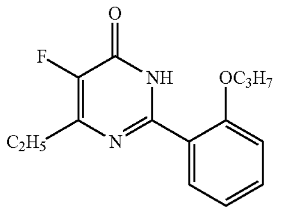

The title compound was prepared with the compound (1.2 g, 5.0 mmol) of preparation example 14 and ethyl 2-fluoro-propionylacetate (0.8 g, 5.1 mmol) as raw materials in the same manner as that of preparation example 18 (yield: 62%). $^1$H NMR ($CDCl_3$) δ: 11.16 (1H, br), 8.45 (1H, d), 7.48 (1H, t), 7.12 (1H, t), 7.04 (1H, d), 4.19 (2H, t), 2.73 (2H, q), 2.00 (2H, m), 1.30 (3H, t), 1.13 (3H, t).

Preparation Example 29

2-(2-n-Propoxyphenyl)-5-methyl-6-ethylpyrimid-4(3H)-one

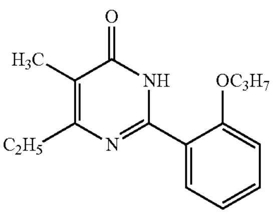

The title compound was prepared with the compound (1.2 g, 5.0 mmol) of preparation example 14 and ethyl 2-methylpropionylacetate (0.8 g, 5.1 mmol) as raw materials in the same manner as that of preparation example 18 (yield: 65%). $^1$H NMR ($CDCl_3$) δ: 11.16 (1H, br), 8.46 (1H, d), 7.46 (1H, t), 7.11 (1H, t), 7.02 (1H, d), 4.16 (2H, t), 2.68 (2H, q), 2.11 (3H, s), 1.98 (2H, m), 1.27 (3H, t), 1.13 (3H, t).

Preparation Example 30

2-(2-Ethoxyphenyl)-5-hydroxy-6-isopropylpyrimid-4(3H)-one

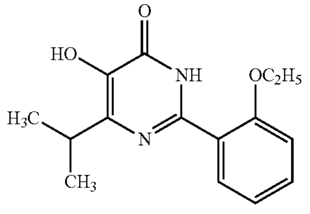

The compound (1.6 g, 5 mmol) of preparation example 23 was suspended in concentrated hydrochloric acid (15 ml), and refluxed for 1 h. The reaction mixture was concentrated under reduced pressure to a small volume, and adjusted to a pH of 8~9 with concentrated ammonia to generate precipitate. The precipitate was distilled water (30 ml×2), and dried to give 1.3 g of a deacetyl compound, 2-(2-ethoxyphenyl)-5-amino-6-isopropylpyrimid-4(3H)-one. The above resulted compound was dissolved in ethanol (15 ml) and cooled under ice-bath, followed by addition of 38% $HBF_4$ (5 ml). Isoamyl nitrite (0.6 g, 6 mmol) was slowly added dropwise there, and incubated for 2 h. Ethylether was added thereinto to generate precipitate. The filtered precipitate was added in batch into a refluxing 1N $H_2SO_4$, reacted for half an hour, and extracted with ethyl acetate (20 ml×2). The organic phase was washed with water (30 ml×2), 10% $NaHCO_3$ (20 ml) and saturated saline (40 ml) respectively, dried with anhydrous $Na_2SO_4$, and concentrated under reduced pressure, and the residue was separated by column chromatography to give 150 mg of the title compound (yield: 11%). $^1$H NMR ($CDCl_3$) δ: 11.36 (1H, br), 8.46 (1H, d), 7.52 (1H, t), 7.14 (1H, t), 7.06 (1H, d), 6.42 (1H, s), 4.32 (2H, q), 3.75 (1H, s), 1.61 (3H, t), 1.54 (6H, s).

Preparation Example 31

2-(2-n-Hexoxylphenyl)-6-isopropylpyrimid-4(3H)-one

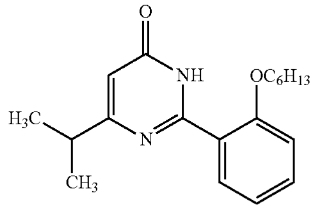

The title compound was prepared with the compound (1.4 g, 5.0 mmol) of preparation example 16 and ethyl isobutyrylacetate (0.8 g, 5.1 mmol) as raw materials in the same manner as that of preparation example 18 (yield: 54%). $^1$H NMR ($CDCl_3$) δ: 11.20 (1H, br), 8.52 (1H, d), 7.48 (1H, t), 7.12 (1H, t), 7.04 (1H, d), 6.29 (1H, s), 4.20 (2H, t), 2.81 (1H, m), 1.98 (2H, m), 1.58-1.30 (6H, m), 1.27 (6H, d), 0.90 (3H, t).

Preparation Example 32

2-(2-Ethoxyphenyl)-6-isopropylpyrimid-4(3H)-one

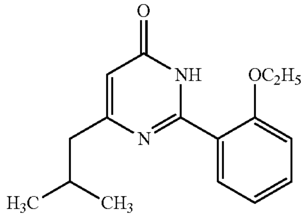 [SMILES: CCOc1ccccc1-c1nc(CC(C)C)cc(=O)[nH]1]

The title compound was prepared with hydrochlorate (1.0 g, 5.0 mmol) of 2-ethoxybenzamidine (the compound of preparation example 13) and ethyl isovalerylacetate (0.9 g, 5.1 mmol) as raw materials in the same manner as that of preparation example 18 (yield: 82%). $^1$H NMR ($CDCl_3$) δ: 11.24 (1H, br), 8.48 (1H, d), 7.49 (1H, t), 7.12 (1H, t), 7.03 (1H, d), 6.16 (1H, s), 4.29 (2H, q), 2.45 (2H, d), 2.18 (1H, m), 1.59 (3H, t), 0.96 (6H, d).

Preparation Example 33

2-(2-n-Propoxyphenyl)-5,6-diethylpyrimid-4(3H)-one

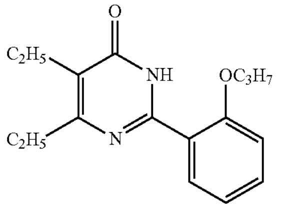

The title compound was prepared with the compound (4.0 g, 20 mmol) of preparation example 14 and methyl 2-ethyl-3-oxopentanoate (3.6 g, 21 mmol) as raw materials in the same manner as that of preparation example 18 (yield: 78%). $^1$H NMR ($CDCl_3$) δ: 11.18 (1H, br), 8.46 (1H, dd), 7.44 (1H, t), 7.09 (1H, t), 7.01 (1H, d), 4.15 (2H, t), 2.66 (2H, q), 2.58 (2H, q), 1.98 (2H, m), 1.29 (3H, t), 1.14 (3H, t).

Preparation Example 34

2-(5-Bromo-2-n-propoxyphenyl)-5,6-diethylpyrimid-4(3H)-one

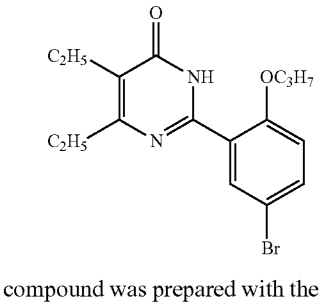

The title compound was prepared with the compound (5.9 g, 20 mmol) of preparation example 17 and methyl 2-ethyl-3-oxopentanoate (3.6 g, 21 mmol) as raw materials in the same manner as that of preparation example 18 (yield: 63%). $^1$H NMR ($CDCl_3$) δ: 7.96 (1H, d), 7.89 (1H, dd), 7.44 (1H, d), 4.13 (2H, t), 2.58 (2H, q), 2.46 (2H, q), 1.76 (2H, m), 1.18 (3H, t), 1.05 (3H, t), 0.96 (3H, t).

Preparation Example 35

2-(5-Bromo-2-n-propoxyphenyl)-6-isopropylpyrimid-4(3H)-one

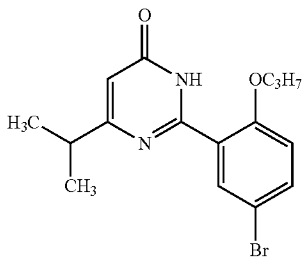

The title compound was prepared with the compound (4.0 g, 20 mmol) of preparation example 17 and ethyl isobutyrylacetate (3.3 g, 21 mmol) as raw materials in the same manner as that of preparation example 18 (yield: 93%). $^1$H NMR ($CDCl_3$) δ: 11.12 (1H, br), 8.60 (1H, d), 7.54 (1H, dd), 6.93 (1H, d), 6.22 (1H, s), 4.15 (2H, t), 2.82 (1H, m), 1.98 (2H, m), 1.27 (6H, d), 1.12 (3H, t).

Preparation Example 36

2-(2-(3-Methoxyn-propoxy)phenyl)-5,6-diethylpyrimid-4(3H)-one

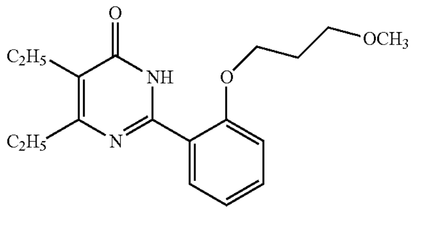 [SMILES: CCc1nc(-c2ccccc2OCCCOC)[nH]c(=O)c1CC]

The title compound was prepared with hydrochlorate (1.22 g, 5.0 mmol) of 2-(3-methoxy-n-propoxy)benzamidine and ethyl 2-ethylpropionylacetate (0.8 g, 5.1 mmol) as raw materials in the same manner as that of preparation example 18 (yield: 73%). $^1$H NMR ($CDCl_3$) δ: 11.08 (1H, br), 8.46 (1H, dd), 7.44 (1H, t), 7.09 (1H, t), 7.01 (1H, d), 4.25 (2H, t), 3.65 (2H, t), 3.42 (3H, s), 2.66 (2H, q), 2.59 (2H, q), 2.22 (2H, m), 1.27 (3H, t), 1.15 (3H, t).

Example 1

6-Isopropyl-2-[2-n-propoxy-5-(4-methyl-piperazin-1-yl-sulfonyl)phenyl]pyrimid-4(3H)-one

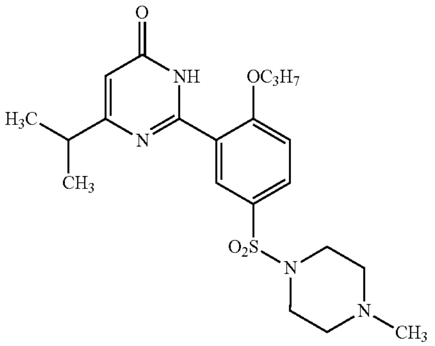

Ethyl isobutyrylacetate (0.5 g, 3.2 mmol) and the compound (1.2 g, 3.2 mmol) of preparation example 7 were added into DMF (10 ml), followed by addition of $K_2CO_3$ (0.9 g, 6.4 mmol). The reaction mixture was heated to 90° C. for 3 h. The cooled reaction mixture was poured into ice water, and extracted with $CH_2Cl_2$ (3×20 ml). The organic phase was washed with saturated brine, dried with anhydrous $Na_2SO_4$, and concentrated. The residue was passed through a neutral alumina column to give 0.7 g of the title compound (yield: 50%). $^1$H NMR (DMSO-$d_6$) δ: 7.89 (1H, d), 7.84 (1H, dd), 7.38 (1H, d), 6.15 (1H, s), 4.12 (2H, t), 2.90 (4H, t), 2.75 (1H, m), 2.36 (4H, t), 2.14 (3H, s), 1.74 (2H, m), 1.35 (3H, t), 1.18 (6H, d).

Examples 2~8

The compounds of Examples 2~8 were prepared by reacting the compound of preparation example 7 with ethyl cyanoacetate, diethyl malonate, diethyl acetamidomalonate, ethyl benzoylacetate, ethyl propionylacetate, ethyl acetamidopropionylacetate, ethyl acetamidocyanoacetate respectively in the same manner as that of preparation example 1.

| Example | Structural Formula | Nomenclature and data of $^1$H-NMR (δ) |
|---|---|---|
| 2 | 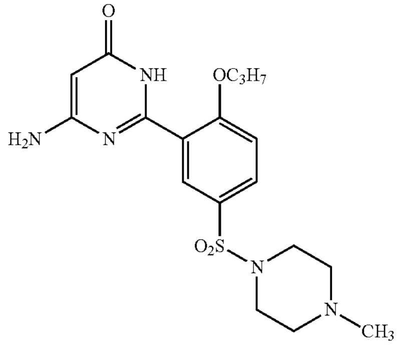 | 6-amino-2-[2-n-propoxy-5-(4-methyl-1-piperazinylsulfonyl)phenyl]pyrimid-4(3H)-one (DMSO-$d_6$) δ: 7.90 (1H, d), 7.81 (1H, dd), 7.38 (1H, d), 6.56 (2H, br), 5.00 (1H, s), 4.12 (2H, t), 2.87 (4H, t), 2.36 (4H, t), 2.14 (3H, s), 1.75 (2H, m), 0.97 (3H, t) |

-continued

| Example | Structural Formula | Nomenclature and data of $^1$H-NMR (δ) |
|---|---|---|
| 3 | 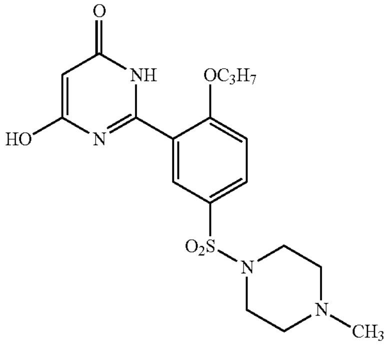 | 6-hydroxy-2-[2-n-propoxy-5-(4-methyl-1-piperazinylsulfonyl)phenyl]pyrimid-4(3H)-one (DMSO-$d_6$) δ: 8.09 (1H, d), 7.76 (1H, dd), 7.36 (1H, d), 6.56 (1H, s), 4.52 (1H, br), 4.15 (2H, t), 2.87 (4H, t), 2.36 (4H, t), 2.13 (3H, s), 1.79 (2H, m), 1.01 (3H, t) |
| 4 | 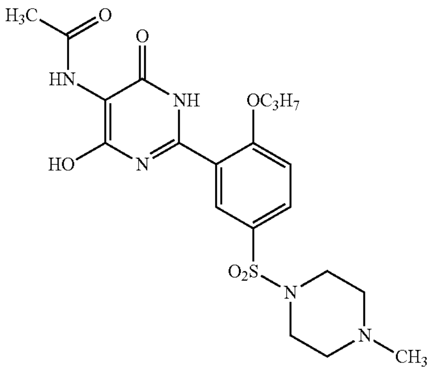 | 5-acetamido-6-hydroxy-2-[2-n-propoxy-5-(4-methyl-1-piperazinylsulfonyl)phenyl]pyrimid-4(3H)-one (DMSO-$d_6$) δ: 7.94 (1H, d), 7.84 (1H, dd), 7.40 (1H, d), 6.56 (1H, s), 4.52 (1H, br), 4.14 (2H, t), 2.88 (4H, t), 2.36 (4H, t), 2.14 (3H, s), 1.99 (3H, s), 1.76 (2H, m), 0.97 (3H, t) |
| 5 | 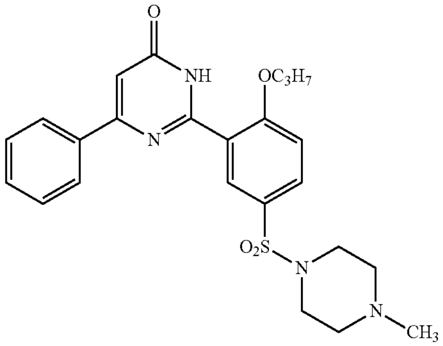 | 6-phenyl-2-[2-n-propoxy-5-(4-methyl-1-piperazinylsulfonyl)phenyl]pyrimid-4(3H)-one (DMSO-$d_6$) δ: 8.09 (2H, m), 8.01 (1H, d), 7.87 (1H, dd), 7.50 (3H, m), 7.43 (1H, d), 6.91 (1H, s), 4.15 (2H, t), 2.92 (4H, t), 2.37 (4H, t), 2.14 (3H, s), 1.76 (2H, m), 0.95 (3H, t) |
| 6 | 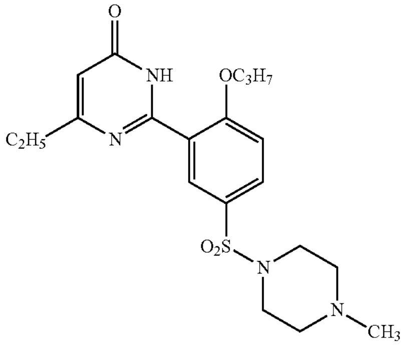 | 6-ethyl-2-[2-n-propoxy-5-(4-methyl-1-piperazinylsulfonyl)phenyl]pyrimid-4(3H)-one (DMSO-$d_6$) δ: 7.89 (1H, d), 7.84 (1H, dd), 7.39 (1H, d), 4.15 (2H, t), 2.89 (4H, t), 2.45 (2H, q), 2.36 (4H, t), 2.16 (3H, s), 1.75 (2H, m), 1.13 (3H, t), 0.96 (3H, t) |

-continued

| Example | Structural Formula | Nomenclature and data of $^{1}$H-NMR (δ) |
|---|---|---|
| 7 | 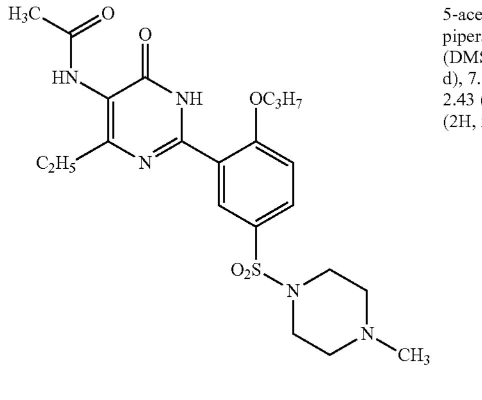 | 5-acetamido-6-ethyl-2-[2-n-propoxy-5-(4-methyl-1-piperazinylsulfonyl)phenyl]pyrimid-4(3H)-one (DMSO-$d_6$) δ: 12.48 (1H, br), 9.22 (1H, br), 7.88 (1H, d), 7.84 (1H, dd), 7.39 (1H, d), 4.13 (2H, t), 2.91 (4H, t), 2.43 (2H, q), 2.40 (4H, t), 2.16 (3H, s), 2.02 (3H, s), 1.76 (2H, m), 1.13 (3H, t), 0.96 (3H, t) |
| 8 | 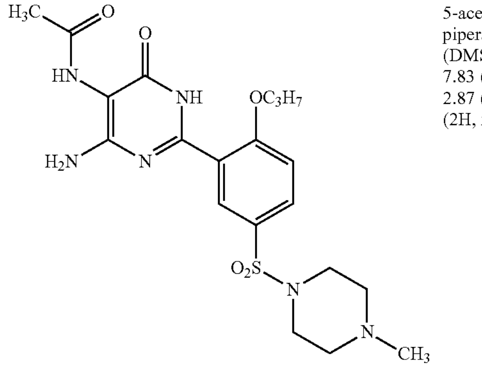 | 5-acetamido-6-amino-2-[2-n-propoxy-5-(4-methyl-1-piperazinylsulfonyl)phenyl]pyrimid-4(3H)-one (DMSO-$d_6$) δ: 11.57 (2H, s), 8.69 (1H, br), 7.90 (1H, d), 7.83 (1H, dd), 7.39 (1H, d), 6.35 (2H, s), 4.13 (2H, t), 2.87 (4H, t), 2.36 (4H, t), 2.14 (3H, s), 1.96 (3H, s), 1.77 (2H, m), 0.97 (3H, t) |

Example 9

6-Acetamido-2-[2-n-propoxy-5-(4-methyl-1-piperazinylsulfonyl)phenyl]pyrimid-4(3H)-one

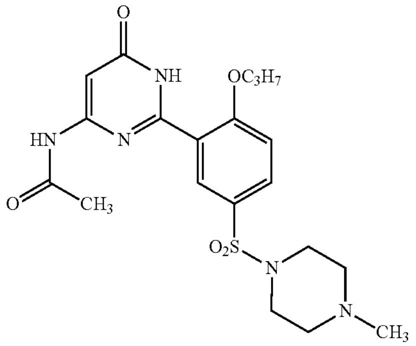

The compound (0.20 g, 0.5 mmol) of Example 2 was suspended in acetic anhydride (5 ml), and stirred at 100° C. for 1 h. The cooled reaction mixture was poured into ice water to generate a white solid. After filtered, the solid was washed with clear water (3×10 ml), and dried at 60° C. to give 0.12 g of the title compound (yield: 53%). $^{1}$H NMR (DMSO-$d_6$) δ: 12.16 (1H, br), 10.54 (1H, br), 7.92 (1H, d), 7.84 (1H, dd), 7.40 (1H, d), 6.89 (1H, s), 4.12 (2H, t), 2.88 (4H, t), 2.36 (4H, t), 2.14 (3H, s), 2.08 (3H, s), 1.74 (2H, m), 0.95 (3H, t).

Example 10

5-Bromo-6-isopropyl-2-[2-n-propoxy-5-(4-methyl-1-piperazinylsulfonyl)phenyl]pyrimid-4(3H)-one

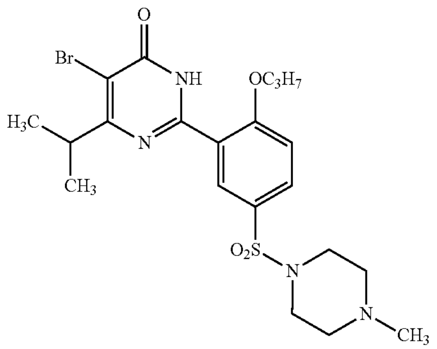

The compound (0.35 g, 1.0 mmol) of preparation example 19 was slowly added into chlorosulfonic acid (5 ml) under ice-bath, and then the ice-bath was removed. After stirred at room temperature for 2 h, the reaction mixture was charily added dropwise into brash ice to generate a faint yellow precipitate. After filtered, the solid was washed with ice water, dissolved in $CH_2Cl_2$ (50 ml), and added dropwise into $CH_2Cl_2$ (30 ml) containing N-methylpiperazine (0.11 g, 1.1 mmol) and triethylamine (1 ml) under ice-bath, followed by stirring for 30 min. The organic phase was washed with water (3×20 ml) and saturated saline (20 ml), and evaporated off solvent to dryness. The residue was recrystallized from ethyl acetate/petroleum ether to give the title compound (0.41 g, total yield of two steps: 80%). $^1$H NMR (DMSO-$d_6$) δ: 7.91 (1H, d), 7.85 (1H, dd), 7.39 (1H, d), 4.13 (2H, t), 2.90 (4H, t), 2.75 (1H, m), 2.36 (4H, t), 2.14 (3H, s), 1.74 (2H, m), 1.35 (3H, t), 1.18 (6H, d).

Examples 11~21

The compounds of preparation examples 20~30 were reacted sequentially with chlorosulfonic acid and N-methylpiperazine in the same manner as that of preparation example 10 to prepare the compounds of Examples 11~21.

| Example | Structural Formula | Nomenclature and data of $^1$H-NMR (δ) |
|---|---|---|
| 11 | 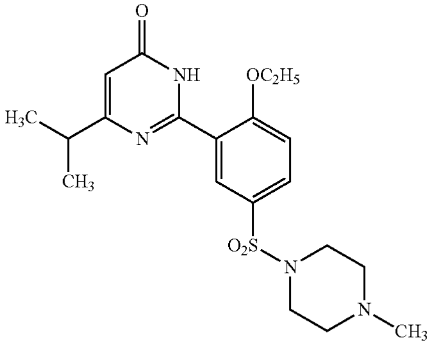 | 6-isopropyl-2-[2-ethoxy-5-(4-methyl-1-piperazinylsulfonyl)phenyl]pyrimid-4(3H)-one (DMSO-$d_6$) δ: 7.89 (1H, d), 7.84 (1H, dd), 7.38 (1H, d), 6.15 (1H, s), 4.22 (2H, q), 2.90 (4H, t), 2.75 (1H, m), 2.36 (4H, t), 2.14 (3H, s), 1.35 (3H, t), 1.18 (6H, d) |
| 12 | 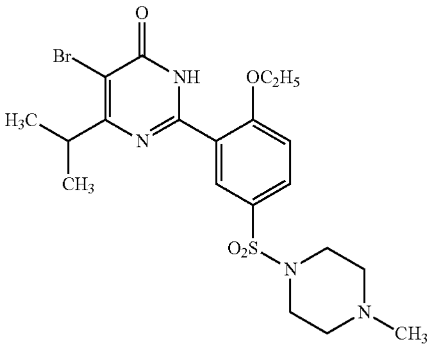 | 5-bromo-6-isopropyl-2-[2-ethoxy-5-(4-methyl-1-piperazinylsulfonyl)phenyl]pyrimid-4(3H)-one (DMSO-$d_6$) δ: 7.91 (1H, d), 7.85 (1H, dd), 7.39 (1H, d), 4.21 (2H, q), 3.36 (1H, m), 2.90 (4H, t), 2.37 (4H, t), 2.14 (3H, s), 1.35 (3H, t), 1.17 (6H, d) |
| 13 | 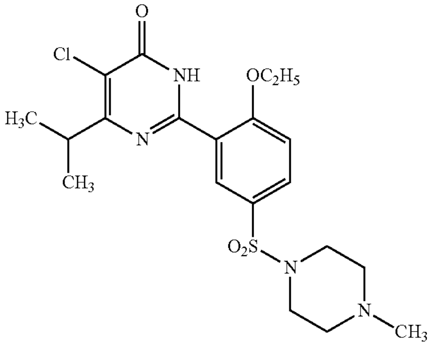 | 5-chloro-6-isopropyl-2-[2-ethoxy-5-(4-methyl-1-piperazinylsulfonyl)phenyl]pyrimid-4(3H)-one $^1$H NMR (DMSO-$d_6$) δ: 7.91 (1H, d), 7.84 (1H, dd), 7.39 (1H, d), 4.21 (2H, q), 3.36 (1H, m), 2.90 (4H, t), 2.37 (4H, t), 2.14 (3H, s), 1.34 (3H, t), 1.17 (6H, d). |

-continued

| Example | Structural Formula | Nomenclature and data of $^1$H-NMR (δ) |
|---|---|---|
| 14 | 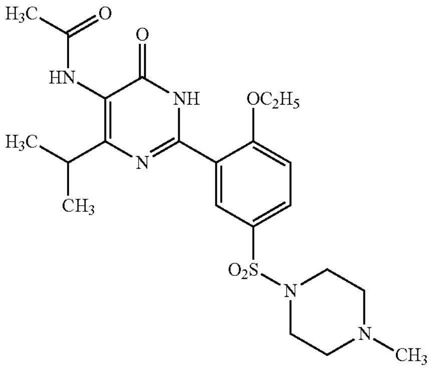 [SMILES: CCOc1ccc(S(=O)(=O)N2CCN(C)CC2)cc1-c1nc(C(C)C)c(NC(C)=O)c(=O)[nH]1] | 5-acetamido-6-isopropyl-2-[2-ethoxy-5-(4-methyl-1-piperazinylsulfonyl)phenyl]pyrimid-4(3H)-one (DMSO-$d_6$) δ: 7.89 (1H, d), 7.84 (1H, dd), 7.40 (1H, d), 4.20 (2H, q), 3.00 (1H, m), 2.91 (4H, t), 2.34 (4H, t), 2.14 (3H, s), 2.01 (3H, s), 1.10 (6H, d), 0.96 (3H, t) |
| 15 | 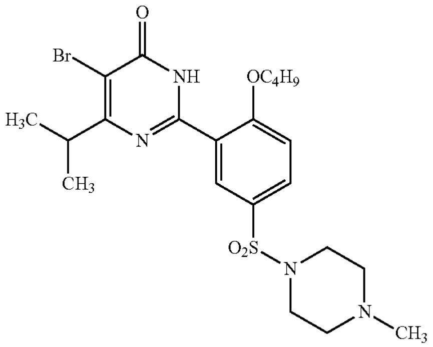 | 5-bromo-6-isopropyl-2-[2-n-butoxyl-5-(4-methyl-1-piperazinylsulfonyl)phenyl]pyrimid-4(3H)-one (DMSO-$d_6$) δ: 7.89 (1H, d), 7.85 (1H, dd), 7.39 (1H, d), 4.14 (2H, t), 3.37 (1H, m), 2.90 (4H, t), 2.37 (4H, t), 2.14 (3H, s), 1.71 (2H, m), 1.35 (2H, m), 1.23 (3H, t), 1.15 (6H, d), 0.81 (3H, t) |
| 16 | 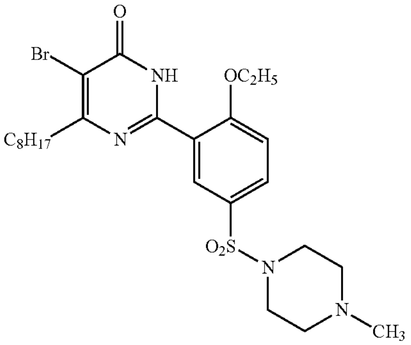 | 5-bromo-6-n-octyl-2-[2-ethoxy-5-(4-methyl-1-piperazinylsulfonyl)phenyl]pyrimid-4(3H)-one (DMSO-$d_6$) δ: 7.89 (1H, d), 7.85 (1H, dd), 7.39 (1H, d), 4.14 (2H, q), 2.90 (4H, t), 2.37 (4H, t), 2.14 (3H, s), 1.71 (2H, m), 1.58 (3H, t), 1.51-1.19 (12H, m), 0.88 (3H, t) |
| 17 | 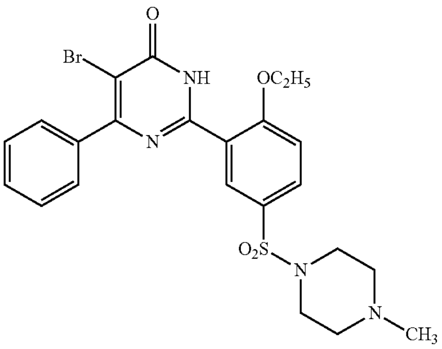 [SMILES: CCOc1ccc(S(=O)(=O)N2CCN(C)CC2)cc1-c1nc(-c2ccccc2)c(Br)c(=O)[nH]1] | 5-bromo-6-phenyl-2-[2-ethoxy-5-(4-methyl-1-piperazinylsulfonyl)phenyl]pyrimid-4(3H)-one (DMSO-$d_6$) δ: 7.93 (1H, d), 7.86 (1H, dd), 7.72 (2H, m), 7.50 (3H, m), 7.40 (1H, d), 4.24 (2H, q), 2.90 (4H, t), 2.38 (4H, t), 2.15 (3H, s), 1.38 (3H, t) |

-continued

| Example | Structural Formula | Nomenclature and data of $^1$H-NMR (δ) |
|---|---|---|
| 18 | 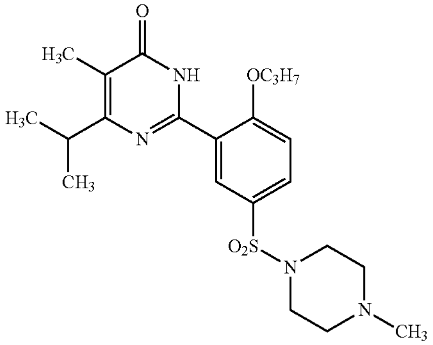 | 5-methyl-6-isopropyl-2-[2-n-propoxy-5-(4-methyl-1-piperazinylsulfonyl)phenyl]pyrimid-4(3H)-one (DMSO-$d_6$) δ: 7.91 (1H, d), 7.84 (1H, dd), 7.40 (1H, d), 4.13 (2H, t), 3.13 (1H, m), 2.94 (4H, t), 2.27 (4H, t), 2.68 (2H, q), 2.11 (3H, s), 1.91 (3H, s), 1.75 (2H, m), 1.14 (6H, d), 0.96 (3H, t) |
| 19 | 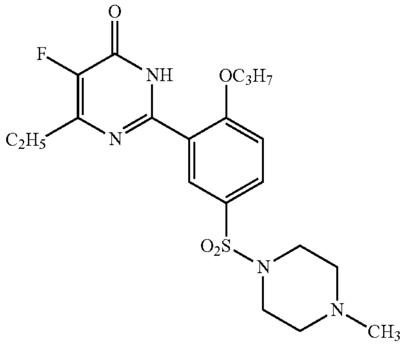 | 5-fluoro-6-ethyl-2-[2-n-propoxy-5-(4-methyl-1-piperazinylsulfonyl)phenyl]pyrimid-4(3H)-one ($CDCl_3$) δ: 8.80 (1H, d), 7.86 (1H, dd), 7.16 (1H, d), 4.26 (2H, t), 3.09 (4H, t), 2.74 (4H, m), 2.51 (4H, t), 2.28 (3H, s), 2.03 (2H, m), 1.28 (3H, t), 1.15 (3H, t) |
| 20 | 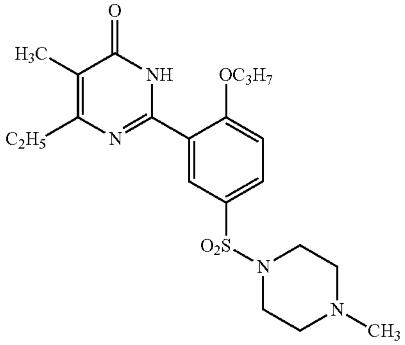 | 5-methyl-6-ethyl-2-[2-n-propoxy-5-(4-methyl-1-piperazinylsulfonyl)phenyl]pyrimid-4(3H)-one ($CDCl_3$) δ: 10.93 (1H, br), 8.85 (1H, d), 7.84 (1H, dd), 7.13 (1H, d), 4.24 (2H, t), 3.09 (4H, t), 2.68 (2H, q), 2.51 (4H, t), 2.28 (3H, s), 2.12 (3H, s), 2.03 (2H, m), 1.26 (3H, t), 1.16 (3H, t) |
| 21 | 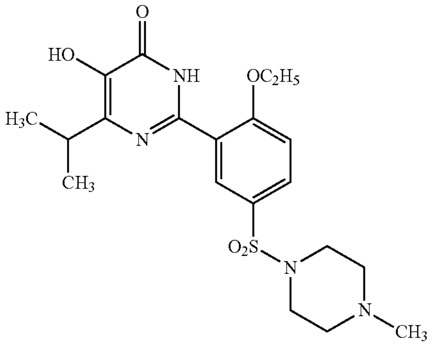 [SMILES: CCOc1ccc(S(=O)(=O)N2CCN(C)CC2)cc1-c1nc(C(C)C)c(O)c(=O)[nH]1] | 5-hydroxy-6-isopropyl-2-[2-ethoxy-5-(4-methyl-1-piperazinylsulfonyl)phenyl]pyrimid-4(3H)-one ($CDCl_3$) δ: 11.36 (1H, br), 8.46 (1H, d), 7.52 (1H, t), 7.14 (1H, t), 7.06 (1H, d), 6.42 (1H, s), 4.32 (2H, q), 3.75 (1H, s), 3.09 (4H, t), 2.51 (4H, t), 2.28 (3H, s), 1.61 (3H, t), 1.54 (6H, s) |

Example 22

5-Amino-6-isopropyl-2-[2-ethoxy-5-(4-methyl-1-piperazinylsulfonyl)phenyl]pyrimid-4(3H)-one

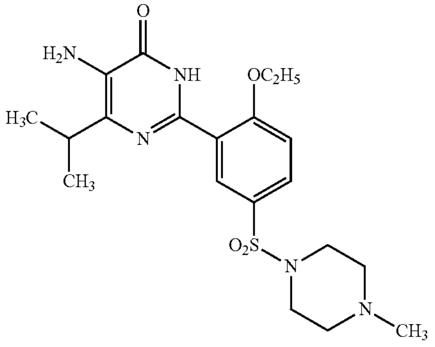 [SMILES: CCOc1ccc(S(=O)(=O)N2CCN(C)CC2)cc1-c1nc(C(C)C)c(N)c(=O)[nH]1]

The compound (60 mg, 0.13 mmol) of Example 14 was suspended in concentrated hydrochloric acid (3 ml), and refluxed for 1 h. The reaction mixture was concentrated under reduced pressure to a small volume, and adjusted to a pH of 8~9 with concentrated ammonia to generate precipitate. The obtained precipitate was washed with distilled water (3 ml) and dried to give the title compound (50 mg, yield: 91%). $^1$H NMR (DMSO-$d_6$) δ: 7.90 (1H, d), 7.75 (1H, dd), 7.33 (1H, d), 4.91 (2H, s), 4.21 (2H, q), 3.09 (1H, m), 2.89 (4H, t), 2.36 (4H, t), 2.13 (3H, s), 1.37 (3H, t), 1.13 (6H, d).

Example 23

5-Bromo-6-isopropyl-2-[2-n-hexyloxy-5-(4-methyl-1-piperazinylsulfonyl)phenyl]pyrimid-4(3H)-one

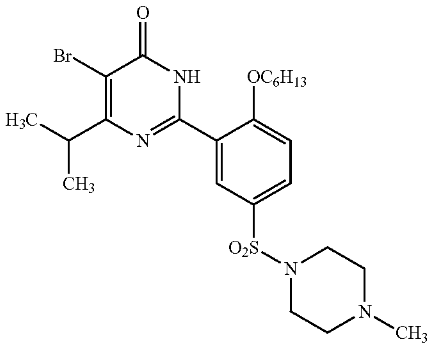

2-(2-n-hexoxylphenyl)-5-bromo-6-isopropylpyrimid-4(3H)-one was prepared from the compound of Preparation example 31 as a raw material in the same manner as the bromization of preparation example 19, and then chlorosulfonated and reacted with N-methylpiperazine in the same manner as that of example 10 to give the title compound (total yield of two steps: 85%). $^1$H NMR (DMSO-$d_6$) δ: 7.90 (1H, d), 7.85 (1H, dd), 7.39 (1H, d), 4.14 (2H, t), 3.37 (1H, m), 2.90 (4H, t), 2.37 (4H, t), 2.14 (3H, s), 1.70 (2H, m), 1.18-1.40 (8H, m), 1.15 (6H, d), 0.81 (3H, t).

Example 24

5-Bromo-6-isobutyl-2-[2-ethoxy-5-(4-methyl-1-piperazinylsulfonyl)phenyl]pyrimid-4(3H)-one

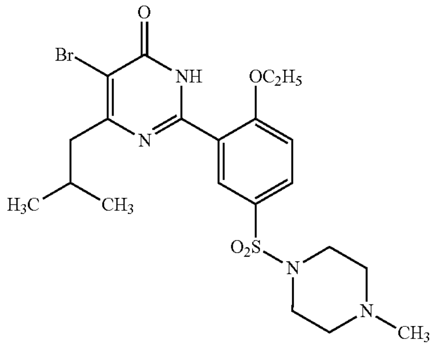 [SMILES: CCOc1ccc(S(=O)(=O)N2CCN(C)CC2)cc1-c1nc(CC(C)C)c(Br)c(=O)[nH]1]

The title compound was prepared from the compound of preparation example 32 as a raw material in the same manner as that of example 23 (total yield: 88%). $^1$H NMR (DMSO-$d_6$) δ: 7.87 (1H, d), 7.83 (1H, dd), 7.38 (1H, d), 4.21 (2H, q), 2.91 (4H, t), 2.65 (2H, d), 2.44 (4H, t), 2.20 (3H, s), 2.17 (1H, m), 1.33 (3H, t), 0.95 (6H, d).

Examples 25~28

In the same manner as that of example 10, the compound of preparation example was first chlorosulfonated and then reacted with N-methylethanolamine, 2-(morpholin-1-yl) ethylamine, 3-(morpholin-1-yl)propylamine and N,N-diethyl ethylendiamine respectively to give the compounds of examples 25~28.

| Example | Structural Formula | Nomenclature and data of $^1$H-NMR(δ) |
| --- | --- | --- |
| 25 | 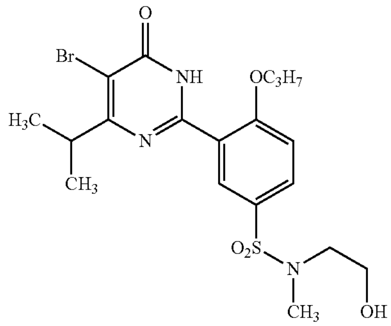 | 5-bromo-6-isopropyl-2-{2-n-propoxy-5-[N-methyl-N-(2-hydroxyethyl)aminosulfonyl]phenyl}pyrimid-4(3H)-one (DMSO-$d_6$) δ: 7.96 (1H, d), 7.89 (1H, dd), 7.37 (1H, d), 4.80 (1H, t), 4.11 (2H, t), 3.52 (2H, q), 3.36 (1H, m), 3.01 (2H, t), 2.73 (3H, s), 1.74 (2H, m), 1.17 (6H, d), 0.94 (3H, t) |

-continued

| Example | Structural Formula | Nomenclature and data of $^{1}$H-NMR(δ) |
|---|---|---|
| 26 | 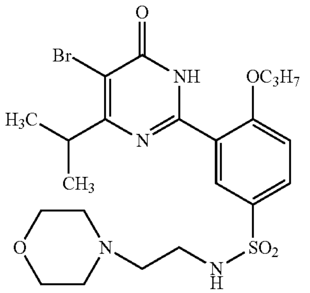 | 5-bromo-6-isopropyl-2-{2-n-propoxy-5-[N-(2-morpholinylethyl)aminosulfonyl]phenyl}pyrimid-4(3H)-one (DMSO-$d_6$) δ: 8.02 (1H, d), 7.92 (1H, dd), 7.60 (1H, t), 7.36 (1H, d), 4.10 (2H, t), 3.48 (4H, t), 3.38 (1H, m), 2.88 (2H, t), 2.30 (2H, t), 2.25 (4H, t), 1.74 (2H, m), 1.18 (6H, d), 0.95 (3H, t) |
| 27 | 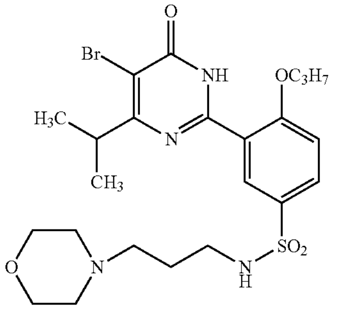 | 5-bromo-6-isopropyl-2-{2-n-propoxy-5-[N-(3-morpholinylpropyl)aminosulfonyl]phenyl}pyrimid-4(3H)-one (DMSO-$d_6$) δ: 8.00 (1H, d), 7.90 (1H, dd), 7.64 (1H, t), 7.36 (1H, d), 4.10 (2H, t), 3.36 (5H, m), 2.79 (2H, t), 2.21 (6H, m), 1.75 (2H, m), 1.52 (2H, m), 1.18 (6H, d), 0.95 (3H, t) |
| 28 | 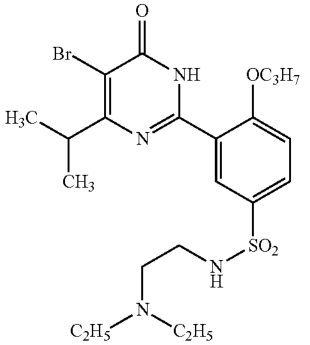 | 5-bromo-6-isopropyl-2-{2-n-propoxy-5-[N-(N',N'-diethylamino)ethylaminosulfonyl]phenyl}pyrimid-4(3H)-one ($CD_3OD$) δ: 8.34 (1H, d), 7.99 (1H, dd), 7.34 (1H, d), 4.19 (2H, t), 3.55 (1H, m), 2.99 (2H, t), 2.55-2.66 (6H, m), 1.88 (2H, m), 1.26 (6H, d), 1.00-1.10 (9H, m) |

Examples 29~32

In the same manner as that of example 10, the compound of preparation example 33 was first chlorosulfonated and then reacted with N-methylpiperazine, N-methylethanolamine, 2-morpholinylethylamine and L-proline respectively to give the compounds of examples 29~32.

| Example | Structural Formula | Nomenclature and data of $^{1}$H-NMR(δ) |
|---|---|---|
| 29 | 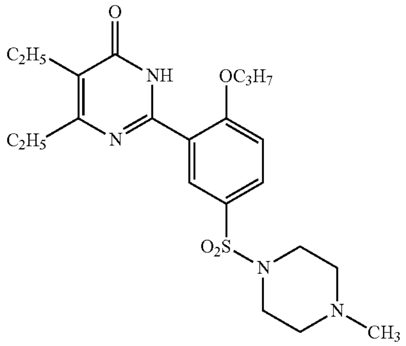 | 5,6-diethyl-2-[2-n-propoxy-5-(4-methyl-1-piperazinylsulfonyl)phenyl]pyrimid-4(3H)-one ($CDCl_3$) δ: 7.96 (1H, d), 7.89 (1H, dd), 7.44 (1H, d), 4.13 (2H, t), 3.09 (4H, t), 2.74 (4H, m), 2.58 (2H, q), 2.46 (2H, q), 2.28 (3H, s), 1.76 (2H, m), 1.18 (3H, t), 1.05 (3H, t), 0.96 (3H, t) |

-continued

| Example | Structural Formula | Nomenclature and data of $^1$H-NMR(δ) |
|---|---|---|
| 30 | 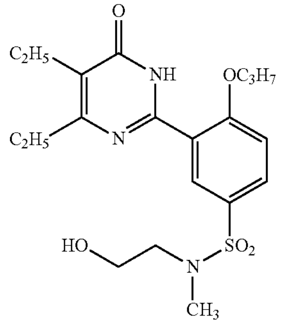 | 5,6-diethyl-2-{2-n-propoxy-5-[N-methyl-N-(hydroxyethyl)aminosulfonyl]phenyl}pyrimid-4(3H)-one<br>($CDCl_3$) δ: 8.86 (1H, d), 7.90 (1H, dd), 7.14 (1H, d), 4.24 (2H, t), 3.80 (2H, t), 3.23 (2H, t), 2.89 (3H, s), 2.69 (2H, q), 2.59 (2H, q), 2.01 (2H, m), 1.28 (3H, t), 1.15 (3H, t), 1.14 (3H, t) |
| 31 | 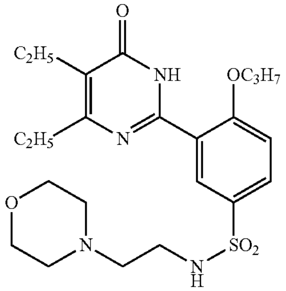 | 5,6-diethyl-2-{2-n-propoxy-5-[N-(2-morpholinylethyl) aminosulfonyl)phenyl}pyrimid-4(3H)-one<br>($CDCl_3$) δ: 8.95 (1H, d), 7.97 (1H, dd), 7.13 (1H, d), 4.24 (2H, t), 3.65 (4H, t), 3.06 (2H, t), 2.67 (2H, q), 2.59 (2H, q), 2.49 (2H, t), 2.36 (4H, t), 2.03 (2H, m), 1.28 (3H, t), 1.16 (3H, t), 1.14 (3H, t) |
| 32 | 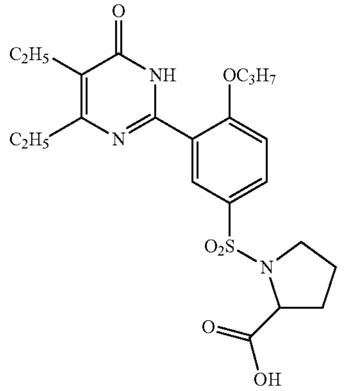 | N-(3-(4,5-diethyl-1,6-dihydro-6-oxopyrimidin-2-yl)-4-n-propoxyphenylsulfonylproline<br>($CDCl_3$) δ: 8.67 (1H, d), 7.99 (1H, dd), 7.07 (1H, d), 4.08 (3H, m), 3.48 (1H, m), 3.12 (1H, m), 2.40-2.86 (6H, m), 1.86 (4H, m), 1.20 (3H, t), 1.10 (3H, t), 1.04 (3H, t) |

Example 33

2-(5-Nitro-2-n-propoxyphenyl)-5-bromo-6-isopropylpyrimid-4(3H)-one

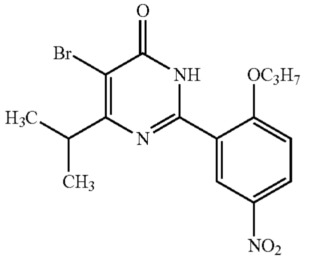

The compound (14.0 g, 40 mmol) of preparation example 19 was dissolved in concentrated sulfuric acid (100 ml) under ice-bath, and slowly added with a 65-68% concentrated nitric acid (100 ml). After stirred at room temperature for 3 h, the reaction mixture was slowly added dropwise into ice water to generate a light yellow precipitate. After filtered, the solid was washed with clear water (3×200 ml) and dried at 60° C. to give the title compound (14.2 g, yield: 90%). $^1$H NMR ($CDCl_3$) δ: 11.20 (1H, br), 9.36 (1H, d), 8.39 (1H, dd), 7.04 (1H, d), 4.32 (2H, t), 3.56 (1H, m), 2.04 (2H, m), 1.30 (6H, d), 1.16 (3H, t).

Example 34

2-(5-Amino-2-n-propoxyphenyl)-5-bromo-6-isopropylpyrimid-4(3H)-one

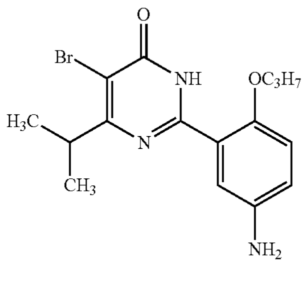

The compound (4.0 g, 10 mmol) of Example 33 was suspended in concentrated hydrochloric acid and heated to be refluxed. Reduced iron powder (1.7 g, 30 mmol) was added into the reaction mixture in batch, and stirred for 1 h. The hot reaction mixture was filtered and cooled to room temperature to generate a yellowish precipitate. After filtered, the solid was dried at 60° C. to give the hydrochlorate of the title compound (3.0 g, yield: 82%). $^1$H NMR (DMSO-$d_6$) δ: 12.55 (1H, br), 10.18 (2H, br), 7.72 (1H, d), 7.50 (1H, dd), 7.27 (1H, d), 4.04 (2H, t), 3.39 (1H, m), 1.73 (2H, m), 1.17 (6H, d), 0.95 (3H, t).

Example 35

1-(3-(4-Isopropyl-5-bromo-1,6-dihydro-6-oxopyrimidin-2-yl)-4-n-propoxyphenyl)-3-ethyl thiourea

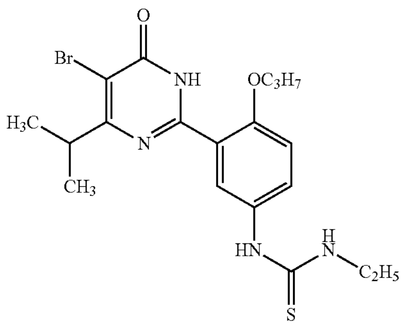

The compound (4.0 g, 10 mmol) of example 34 was suspended in ethanol (10 ml), and added with ethyl isothiocyanate (0.9 g, 1.1 mmol) and triethylamine (1 mL). After refluxed for 3 h, the reaction mixture was concentrated to dryness. The resultant solid was washed with distilled water and recrystallized from ethyl acetate-petroleum ether to give the title compound (3.4 g, yield: 74%). $^1$H NMR (DMSO-$d_6$) δ: 12.38 (1H, br), 9.41 (1H, br), 7.74 (1H, d), 7.54 (1H, dd), 7.15 (1H, d), 4.04 (2H, t), 3.46 (2H, m), 3.37 (1H, m), 1.75 (2H, m), 1.18 (6H, d), 1.11 (3H, t), 0.97 (3H, t).

Example 36

1-[3-(4-Isopropyl-5-bromo-1,6-dihydro-6-oxopyrimidin-2-yl)-4-n-propoxyphenyl]-3-ethyl-2-methyl-isothiourea

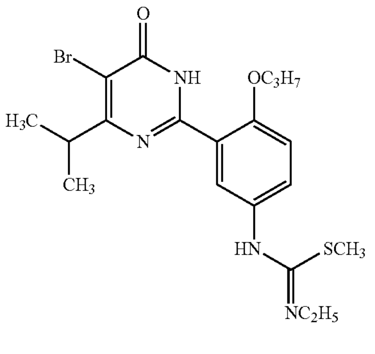

The compound (2.7 g, 6 mmol) of example 35 was suspended in methanol (20 ml), and added with iodomethane (1.0 g, 7 mmol). After refluxed for 3 h, the reaction mixture was concentrated to dryness. The resultant solid was recrystallized from ethylether to obtain the title compound (2.4 g, yield: 85%). $^1$H NMR (DMSO-$d_6$) δ: 7.16 (1H, d), 6.99 (1H, dd), 6.87 (1H, d), 4.00 (2H, t), 3.37 (1H, m), 2.94 (2H, q), 2.56 (3H, s), 1.74 (2H, m), 1.18 (6H, d), 1.11 (3H, t), 0.98 (3H, t).

Example 37

N-[3-(4-Isopropyl-5-bromo-1,6-dihydro-6-oxopyrimidin-2-yl)-4-n-propoxyphenyl]-N',N"-triethylguanidine

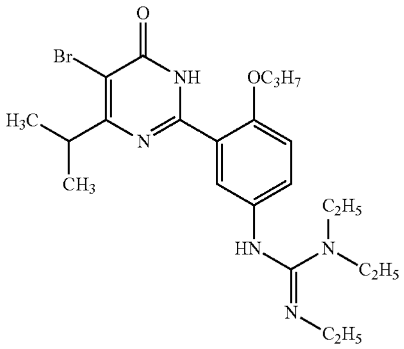

The compound (150 mg, 0.28 mmol) of example 36 was added into 20 ml of ethanol, added with diethylamine (84 mg, 0.8 mmol), and stirred at 70° C. for 15 h. The cooled reaction mixture was concentrated under reduced pressure. The resultant pasty solid was washed with 4 ml of ethyl acetate and dissolved with $CH_2Cl_2$ (100 ml), and then washed with water (30 ml×2), 10% NaOH (20 ml) and saturated saline (40 ml) respectively. The organic phase was dried with anhydrous $Na_2SO_4$ and concentrated under reduced pressure. The residue was recrystallized from ethyl acetate-methanol to obtain a white solid (75 mg, yield: 56%). $^1$H NMR (DMSO-$d_6$) δ: 7.14 (1H, d), 6.98 (1H, dd), 6.85 (1H, d), 3.94 (2H, t), 3.37 (1H, m), 3.21 (4H, q), 2.93 (2H, q), 1.69 (2H, m), 1.14 (6H, d), 1.05 (6H, t), 1.00 (3H, t), 0.94 (3H, t).

Examples 38~40

The compounds of examples 38~40 were prepared by reacting the compound of example 36 with piperidine, pyrrolidine and diethanolamine respectively in the same manner as that of example 37.

| Example | Structural Formula | Nomenclature and data of $^1$H-NMR(δ) |
|---|---|---|
| 38 | 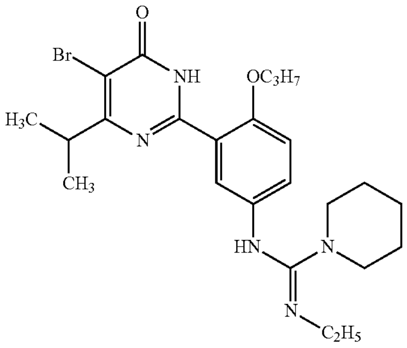 | N-[3-(4-isopropyl-5-bromo-1,6-dihydro-6-oxopyrimidin-2-yl)-4-n-propoxyphenyl]-N'-ethyl-piperidyl-1-formamidine (DMSO-$d_6$) δ: 7.39 (1H, d), 7.01 (1H, dd), 6.87 (1H, d), 4.00 (2H, t), 3.37 (1H, m), 3.06 (4H, br), 2.97 (2H, q), 1.76 (2H, m), 1.47 (6H, br), 1.18 (6H, d), 1.03 (3H, t), 1.01 (3H, t) |
| 39 | 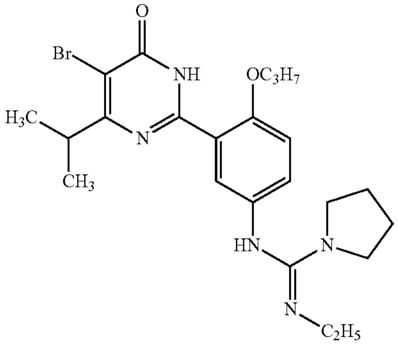 | N-[3-(4-isopropyl-5-bromo-1,6-dihydro-6-oxopyrimidin-2-yl)-4-n-propoxyphenyl]-N'-ethyl-pyrrolyl-1-formamidine ($CDCl_3$) δ: 7.98 (1H, d), 7.20 (1H, dd), 6.97 (1H, d), 4.45 (2H, t), 4.14 (2H, t), 3.44 (4H, m), 3.31 (2H, q), 1.93 (6H, m), 1.27 (6H, d), 1.18 (3H, t), 1.12 (3H, t) |
| 40 | 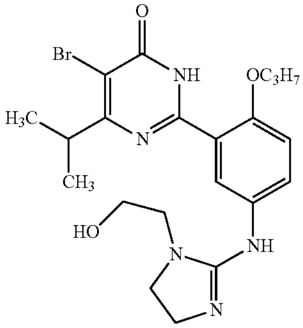 | 2-{2-[3-(4-isopropyl-5-bromo-1,6-dihydro-6-oxopyrimidin-2-yl)-4-n-propoxyphenyl]amino-4,5-dihydro-imidazol-1-yl}-ethanol ($CDCl_3$) δ: 8.25 (1H, d), 7.20 (1H, dd), 6.91 (1H, d), 4.45 (2H, t), 4.13 (2H, t), 3.92 (2H, t), 3.70 (2H, t), 3.56 (2H, t), 3.49 (1H, m), 1.95 (2H, m), 1.27 (6H, d), 1.11 (3H, t) |

Example 41

2-(5-Nitro-2-n-propoxyphenyl)-5,6-diethylpyrimid-4(3H)-one

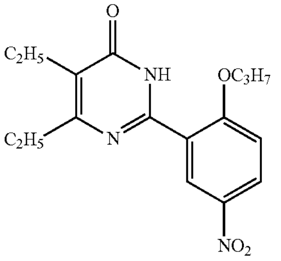

The title compound was prepared from the compound of preparation example 33 as a raw material in the same manner as that of example 33. Yield: 89%. $^1$H NMR ($CDCl_3$) δ: 9.29 (1H, d), 8.35 (1H, dd), 7.14 (1H, d), 4.30 (2H, t), 2.73 (2H, q), 2.60 (2H, q), 2.02 (2H, m), 1.32 (3H, t), 1.15 (6H, t).

Example 42

2-(5-Amino-2-n-propoxyphenyl)-5,6-diethylpyrimid-4(3H)-one

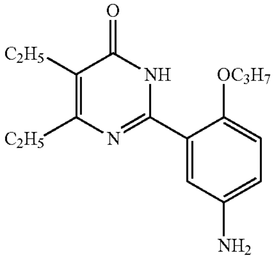

The compound (16.5 g, 50 mmol) of example 41 was dissolved in methanol, added with 0.4 g 10% Pd/C, and hydrogenized at the normal temperature and pressure. When hydrogen was not absorbed by the reaction mixture any more, the reaction was quenched and Pd/C was filtered off. The filtrate was concentrated to a small volume, and fed with HCl gas to generate a white solid. The obtained solid was filtered and dried to give the hydrochlorate of the title compound (16.4 g. yield: 97%). $^1$H NMR $^1$H NMR ($CDCl_3$) δ: 7.68 (1H, d), 7.43 (1H, dd), 7.24 (1H, d), 4.04 (2H, t), 2.57 (2H, q), 2.46 (2H, q), 1.75 (2H, m), 1.19 (3H, t), 1.04 (3H, t), 0.96 (3H, t).

Example 43

1-(3-(4,5-Diethyl-1,6-dihydro-6-oxopyrimidin-2-yl)-4-n-propoxyphenyl)-3-ethylthiourea

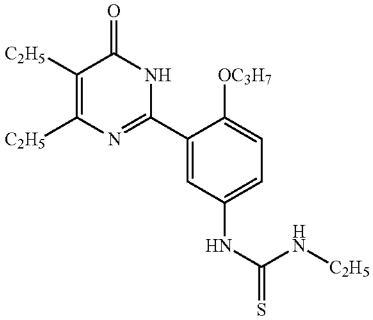

The title compound was prepared from the compound of example 42 in the same manner as that of example 35. Yield: 83%. $^1$H NMR (DMSO-$d_6$) δ: 11.79 (1H, br), 9.40 (1H, br), 7.73 (1H, d), 7.52 (1H, dd), 7.13 (1H, d), 4.05 (2H, t), 3.46 (2H, q), 2.56 (2H, q), 2.45 (2H, q), 1.76 (2H, m), 1.18 (3H, t), 1.10 (3H, t), 1.04 (3H, t), 0.98 (3H, t).

Example 44

1-[3-(4,5-Diethyl-1,6-dihydro-6-oxopyrimidin-2-yl)-4-n-propoxyphenyl]-3-ethyl-2-methyl isothiourea

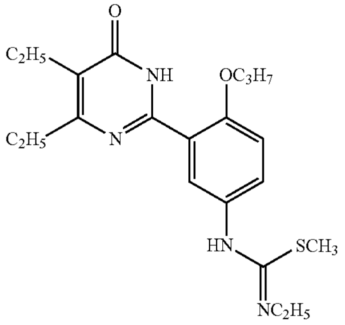

The title compound was prepared from the compound of example 43 in the same manner as that of example 36. Yield: 87%. $^1$H NMR (DMSO-$d_6$) δ: 7.78 (1H, d), 7.56 (1H, dd), 7.13 (1H, d), 4.07 (2H, t), 3.46 (2H, q), 2.67 (3H, s), 2.56 (2H, q), 2.45 (2H, q), 1.76 (2H, m), 1.18 (3H, t), 1.11 (3H, t), 1.04 (3H, t), 0.97 (3H, t).

Examples 45~47

The compounds of example 45~47 were prepared by reacting the compound of example 44 with piperidine, diethylamine and diethanolamine respectively, in the same manner as that of example 37.

| Example | Structural Formula | Nomenclature and data of $^1$H-NMR(δ) |
|---|---|---|
| 45 | 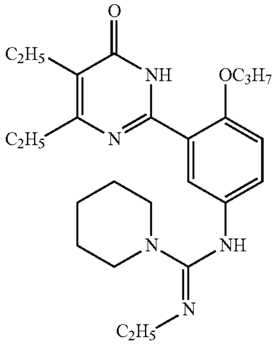 | N-[3-(4,5-diethyl-1,6-dihydro-6-oxopyrimidin-2-yl)-4-n-propoxyphenyl]-N'-ethyl-piperidyl-1-formamidine (DMSO-$d_6$) δ: 7.38 (1H, d), 7.01 (1H, dd), 6.86 (1H, d), 4.01 (2H, t), 3.06 (4H, br), 2.97 (2H, q), 2.56 (2H, q), 2.45 (2H, q), 1.76 (2H, m), 1.47 (6H, br), 1.18 (3H, t), 1.03 (3H, t), 1.01 (3H, t), 0.99 (3H, t) |
| 46 | 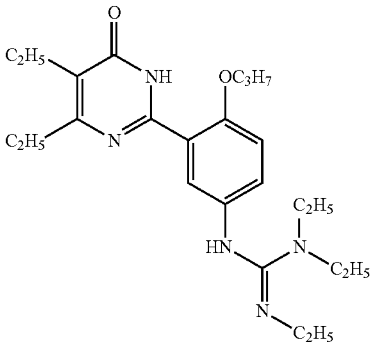 | N-[3-(4,5-diethyl-1,6-dihydro-6-oxopyrimidin-2-yl)-4-n-propoxyphenyl]-N',N''-triethylguanidine (DMSO-$d_6$) δ: 11.84 (1H, br), 9.43 (1H, s), 7.53 (1H, dd), 7.24 (1H, d), 4.06 (2H, t), 3.37 (4H, q), 3.12 (2H, q), 2.56 (2H, q), 2.46 (2H, q), 1.76 (2H, m), 1.18 (3H, t), 1.13 (6H, t), 1.11 (3H, t), 1.04 (3H, t), 0.98 (3H, t) |

-continued

| Example | Structural Formula | Nomenclature and data of ¹H-NMR(δ) |
|---|---|---|
| 47 | 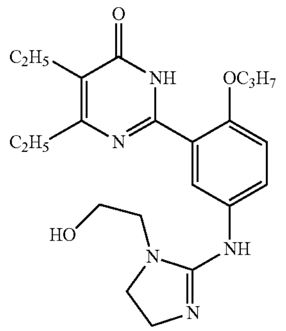 | 2-{2-[3-(4,5-diethyl-1,6-dihydro-6-oxopyrimidin-2-yl)-4-n-propoxyphenyl]amino-4,5-dihydro-imidazol-1-yl}-ethanol (DMSO-$d_6$) δ: 7.41 (1H, d), 7.06 (1H, dd), 6.99 (1H, d), 4.86 (1H, br), 4.31 (2H, t), 4.00 (2H, t), 3.60 (4H, t), 3.40 (2H, t), 2.55 (2H, q), 2.45 (2H, q), 1.73 (2H, m), 1.18 (3H, t), 1.03 (3H, t), 0.97 (3H, t) |

Examples 48 and 49

The compound (0.40 g, 1.0 mmol) of Example 44 was added in 20 ml of ethanol, added with pyrrolidine (0.28 g, 4 mmol), and stirred at 70° C. for 15 h. The cooled reaction mixture was concentrated under reduced pressure, dissovled in $CH_2Cl_2$ (100 ml), washed with water (30 ml×2), 10% NaOH (20 ml) and saturated saline (40 ml) respectively. The organic phase was dried with anhydrous $Na_2SO_4$, and concentrated under reduced pressure. The residue was passed through a silica gel column using ethyl acetate-methanol as an eluant, to give 150 mg of the compound of Example 48 and 85 mg of the compound of Example 49.

| Example | Structural Formula | Nomenclature and data of ¹H-NMR(δ) |
|---|---|---|
| 48 | 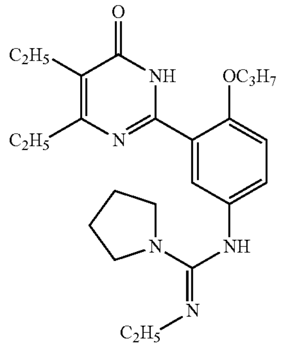 | N-[3-(4,5-diethyl-1,6-dihydro-6-oxopyrimidin-2-yl)-4-n-propoxyphenyl]-N'-ethyl-pyrrolyl-1-formamidine (DMSO-$d_6$) δ: 7.30 (1H, d), 7.02 (1H, dd), 6.89 (1H, d), 4.01 (2H, t), 3.22 (4H, m), 2.99 (2H, q), 2.55 (2H, q), 2.45 (2H, q), 1.76 (6H, m), 1.18 (3H, t), 1.03 (3H, t), 1.00 (6H, t) |
| 49 | 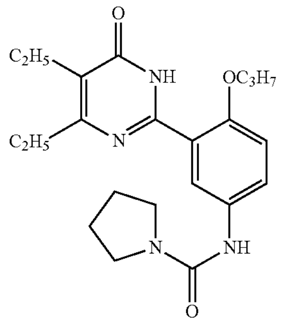 | N-[3-(4,5-diethyl-1,6-dihydro-6-oxopyrimidin-2-yl)-4-n-propoxyphenyl]-pyrrolyl-1-formamide (DMSO-$d_6$) δ: 11.77 (1H, br), 8.17 (1H, br), 7.87 (1H, d), 7.65 (1H, dd), 7.06 (1H, d), 4.01 (2H, t), 3.31 (4H, m), 2.56 (2H, q), 2.46 (2H, q), 1.84 (4H, m), 1.74 (2H, m), 1.19 (3H, t), 1.04 (3H, t), 0.97 (3H, t) |

Example 50

5-Bromo-6-isopropyl-2-(2-n-propoxy-5-mesylamidophenyl)pyrimid-4(3H)-one

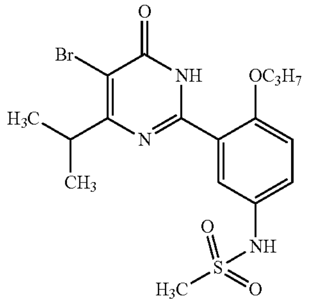

The compound (0.37 g, 1 mmol) of Example 34 was dissolved in dichloromethane (20 ml), and added with triethylamine (1 ml), followed by slow addition of mesyl chloride (81 μL, 1 mmol) under ice water bath. After stirred for 0.5 h, the reaction mixture was washed with water (10 ml), 1N HCl (5 ml), saturated sodium bicarbonate solution (10 ml), saturated saline respectively. The organic phase was dried with anhydrous $Na_2SO_4$ and concentrated under reduced pressure to obtain an oil, which was passed through a silica gel column using ethyl acetate-petroleum ether as a eluent, to give the title compound (160 mg, yield: 36%). $^1$H NMR (DMSO-$d_6$) δ: 7.63 (1H, d), 7.37 (1H, dd), 7.18 (1H, d), 6.15 (1H, s), 4.02 (2H, t), 3.38 (1H, m), 2.95 (3H, s), 1.74 (2H, m), 1.18 (6H, d), 0.95 (3H, t).

Example 51

5,6-Diethyl-2-(2-n-propoxy-5-mesylamidophenyl)pyrimid-4(3H)-one

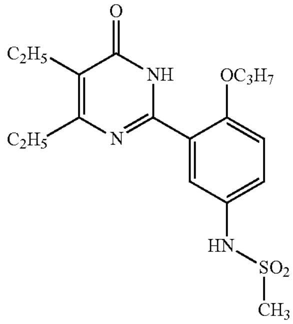

The title compound was prepared by reacting the compound of Example 42 with mesyl chloride in the same manner as that of Example 50. $^1$H NMR ($CDCl_3$) δ: 8.28 (1H, d), 7.50 (1H, dd), 7.11 (1H, br), 7.02 (1H, d), 4.15 (2H, t), 3.00 (3H, s), 2.66 (2H, q), 2.58 (2H, q), 1.97 (2H, m), 1.28 (3H, t), 1.14 (3H, t), 1.12 (3H, t).

Examples 52~54

The compound of example 52 was prepared by reacting the compound of Example 34 with acetyl chloride, and the compounds of examples 53 and 54 were prepared by reacting the compound of Example 42 with acetyl chloride and propionyl chloride, in the same manner as that of Example 50.

| Example | Structural Formula | Nomenclature and data of 1H-NMR(δ) |
|---|---|---|
| 52 | 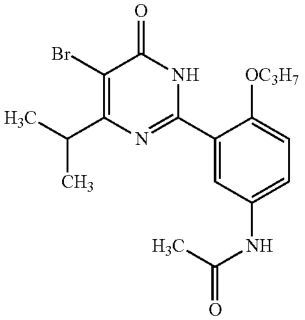 | N-(3-(1,6-dihydro-4-isopropyl-5-bromo-6-oxopyrimidin-2-yl)-4-propoxyphenyl)acetamide ($CDCl_3$) δ: 8.34 (1H, d), 7.99 (1H, dd), 7.44 (1H, br), 7.01 (1H, d), 4.45 (2H, t), 4.17 (2H, t), 3.50 (1H, m), 2.22 (3H, s), 1.97 (2H, m), 1.26 (6H, d), 1.12 (3H, t) |
| 53 | 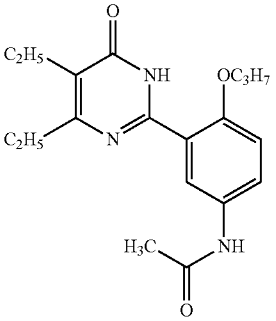 | N-(3-(1,6-dihydro-4,5-diethyl-6-oxopyrimidin-2-yl)-4-propoxyphenyl)acetamide ($CDCl_3$) δ: 8.24 (1H, d), 7.99 (1H, dd), 7.47 (1H, br), 6.99 (1H, d), 4.13 (2H, t), 2.65 (2H, q), 2.58 (2H, q), 2.19 (3H, s), 1.96 (2H, m), 1.28 (3H, t), 1.14 (3H, t), 1.12 (3H, t) |

-continued

| Example | Structural Formula | Nomenclature and data of 1H-NMR(δ) |
|---|---|---|
| 54 | 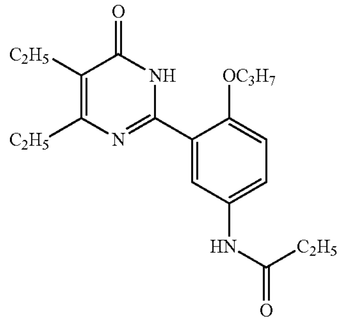 | N-(3-(1,6-dihydro-4,5-diethyl-6-oxopyrimidin-2-yl)-4-propoxyphenyl)propionamide<br>($CDCl_3$) δ: 8.22 (1H, d), 8.04 (1H, dd), 7.45 (1H, br), 6.98 (1H, d), 4.13 (2H, t), 2.65 (2H, q), 2.58 (2H, q), 2.41 (2H, q), 1.96 (2H, m), 1.28 (3H, t), 1.26 (3H, t), 1.14 (3H, t), 1.12 (3H, t) |

Example 55

N-(3-(1,6-dihydro-4,5-diethyl-6-oxopyrimidin-2-yl)-4-propoxyphenyl)cyclohexamide

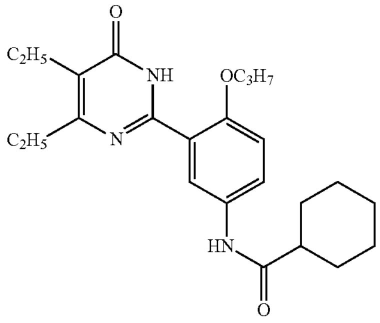

Cyclohexylformic acid (100 mg, 0.78 mmol) was dissolved in dichloromethane (20 ml), added with EDCI (130 mg, 0.78 mmol), and stirred for 0.5 h. 1-hydroxy-benzotriazole (HOBT) (100 mg, 0.78 mmol) was added thereinto and stirred for 12 h, followed by addition of the compound (235 mg, 0.78 mmol) of example 42. After stirred at room temperature for 2 h, the reaction mixture was washed with water (10 ml) and saturated saline. The organic phase was dried with anhydrous $Na_2SO_4$ and concentrated under reduced pressure to give an oil, which was then passed through a silica gel column to give the title compound (250 mg, yield: 78%). $^1H$ NMR ($CDCl_3$) δ: 8.21 (1H, d), 8.08 (1H, dd), 7.55 (1H, br), 6.98 (1H, d), 4.13 (2H, t), 2.66 (2H, q), 2.58 (2H, q), 2.50-1.60 (13H, m), 1.28 (3H, t), 1.14 (3H, t), 1.12 (3H, t).

Examples 56 and 57

The compounds of examples 56 and 57 were prepared by condensing the compound of example 42 with formic acid and N-Boc-4-hydroxypraline respectively in the same manner as that of Example 55.

| Example | Structural Formula | Nomenclature and data of 1H-NMR(δ) |
|---|---|---|
| 56 | 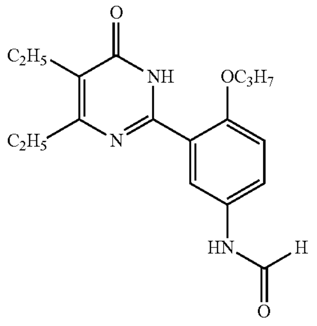 | N-(3-(1,6-dihydro-4,5-diethyl-6-oxopyrimidin-2-yl)-4-propoxyphenyl)formamide<br>($CDCl_3$) δ: 8.24 (1H, d), 7.98 (1H, dd), 7.51 (1H, br), 6.97 (1H, d), 4.13 (2H, t), 2.66 (2H, q), 2.58 (2H, q), 2.00 (2H, m), 1.29 (3H, t), 1.16 (3H, t), 1.13 (3H, t). |
| 57 | 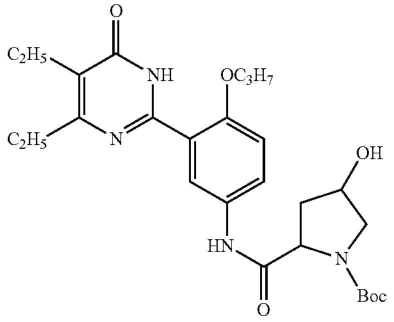 | N-(3-(1,6-dihydro-4,5-diethyl-6-oxopyrimidin-2-yl)-4-propoxyphenyl)-1-t-butyloxycarbonyl-4-hydroxy-prolylamide<br>($CDCl_3$) δ: 8.26 (1H, d), 8.00 (1H, dd), 7.50 (1H, br), 6.99 (1H, d), 4.14 (2H, t), 2.67 (2H, q), 2.59 (2H, q), 2.19 (3H, br), 1.97 (2H, m), 1.29 (3H, t), 1.15 (3H, t), 1.13 (3H, t) |

Example 58

4-n-Propoxy-3-(1,6-dihydro-4,5-diethyl-6-oxopyrimidin-2-yl)benzoic acid

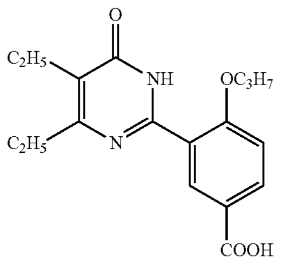

The compound (1.0 g, 2.74 mmol) of preparation example 34 was dissolved in DMF (12 ml), added with CuCN (0.28 g, 3.1 mmol) and pyridine (1.2 ml), and refluxed for 24 h. The reaction mixture was cooled down to the room temperature, added with a saturated $Na_2S_2O_3$ aqueous solution (20 ml), and extracted with ethyl acetate (15 ml×3). The organic phase was concentrated to dryness. The resultant solid was dissolved in a mixed solution of 2N NaOH aqueous solution (10 ml) and methanol (10 ml) and refluxed for 4 h. After the reaction finished, most of methanol and water were evaporated off. The residue was extracted with $CH_2Cl_2$ (15 ml×3), and the water layer was adjusted to a pH of 6~7 with concentrated hydrochloric acid. The resultant white solid was filtered and dried to obtain the title compound (0.25 g, yield: 28%).

Example 59

(Morpholin-1-yl)(3-(4,5-diethyl-1,6-dihydro-6-oxopyrimidin-2-yl)-4-n-propoxy)benzophenone

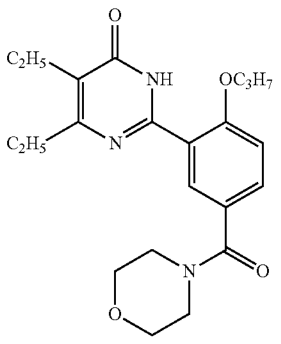

The compound (100 mg, 0.3 mmol) of example 58 was dissolved in dichloromethane (20 ml), added with EDCI (50 mg, 0.3 mmol), and stirred for 0.5 h. HOBT (41 mg, 0.3 mmol) was added thereinto and stirred for 12 h. Then morpholine (27 mg, 0.3 mmol) was added thereinto, and the stirring continued at room temperature for 2 h. The reaction mixture was washed with water (10 ml), saturated sodium bicarbonate solution (10 ml) and saturated saline respectively. The organic phase was dried with anhydrous $Na_2SO_4$ and concentrated under reduced pressure to obtain an oil, which was passed through a silica gel column to give the title compound (60 mg, yield: 50%). $^1H$ NMR ($CDCl_3$) δ: 8.57 (1H, d), 7.59 (1H, dd), 7.08 (1H, d), 4.20 (2H, t), 3.74 (8H, br), 2.67 (2H, q), 2.59 (2H, q), 2.00 (2H, m), 1.29 (3H, t), 1.14 (6H, t).

Examples 60 and 61

The compounds of examples 60 and 61 were prepared by condensing the compound of example 58 with piperidine and L-prolylamide respectively, in the same manner as that of example 59.

| Example | Structural Formula | Nomenclature and data of 1H-NMR(δ) |
| --- | --- | --- |
| 60 | 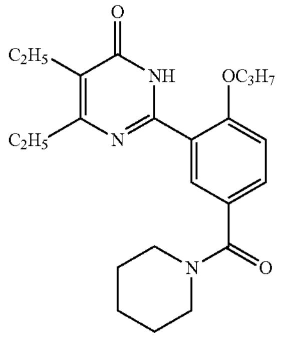 | (piperid-1-yl)(3-(4,5-diethyl-1,6-dihydro-6-oxopyrimidin-2-yl)-4-n-propoxy)benzophenone ($CDCl_3$) δ: 8.56 (1H, d), 7.56 (1H, dd), 7.05 (1H, d), 4.20 (2H, t), 3.56 (4H, br), 2.67 (2H, q), 2.59 (2H, q), 2.00 (2H, m), 1.69 (6H, br), 1.29 (3H, t), 1.14 (6H, t) |

-continued

| Example | Structural Formula | Nomenclature and data of 1H-NMR(δ) |
|---|---|---|
| 61 | 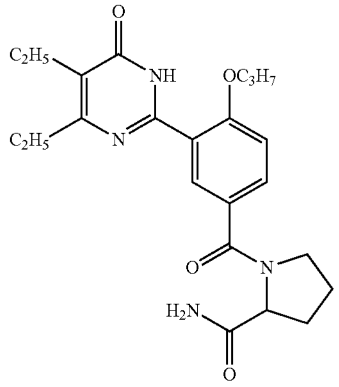 | (2-aminoformylpyrrol-1-yl)(3-(4,5-diethyl-1,6-dihydro-6-oxopyrimidin-2-yl)-4-n-propoxy)benzophenone ($CDCl_3$) δ: 8.69 (1H, d), 7.70 (1H, dd), 7.06 (1H, d), 6.96 (1H, br), 5.56 (1H, br), 4.79 (1H, t), 4.20 (2H, t), 3.62 (2H, t), 2.66 (2H, q), 2.58 (2H, q), 2.00 (2H, m), 2.19-1.79 (6H, m), 1.27 (3H, t), 1.14 (6H, t) |

Example 62

4-n-Propoxy-3-(1,6-dihydro-4-isopropyl-6-oxopyrimidin-2-yl)benzoic acid

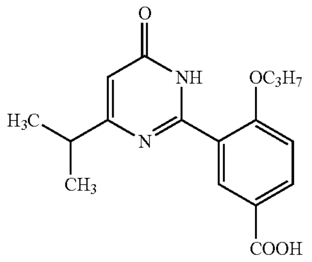

The compound (4.0 g, 14 mmol) of preparation example 12 and $K_2CO_3$ (7.7 g, 56 mmol) were mixed and suspended in DMF (30 ml), and then added with ethyl isobutyrylacetate (2.7 g, 17 mmol) in one batch. The reaction mixture was stirred overnight at 100° C. under nitrogen protection, cooled, poured into ice water, and adjusted to a pH of 4~5 by addition of glacial acetic acid to give a yellowish solid crude. After filtered, the solid was washed with water (250 mL) and dried at 60° C. The crude was recrystallized from ethyl acetate to give the white title compound (3.4 g, yield: 77%). $^1H$ NMR ($CD_3OD$) δ: 8.57 (1H, d), 8.19 (1H, dd), 7.26 (1H, d), 6.25 (1H, s), 4.20 (2H, t), 2.86 (1H, m), 1.89 (2H, m), 1.29 (6H, d), 1.06 (3H, t).

Example 63

(Morpholin-1-yl)(3-(4-isopropyl-5-bromo-1,6-dihydro-6-oxopyrimidin-2-yl)-4-n-propoxy)benzophenone

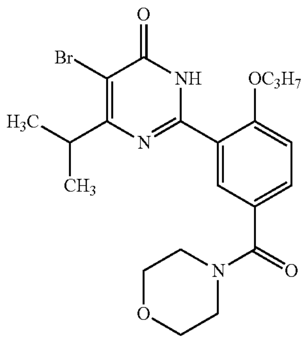

(morpholin-1-yl) (3-(4-isopropyl-1,6-dihydro-6-oxopyrimidin-2-yl)-4-n-propoxy)benzophenone was first prepared from the compound of example 62 as a raw material in the same manner as that of example 59, and then brominized in the same manner as that of preparation example 19 to prepare the title compound (yield: 30%). $^1H$ NMR ($CDCl_3$) δ: 8.60 (1H, d), 7.65 (1H, dd), 7.11 (1H, d), 4.24 (2H, t), 3.75 (8H, br), 3.51 (1H, m), 2.01 (2H, m), 1.26 (6H, d), 1.14 (3H, t).

Examples 64 and 65

The compounds of examples 64 and 65 were prepared by condensing the compound of example 62 with piperidine and N-methylpiperazine respectively and then bromizing in the same manner as that of example 63.

| Example | Structural Formula | Nomenclature and data of 1H-NMR(δ) |
|---|---|---|
| 64 | 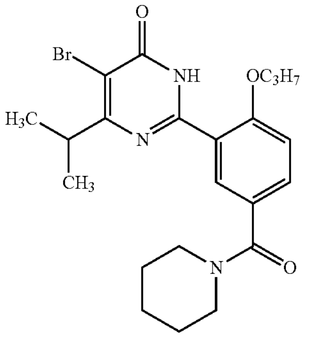 | (piperid-1-yl)(3-(4-isopropyl-5-bromo-1,6-dihydro-6-oxo-pyrimidin-2-yl)-4-n-propoxy)benzophenone ($CDCl_3$) δ: 8.60 (1H, d), 7.63 (1H, dd), 7.08 (1H, d), 4.24 (2H, t), 3.67 (4H, br), 3.51 (1H, m), 2.00 (2H, m), 1.68 (6H, br), 1.26 (6H, d), 1.14 (3H, t) |
| 65 | 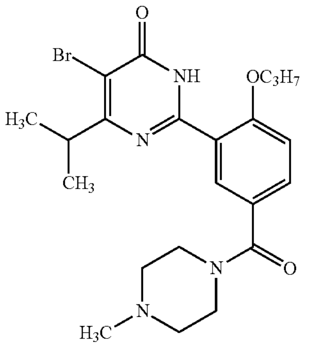 | (4-methyl-piperazin-1-yl)(3-(4-isopropyl-5-bromo-1,6-di-hydro-6-oxopyrimidin-2-yl)-4-n-propoxy)benzophenone ($CDCl_3$) δ: 8.59 (1H, d), 7.62 (1H, dd), 7.06 (1H, d), 4.20 (2H, t), 3.51 (1H, m), 2.89 (4H, t), 2.36 (4H, t), 2.13 (3H, s), 1.98 (2H, m), 1.26 (6H, d), 1.13 (3H, t) |

Example 66

2-(5-(N,N-dimethylamino-2-n-propoxyphenyl)-5,6-diethylpyrimid-4(3H)-one

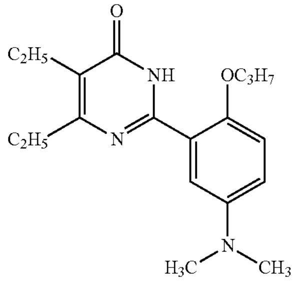

The compound (100 mg, 0.3 mmol) of example 42 was suspended in water (10 ml), added with paraformaldehyde (20 mg, 0.66 mmol) and formic acid (0.1 ml) orderly, and heated to reflux and stirred for 2 h. The reaction mixture was concentrated to dryness, and dissolved in dichloromethane (20 ml), and washed orderly with water (10 ml), 1N HCl (5 ml), saturated sodium bicarbonate solution (10 ml), saturated saline. The organic phase was dried with anhydrous $Na_2SO_4$ and concentrated under reduced pressure to give an oil, which was passed through a silica gel column using ethyl acetate-petroleum ether as a eluant, to obtain the title compound (100 mg, yield: 91%). $^1H$ NMR ($CDCl_3$) δ: 11.33 (1H, br), 7.92 (1H, d), 7.57 (1H, dd), 6.93 (1H, d), 4.08 (2H, t), 2.95 (6H, s), 2.67 (2H, q), 2.58 (2H, q), 1.94 (2H, m), 1.29 (3H, t), 1.14 (3H, t), 1.11 (3H, t).

Example 67

1-(3-(4,5-Diethyl-1,6-dihydro-6-oxopyrimidin-2-yl)-4-n-propoxyphenyl)urea

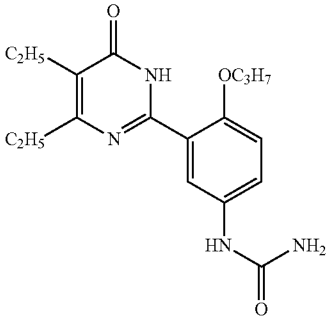

The compound (200 mg, 0.6 mmol) of example 42 was suspended in a mixed solution of water (5 ml) and acetic acid (5 ml), added with potassium cyanate (81 mg, 1 mmol), and heated to reflux and stirred for 2 h. The cooled reaction mixture was poured into water to generate a white solid, which was washed with water (10 ml×3) and dried to give the title compound (210 mg, yield: 91%). $^1H$ NMR (DMSO-$d_6$) δ: 11.76 (1H, br), 8.56 (1H, br), 7.76 (1H, d), 7.59 (1H, dd), 7.06 (1H, d), 5.78 (1H, br), 4.00 (2H, t), 2.56 (2H, q), 2.46 (2H, q), 1.74 (2H, m), 1.19 (3H, t), 1.04 (3H, t), 0.97 (3H, t).

Example 68

1-(3-(4,5-Diethyl-1,6-dihydro-6-oxopyrimidin-2-yl)-4-n-propoxyphenyl)-3-ethylurea

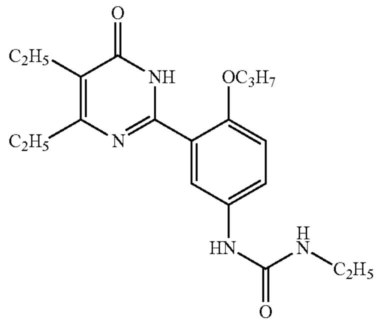

The title compound was prepared by reacting the compound of example 42 with ethyl isocyanate in the same manner as that of example 35. Yield: 90%. $^1$H NMR (DMSO-$d_6$) δ: 11.76 (1H, br), 8.46 (1H, br), 7.77 (1H, d), 7.57 (1H, dd), 7.06 (1H, d), 6.01 (1H, t), 4.00 (2H, t), 3.09 (2H, m), 2.56 (2H, q), 2.45 (2H, q), 1.73 (2H, m), 1.19 (3H, t), 1.03 (6H, t), 0.97 (3H, t).

Example 69

1-(3-(4-Isopropyl-5-bromo-1,6-dihydro-6-oxopyrimidin-2-yl)-4-n-propoxyphenyl)-3-phen ylthiourea

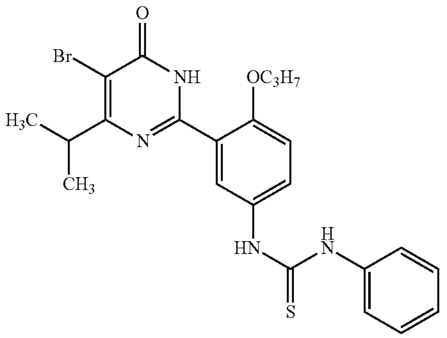

The title compound was prepared by reacting the compound of example 34 with phenyl isosulfocyanate in the same manner as that of example 35. Yield: 89%. $^1$H NMR (DMSO-$d_6$) δ: 12.38 (1H, br), 9.79 (1H, br), 7.84 (1H, d), 7.65 (1H, dd), 7.53-7.07 (6H, m), 4.06 (2H, t), 3.37 (1H, m), 1.75 (2H, m), 1.17 (6H, d), 0.97 (3H, t).

Example 70

1-(3-(4,5-Diethyl-1,6-dihydro-6-oxopyrimidin-2-yl)-4-n-propoxyphenyl)-guanidine

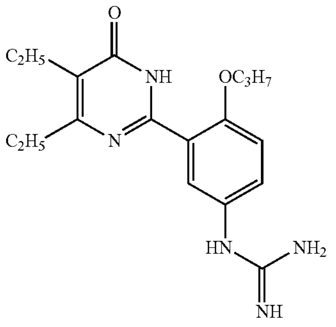

The compound (140 mg, 0.41 mmol) of example 42 was suspended in a mixed solution of water (2.5 ml) and acetic acid (2.5 ml), added with S-methylisothiourea (64 mg, 0.45 mmol), and heated to reflux under stirring for 10 h. The reaction mixture was concentrated to dryness, dissolved in dichloromethane (20 ml), and washed orderly with 1N NaOH (5 ml), water (10 ml) and saturated saline. The organic phase was dried with anhydrous $Na_2SO_4$ and concentrated under reduced pressure to give an oil, which was passed through a silica gel column using ethyl acetate-petroleum ether as an eluant to obtain the title compound (35 mg, yield: 25%). $^1$H NMR ($CDCl_3$) δ: 8.26 (1H, d), 8.00 (1H, dd), 7.50 (1H, br), 6.99 (1H, d), 4.14 (2H, t), 2.67 (2H, q), 2.59 (2H, q), 1.97 (2H, m), 1.29 (3H, t), 1.15 (3H, t), 1.13 (3H, t).

Example 71

5-Bromo-6-isopropyl-2-(5-(2-bromoacetyl)-2-n-propoxyphenyl)pyrimid-4(3H)-one

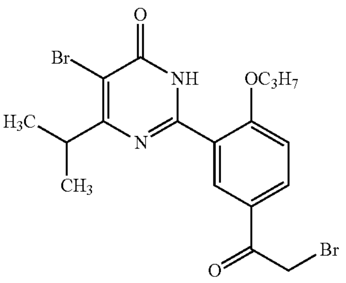

The compound (2.5 g, 7.1 mmol) of preparation example 35 was dissolved in DMF (50 ml), added with vinyl n-butyl ether (4.7 ml), 1,4-bis(diphenylphosphine)butane (0.47 g, 1.1 mmol), $Pd(OAc)_2$ (0.14 g, 0.62 mmol) and triethylamine (1.2 ml), followed by stirring at 100° C. for 36 h. The reaction mixture was cooled to the room temperature, added with water (40 ml), and extracted with $CH_2Cl_2$ (30 ml×3). The organic phase was concentrated to dryness, added with a mixed solution of 10% hydrochloric acid (30 ml) and THF (30 ml) followed by stirring at room temperature for 4 h. THF was evaporated off and the reaction mixture was cooled down to room temperature, adjusted to a pH of 6~7 with 2N NaOH, and extracted with $CH_2Cl_2$ (20 ml×3). The organic phase was washed with saturated saline (20 ml×3), dried with anhydrous $Na_2SO_4$, and concentrated under reduced pressure to give an oil. The oil was dissolved in 25 ml of glacial acetic acid, added dropwise with liquid bromine (0.5 ml) at room temperature, stirred at 30° C. for 3 h, and added with 30 ml of water, followed by extraction with ethyl acetate (30 ml×3). The organic layer was washed with saturated saline (20 ml×3), dried with anhydrous $Na_2SO_4$, and concentrated under reduced pressure, and the residue was passed through a silica gel column using ethyl acetate-petroleum ether as a eluant to give the title compound (0.61 g, total yield: 18%). $^1$H NMR ($CDCl_3$) δ: 11.20 (1H, br), 9.21 (1H, d), 8.17 (1H, dd), 7.15 (1H, d), 4.45 (2H, s), 4.30 (2H, t), 3.52 (1H, m), 2.03 (2H, m), 1.30 (6H, d), 1.16 (3H, t).

Example 72

5-Bromo-6-isopropyl-2-(5-(2-morpholinylacetyl)-2-n-propoxyphenyl)pyrimid-4(3H)-one

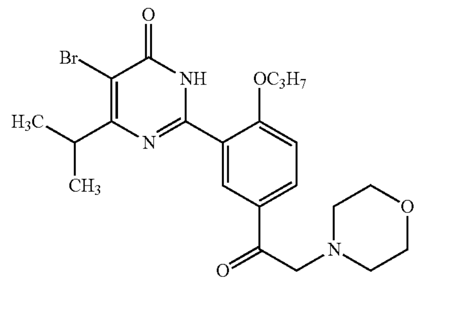

The compound (150 mg, 0.32 mmol) of example 71 was dissolved in dichloromethane (20 ml), added with triethylamine (0.5 ml) and morpholine (40 mg, 0.46 mmol), followed by stirring for 12 h. The reaction mixture was washed orderly with water (10 ml) and saturated saline. The organic phase was dried with anhydrous $Na_2SO_4$, and concentrated under reduced pressure to give an oil, which was passed through a silica gel column to obtain the title compound (60 mg, yield: 39%). $^1H$ NMR ($CDCl_3$) δ: 11.20 (1H, br), 9.21 (1H, d), 8.17 (1H, dd), 7.15 (1H, d), 4.30 (2H, t), 3.75-3.64 (10H, br), 3.52 (1H, m), 2.03 (2H, m), 1.30 (6H, d), 1.16 (3H, t).

Example 73

5-Bromo-6-isopropyl-2-(5-(2-(4-methyl-piperazin-1-yl)acetyl)-2-n-propoxyphenyl)pyrimid-4(3H)-one

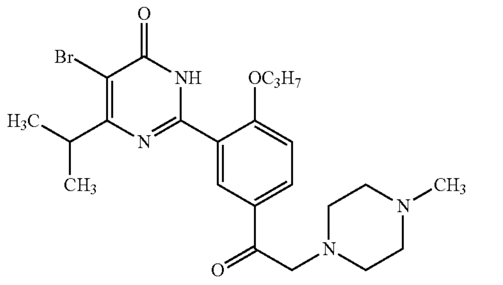

The title compound was prepared by reacting the compound of example 71 with N-methyl piperazine, in the same manner as that of example 72. $^1H$ NMR ($CDCl_3$) δ: 9.23 (1H, d), 8.19 (1H, dd), 7.10 (1H, d), 4.28 (2H, t), 3.77 (2H, s), 3.53 (1H, m), 2.66 (4H, t), 2.52 (4H, t), 2.31 (3H, s), 2.02 (2H, m), 1.29 (6H, d), 1.15 (3H, t).

Example 74

5,6-Diethyl-2-(5-(2-bromo acetyl)-2-n-propoxyphenyl)pyrimid-4(3H)-one

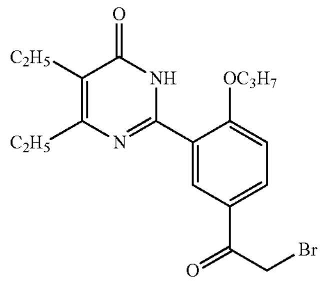

The title compound was prepared from the compound of preparation example 34 in the same manner as that of example 71. $^1H$ NMR ($CDCl_3$) δ: 11.20 (1H, br), 8.60 (1H, d), 7.59 (1H, dd), 7.10 (1H, d), 4.45 (2H, s), 4.20 (2H, t), 2.65 (2H, q), 2.58 (2H, q), 2.03 (2H, m), 1.28 (3H, t), 1.14 (6H, t).

Examples 75 and 76

The compounds of examples 75 and 76 were prepared by reacting the compound of example 74 with N-methylpiperazine and morpholine respectively in the same manner as that of example 72.

| Example | Structural Formula | Nomenclature and data of 1H-NMR(δ) |
|---|---|---|
| 75 | 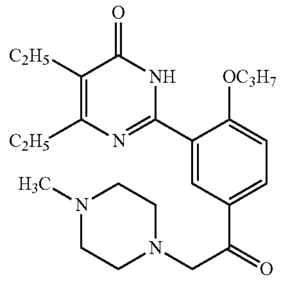 | 5,6-diethyl-2-(5-(2-(4-methyl-piperazin-1-yl)acetyl)-2-n-propoxyphenyl)pyrimid-4(3H)-one ($CDCl_3$) δ: 11.08 (1H, br), 8.58 (1H, d), 7.57 (1H, dd), 7.06 (1H, d), 4.20 (2H, t), 3.77 (2H, s), 2.97 (4H, t), 2.65 (2H, q), 2.58 (2H, q), 2.46 (4H, t), 2.33 (3H, s), 2.00 (2H, m), 1.28 (3H, t), 1.14 (6H, t) |

-continued

| Example | Structural Formula | Nomenclature and data of 1H-NMR(δ) |
|---|---|---|
| 76 | 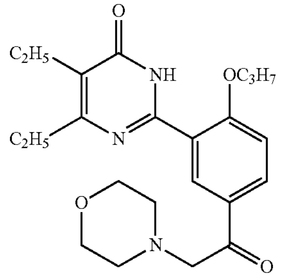 | 5,6-diethyl-2-(5-(2-morpholinylacetyl)-2-n-propoxyphenyl)pyrimid-4(3H)-one (CDCl$_3$) δ: 11.08 (1H, br), 8.58 (1H, d), 7.57 (1H, dd), 7.06 (1H, d), 4.20 (2H, t), 3.78 (2H, s), 3.67 (4H, t), 3.48 (4H, t), 2.65 (2H, q), 2.58 (2H, q), 2.00 (2H, m), 1.28 (3H, t), 1.14 (3H, t), 1.12 (3H, t) |

Example 77

5-Bromo-6-isopropyl-2-(2-n-propoxy-5-(tetrahydro-3,4,5-trihydroxy-6-(hydroxymethyl)-2H-pyran-2-ylamino)phenyl)pyrimid-4(3H)-one

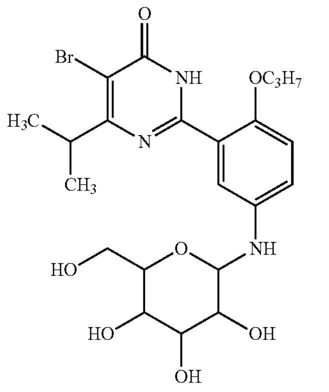

The compound of example 34 (200 mg, 0.55 mmol) was dissolved in n-butanol (10 ml), and added with glucose (200 mg, 1 mmol) and one drop of glacial acetic acid. The reaction mixture was heated under nitrogen protection to reflux for 12 h. The cooled reaction mixture was concentrated to dryness, and added with dichloromethane. The organic layer was washed with saturated saline (20 ml×3), dried with anhydrous $Na_2SO_4$, and concentrated under reduced pressure. The residue was passed through a silica gel column to give the title compound (60 mg, yield: 21%). $^1$H NMR (DMSO-d$_6$) δ: 7.47 (1H, d), 7.21 (1H, dd), 7.09 (1H, d), 4.31 (1H, d), 4.01 (3H, t), 3.63 (1H, d), 3.46 (1H, d), 3.09-3.29 (4H, m), 2.57 (2H, q), 2.46 (2H, q), 1.72 (2H, m), 1.18 (6H, d), 0.95 (3H, t).

Example 78

5-Bromo-6-isopropyl-2-(2-n-propoxy-5-(tetrahydro-3,4-dihydroxy-5-(1,2-dihydroxyethyl)fur-2-ylamino)phenyl)pyrimid-4(3H)-one

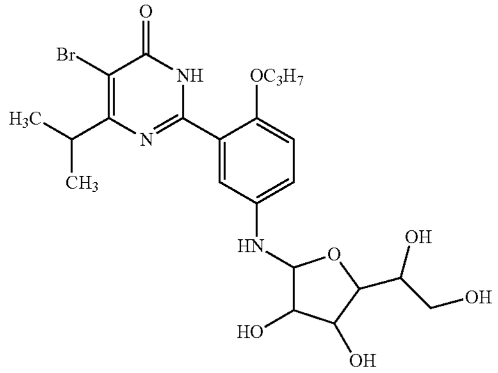

The title compound was prepared by reacting the compound of example 34 with mannose in the same manner as that of example 77. $^1$H NMR (DMSO-d$_6$) δ: 7.47 (1H, d), 7.21 (1H, dd), 7.09 (1H, d), 4.75 (1H, d), 4.01 (2H, t), 3.78-3.37 (7H, m), 2.57 (2H, q), 2.46 (2H, q), 1.72 (2H, m), 1.18 (6H, d), 0.95 (3H, t).

Examples 79 and 80

The compounds of examples 79 and 80 were prepared by reacting the compound of example 42 with mannose and glucose in the same manner as that of example 77.

| Example | Structural Formula | Nomenclature and data of 1H-NMR(δ) |
|---|---|---|
| 79 | 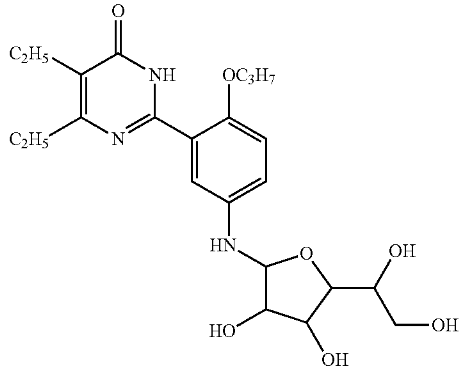 | 5,6-diethyl-2-(2-n-propoxy-5-(tetrahydro-3,4-dihydroxy-5-(1,2-dihydroxyethyl)fur-2-ylamino)phenyl)pyrimid-4(3H)-one (DMSO-$d_6$) δ: 7.48 (1H, d), 7.20 (1H, dd), 7.10 (1H, d), 4.77 (1H, d), 4.01 (2H, t), 3.78-3.37 (6H, m), 2.57 (2H, q), 2.46 (2H, q), 1.74 (2H, m), 1.19 (3H, t), 1.04 (3H, t), 0.96 (3H, t) |
| 80 | 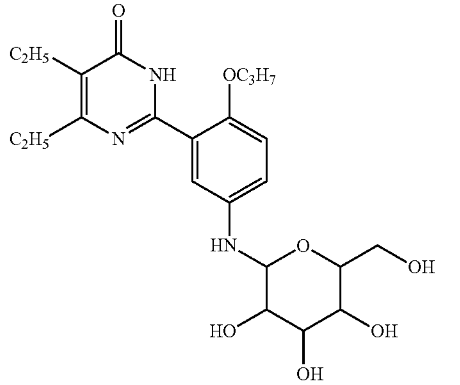 | 5,6-diethyl-2-(2-n-propoxy-5-(tetrahydro-3,4,5-trihydroxy-6-(hydroxymethyl)-2H-pyran-2-ylamino)phenyl)pyrimid-4(3H)-one (DMSO-$d_6$) δ: 7.48 (1H, d), 7.20 (1H, dd), 7.10 (1H, d), 4.31 (1H, d), 4.01 (3H, t), 3.63 (1H, d), 3.46 (1H, d), 3.09-3.29 (4H, m), 2.57 (2H, q), 2.46 (2H, q), 1.72 (2H, m), 1.18 (3H, t), 1.03 (3H, t), 0.96 (3H, t) |

Example 81

2-(5-Hydroxy-2-n-propoxyphenyl)-5,6-diethylpyrimid-4(3H)-one

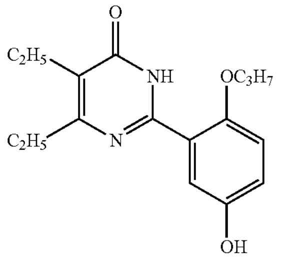

The title compound was prepared by reacting methyl 2-ethyl-3-oxovalerate with the compound of preparation example 11 in the same manner as that of example 1. $^1$H NMR ($CDCl_3$) δ: 7.98 (1H, d), 7.00 (1H, dd), 6.88 (1H, d), 4.06 (2H, t), 2.65 (2H, q), 2.59 (2H, q), 1.92 (2H, m), 1.26 (3H, t), 1.15 (3H, t), 1.08 (3H, t).

Example 82

(3-(4,5-Diethyl-1,6-dihydro-6-oxopyrimidin-2-yl)-4-n-propoxyphenyl)acetate

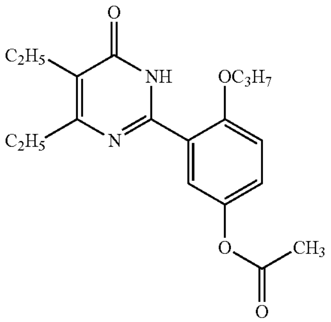

The compound of example 82 was prepared by reacting the compound of example 81 with acetyl chloride in the same manner as that of example 50. $^1$H NMR ($CDCl_3$) δ: 8.20 (1H, d), 7.20 (1H, dd), 7.02 (1H, d), 4.17 (2H, t), 2.67 (2H, q), 2.59 (2H, q), 2.33 (3H, s), 1.99 (2H, m), 1.29 (3H, t), 1.15 (6H, t).

Example 83

3-(4,5-Diethyl-1,6-dihydro-6-oxopyrimidin-2-yl)-4-n-propoxyphenyl ethylaminoformate

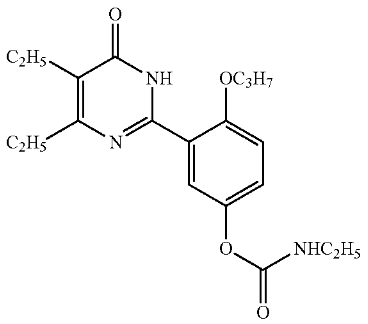

The title compound was prepared by reacting the compound of example 81 with ethyl isocyanate in the same manner as that of example 35. $^1H$ NMR ($CDCl_3$) δ: 8.20 (1H, d), 7.25 (1H, dd), 6.99 (1H, d), 5.06 (1H, br), 4.14 (2H, t), 3.32 (2H, m), 2.66 (2H, q), 2.58 (2H, q), 1.98 (2H, m), 1.28 (3H, t), 1.22 (3H, t), 1.14 (3H, t), 1.13 (3H, t).

Example 84

5,6-Diethyl-2-(2-n-propoxy-5-(tetrahydro-3,4,5-trihydroxy-6-(hydroxymethyl)-2H-pyran-2-yloxy)phenyl)pyrimid-4(3H)-one

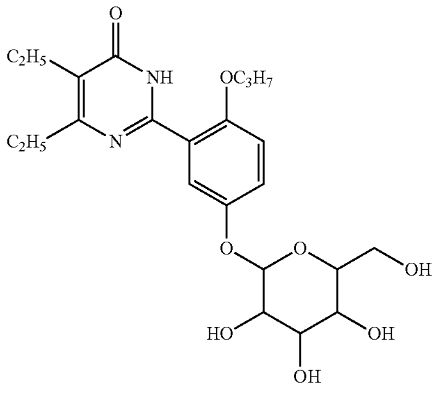

The compound (500 mg, 1.6 mmol) of example 81 was dissolved in dichloromethane (20 ml), and added with borontrifluorideetherate (2 ml) and 2,3,4,6-tetra-o-acetyl-α-d-glucopyranose trichloroacetylimide ester (800 mg, 1.6 mmol) (the preparation thereof refers to Upreti, M. et al. *Tetrahedron,* 2000, 56, 6577.), followed by stirring at room temperature for 12 h. The reaction mixture was concentrated to dryness to give an oil. The oil was dissolved in a mixed solution of methanol (10 ml) and water (10 ml), and added with potassium carbonate (900 mg, 6.5 mmol), followed by refluxing for 2 h. The reaction mixture was concentrated to dryness, and the residue was passed through a silica gel column to obtain the title compound (155 mg, total yield of two steps: 20%. $^1H$ NMR (DMSO-$d_6$) δ: 7.48 (1H, d), 7.20 (1H, dd), 7.10 (1H, d), 4.75 (1H, d), 4.01 (2H, t), 3.69-3.48 (2H, m), 3.33-3.14 (4H, m), 2.57 (2H, q), 2.46 (2H, q), 1.72 (2H, m), 1.18 (3H, t), 1.03 (3H, t), 0.96 (3H, t).

Example 85

3-(4,5-Diethyl-1,6-dihydro-6-oxopyrimidin-2-yl)-4-n-propoxyphenyl mesylate

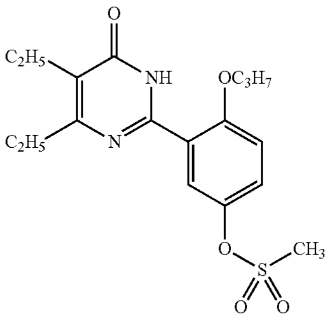

The title compound was prepared by reacting the compound of example 81 with mesyl chloride in the same manner as that of example 50. $^1H$ NMR ($CDCl_3$) δ: 8.39 (1H, d), 7.43 (1H, dd), 7.06 (1H, d), 4.18 (2H, t), 3.20 (3H, s), 2.68 (2H, q), 2.58 (2H, q), 2.00 (2H, m), 1.28 (3H, t), 1.14 (6H, t).

Example 86

2-(5-(2,5-Dimethyl-1H-pyrrol-1-yl)-2-propoxyphenyl)-5,6-diethylpyrimid-4(3H)-one

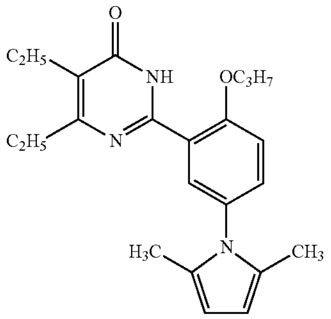

The compound (200 mg, 0.66 mmol) of example 42 and 2,5-hexanedione (76 mg, 0.66 mmol) were dissolved in ethanol (10 ml) and added with glacial acetic acid (0.1 ml), followed by refluxing for 12 h. The reaction mixture was concentrated to dryness, dissolved in $CH_2Cl_2$ (10 ml), and washed with saturated $NaHCO_3$ (10 ml) and saturated saline (10 ml), dried and concentrated. The residue was passed through a silica gel column to give the title compound (110 mg, yield: 44%). $^1H$ NMR ($CDCl_3$) δ: 11.20 (1H, br), 8.42 (1H, d), 7.30 (1H, dd), 7.10 (1H, d), 5.93 (2H, s), 4.23 (2H, t), 2.63 (2H, q), 2.59 (2H, q), 2.06 (6H, s), 2.04 (2H, m), 1.24 (3H, t), 1.18 (3H, t), 1.15 (3H, t).

Example 87

2,2'-(4-n-Propoxy-1,3-phenylene)bis(5,6-diethylpyrimid-4(3H)-one)

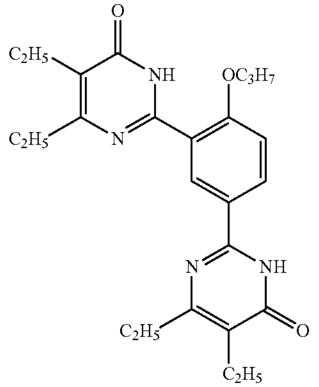

The title compound was prepared by reacting the compound of example 10 with methyl 2-ethyl-3-oxovalerate in the same manner as that of example 1. $^1$H NMR ($CDCl_3$) δ: 9.08 (1H, d), 8.34 (1H, dd), 7.08 (1H, d), 4.19 (2H, t), 2.74-2.48 (8H, m), 1.97 (2H, m), 1.30 (3H, t), 1.27 (3H, t), 1.15 (3H, t), 1.13 (3H, t), 1.07 (3H, t).

Example 88

2-(5-(1,3,4-Oxadiazol-2-yl)-2-propoxyphenyl)-5,6-diethylpyrimid-4(3H)-one

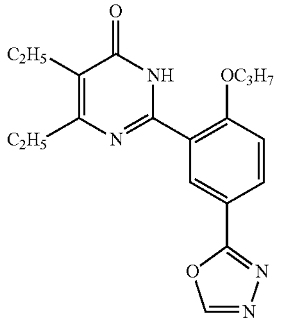

The title compound was prepared by reacting the compound of example 8 with methyl 2-ethyl-3-oxovalerate in the same manner as that of example 1. $^1$H NMR ($CDCl_3$) δ: 8.69

(1H, d), 8.51 (1H, dd), 7.05 (1H, d), 4.14 (2H, t), 2.69 (4H, m), 1.92 (2H, m), 1.31 (3H, t), 1.21 (3H, t), 1.12 (3H, t).

Example 89

Ethyl 2-(3-(4,5-diethyl-1,6-dihydro-6-oxopyrimidin-2-yl)-4-n-propoxybenzamido)acetate

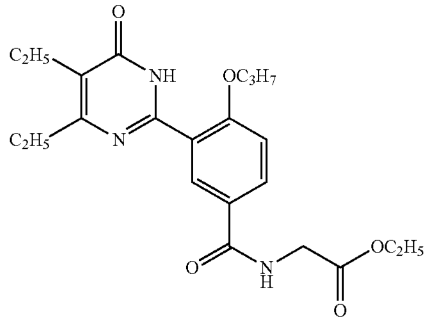

The compound (250 mg, 0.76 mmol) of example 58 was suspended in dichloromethane (20 ml), and added with thionyl chloride (2 ml), followed by refluxing for 2 h to clear the reaction mixture. The reaction mixture was concentrated off thionyl chloride, and added with dichloromethane. Under ice-bath, the reaction mixture was added dropwise into a dichloromethane solution (20 ml) containing ethyl 2-aminoacetate (80 mg, 0.727 mmol) and triethylamine (0.2 ml, 1.454 mmol), followed by stirring for 0.5 h. The reaction mixture was then washed with water (20 ml) and saturated saline (20 ml) respectively. The organic layer was dried with anhydrous sodium sulfate, and concentrated. The residue was passed through a silica gel column to give the white title compound (100 mg, yield: 33%). $^1$H NMR ($CDCl_3$) δ: 11.01 (1H, br), 8.87 (1H, d), 8.00 (1H, dd), 7.08 (1H, d), 6.87 (1H, br), 4.27 (2H, q), 4.25 (2H, t), 4.21 (2H, t), 2.69 (2H, q), 2.59 (2H, q), 2.00 (2H, m), 1.32 (3H, t), 1.30 (3H, t), 1.15 (6H, t).

Examples 90~97

In the same manner as that of example 89, the compound of example 58 was first reacted with thionyl chloride to obtain a product, which was then reacted with N-aminoethylmorpholine, diethanolamine, 3-aminocyclocaprolactam, 1-(2,3-dichlorophenyl)piperazine, 3-isopropylpyrazole, cyclohexylamine, 2-aminomethylpyridine and methyl 3,3-dimethylbutyrate respectively to give the title compounds of examples 90~97.

| Example | Structural Formula | Nomenclature and data of 1H-NMR(δ) |
|---|---|---|
| 90 | 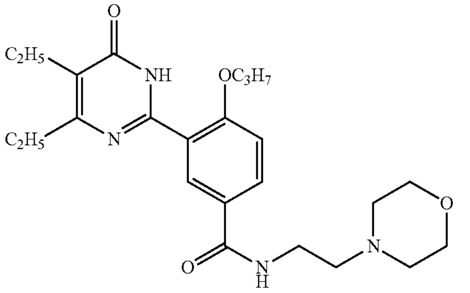 | 3-(4,5-diethyl-1,6-dihydro-6-oxopyrimidin-2-yl)-N-(2-morpholinylethyl)-4-n-propoxybenzamide ($CDCl_3$) δ: 11.07 (1H, br), 8.82 (1H, d), 8.05 (1H, dd), 7.10 (1H, d), 7.03 (1H, br), 4.22 (2H, t), 3.77 (2H, t), 3.59 (2H, m), 2.68 (2H, q), 2.65 (2H, t), 2.58 (2H, q), 2.56 (4H, t), 2.01 (2H, m), 1.31 (3H, t), 1.15 (6H, t) |
| 91 | 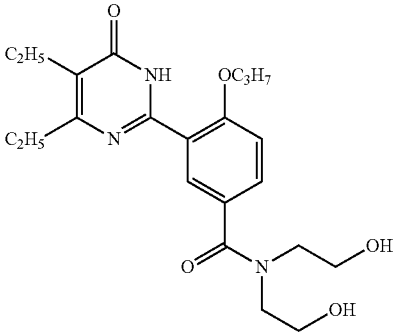 | 3-(4,5-diethyl-1,6-dihydro-6-oxopyrimidin-2-yl)-N,N-di(2-hydroxyethyl)-4-n-propoxybenzamide ($CDCl_3$) δ: 8.60 (1H, d), 7.70 (1H, dd), 7.04 (1H, d), 7.03 (1H, br), 4.18 (2H, t), 4.05-3.40 (8H, m), 2.66 (2H, q), 2.58 (2H, q), 1.99 (2H, m), 1.28 (3H, t), 1.14 (3H, t), 1.13 (3H, t) |
| 92 | 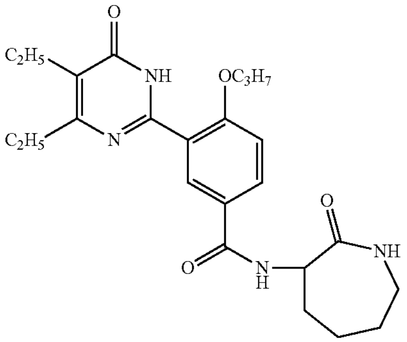 | 3-(4,5-diethyl-1,6-dihydro-6-oxopyrimidin-2-yl)-N-(2-caprolactam-3-yl)-4-n-propoxybenzamide ($CDCl_3$) δ: 11.10 (1H, br), 8.94 (1H, d), 7.98 (1H, dd), 7.73 (1H, br), 7.10 (1H, d), 6.20 (1H, br), 4.74 (1H, t), 4.24 (2H, t), 3.35 (2H, m), 2.72 (2H, q), 2.62 (2H, q), 2.27 (1H, d), 2.14-1.40 (7H, m), 1.34 (3H, t), 1.17 (6H, t) |
| 93 | 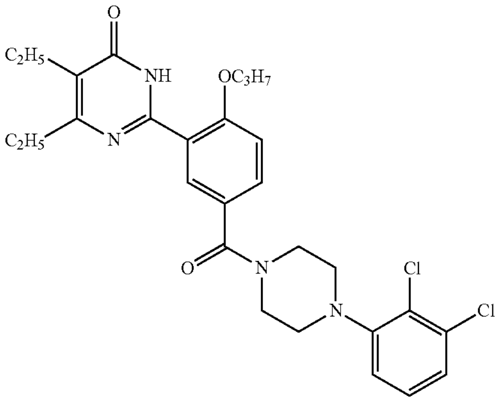 | (4-(2,3-dichlorophenyl)piperazin-1-yl)(3-(4,5-diethyl-1,6-dihydro-6-oxopyrimidin-2-yl)-4-n-propoxy)benzophenone ($CDCl_3$) δ: 11.10 (1H, br), 8.65 (1H, d), 7.64 (1H, dd), 7.24 (1H, dd), 7.21 (1H, q), 7.11 (1H, d), 6.97 (1H, dd), 4.24 (2H, t), 3.99 (2H, br), 3.75 (2H, br), 3.11 (4H, br), 2.69 (2H, q), 2.62 (2H, q), 2.04 (2H, m), 1.32 (3H, t), 1.18 (3H, t), 1.17 (3H, t) |

-continued

| Example | Structural Formula | Nomenclature and data of 1H-NMR(δ) |
|---|---|---|
| 94 | 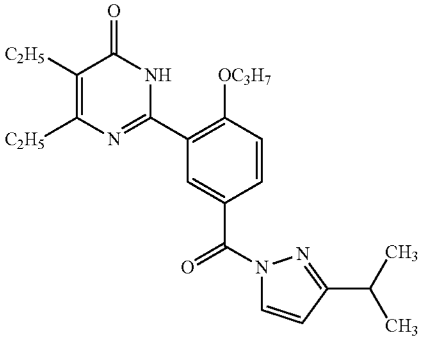 | (3-isopropylpyrazol-1-yl)(3-(4,5-diethyl-1,6-dihydro-6-oxopyrimidin-2-yl)-4-n-propoxy)benzophenone<br>($CDCl_3$) δ: 11.06 (1H, br), 9.52 (1H, d), 8.40 (1H, dd), 8.38 (1H, d), 7.16 (1H, d), 6.42 (1H, d), 4.29 (2H, t), 3.08 (1H, m), 2.68 (2H, q), 2.62 (2H, q), 2.06 (2H, m), 1.35 (3H, t), 1.33 (3H, t), 1.30 (3H, t), 1.19 (3H, t), 1.18 (3H, t) |
| 95 | 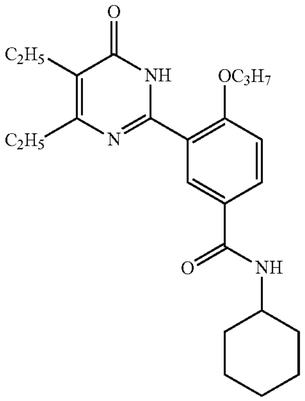 | N-cyclohexyl-3-(4,5-diethyl-1,6-dihydro-6-oxopyrimidin-2-yl)-4-n-propoxybenzamide<br>($CDCl_3$) δ: 10.98 (1H, br), 8.75 (1H, d), 7.95 (1H, dd), 7.05 (1H, d), 6.13 (1H, br), 4.19 (2H, t), 3.99 (1H, m), 2.69 (2H, q), 2.60 (2H, q), 2.05 (2H, m), 2.01 (2H, m), 1.83-1.62 (4H, m), 1.44 (2H, m), 1.31 (5H, m), 1.16 (3H, t), 1.15 (3H, t) |
| 96 | 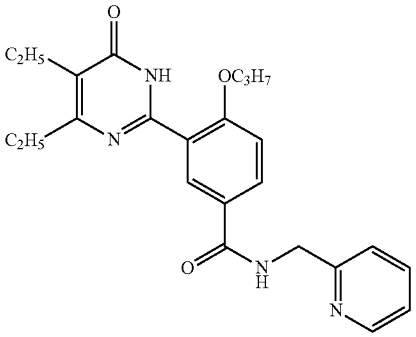 | N-((pyrid-2-yl)methyl)-3-(4,5-diethyl-1,6-dihydro-6-oxo-pyrimidin-2-yl)-4-n-propoxybenzamide<br>($CDCl_3$) δ: 8.56 (1H, d), 8.21 (1H, d), 7.98 (1H, dd), 7.69 (1H, t), 7.50 (1H, br), 7.35 (1H, d), 7.22 (1H, t), 7.04 (1H, d), 4.77 (2H, d), 4.04 (2H, t), 2.90 (2H, q), 2.85 (2H, q), 1.80 (2H, m), 1.37 (3H, t), 1.27 (3H, t), 1.02 (3H, t) |
| 97 | 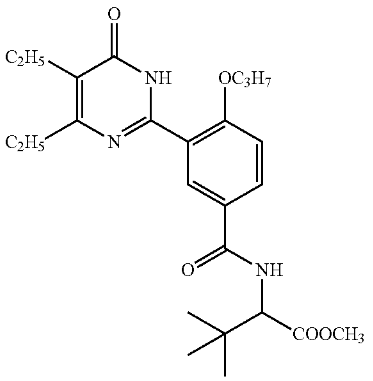 | methyl<br>2-(3-(4,5-diethyl-1,6-dihydro-6-oxopyrimidin-2-yl)-4-n-propoxybenzamido)-3,3-dimethylbutyrate<br>($CDCl_3$) δ: 11.03 (1H, br), 8.90 (1H, d), 7.96 (1H, dd), 7.09 (1H, d), 6.74 (1H, br), 4.69 (1H, d), 4.22 (2H, t), 3.76 (3H, s), 2.70 (2H, q), 2.59 (2H, q), 2.01 (2H, m), 1.32 (3H, t), 1.15 (6H, t), 1.07 (9H, s) |

Examples 98~405

The compound of example 42 was reacted with trifluoroacetyl chloride, ethyl oxalyl monochloride, acrolyl chloride, crotonyl chloride, ethyl malonyl chloride, 2-ethoxybenzoyl chloride, nicotinoyl chloride, 5-isopropylthiazoleformyl chloride respectively to give the title compounds of examples 98~105, in the same manner as that of example 50.

| Example | Structural Formula | Nomenclature and data of 1H-NMR(δ) |
|---|---|---|
| 98 | 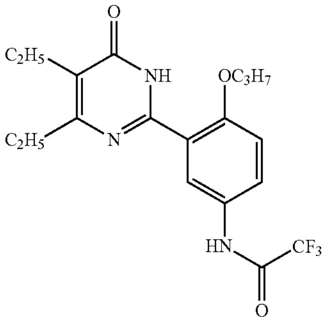 | N-(3-(4,5-diethyl-1,6-dihydro-6-oxopyrimidin-2-yl)-4-n-propoxyphenyl)-2,2,2-trifluoroacetamide<br>($CDCl_3$) δ: 8.43 (1H, d), 8.23 (1H, br), 7.99 (1H, dd), 7.06 (1H, d), 4.18 (2H, t), 2.67 (2H, q), 2.59 (2H, q), 1.98 (2H, m), 1.29 (3H, t), 1.14 (6H, t) |
| 99 | 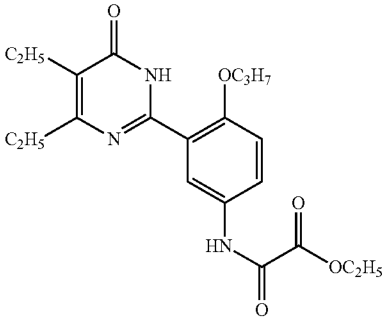 | ethyl N-(3-(4,5-diethyl-1,6-dihydro-6-oxopyrimidin-2-yl)-4-n-propoxyphenyl)aminoformylformate<br>($CDCl_3$) δ: 8.47 (1H, d), 8.08 (1H, dd), 7.06 (1H, d), 4.44 (2H, q), 4.18 (2H, t), 2.68 (2H, q), 2.60 (2H, q), 2.00 (2H, m), 1.45 (3H, t), 1.31 (3H, t), 1.15 (6H, t) |
| 100 | 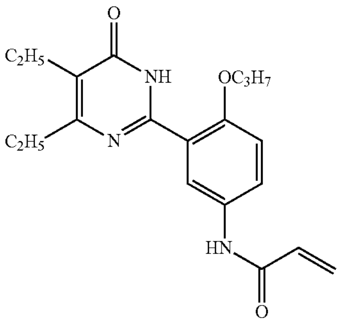 | N-(3-(4,5-diethyl-1,6-dihydro-6-oxopyrimidin-2-yl)-4-n-propoxyphenyl)acrylamide<br>($CDCl_3$) δ: 8.30 (1H, d), 8.11 (1H, dd), 7.79 (1H, br), 6.99 (1H, d), 6.45 (1H, d), 6.29 (1H, dd), 5.77 (1H, d), 4.13 (2H, t), 2.64 (2H, q), 2.58 (2H, q), 1.95 (2H, m), 1.27 (3H, t), 1.14 (3H, t), 1.12 (3H, t) |
| 101 | 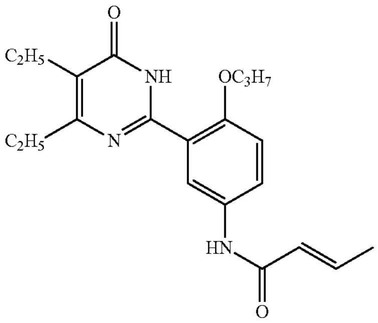 | N-(3-(4,5-diethyl-1,6-dihydro-6-oxopyrimidin-2-yl)-4-n-propoxyphenyl)-2-crotonamide<br>($CDCl_3$) δ: 8.22 (1H, d), 8.00 (1H, dd), 7.47 (1H, br), 7.01 (1H, m), 6.99 (1H, d), 5.97 (1H, d), 4.13 (2H, t), 2.65 (2H, q), 2.58 (2H, q), 1.96 (2H, m), 1.92 (3H, t), 1.28 (3H, t), 1.15 (3H, t), 1.13 (3H, t) |
| 102 | 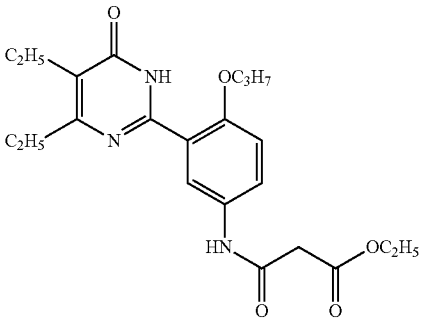 | ethyl N-(3-(4,5-diethyl-1,6-dihydro-6-oxopyrimidin-2-yl)-4-n-propoxyphenyl)aminoformylacetate<br>($CDCl_3$) δ: 9.25 (1H, br), 8.36 (1H, d), 7.95 (1H, dd), 7.00 (1H, d), 4.28 (2H, q), 4.15 (2H, t), 3.49 (2H, s), 2.68 (2H, q), 2.59 (2H, q), 1.98 (2H, m), 1.34 (3H, t), 1.30 (3H, t), 1.15 (3H, t), 1.14 (3H, t) |

-continued

| Example | Structural Formula | Nomenclature and data of 1H-NMR(δ) |
|---|---|---|
| 103 | 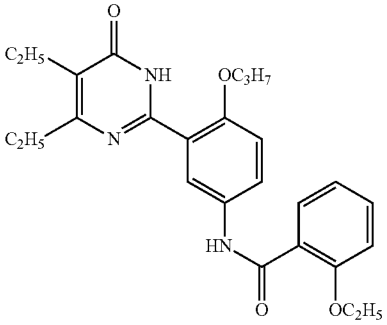 | 2-ethoxy-N-(3-(4,5-diethyl-1,6-dihydro-6-oxopyrimidin-2-yl)-4-n-propoxyphenyl)benzamide ($CDCl_3$) δ: 11.25 (1H, br), 10.28 (1H, br), 8.35 (1H, dd), 8.32 (1H, d), 8.30 (1H, dd), 7.49 (1H, t), 7.13 (1H, t), 7.05 (1H, d), 7.02 (1H, d), 4.31 (2H, q), 4.18 (2H, t), 2.67 (2H, q), 2.60 (2H, q), 1.99 (2H, m), 1.71 (3H, t), 1.31 (3H, t), 1.15 (6H, t) |
| 104 | 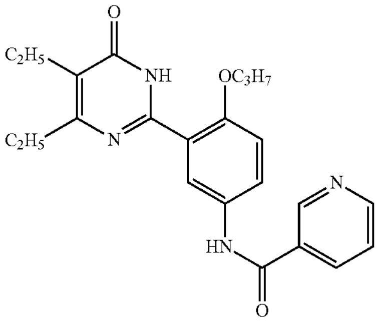 | N-(3-(4,5-diethyl-1,6-dihydro-6-oxopyrimidin-2-yl)-4-n-propoxyphenyl)nicotinamide ($CDCl_3$) δ: 9.17 (1H, br), 8.78 (1H, d), 8.40 (2H, d), 8.27 (1H, d), 8.11 (1H, dd), 7.45 (1H, dd), 7.04 (1H, d), 4.15 (2H, t), 3.49 (2H, s), 2.63 (2H, q), 2.58 (2H, q), 1.97 (2H, m), 1.14 (3H, t), 1.13 (3H, t) |
| 105 | 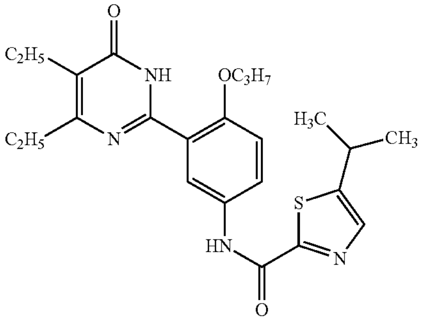 | N-(3-(4,5-diethyl-1,6-dihydro-6-oxopyrimidin-2-yl)-4-n-propoxyphenyl)-5-isopropylthiazolyl-2-formamide (DMSO-$d_6$) δ: 11.85 (1H, br), 10.60 (1H, br), 8.24 (1H, d), 7.94 (1H, dd), 7.68 (1H, s), 7.19 (1H, d), 4.05 (2H, t), 3.16 (1H, m), 2.58 (2H, q), 2.47 (2H, q), 1.76 (2H, m), 1.33 (6H, d), 1.21 (3H, t), 1.05 (3H, t), 0.98 (3H, t) |

Example 106 t-Butyl 3-(N-(3-(4,5-diethyl-1,6-dihydro-6-oxopyrimidin-2-yl)-4-n-propoxyphenyl)aminoformyl)propylaminoformate

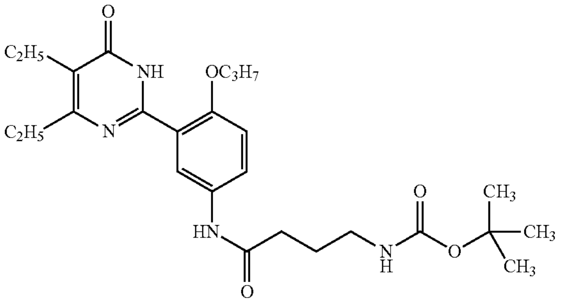

N-Boc-4-aminobutyric acid (203 mg, 1 mmol) was dissolved in dichloromethane (50 ml), and added with EDCI (180 mg, 1 mmol) and HOBT (135 mg, 1 mmol), followed by stirring at room temperature for 12 h. The compound of example 42 (300 mg, 1 mmol) was added thereinto and the stirring continued at room temperature for 6 h. The reaction mixture was washed with water (50 ml) and saturated saline (50 ml) respectively. The organic layer was dried with anhydrous sodium sulfate, and concentrated, and the residue was passed through a silica gel column to give the white title compound (200 mg, yield: 41%). $^1H$ NMR ($CDCl_3$) δ: 9.00 (1H, br), 8.39 (1H, d), 8.09 (1H, dd), 6.99 (1H, d), 4.83 (1H, t), 4.14 (2H, t), 3.27 (2H, m), 2.65 (2H, q), 2.59 (2H, q), 2.41 (2H, t), 1.97 (2H, m), 1.89 (2H, m), 1.48 (9H, s), 1.29 (3H, t), 1.14 (3H, t), 1.13 (3H, t).

Example 107

4-Acetamido-N-(3-(4,5-diethyl-1,6-dihydro-6-oxopyrimidin-2-yl)-4-n-propoxyphenyl)butyramide

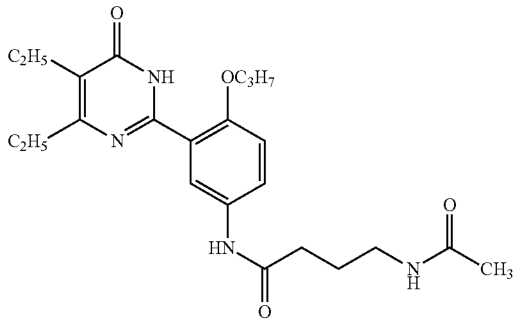

The compound (200 mg, 0.412 mmol) of example 106 was dissolved in dichloromethane (30 ml) and added with trifluoroacetic acid (2 ml), followed by stirring at room temperature for 0.5 h. The reaction mixture was directly concentrated to dryness. The resultant oil was dissolved in dichloromethane (30 ml) and added with triethylamine (1 ml). Under ice-water both, acetyl chloride (33 mg, 0.42 mmol) was added dropwise thereinto. 0.5 h later, TLC showed that the reaction was complete. The reaction mixture was washed with water (50 ml) and saturated saline (50 ml). The organic layer was dried with anhydrous sodium sulfate, and concentrated, and the residue was passed through a silica gel column to give the white title compound (50 mg, yield: 28%). $^1H$ NMR ($CDCl_3$) δ: 8.79 (1H, br), 8.51 (1H, d), 7.93 (1H, dd), 6.99 (1H, d), 6.05 (1H, br), 4.15 (2H, t), 3.40 (2H, t), 2.68 (2H, q), 2.60 (2H, q), 2.44 (2H, t), 2.03 (3H, s), 1.97 (2H, m), 1.94 (2H, m), 1.32 (3H, t), 1.16 (3H, t), 1.14 (3H, t).

Examples 108~112

According to the same manner as those of example 106 and example 107, the compound of example 42 was reacted with N-Boc-proline, N-Boc-valine, N-Boc-phenylalanine, N-Boc-lactamine and N-Boc-lysine respectively, and then removed the Boc-protecting group and acetylated to obtain the compounds of examples 108~112.

| Example | Structural Formula | Nomenclature and data of 1H-NMR(δ) |
|---|---|---|
| 108 | 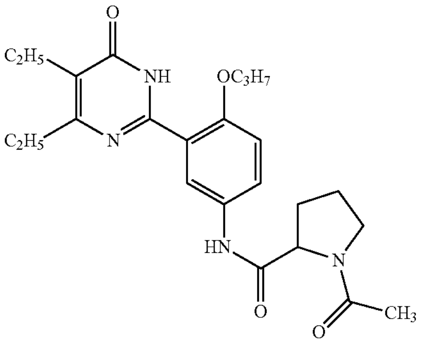 | 1-acetyl-N-(3-(4,5-diethyl-1,6-dihydro-6-oxopyrimidin-2-yl)-4-n-propoxyphenyl)pyrrolidinyl-2-formamide ($CDCl_3$) δ: 9.61 (1H, br), 8.35 (1H, d), 7.83 (1H, dd), 6.94 (1H, d), 4.78 (1H, d), 4.12 (2H, t), 3.60 (1H, m), 3.46 (1H, m), 2.67 (2H, q), 2.58 (2H, q), 2.16 (3H, s), 2.07 (2H, m), 1.95 (2H, m), 1.85 (2H, m), 1.30 (3H, t), 1.14 (3H, t), 1.12 (3H, t) |
| 109 | 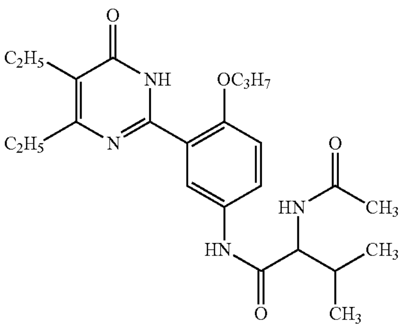 | 2-acetamido-N-(3-(4,5-diethyl-1,6-dihydro-6-oxopyrimidin-2-yl)-4-n-propoxyphenyl)-3-methylbutyramide ($CDCl_3$) δ: 11.19 (1H, br), 8.91 (1H, br), 8.36 (1H, d), 7.94 (1H, dd), 6.98 (1H, d), 6.44 (1H, br), 4.53 (1H, d), 4.14 (2H, t), 2.66 (2H, q), 2.59 (2H, q), 2.20 (1H, m), 2.12 (3H, s), 1.98 (2H, m), 1.29 (3H, t), 1.16 (3H, t), 1.14 (3H, t), 1.06 (3H, d), 1.04 (3H, d) |

-continued

| Example | Structural Formula | Nomenclature and data of 1H-NMR(δ) |
|---|---|---|
| 110 | 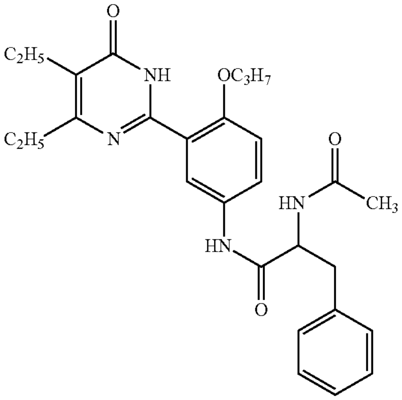 | 2-acetamido-N-(3-(4,5-diethyl-1,6-dihydro-6-oxopyrimidin-2-yl)-4-n-propoxyphenyl)-3-phenylpropionamide ($CDCl_3$) δ: 11.18 (1H, br), 8.14 (1H, d), 7.77 (1H, dd), 7.42-7.36 (5H, m), 6.95 (1H, d), 6.46 (1H, d), 4.88 (1H, q), 4.13 (2H, t), 3.17 (2H, m), 2.66 (2H, q), 2.60 (2H, q), 2.05 (3H, s), 1.97 (2H, m), 1.30 (3H, t), 1.16 (3H, t), 1.13 (3H, t) |
| 111 | 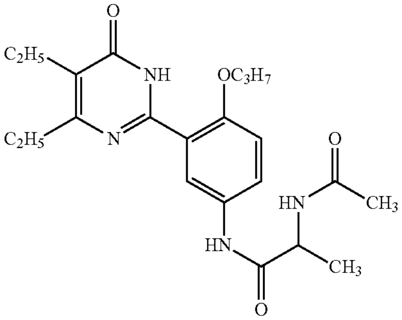 | 2-acetamido-N-(3-(4,5-diethyl-1,6-dihydro-6-oxopyrimidin-2-yl)-4-n-propoxyphenyl)propionamide ($CDCl_3$) δ: 8.99 (1H, br), 8.36 (1H, d), 7.88 (1H, dd), 6.94 (1H, d), 6.49 (1H, d), 4.77 (1H, m), 4.11 (2H, t), 2.64 (2H, q), 2.57 (2H, q), 2.08 (3H, s), 1.95 (2H, m), 1.49 (3H, d), 1.27 (3H, t), 1.13 (3H, t), 1.11 (3H, t) |
| 112 | 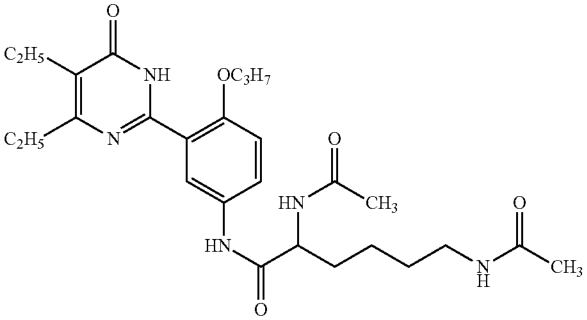 | 2,6-diacetamido-N-(3-(4,5-diethyl-1,6-dihydro-6-oxopyrimidin-2-yl)-4-n-propoxyphenyl)hexanamide ($DMSO-d_6$) δ: 11.79 (1H, br), 10.07 (1H, br), 8.11 (1H, d), 8.02 (1H, d), 7.79 (1H, t), 7.75 (1H, dd), 7.13 (1H, d), 4.33 (1H, m), 4.02 (2H, t), 3.00 (2H, q), 2.57 (2H, q), 2.46 (2H, q), 1.86 (3H, s), 1.76 (3H, s), 1.74 (2H, m), 1.20 (3H, t), 1.04 (3H, t), 0.97 (3H, t) |

Example 113

$N^1$-(3-(4,5-diethyl-1,6-dihydro-6-oxopyrimidin-2-yl)-4-n-propoxyphenyl)propanediamide

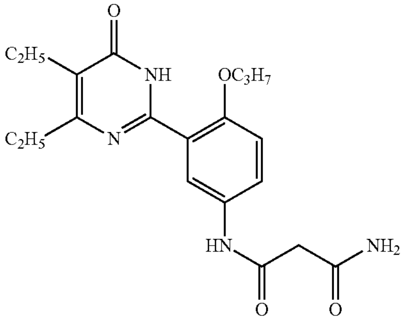

The compound of Example 102 (100 mg) was sealed in a 25 ml tube, added with a saturated solution (15 ml) of ammonia in ethanol (15 ml), and heated to 120° C. to react for 12 h. The reaction mixture was concentrated to dryness, and the residue was recrystallized from ethyl acetate to give the white title compound (60 mg, yield: 64%). $^1H$ NMR ($CDCl_3$) δ: 9.57 (1H, br), 8.38 (1H, d), 7.87 (1H, dd), 7.02 (1H, br), 6.96 (1H, d), 5.93 (1H, br), 4.12 (2H, t), 3.44 (2H, s), 2.64 (2H, q), 2.57 (2H, q), 1.95 (2H, m), 1.27 (3H, t), 1.14 (3H, t), 1.11 (3H, t).

Examples 114~115

The compounds of examples 114~115 were prepared by respectively reacting the compounds of examples 99 and 89 with the saturated solution of ammonia in ethanol in the same manner as that of example 113.

| Example | Structural Formula | Nomenclature and data of 1H-NMR(δ) |
|---|---|---|
| 114 | 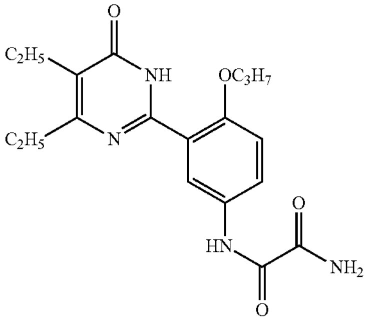 | $N^1$-(3-(4,5-diethyl-1,6-dihydro-6-oxopyrimidin-2-yl)-4-n-propoxyphenyl)oxalamide (DMSO-$d_6$) δ: 11.81 (1H, br), 10.67 (1H, br), 8.30 (1H, d), 7.96 (1H, br), 7.87 (1H, dd), 7.16 (1H, d), 4.04 (2H, t), 2.56 (2H, q), 2.46 (2H, q), 1.75 (2H, m), 1.20 (3H, t), 1.04 (3H, t), 0.97 (3H, t) |
| 115 | 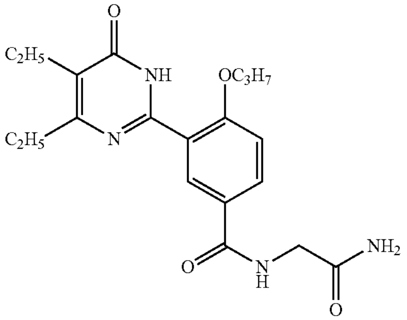 | N-(aminoformylmethyl)-3-(4,5-diethyl-1,6-dihydro-6-oxo-pyrimidin-2-yl)-4-n-propoxybenzamide (DMSO-$d_6$) δ: 12.00 (1H, br), 8.66 (1H, t), 8.17 (1H, d), 8.01 (1H, dd), 7.38 (1H, br), 7.23 (1H, d), 7.02 (1H, br), 4.09 (2H, t), 3.80 (2H, d), 2.58 (2H, q), 2.47 (2H, q), 1.75 (2H, m), 1.20 (3H, t), 1.04 (3H, t), 0.97 (3H, t) |

Example 116

5,6-Diethyl-2-{2-n-propoxy-5-[(2-(1-methylpyrrol-2-yl)ethyl)aminosulfonyl]phenyl}pyrimid-4(3H)-one

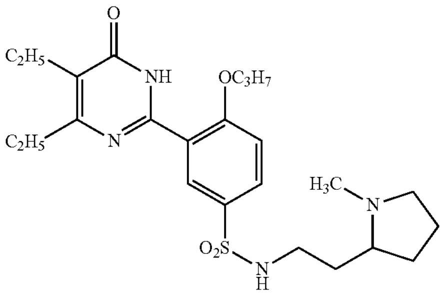

According to the same manner as that of example 10, the compound of preparation example 33 was first chlorosulfonated, and then reacted with 2-(1-methylpyrrol-2-yl)ethylamine to give the compound of example 116. $^1$H NMR (DMSO-$d_6$) δ: 12.04 (1H, br), 8.02 (1H, d), 7.87 (1H, dd), 7.60 (1H, br), 7.35 (1H, d), 4.11 (2H, t), 2.88 (1H, m), 2.75 (2H, m), 2.57 (2H, q), 2.47 (2H, q), 2.12 (3H, s), 2.00 (2H, m), 1.85-1.62 (4H, m), 1.55 (2H, m), 1.29 (2H, m), 1.19 (3H, t), 1.04 (3H, t), 0.96 (3H, t).

Example 117

3-(4,5-Diethyl-1,6-dihydro-6-oxopyrimidin-2-yl)-N-(2-(1-methylpyrrol-2-yl)ethyl)-4-n-propoxybenzamide

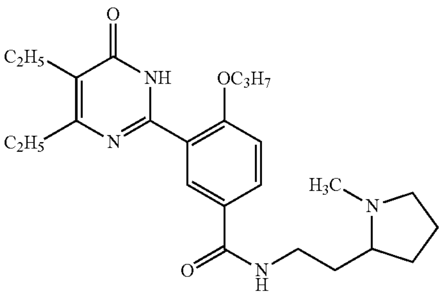

According to the same manner as that of example 89, the compound of example 58 was reacted with 2-(1-methylpyrrol-2-yl)ethylamine to give the compound of example 117. $^1$H NMR (DMSO-$d_6$) δ: 12.01 (1H, br), 8.50 (1H, t), 8.12 (1H, d), 7.96 (1H, dd), 7.22 (1H, d), 4.08 (2H, t), 3.28 (2H, m), 2.98 (1H, m), 2.58 (2H, q), 2.47 (2H, q), 2.25 (3H, s), 2.13 (2H, m), 1.90 (2H, m), 1.75 (2H, m), 1.64 (2H, m), 1.45 (2H, m), 1.19 (3H, t), 1.04 (3H, t), 0.96 (3H, t).

Examples 118~436

According to the same manner as that of example 10, the compound of preparation example 33 was first chlorosulfonated, and then reacted with citrulline, ornithine, valine, lactamine, serine, ethyl lactamate, homotaurine, taurine, asparamide, tryptophan, glycocine, t-leucine, glutamine, ethyl isoleucinate, methyl 6-acetyllysinate, hydroxyethylpiperazine, 1-propanolamine, N-hydroxyethyl-2-(morpholin-1-yl)ethylamine, N-methyl-2-(pyrrolidin-1-yl)ethylamine respectively, to obtain the compounds of examples 118~136.

| Example | Structural Formula | Nomenclature and data of 1H-NMR(δ) |
|---|---|---|
| 118 | 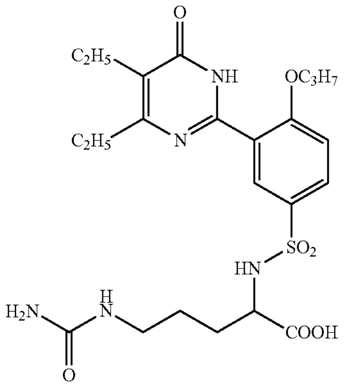 | 2-(N-(3-(4,5-diethyl-1,6-dihydro-6-oxopyrimidin-2-yl)-4-n-propoxyphenyl)sulfonyl)amino-5-ureavaleric acid (DMSO-$d_6$) δ: 8.04 (1H, d), 7.86 (1H, dd), 7.31 (1H, d), 4.10 (2H, t), 3.63 (1H, m), 2.83 (2H, m), 2.56 (2H, q), 2.44 (2H, q), 1.75 (2H, m), 1.50 (2H, m), 1.29 (2H, m), 1.19 (3H, t), 1.04 (3H, t), 0.96 (3H, t) |
| 119 | 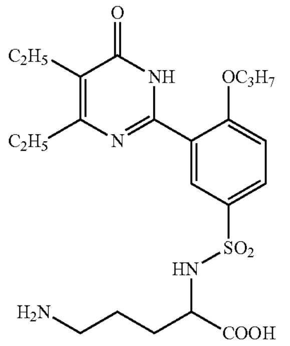 | 2-(N-(3-(4,5-diethyl-1,6-dihydro-6-oxopyrimidin-2-yl)-4-n-propoxyphenyl)sulfonyl)amino-5-aminovaleric acid (DMSO-$d_6$) δ: 8.04 (1H, d), 7.86 (1H, dd), 7.31 (1H, d), 4.10 (2H, t), 3.63 (1H, m), 2.83 (2H, m), 2.56 (2H, q), 2.44 (2H, q), 1.75 (2H, m), 1.50 (2H, m), 1.38 (2H, m), 1.16 (3H, t), 1.04 (3H, t), 0.96 (3H, t) |
| 120 | 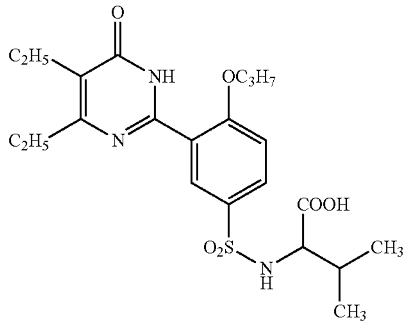 | 2-(N-(3-(4,5-diethyl-1,6-dihydro-6-oxopyrimidin-2-yl)-4-n-propoxyphenyl)sulfonyl)amino-3-methylbutyric acid (DMSO-$d_6$) δ: 8.08 (1H, d), 7.87 (1H, dd), 7.32 (1H, d), 4.11 (2H, t), 3.50 (1H, d), 2.58 (2H, q), 2.47 (2H, q), 1.95 (1H, m), 1.77 (2H, m), 1.20 (3H, t), 1.05 (3H, t), 0.98 (3H, t), 0.83 (3H, d), 0.80 (3H, d) |
| 121 | 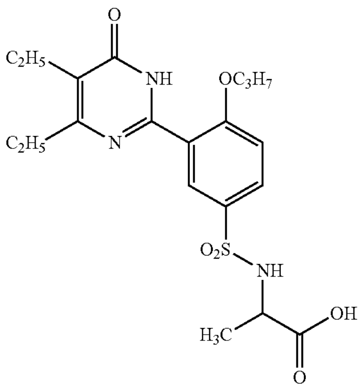 | 2-(N-(3-(4,5-diethyl-1,6-dihydro-6-oxopyrimidin-2-yl)-4-n-propoxyphenyl)sulfonyl)aminopropionic acid (DMSO-$d_6$) δ: 8.06 (1H, d), 7.88 (1H, dd), 7.33 (1H, d), 4.11 (2H, t), 3.75 (1H, q), 2.57 (2H, q), 2.46 (2H, q), 1.76 (2H, m), 1.18 (3H, d), 1.15 (3H, t), 1.04 (3H, t), 0.96 (3H, t) |

-continued

| Example | Structural Formula | Nomenclature and data of 1H-NMR(δ) |
|---|---|---|
| 122 | 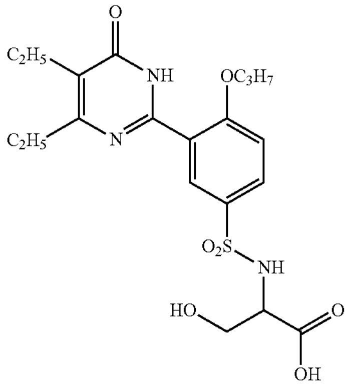 | 2-(N-(3-(4,5-diethyl-1,6-dihydro-6-oxopyrimidin-2-yl)-4-n-propoxyphenyl)sulfonyl)amino-3-hydroxypropionic acid ($DMSO-d_6$) δ: 8.09 (1H, d), 7.89 (1H, dd), 7.32 (1H, d), 4.10 (2H, t), 3.74 (1H, t), 3.44 (2H, d), 2.58 (2H, q), 2.46 (2H, q), 1.76 (2H, m), 1.19 (3H, t), 1.04 (3H, t), 0.96 (3H, t) |
| 123 | 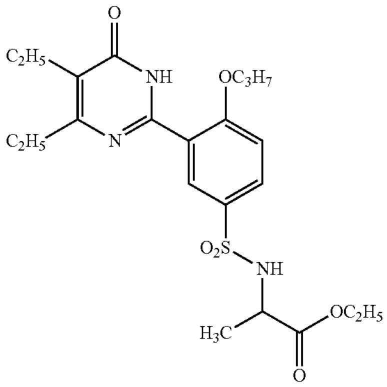 | ethyl 2-(N-(3-(4,5-diethyl-1,6-dihydro-6-oxopyrimidin-2-yl)-4-n-propoxyphenyl)sulfonyl)aminopropionate ($CDCl_3$) δ: 11.01 (1H, br), 8.84 (1H, d), 7.97 (1H, dd), 7.07 (1H, d), 6.86 (1H, d), 4.78 (1H, m), 4.25 (2H, q), 4.20 (2H, t), 2.68 (2H, q), 2.59 (2H, q), 2.00 (2H, m), 1.54 (3H, d), 1.31 (3H, t), 1.30 (3H, t), 1.14 (6H, t) |
| 124 | 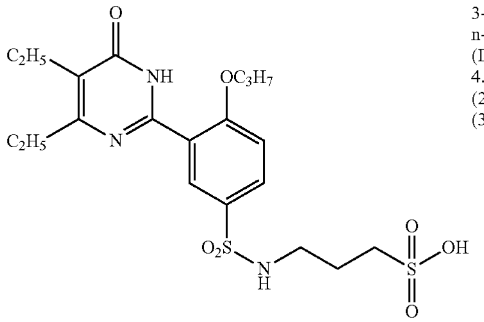 | 3-(N-(3-(4,5-diethyl-1,6-dihydro-6-oxopyrimidin-2-yl)-4-n-propoxyphenyl)sulfonyl)aminopropylsulfonic acid ($DMSO-d_6$) δ: 8.08 (1H, d), 7.96 (1H, dd), 7.42 (1H, d), 4.12 (2H, t), 2.90 (2H, t), 2.68 (2H, q), 2.57 (2H, q), 2.35 (2H, t), 1.73 (2H, m), 1.58 (2H, m), 1.21 (3H, t), 1.07 (3H, t), 0.93 (3H, t) |
| 125 | 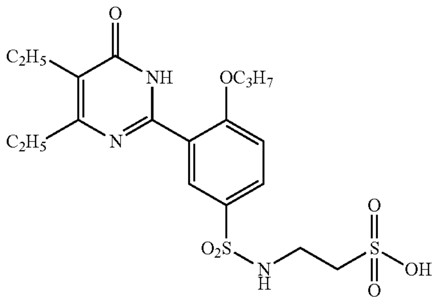 | 2-(N-(3-(4,5-diethyl-1,6-dihydro-6-oxopyrimidin-2-yl)-4-n-propoxyphenyl)sulfonyl)aminoethylsulfonic acid ($DMSO-d_6$) δ: 8.09 (1H, d), 7.97 (1H, dd), 7.45 (1H, d), 4.13 (2H, t), 2.98 (2H, t), 2.68 (2H, t), 2.65 (2H, q), 2.54 (2H, q), 1.74 (2H, m), 1.20 (3H, t), 1.06 (3H, t), 0.93 (3H, t) |

-continued

| Example | Structural Formula | Nomenclature and data of 1H-NMR(δ) |
| --- | --- | --- |
| 126 | 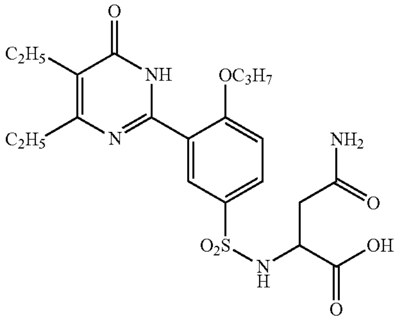 | 2-(N-(3-(4,5-diethyl-1,6-dihydro-6-oxopyrimidin-2-yl)-4-n-propoxyphenyl)sulfonyl)amino-3-aminoformylpropionic acid ($DMSO-d_6$) δ: 8.05 (1H, d), 7.87 (1H, dd), 7.31 (1H, d), 4.09 (3H, m), 2.57 (2H, q), 2.46 (2H, q), 2.29 (2H, d), 1.75 (2H, m), 1.19 (3H, t), 1.04 (3H, t), 0.96 (3H, t) |
| 127 | 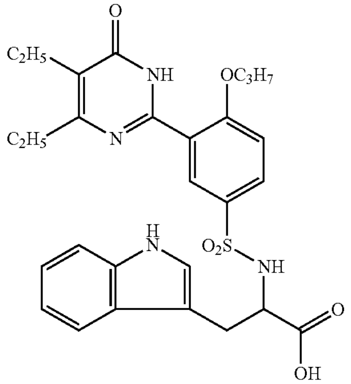 | 2-(N-(3-(4,5-diethyl-1,6-dihydro-6-oxopyrimidin-2-yl)-4-n-propoxyphenyl)sulfonyl)amino-3-indylpropionic acid ($DMSO-d_6$) δ: 8.00 (1H, d), 7.56 (1H, dd), 7.31 (1H, d), 7.24 (1H, d), 7.05 (1H, d), 7.00 (1H, s), 6.96 (1H, d), 6.85 (1H, t), 4.08 (2H, t), 3.91 (1H, dd), 3.05 (1H, dd), 2.83 (1H, dd), 2.57 (2H, q), 2.47 (2H, q), 1.79 (2H, m), 1.18 (3H, t), 1.06 (3H, t), 1.00 (3H, t) |
| 128 | 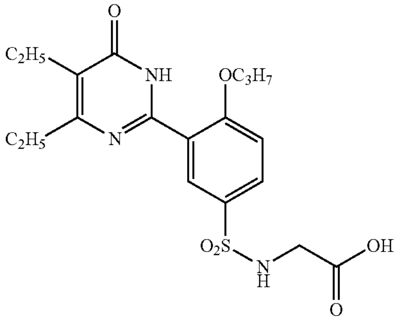 | 2-(N-(3-(4,5-diethyl-1,6-dihydro-6-oxopyrimidin-2-yl)-4-n-propoxyphenyl)sulfonyl)aminoacetic acid ($DMSO-d_6$) δ: 8.04 (1H, d), 7.89 (1H, dd), 7.33 (1H, d), 4.10 (2H, t), 3.56 (2H, s), 2.57 (2H, q), 2.46 (2H, q), 1.76 (2H, m), 1.19 (3H, t), 1.04 (3H, t), 0.96 (3H, t) |
| 129 | 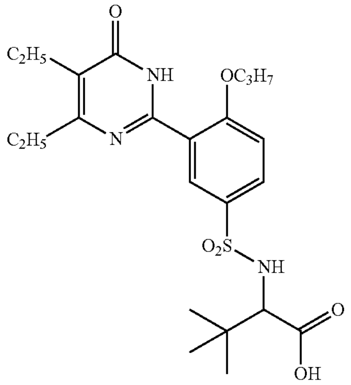 | 2-(N-(3-(4,5-diethyl-1,6-dihydro-6-oxopyrimidin-2-yl)-4-n-propoxyphenyl)sulfonyl)amino-3,3-dimethylbutyric acid ($DMSO-d_6$) δ: 8.08 (1H, d), 7.85 (1H, dd), 7.31 (1H, d), 4.10 (3H, m), 2.58 (2H, q), 2.46 (2H, q), 1.76 (2H, m), 1.19 (3H, t), 1.04 (3H, t), 0.97 (3H, t), 0.86 (9H, s) |

-continued

| Example | Structural Formula | Nomenclature and data of 1H-NMR(δ) |
|---|---|---|
| 130 | 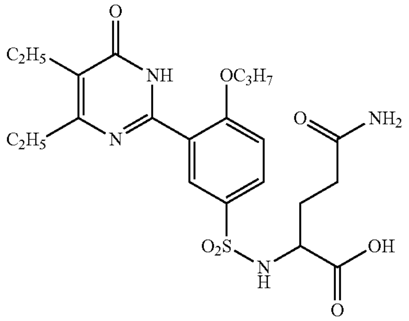 | 2-(N-(3-(4,5-diethyl-1,6-dihydro-6-oxopyrimidin-2-yl)-4-n-propoxyphenyl)sulfonyl)amino-4-aminoformylbutyric acid (DMSO-$d_6$) δ: 8.18 (1H, d), 8.07 (1H, d), 7.85 (1H, dd), 7.31 (1H, d), 4.10 (2H, t), 3.70 (1H, d), 2.57 (2H, q), 2.46 (2H, q), 2.06 (2H, t), 1.93-1.57 (4H, m), 1.19 (3H, t), 1.04 (3H, t), 0.97 (3H, t) |
| 131 | 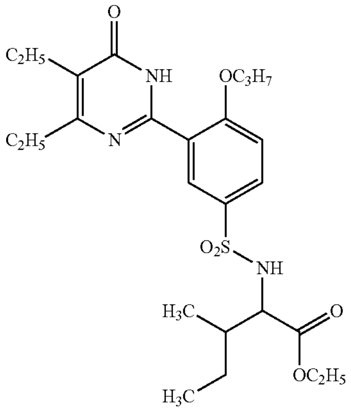 | ethyl 2-(N-(3-(4,5-diethyl-1,6-dihydro-6-oxopyrimidin-2-yl)-4-n-propoxyphenyl)sulfonyl)amino-3-methylvalerate ($CDCl_3$) δ: 10.99 (1H, br), 8.89 (1H, d), 7.90 (1H, dd), 7.09 (1H, d), 5.31 (1H, d), 4.21 (2H, t), 3.99-3.78 (3H, m), 2.66 (2H, q), 2.57 (2H, q), 2.00 (2H, m), 1.79 (1H, m), 1.42 (1H, m), 1.28 (3H, t), 1.17 (1H, m), 1.13 (6H, t), 1.05 (3H, t), 0.91 (3H, d), 0.86 (3H, t) |
| 132 | 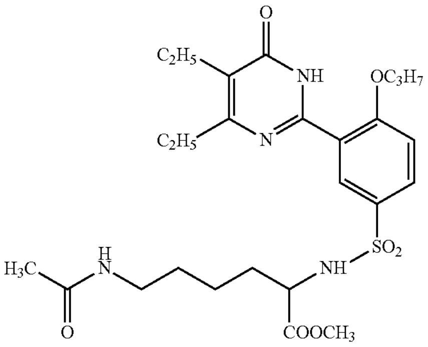 | methyl 2-(3-(4,5-diethyl-1,6-dihydro-6-oxopyrimidin-2-yl)-4-n-propoxyphenylsulfonamido)-6-acetamidocaproate (DMSO-$d_6$) δ: 12.03 (1H, br), 8.20 (1H, d), 8.02 (1H, d), 7.86 (1H, dd), 7.58 (1H, t), 7.34 (1H, d), 4.11 (3H, m), 3.60 (3H, s), 2.70 (2H, m), 2.57 (2H, q), 2.46 (2H, q), 1.83 (3H, s), 1.76 (2H, m), 1.56 (2H, m), 1.36 (2H, m), 1.26 (2H, m), 1.18 (3H, t), 1.04 (3H, t), 0.97 (3H, t) |
| 133 | 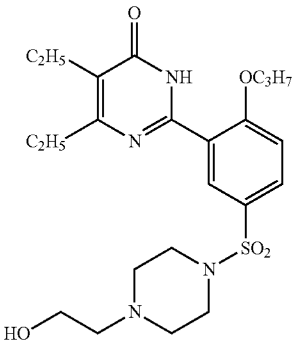 | 5,6-diethyl-2-(2-n-propoxy-5-(4-hydroxyethyl-1-piperazinylsulfonyl)phenyl]pyrimid-4(3H)-one ($CDCl_3$) δ: 10.97 (1H, br), 8.86 (1H, d), 7.83 (1H, dd), 7.15 (1H, d), 4.25 (2H, t), 3.57 (2H, t), 3.08 (4H, t), 2.72-2.50 (10H, m), 2.36 (1H, br), 2.03 (2H, m), 1.27 (3H, t), 1.16 (3H, t), 1.13 (3H, t) |

-continued

| Example | Structural Formula | Nomenclature and data of 1H-NMR(δ) |
|---|---|---|
| 134 | 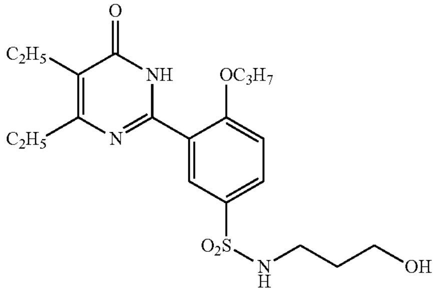 | 5,6-diethyl-2-(2-n-propoxy-5-(3-hydroxypropylamino sulfonyl)phenyl]pyrimid-4(3H)-one ($CDCl_3$) δ: 10.93 (1H, br), 8.86 (1H, d), 7.97 (1H, dd), 7.12 (1H, d), 5.26 (1H, t), 4.23 (2H, t), 3.72 (2H, t), 3.16 (2H, q), 2.67 (2H, q), 2.59 (2H, q), 2.02 (2H, m), 1.70 (2H, m), 1.28 (3H, t), 1.15 (6H, t) |
| 135 | 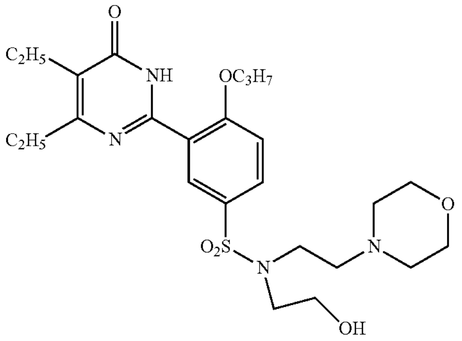 | 5,6-diethyl-2-(2-n-propoxy-5-(N-(2-morpholinylethyl)-N-(2-hydroxyethyl)aminosulfonyl)phenyl)pyrimid-4(3H)-one (DMSO-$d_6$) δ: 12.09 (1H, br), 8.00 (1H, d), 7.92 (1H, dd), 7.33 (1H, d), 5.00 (1H, br), 4.11 (2H, t), 3.52 (6H, t), 3.25 (2H, t), 3.16 (2H, t), 2.57 (2H, q), 2.47 (2H, q), 2.45 (2H, t), 2.36 (4H, t), 1.75 (2H, m), 1.18 (3H, t), 1.04 (3H, t), 0.96 (3H, t) |
| 136 | 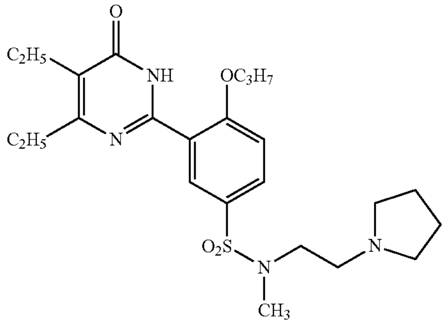 | 5,6-diethyl-2-(2-n-propoxy-5-(N-methyl-N-(2-(pyrrolidin-1-yl)ethyl)aminosulfonyl)phenyl)pyrimid-4(3H)-one ($CDCl_3$) δ: 8.90 (1H, d), 7.89 (1H, dd), 7.14 (1H, d), 4.25 (2H, t), 3.23 (2H, t), 2.85 (3H, s), 2.74 (2H, t), 2.67 (2H, q), 2.60 (6H, m), 2.03 (2H, m), 1.79 (4H, m), 1.28 (3H, t), 1.17 (3H, t), 1.15 (3H, t) |

Example 137

5,6-Diethyl-2-(2-n-propoxy-5-(2-(N,N-diethyl)aminoethylaminosulfonyl)phenyl]pyrimid-4(3H)-one maleate

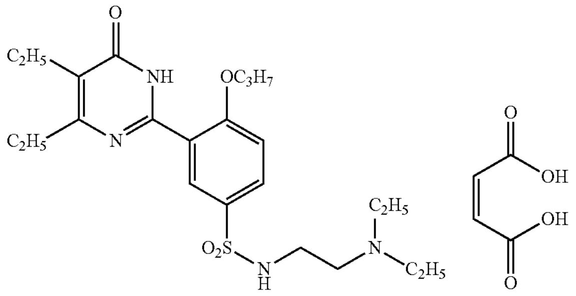

The compound (0.35 g, 1.0 mmol) of preparation example 33 was slowly added into chlorosulfonic acid (5 ml) under ice-bath. The ice-bath was removed, and the reaction mixture was stirred at room temperature for 2 h, and then carefully added dropwise into brash ice to generate a yellowish precipitate, and filtered. The resultant solid was washed with ice water, dissolved in $CH_2Cl_2$ (50 ml), and added dropwise into a $CH_2Cl_2$ solution (30 ml) containing N,N-diethylethylendiamine (0.13 g, 1.1 mmol) and triethylamine (1 ml) under ice-bath. After addition, the stirring continued for 30 min. The organic phase was washed with water (3×20 ml) and saturated saline (20 ml), and distilled off solvent to give an oil. The oil was dissolved in anhydrous ethanol (5 ml), added with maleic acid (0.13 g, 1.1 mmol), and heated to 50° C. to stir for 15 min. The reaction mixture was stirred for 2 h under ice-bath, filtered and dried to give the title compound (0.45 g, total yield of two steps: 77.6%). $^1H$ NMR (DMSO-$d_6$) δ: 8.05 (1H, d), 7.92 (1H, dd), 7.38 (1H, d), 6.04 (2H, s), 4.12 (2H, t), 3.18-3.02 (8H, m), 2.57 (2H, q), 2.46 (2H, q), 1.76 (2H, m), 1.18 (3H, t), 1.16 (3H, t), 1.04 (3H, t), 0.96 (3H, t).

Examples 138~153

According to the same manner as that of example 89, the compound of example 58 was first reacted with thionyl chloride, and the resultant products were reacted with phenylalanine, methyl prolinate, methyl tyrosinate, ethyl tryptophanate, methyl valinate, methyl histidinate, ethyl isoleucinate, lactamine, asparamide, glutamine, serine, arginine, methyl phenylalaninate, methyl lactaminate, methyl leucinate, ethyl lactaminate respectively to obtain the compounds of examples 138~153.

| Example | Structural Formula | Nomenclature and data of 1H-NMR(δ) |
| --- | --- | --- |
| 138 | 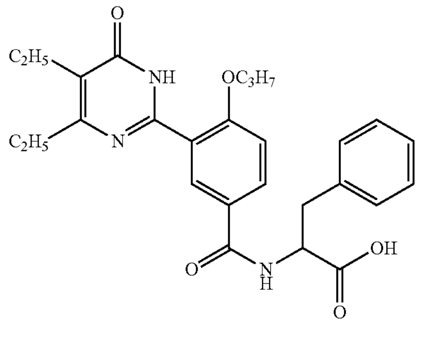 | 2-(3-(4,5-diethyl-1,6-dihydro-6-oxopyrimidin-2-yl)-4-n-propoxybenzamido)-3-phenylpropionic acid (DMSO-$d_6$) δ: 8.09 (1H, d), 7.89 (1H, dd), 7.32-7.08 (6H, m), 4.48 (1H, m), 4.05 (2H, t), 3.21 (1H, dd), 3.04 (1H, dd), 2.57 (2H, q), 2.45 (2H, q), 1.73 (2H, m), 1.18 (3H, t), 1.03 (3H, t), 0.95 (3H, t) |
| 139 | 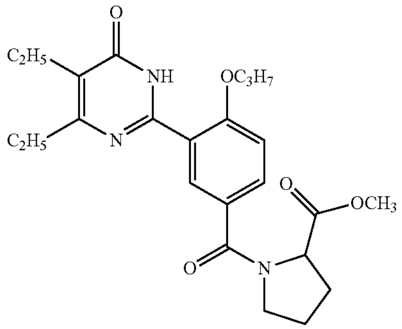 | methyl N-(3-(4,5-diethyl-1,6-dihydro-6-oxopyrimidin-2-yl)-4-n-propoxybenzoylprolinate ($CDCl_3$) δ: 8.76 (1H, d), 7.76 (1H, dd), 7.05 (1H, d), 4.68 (1H, t), 4.20 (2H, t), 3.78 (3H, s), 3.68 (2H, m), 2.67 (2H, q), 2.58 (2H, q), 2.33 (1H, m), 2.01 (5H, m), 1.28 (3H, t), 1.14 (6H, t) |
| 140 | 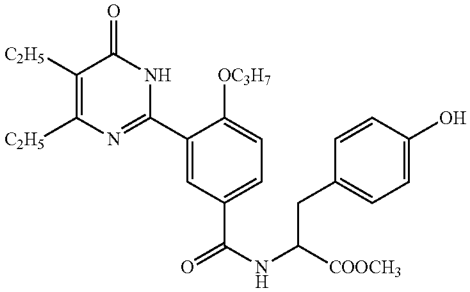 | methyl 2-(3-(4,5-diethyl-1,6-dihydro-6-oxopyrimidin-2-yl)-4-n-propoxybenzamido)-3-(4-hydroxyphenyl)propionate ($CDCl_3$) δ: 11.04 (1H, br), 8.77 (1H, d), 7.89 (1H, dd), 7.06 (1H, d), 7.00 (2H, dd), 6.76 (2H, dd), 5.03 (1H, m), 4.18 (2H, t), 3.78 (3H, s), 3.18 (2H, d), 2.68 (2H, q), 2.59 (2H, q), 1.97 (2H, m), 1.30 (3H, t), 1.14 (3H, t), 1.12 (3H, t) |
| 141 | 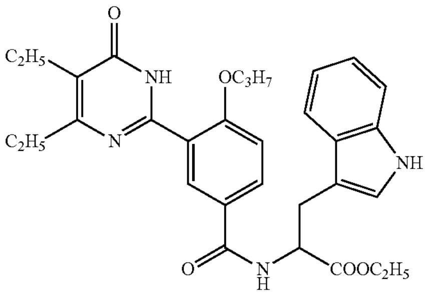 | ethyl 2-3-(4,5-diethyl-1,6-dihydro-6-oxopyrimidin-2-yl)-4-n-propoxybenzamido)-3-(1H-indol-3-yl)propionate ($CDCl_3$) δ: 10.97 (1H, br), 8.82 (1H, d), 8.22 (1H, br), 7.82 (1H, dd), 7.57 (1H, d), 7.35 (1H, d), 7.15 (1H, t), 7.08 (1H, s), 7.05 (1H, t), 7.01 (1H, d), 6.81 (1H, br), 5.10 (1H, m), 4.17 (2H, t), 3.46 (2H, d), 2.68 (2H, q), 2.59 (2H, q), 1.97 (2H, m), 1.28 (3H, t), 1.24 (3H, t), 1.16 (3H, t), 1.12 (3H, t) |

-continued

| Example | Structural Formula | Nomenclature and data of 1H-NMR(δ) |
|---|---|---|
| 142 | 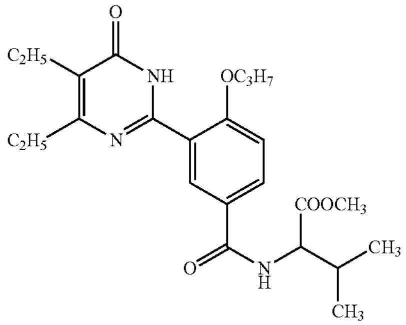 | methyl 2-(3-(4,5-diethyl-1,6-dihydro-6-oxopyrimidin-2-yl)-4-n-propoxybenzamido)-3-methylbutyrate ($CDCl_3$) δ: 11.02 (1H, br), 8.91 (1H, d), 7.98 (1H, dd), 7.09 (1H, d), 6.78 (1H, br), 4.76 (1H, dd), 4.22 (2H, t), 3.78 (3H, s), 2.71 (2H, q), 2.60 (2H, q), 2.30 (1H, m), 2.01 (2H, m), 1.32 (3H, t), 1.15 (6H, t), 1.03 (3H, d), 1.02 (3H, d) |
| 143 | 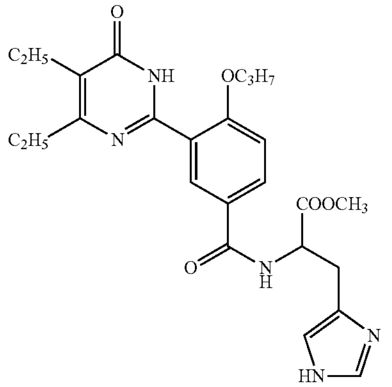 | methyl 2-(3-(4,5-diethyl-1,6-dihydro-6-oxopyrimidin-2-yl)-4-n-propoxybenzamido)-3-(1H-imidazol-4-yl)propionate ($CDCl_3$) δ: 8.94 (1H, d), 8.26 (1H, br), 8.03 (1H, dd), 7.62 (1H, s), 7.06 (1H, dd), 6.87 (1H, s), 4.98 (1H, m), 4.19 (2H, t), 3.71 (3H, s), 3.23 (2H, dd), 2.68 (2H, q), 2.58 (2H, q), 1.98 (2H, m), 1.31 (3H, t), 1.14 (3H, t), 1.13 (3H, t) |
| 144 | 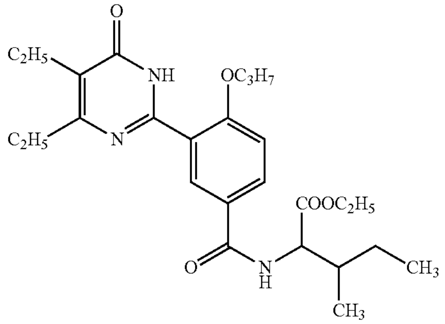 | ethyl 2-3-(4,5-diethyl-1,6-dihydro-6-oxopyrimidin-2-yl)-4-n-propoxybenzamido)-3-methylvalerate ($CDCl_3$) δ: 11.02 (1H, br), 8.89 (1H, d), 7.97 (1H, dd), 7.08 (1H, d), 6.77 (1H, br), 4.79 (1H, dd), 4.23 (4H, m), 2.70 (2H, q), 2.59 (2H, q), 2.00 (3H, m), 1.56 (2H, m), 1.31 (6H, t), 1.15 (6H, t), 0.99 (3H, d), 0.98 (3H, t) |
| 145 | 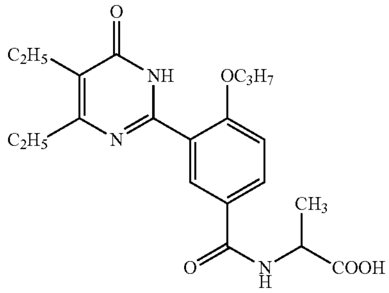 | 2-(3-(4,5-diethyl-1,6-dihydro-6-oxopyrimidin-2-yl)-4-n-propoxybenzamido)propionic acid ($DMSO-d_6$) δ: 8.67 (1H, d), 8.18 (1H, d), 8.04 (1H, dd), 7.24 (1H, d), 4.41 (1H, m), 4.09 (2H, t), 2.59 (2H, q), 2.47 (2H, q), 1.75 (2H, m), 1.39 (3H, d), 1.19 (3H, t), 1.05 (3H, t), 0.96 (3H, t) |

-continued

| Example | Structural Formula | Nomenclature and data of 1H-NMR(δ) |
|---|---|---|
| 146 | 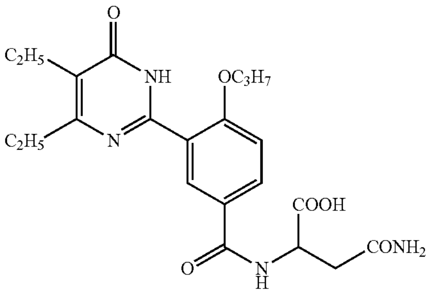 | 2-(3-(4,5-diethyl-1,6-dihydro-6-oxopyrimidin-2-yl)-4-n-propoxybenzamido)-3-aminoformylpropionic acid (DMSO-$d_6$) δ: 8.13 (1H, d), 7.97 (1H, dd), 7.05 (1H, d), 4.71 (1H, m), 4.09 (2H, t), 2.66 (2H, m), 2.58 (2H, q), 2.47 (2H, q), 1.75 (2H, m), 1.19 (3H, t), 1.04 (3H, t), 0.96 (3H, t) |
| 147 | 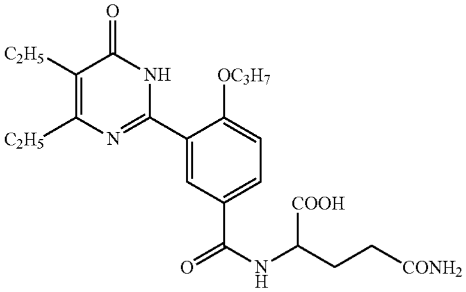 | 2-(3-(4,5-diethyl-1,6-dihydro-6-oxopyrimidin-2-yl)-4-n-propoxybenzamido)-4-aminoformylbutyric acid (DMSO-$d_6$) δ: 8.18 (1H, d), 8.02 (1H, dd), 7.24 (1H, d), 4.34 (1H, m), 4.09 (2H, t), 2.58 (2H, q), 2.47 (2H, q), 2.21 (2H, t), 2.00 (2H, m), 1.75 (2H, m), 1.19 (3H, t), 1.04 (3H, t), 0.96 (3H, t) |
| 148 | 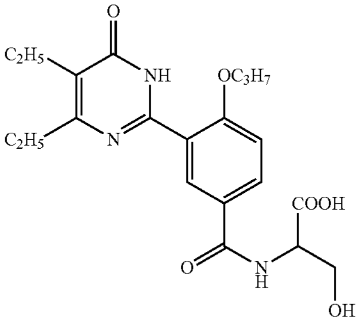 | 2-(3-(4,5-diethyl-1,6-dihydro-6-oxopyrimidin-2-yl)-4-n-propoxybenzamido)-3-hydroxypropionic acid (DMSO-$d_6$) δ: 8.18 (1H, d), 8.03 (1H, dd), 7.24 (1H, d), 4.43 (1H, m), 4.09 (2H, t), 3.77 (2H, d), 2.58 (2H, q), 2.47 (2H, q), 1.75 (2H, m), 1.19 (3H, t), 1.04 (3H, t), 0.96 (3H, t) |
| 149 | 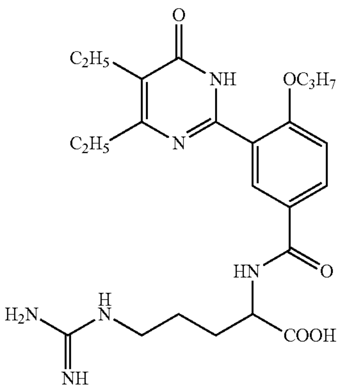 | 2-(3-(4,5-diethyl-1,6-dihydro-6-oxopyrimidin-2-yl)-4-n-propoxybenzamido)-5-guanidylvaleric acid (DMSO-$d_6$) δ: 8.09 (1H, d), 7.92 (1H, dd), 6.97 (1H, d), 4.19 (1H, m), 3.96 (2H, t), 3.04 (2H, m), 2.56 (2H, q), 2.44 (2H, q), 1.82 (2H, m), 1.67 (2H, m), 1.51 (2H, m), 1.17 (3H, t), 1.03 (3H, t), 0.91 (3H, t) |

-continued

| Example | Structural Formula | Nomenclature and data of 1H-NMR(δ) |
|---|---|---|
| 150 | 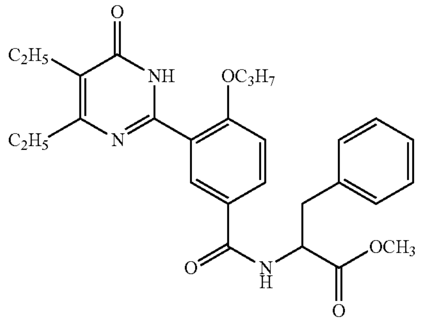 | methyl 2-(3-(4,5-diethyl-1,6-dihydro-6-oxopyrimidin-2-yl)-4-n-propoxybenzamido)-3-phenylpropionate (DMSO-$d_6$) δ: 12.01 (1H, br), 8.84 (1H, d), 8.11 (1H, d), 7.94 (1H, dd), 7.24 (6H, m), 4.64 (1H, m), 4.08 (2H, t), 3.64 (3H, s), 3.16 (1H, dd), 3.08 (1H, dd), 2.58 (2H, q), 2.47 (2H, q), 1.74 (2H, m), 1.20 (3H, t), 1.04 (3H, t), 0.96 (3H, t) |
| 151 | 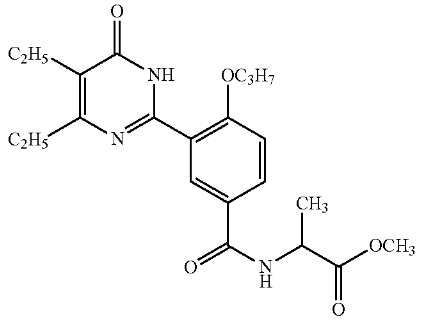 | methyl 2-(3-(4,5-diethyl-1,6-dihydro-6-oxopyrimidin-2-yl)-4-n-propoxybenzamido)propionate ($CDCl_3$) δ: 11.00 (1H, br), 8.87 (1H, d), 7.99 (1H, dd), 7.08 (1H, d), 6.83 (1H, br), 4.80 (1H, m), 4.22 (2H, t), 3.81 (3H, s), 2.70 (2H, q), 2.59 (2H, q), 2.01 (2H, m), 1.55 (3H, d), 1.31 (3H, t), 1.15(6H, t) |
| 152 | 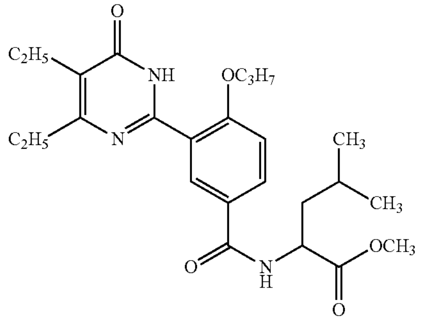 | methyl 2-(3-(4,5-diethyl-1,6-dihydro-6-oxopyrimidin-2-yl)-4-n-propoxybenzamido)-4-methylvalerate ($CDCl_3$) δ: 8.91 (1H, d), 8.00 (1H, dd), 7.09 (1H, d), 4.85 (1H, m), 4.22 (2H, t), 3.77 (3H, s), 2.73 (2H, q), 2.60 (2H, q), 2.01 (2H, m), 1.77 (3H, m), 1.32 (3H, t), 1.16 (3H, t), 1.15 (3H, t), 1.00 (3H, d), 0.99 (3H, d) |
| 153 | 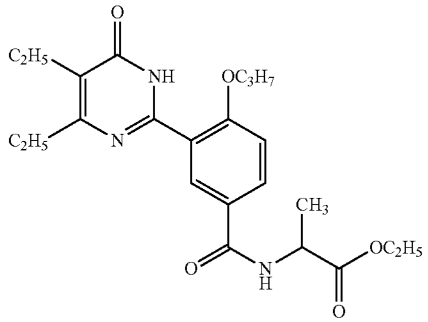 | ethyl 2-(3-(4,5-diethylmethyl-1,6-dihydro-6-oxopyrimidin-2-yl)-4-n-propoxybenzamido)propionate (DMSO-$d_6$) δ: 12.05 (1H, br), 8.76 (1H, d), 8.17 (1H, d), 8.02 (1H, dd), 7.24 (1H, d), 4.44 (1H, m), 4.09 (4H, m), 2.57 (2H, q), 2.47 (2H, q), 1.75 (2H, m), 1.39 (3H, d), 1.18 (6H, t), 1.04 (3H, t), 0.96 (3H, t) |

Examples 154~155

The compounds of examples 154~155 were prepared by reacting the compound of example 151 with N-methylpiperazine and saturated solution of ammonia in ethanol respectively in the same manner as that of example 113.

| Example | Structural Formula | Nomenclature and data of 1H-NMR(δ) |
|---|---|---|
| 154 | 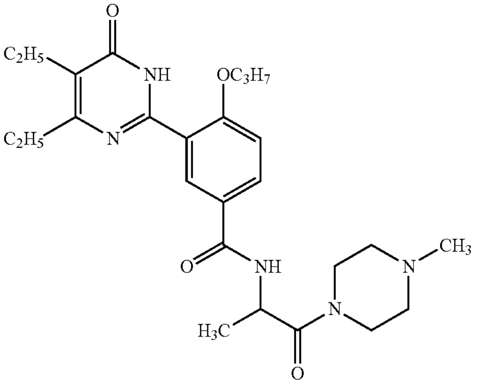 | 3-(4,5-diethyl-1,6-dihydro-6-oxopyrimidin-2-yl)-N-(1-(4-methylpiperazin-l-yl)-1-oxopropan-2-yl)-4-n-propoxybenzamide (DMSO-$d_6$) δ: 11.00 (1H, d), 8.87 (1H, d), 7.95 (1H, dd), 7.41 (1H, d), 7.05 (1H, d), 5.08 (1H, m), 4.20 (2H, t), 3.63 (4H, m), 2.68 (2H, q), 2.58 (2H, q), 2.43 (4H, m), 2.31 (3H, s), 1.99 (2H, m), 1.44 (3H, d), 1.30 (3H, t), 1.14 (3H, t) |
| 155 | 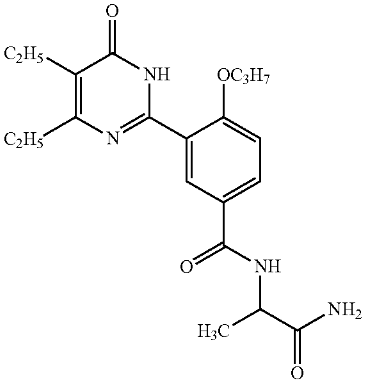 | N-(1-aminoformylethyl)-3-(4,5-diethyl-1,6-dihydro-6-oxo-pyrimidin-2-yl)-4-n-propoxybenzamide ($CDCl_3$) δ: 11.03 (1H, br), 8.74 (1H, d), 7.91 (1H, dd), 7.02 (1H, d), 6.54 (1H, br), 5.81 (1H, br), 4.73 (1H, m), 4.16 (2H, t), 2.66 (2H, q), 2.58 (2H, q), 1.97 (2H, m), 1.54 (3H, d), 1.28 (3H, t), 1.14 (3H, t), 1.12 (3H, t) |

Examples 156~175

According to the same manner as that of Example 89, the compound of example 58 was first reacted with thionyl chloride, and the resultant products were reacted with ammonia water, 2-thienylethylamine, furfurylamine, t-butylamine, isobutylamine, allylamine, 1-(2-pyridyl)piperazine, hydroxylethoxyethylpiperazine, hydroxyethylpiperazine, 1-propanolamine, 2-propanolamine, N-ethylethanolamine, N,N-diethylethylendiamine, homotaurine, taurine, N-methylethanolamine, N-benzylpiperazine, N-methyl-2-(pyrrolidin-1-yl)ethylamine, methyl 5-aminopiperidine-2-carboxylate and N,O-dimethylhydroxylamine respectively, to obtain the compounds of examples 156~175.

| Example | Structural Formula | Nomenclature and data of 1H-NMR(o) |
|---|---|---|
| 156 | 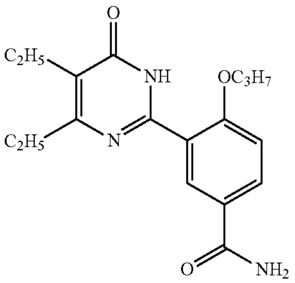 | 3-(4,5-diethyl-1,6-dihydro-6-oxopyrimidin-2-yl)-4-n-propoxybenzamide ($CDCl_3$) δ: 8.85 (1H, d), 8.05 (1H, dd), 7.09 (1H, d), 4.21 (2H, t), 2.70 (2H, q), 2.59 (2H, q), 2.00 (2H, m), 1.30 (3H, t), 1.15 (3H, t), 1.14 (3H, t) |

-continued

| Example | Structural Formula | Nomenclature and data of 1H-NMR(o) |
|---|---|---|
| 157 | 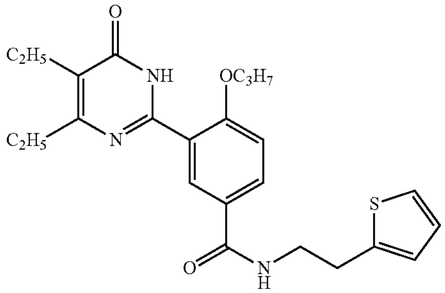 | 3-(4,5-diethyl-1,6-dihydro-6-oxopyrimidin-2-yl)-4-n-propoxy-N-(2-(thien-2-yl)ethyl)benzamide ($CDCl_3$) δ: 11.03 (1H, br), 8.76 (1H, d), 7.97 (1H, dd), 7.18 (1H, d), 7.07 (1H, dd), 6.97 (1H, t), 6.90 (1H, d), 4.20 (2H, t), 3.75 (2H, t), 3.17 (2H, t), 2.68 (2H, q), 2.59 (2H, q), 1.99 (2H, m), 1.30 (3H, t), 1.15 (3H, t), 1.14 (3H, t) |
| 158 | 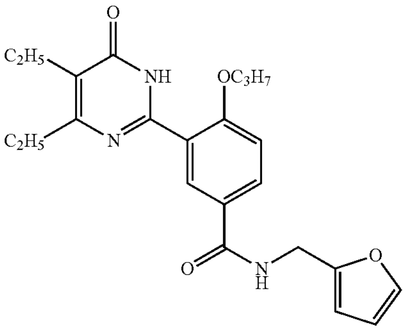 | 3-(4,5-diethyl-1,6-dihydro-6-oxopyrimidin-2-yl)-4-n-propoxy-N-((fur-2-yl)methyl)benzamide ($CDCl_3$) δ: 11.00 (1H, br), 8.81 (1H, d), 8.00 (1H, dd), 7.38 (1H, d), 7.07 (1H, d), 6.64 (1H, br), 6.33 (2H, m), 4.66 (2H, d), 4.20 (2H, t), 2.68 (2H, q), 2.58 (2H, q), 1.99 (2H, m), 1.29 (3H, t), 1.15 (3H, t), 1.14 (3H, t) |
| 159 | 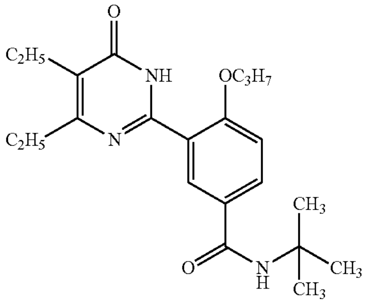 | N-t-butyl-3-(4,5-diethyl-1,6-dihydro-6-oxopyrimidin-2-yl)-4-n-propoxybenzamide ($CDCl_3$) δ: 11.04 (1H, br), 8.76 (1H, d), 7.94 (1H, dd), 7.06 (1H, d), 4.20 (2H, t), 4.15 (2H, q), 2.75 (2H, t), 2.71 (2H, q), 2.59 (2H, q), 2.00 (2H, m), 1.49 (9H, s), 1.31 (3H, t), 1.16 (3H, t), 1.15 (3H, t) |
| 160 | 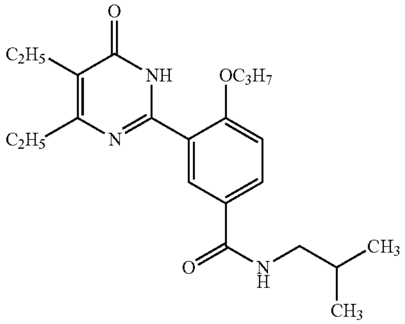 | 3-(4,5-diethyl-1,6-dihydro-6-oxopyrimidin-2-yl)-N-isobutyl-4-n-propoxybenzamide ($CDCl_3$) δ: 11.03 (1H, br), 8.80 (1H, d), 7.98 (1H, dd), 7.07 (1H, d), 6.38 (1H, br), 4.20 (2H, t), 3.31 (2H, t), 2.69 (2H, q), 2.59 (2H, q), 1.97 (3H, m), 1.30 (3H, t), 1.15 (3H, t), 1.14 (3H, t), 1.00 (6H, d) |
| 161 | 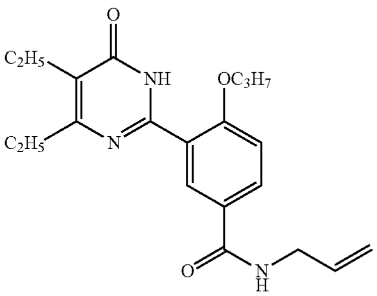 | 3-(4,5-diethyl-1,6-dihydro-6-oxopyrimidin-2-yl)-N-allyl-4-n-propoxybenzamide ($CDCl_3$) δ: 11.02 (1H, br), 8.81 (1H, d), 8.00 (1H, dd), 7.08 (1H, d), 6.41 (1H, br), 5.97 (1H, m), 5.24 (2H, dd), 4.21 (2H, t), 4.12 (2H, t), 2.69 (2H, q), 2.59 (2H, q), 2.00 (2H, m), 1.30 (3H, t), 1.15 (6H, t) |

-continued

| Example | Structural Formula | Nomenclature and data of 1H-NMR(o) |
|---|---|---|
| 162 | 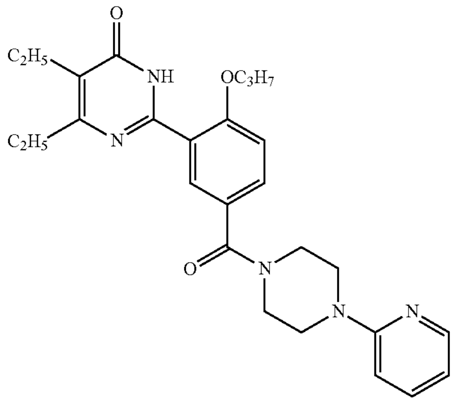 | (4-(pyrid-2-yl)piperazin-1-yl)(3-(4,5-diethyl-1,6-dihydro-6-oxopyrimidin-2-yl)-4-n-propoxybenzophenone ($CDCl_3$) δ: 11.08 (1H, br), 8.62 (1H, d), 8.20 (1H, dd), 7.61 (1H, dd), 7.53 (1H, t), 7.08 (1H, d), 6.69 (1H, t), 6.67 (1H, d), 4.22 (2H, t), 3.77 (4H, t), 3.63 (4H, t), 2.65 (2H, q), 2.58 (2H, q), 2.01 (2H, m), 1.27 (3H, t), 1.16 (3H, t), 1.14 (3H, t) |
| 163 | 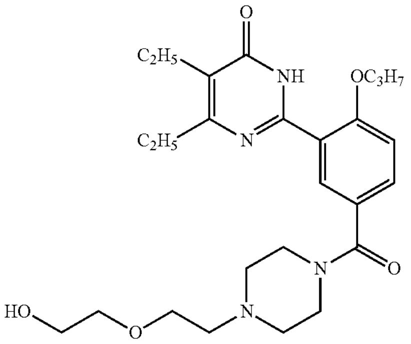 | (4-(hydroxylethoxyethyl)piperazin-1-yl)(3-(4,5-diethyl-1,6-dihydro-6-oxopyrimidin-2-yl)-4-n-propoxybenzophenone ($CDCl_3$) δ: 11.08 (1H, br), 8.58 (1H, d), 7.56 (1H, dd), 7.05 (1H, d), 4.20 (2H, t), 3.90-3.50 (10H, m), 2.70-2.55 (10H, m), 2.00 (2H, m), 1.27 (3H, t), 1.14 (3H, t), 1.13 (3H, t) |
| 164 | 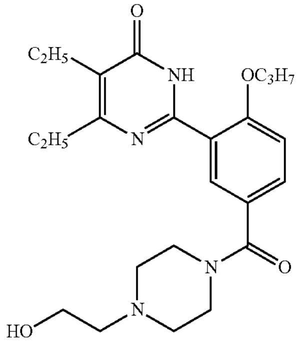 | (4-(hydroxylethyl)piperazin-l-yl)(3-(4,5-diethyl-1,6-dihydro-6-oxopyrimidin-2-yl)-4-n-propoxybenzophenone ($CDCl_3$) δ: 11.06 (1H, br), 8.59 (1H, d), 7.58 (1H, dd), 7.07 (1H, d), 4.20 (2H, t), 3.80 (4H, t), 3.66 (2H, t), 2.70-2.55 (10H, m), 2.01 (2H, m), 1.28 (3H, t), 1.15 (6H, t) |
| 165 | 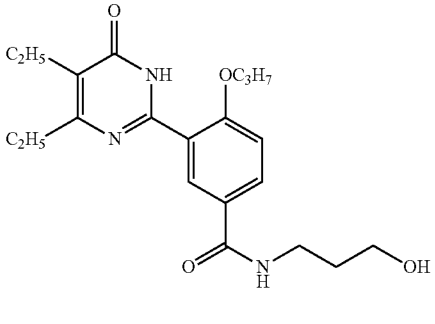 | 3-(4,5-diethyl-1,6-dihydro-6-oxopyrimidin-2-yl)-N-(3-hydroxylpropyl)-4-n-propoxybenzamide ($CDCl_3$) δ: 10.94 (1H, br), 8.76 (1H, d), 7.97 (1H, dd), 7.01 (1H, d), 4.15 (2H, t), 3.76 (2H, t), 3.66 (2H, t), 3.33 (1H, br), 2.65 (2H, q), 2.57 (2H, q), 1.96 (2H, m), 1.84 (2H, m), 1.28 (3H, t), 1.14 (3H, t), 1.12 (3H, t) |

-continued

| Example | Structural Formula | Nomenclature and data of 1H-NMR(o) |
|---|---|---|
| 166 | 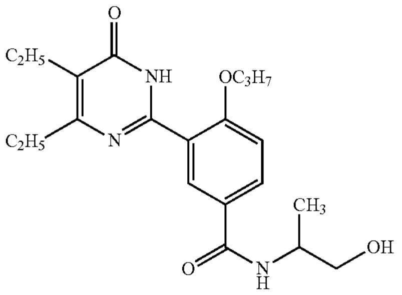 | 3-(4,5-diethyl-1,6-dihydro-6-oxopyrimidin-2-yl)-N-(1-hydroxyprop-2-yl)-4-n-propoxybenzamide ($CDCl_3$) δ: 8.75 (1H, d), 7.94 (1H, dd), 6.97 (1H, d), 4.28 (1H, m), 4.10 (2H, t), 3.84 (1H, dd), 3.69 (1H, dd), 2.66 (2H, q), 2.57 (2H, q), 1.92 (2H, m), 1.33 (3H, d), 1.28 (3H, t), 1.16 (3H, t), 1.10 (3H, t) |
| 167 | 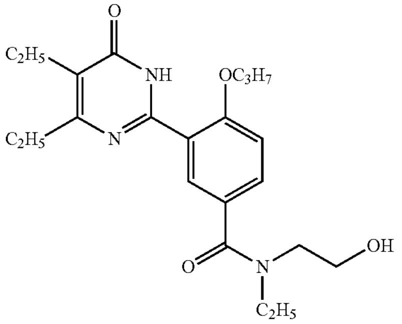 | N-ethyl-3-(4,5-diethyl-1,6-dihydro-6-oxopyrimidin-2-yl)-N-(2-hydroxyethyl)-4-n-propoxybenzamide ($CDCl_3$) δ: 11.14 (1H, br), 8.62 (1H, d), 7.61 (1H, dd), 7.07 (1H, d), 4.20 (2H, t), 3.90 (2H, t), 3.71 (2H, t), 3.42 (2H, q), 2.66 (2H, q), 2.58 (2H, q), 2.00 (2H, m), 1.27 (3H, t), 1.26 (3H, t), 1.15 (3H, t), 1.14 (3H, t) |
| 168 | 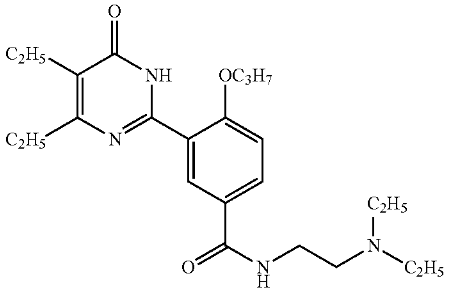 | 3-(4,5-diethyl-1,6-dihydro-6-oxopyrimidin-2-yl)-N-(2-diethylaminoethyl)-4-n-propoxybenzamide ($CDCl_3$) δ: 11.08 (1H, br), 8.84 (1H, d), 8.04 (1H, dd), 7.09 (1H, d), 4.22 (2H, t), 3.49 (2H, m), 2.71-2.53 (10H, m), 2.01 (2H, m), 1.29 (3H, t), 1.15 (6H, t), 1.07 (6H, t) |
| 169 | 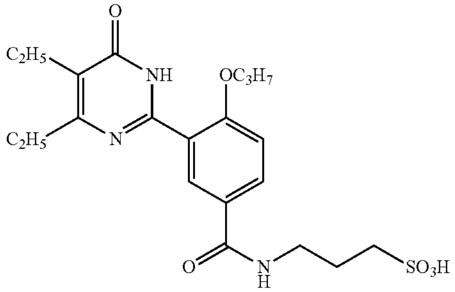 | 3-(3-(4,5-diethyl-1,6-dihydro-6-oxopyrimidin-2-yl)-4-n-propoxybenzamido)propyl-1-sulfonic acid (DMSO-$d_6$) δ: 8.22 (1H, d), 8.13 (1H, dd), 7.33 (1H, d), 4.11 (2H, t), 3.32 (2H, t), 2.68 (2H, q), 2.57 (4H, m), 1.83 (2H, m), 1.73 (2H, m), 1.22 (3H, t), 1.08 (3H, t), 0.93 (3H, t) |
| 170 | 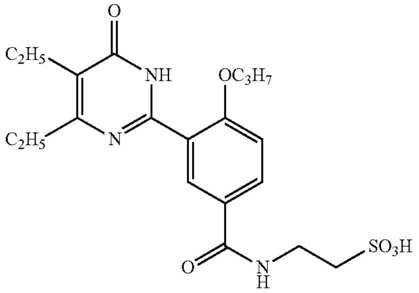 | 2-(3-(4,5-diethyl-1,6-dihydro-6-oxopyrimidin-2-yl)-4-n-propoxybenzamido)ethylsulfonic acid (DMSO-$d_6$) δ: 8.17 (1H, d), 8.06 (1H, dd), 7.35 (1H, d), 4.11 (2H, t), 3.53 (2H, t), 2.68 (4H, m), 2.58 (2H, q), 1.73 (2H, m), 1.22 (3H, t), 1.08 (3H, t), 0.93 (3H, t) |

-continued

| Example | Structural Formula | Nomenclature and data of 1H-NMR(o) |
|---|---|---|
| 171 | 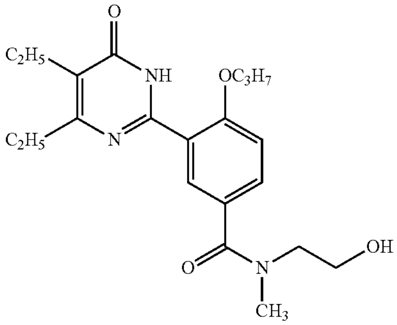 | 3-(4,5-diethyl-1,6-dihydro-6-oxopyrimidin-2-yl)-N-(2-hydroxyethyl)-N-methyl-4-n-propoxybenzamide ($CDCl_3$) δ: 11.08 (1H, br), 8.60 (1H, d), 7.62 (1H, dd), 7.05 (1H, d), 4.19 (2H, t), 3.91 (2H, t), 3.74 (2H, t), 3.12 (3H, s), 2.66 (2H, q), 2.58 (2H, q), 2.00 (2H, m), 1.27 (3H, t), 1.14 (6H, t) |
| 172 | 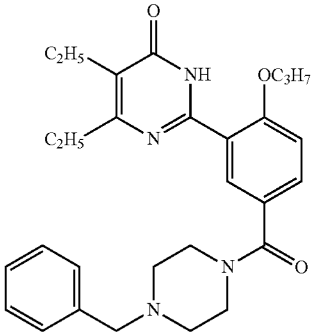 | (4-benzylpiperazin-1-yl)(3-(4,5-diethyl-1,6-dihydro-6-oxopyrimidin-2-yl)-4-n-propoxybenzophenone ($CDCl_3$) δ: 11.08 (1H, br), 8.58 (1H, d), 7.57 (1H, dd), 7.31 (5H, m), 7.05 (1H, d), 4.19 (2H, t), 3.78 (4H, br), 3.55 (2H, s), 2.66 (2H, q), 2.58 (2H, q), 2.50 (4H, br), 2.00 (2H, m), 1.29 (3H, t), 1.14 (6H, t) |
| 173 | 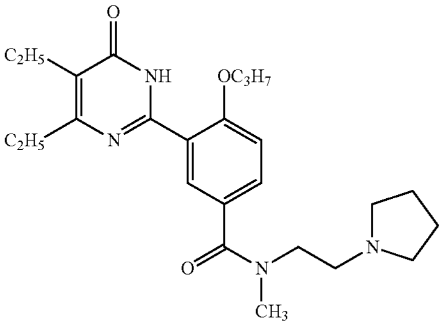 | 3-(4,5-diethyl-1,6-dihydro-6-oxopyrimidin-2-yl)-N-methyl-N-(2-(pyrrolidin-1-yl)ethyl)-4-n-propoxybenzamide ($DMSO-d_6$) δ: 7.84 (1H, d), 7.79 (1H, dd), 7.26 (1H, d), 4.09 (2H, t), 3.79 (2H, t), 3.49 (2H, t), 3.41 (2H, t), 3.06 (2H, t), 3.02 (3H, s), 2.63 (2H, q), 2.54 (2H, q), 1.99 (2H, m), 1.88 (2H, m), 1.74 (2H, m), 1.19 (3H, t), 1.05 (3H, t), 0.95 (3H, t) |
| 174 | 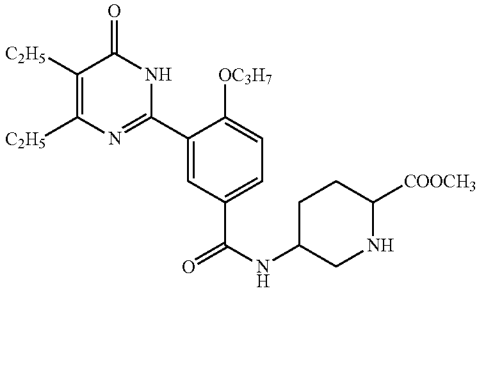 | methyl 5-(3-(4,5-diethyl-1,6-dihydro-6-oxopyrimidin-2-yl)-4-n-propoxybenzamido)piperidine-2-formate ($DMSO-d_6$) δ: 8.16 (1H, d), 8.11 (1H, d), 7.97 (1H, dd), 7.20 (1H, d), 4.07 (2H, t), 3.78 (1H, br), 3.63 (3H, s), 3.22 (1H, m), 3.05 (1H, m), 2.57 (2H, q), 2.46 (2H, q), 2.40 (2H, m), 1.94 (2H, m), 1.73 (2H, m), 1.47 (2H, m), 1.18 (3H, t), 1.03 (3H, t), 0.95 (3H, t) |

-continued

| Example | Structural Formula | Nomenclature and data of 1H-NMR(o) |
| --- | --- | --- |
| 175 | 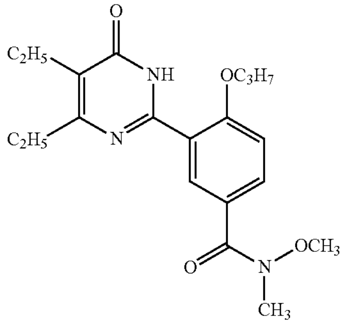 | 3-(4,5-diethyl-1,6-dihydro-6-oxopyrimidin-2-yl)-N-methoxy-N-methyl-4-n-propoxybenzamide ($CDCl_3$) δ: 11.08 (1H, br), 8.91 (1H, d), 7.87 (1H, dd), 7.05 (1H, d), 4.21 (2H, t), 3.62 (3H, s), 3.38 (3H, s), 2.66 (2H, q), 2.59 (2H, q), 2.01 (2H, m), 1.28 (3H, t), 1.15 (3H, t), 1.14 (3H, t) |

Example 176

5,6-Diethyl-2-[2-(3-methoxy-n-propoxy)-5-(4-methyl-1-piperazinylsulfonyl)phenyl]pyrimid-4(3H)-one

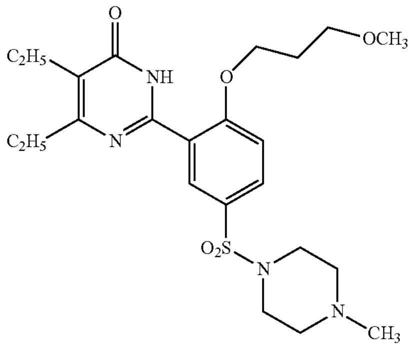 [SMILES: CCc1nc(-c2cc(S(=O)(=O)N3CCN(C)CC3)ccc2OCCCOC)[nH]c(=O)c1CC]

According to the same manner as that of example 10, the compound of preparation example 36 was first chlorosulfonated, and then reacted with N-methylpiperazine to obtain the title compound. $^1H$ NMR ($CDCl_3$) δ: 11.08 (1H, br), 8.78 (1H, d), 7.83 (1H, dd), 7.14 (1H, d), 4.38 (2H, t), 3.65 (2H, t), 3.40 (3H, s), 3.10 (4H, t), 2.66 (2H, q), 2.59 (2H, q), 2.53 (4H, t), 2.30 (3H, s), 2.22 (2H, m), 1.27 (3H, t), 1.15 (3H, t).

Example 177

2-Chloro-N-3-(4,5-diethyl-1,6-dihydro-6-oxopyrimidin-2-yl)-4-n-propoxyphenyl)acetamide

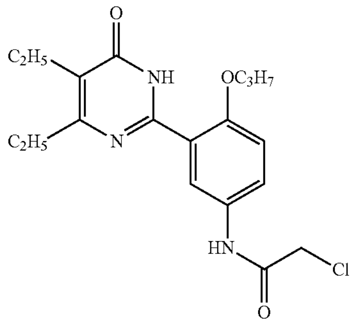

The compound (0.74 g, 2 mmol) of example 34 was dissolved in dichloromethane (20 ml), added with triethylamine (2 ml), followed by slow addition of chloroacetyl chloride (0.23 g, 2.05 mmol) under ice water bath. After stirred for 0.5 h, the reaction mixture was washed with water (10 ml), 1N HCl (5 ml), saturated sodium bicarbonate solution (10 ml) and saturated saline respectively. The organic phase was dried with anhydrous $Na_2SO_4$ and concentrated. The resultant oil was recrystallized from ethyl acetate-petroleum ether to give the title compound (0.71 g, yield: 94%). $^1H$ NMR ($CDCl_3$) δ: 11.16 (1H, br), 9.09 (1H, br), 8.27 (1H, d), 8.00 (1H, dd), 7.01 (1H, d), 4.15 (2H, t), 3.18 (2H, s), 2.68 (2H, q), 2.58 (2H, q), 1.97 (2H, m), 1.31 (3H, t), 1.15 (3H, t), 1.13 (3H, t).

Example 178

2-(Dimethylamino)-N-3-(4,5-diethyl-1,6-dihydro-6-oxopyrimidin-2-yl)-4-n-propoxyphenyl)acetamide

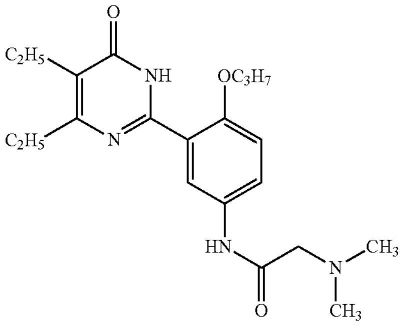

The compound (0.38 g, 1 mmol) of example 177 was suspended in a 33% dimethylamine solution (20 ml), sealed into a tube, and heated to 60° C. to stir for 10 h. The reaction mixture was concentrated to dryness, washed with water and dried. The resultant solid was recrystallized from ethyl acetate to obtain the title compound (0.36 g, yield: 93.2%). $^1H$ NMR (DMSO-$d_6$) δ: 11.81 (1H, br), 9.82 (1H, br), 8.03 (1H, d), 7.78 (1H, dd), 7.12 (1H, d), 4.02 (2H, t), 3.09 (2H, s), 2.57 (2H, q), 2.46 (2H, q), 2.29 (6H, s), 1.74 (2H, m), 1.20 (3H, t), 1.04 (3H, t), 0.97 (3H, t).

Examples 179~482

The title compounds were prepared by reacting the compound of example 77 with N-methylpiperazine, morpholine, piperidine and trimethyl phosphite respectively in the same manner as that of example 178.

| Example | Structural Formula | Nomenclature and data of 1H-NMR(δ) |
|---|---|---|
| 179 | 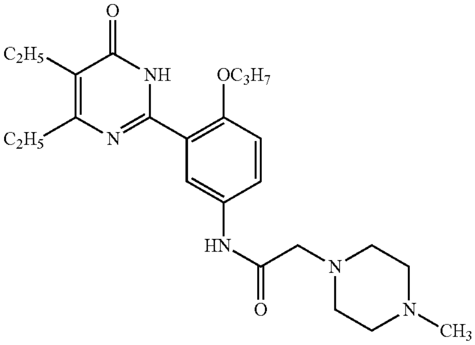 | N-(3-(4,5-diethyl-1,6-dihydro-6-oxopyrimidin-2-yl)-4-n-propoxyphenyl)-2-(4-methylpiperazin-1-yl)acetamide ($CDCl_3$) δ: 11.17 (1H, br), 9.10 (1H, br), 8.27 (1H, d), 7.99 (1H, dd), 7.00 (1H, d), 4.15 (2H, t), 3.16 (2H, s), 2.80-2.50 (12H, m), 2.36 (3H, s), 1.97 (2H, m), 1.31 (3H, t), 1.14 (3H, t), 1.13 (3H, t) |
| 180 | 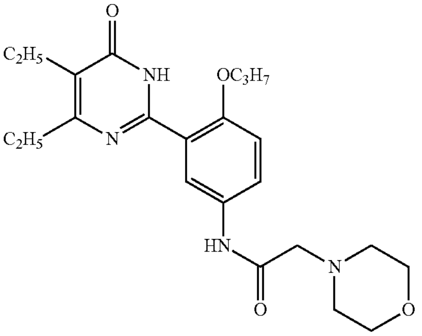 | N-(3-(4,5-diethyl-1,6-dihydro-6-oxopyrimidin-2-yl)-4-n-propoxyphenyl)-2-morpholinyl)acetamide ($CDCl_3$) δ: 11.16 (1H, br), 9.09 (1H, br), 8.27 (1H, d), 8.00 (1H, dd), 7.01 (1H, d), 4.15 (2H, t), 3.81 (4H, t), 3.18 (2H, s), 2.68 (2H, q), 2.66 (4H, t), 2.58 (2H, q), 1.97 (2H, m), 1.31 (3H, t), 1.15 (3H, t), 1.13 (3H, t) |
| 181 | 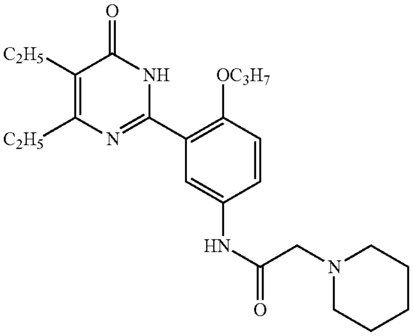 | N-(3-(4,5-diethyl-1,6-dihydro-6-oxopyrimidin-2-yl)-4-n-propoxyphenyl)-2-(piperid-1-yl)acetamide ($CDCl_3$) δ: 11.17 (1H, br), 9.27 (1H, br), 8.28 (1H, d), 7.99 (1H, dd), 7.01 (1H, d), 4.15 (2H, t), 3.10 (2H, s), 2.68 (2H, q), 2.59 (2H, q), 2.56 (4H, t), 1.97 (2H, m), 1.66 (4H, m), 1.50 (2H, m), 1.31 (3H, t), 1.15 (3H, t), 1.13 (3H, t) |
| 182 | 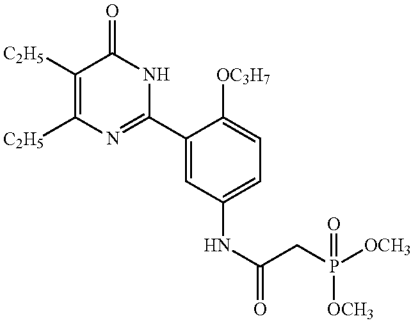 | dimethyl (3-(4,5-diethyl-1,6-dihydro-6-oxopyrimidin-2-yl)-4-n-propoxyphenylaminoformyl)methylphosphate ($CDCl_3$) δ: 11.10 (1H, br), 8.87 (1H, br), 8.34 (1H, d), 7.87 (1H, dd), 6.93 (1H, d), 4.11 (2H, t), 3.85 (6H, d), 3.07 (2H, d), 2.65 (2H, q), 2.58 (2H, q), 1.96 (2H, m), 1.27 (3H, t), 1.14 (3H, t), 1.12 (3H, t) |

Examples 183~188

The compounds of examples 183~188 were prepared by reacting the compound of example 42 with isobutyryl chloride, isovaleryl chloride, phenylacetyl chloride, benzoyl chloride and ethyl succinyl chloride and pyroglutamyl chloride respectively in the same manner as that of example 50.

| Example | Structural Formula | Nomenclature and data of 1H-NMR(δ) |
|---|---|---|
| 183 | 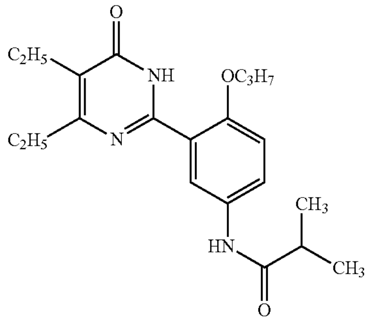 | N-(3-(4,5-diethyl-1,6-dihydro-6-oxopyrimidin-2-yl)-4-n-propoxyphenyl)isobutyramide ($CDCl_3$) δ: 8.21 (1H, d), 8.09 (1H, dd), 7.33 (1H, br), 6.99 (1H, d), 4.14 (2H, t), 2.66 (2H, q), 2.58 (2H, q), 2.53 (1H, q), 1.97 (2H, m), 1.29 (3H, t), 1.27 (6H, d), 1.15 (3H, t), 1.13 (3H, t) |
| 184 | 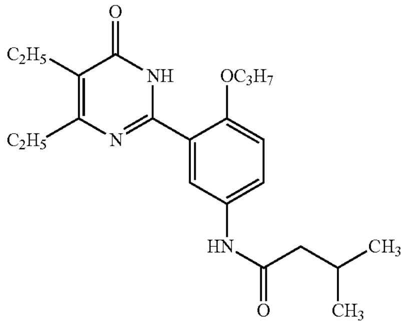 | N-(3-(4,5-diethyl-1,6-dihydro-6-oxopyrimidin-2-yl)-4-n-propoxyphenyl)-3-methylbutyramide ($CDCl_3$) δ: 8.22 (1H, d), 8.07 (1H, dd), 7.39 (1H, br), 6.99 (1H, d), 4.13 (2H, t), 2.66 (2H, q), 2.58 (2H, q), 2.23 (2H, d), 2.20 (1H, m), 1.96 (2H, m), 1.28 (3H, t), 1.14 (3H, t), 1.12 (3H, t), 1.02 (6H, d) |
| 185 | 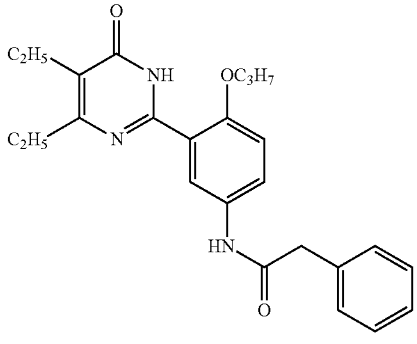 | N-(3-(4,5-diethyl-1,6-dihydro-6-oxopyrimidin-2-yl)-4-n-propoxyphenyl)-2-phenylacetamide ($CDCl_3$) δ: 8.11 (1H, d), 7.93 (1H, dd), 7.37 (5H, m), 6.96 (1H, d), 4.11 (2H, t), 3.75 (2H, s), 2.64 (2H, q), 2.57 (2H, q), 1.95 (2H, m), 1.26 (3H, t), 1.13 (3H, t), 1.11 (3H,t) |
| 186 | 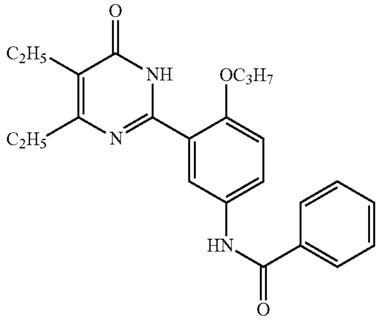 | N-(3-(4,5-diethyl-1,6-dihydro-6-oxopyrimidin-2-yl)-4-n-propoxyphenyl)benzamide ($CDCl_3$) δ: 8.37 (1H, d), 8.11 (1H, dd), 8.04 (1H, br), 7.91 (2H, d), 7.52 (3H, m), 7.05 (1H, d), 4.17 (2H, t), 2.67 (2H, q), 2.58 (2H, q), 1.98 (2H, m), 1.29 (3H, t), 1.15 (3H, t), 1.14 (3H, t) |

-continued

| Example | Structural Formula | Nomenclature and data of 1H-NMR(δ) |
|---|---|---|
| 187 | 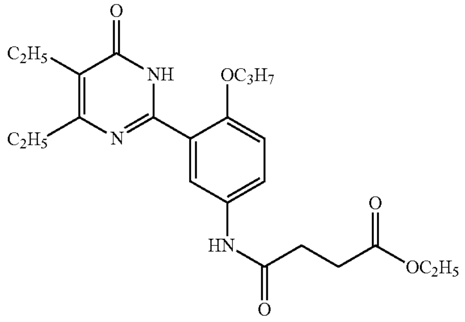 | ethyl 3-(3-(4,5-diethyl-1,6-dihydro-6-oxopyrimidin-2-yl)-4-n-propoxyphenylaminoformyl)propionate ($CDCl_3$) δ: 8.26 (1H, d), 7.99 (1H, dd), 7.66 (1H, br), 6.98 (1H, d), 4.18 (2H, t), 4.15 (2H, q), 2.75 (2H, t), 2.66 (4H, m), 2.58 (2H, q), 1.96 (2H, m), 1.30 (3H, t), 1.27 (3H, t), 1.15 (3H, t), 1.12 (3H, t) |
| 188 | 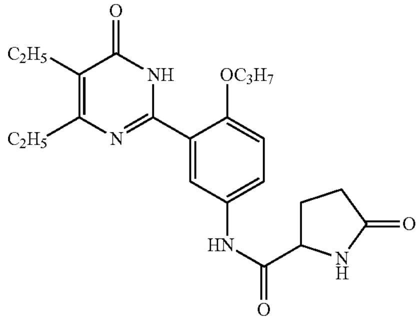 | N-(3-(4,5-diethyl-1,6-dihydro-6-oxopyrimidin-2-yl)-4-n-propoxyphenyl)-5-oxopyrrolidine-2-formamide (DMSO-$d_6$) δ: 10.13 (1H, br), 8.02 (1H, d), 7.97 (1H, dd), 7.15 (1H, d), 4.16 (1H, dd), 4.03 (2H, t), 2.56 (2H, q), 2.46 (2H, q), 2.39-1.92 (4H, m), 1.75 (2H, m), 1.19 (3H, t), 1.03 (3H, t), 0.97 (3H, t), |

Examples 189~193

According to the same manner as those of example 106 and example 107, the compound of example 42 was reacted with N-Boc-leucine, N-Boc-tryptophan, N-Boc-glutamine, N-Boc-threonine and N-Boc-serine respectively, and then removed the Boc-protecting group and acetylated to obtain the compounds of examples 189~193.

| Example | Structural Formula | Nomenclature and data of 1H-NMR(δ) |
|---|---|---|
| 189 | 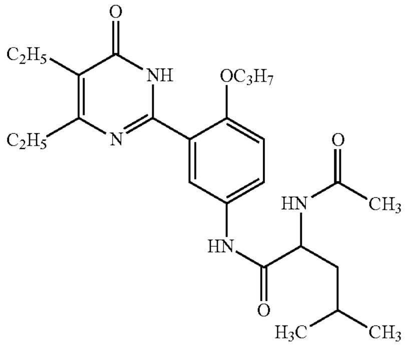 | 2-acetamido-N-3-(4,5-diethyl-1,6-dihydro-6-oxopyrimidin-2-yl)-4-n-propoxyphenyl)-4-methylvaleramide ($CDCl_3$) δ: 8.99 (1H, br), 8.34 (1H, d), 7.91 (1H, dd), 6.94 (1H, d), 6.39 (1H, br), 4.70 (1H, m), 4.11 (2H, t), 2.75 (2H, t), 2.65 (2H, q), 2.58 (2H, q), 2.07 (3H, s), 1.95 (2H, m), 1.82-1.56 (3H, m), 1.27 (3H, t), 1.14 (3H, t), 1.11 (3H, t), 0.94 (6H, d) |
| 190 | 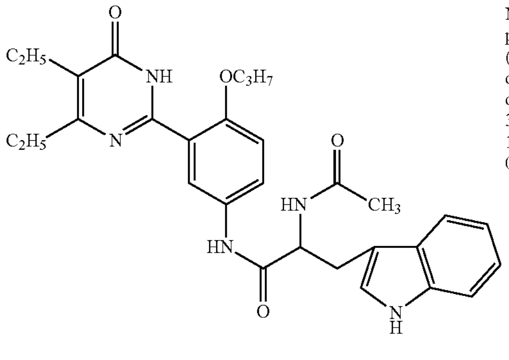 | N-(3-(4,5-diethyl-1,6-dihydro-6-oxopyrimidin-2-yl)-4-n-propoxyphenyl)-2-acetamido-3-(1H-indol-3-yl)propionamide (DMSO-$d_6$) δ: 10.17 (1H, br), 8.02 (1H, d), 7.74 (1H, dd), 7.64 (1H, d), 7.31 (1H, d), 7.16 (1H, s), 7.13 (1H, d), 7.05 (1H, t), 6.97 (1H, t), 4.67 (1H, dd), 4.02 (2H, t), 3.15 (1H, dd), 2.98 (1H, dd), 2.57 (2H, q), 2.46 (2H, q), 1.81 (3H, s), 1.74 (2H, m), 1.20 (3H, t), 1.04 (3H, t), 0.97(3H, t) |

-continued

| Example | Structural Formula | Nomenclature and data of 1H-NMR(δ) |
|---|---|---|
| 191 | 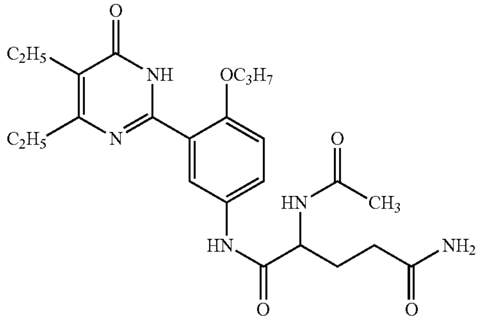 | 2-acetamido-N-(3-(4,5-diethyl-1,6-dihydro-6-oxopyrimidin-2-yl)-4-n-propoxyphenyl)glutaramide (DMSO-$d_6$) δ: 8.05 (1H, d), 7.76 (1H, dd), 7.13 (1H, d), 4.32 (1H, m), 4.02 (2H, t), 2.56 (2H, q), 2.45 (2H, q), 2.13 (2H, m), 1.91 (2H, m), 1.87 (3H, s), 1.74 (2H, m), 1.19 (3H, t), 1.03 (3H, t), 0.96 (3H, t) |
| 192 | 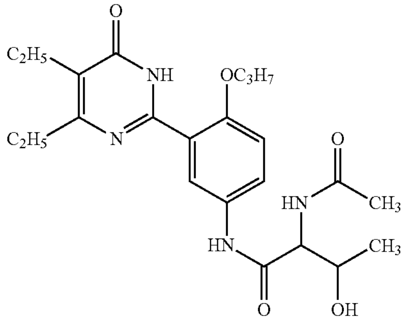 | 2-acetamido-N-(3-(4,5-diethyl-1,6-dihydro-6-oxopyrimidin-2-yl)-4-n-propoxyphenyl)-3-hydroxybutyramide (DMSO-$d_6$) δ: 9.95 (1H, br), 8.02 (1H, d), 7.75 (1H, dd), 7.14 (1H, d), 4.30 (1H, d), 4.02 (3H, m), 2.57 (2H, q), 2.46 (2H, q), 1.92 (3H, s), 1.74 (2H, m), 1.19 (3H, t), 1.08 (3H, d), 1.03 (3H, t), 0.96 (3H, t) |
| 193 | 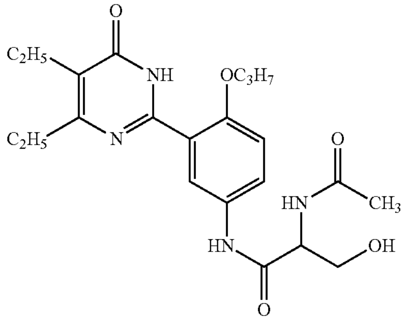 | 2-acetamido-N-(3-(4,5-diethyl-1,6-dihydro-6-oxopyrimidin-2-yl)-4-n-propoxyphenyl)-3-hydroxypropionamide (DMSO-$d_6$) δ: 10.05 (1H, br), 8.07 (1H, d), 8.06 (1H, d), 7.76 (1H, dd), 7.13 (1H, d), 4.42 (1H, m), 4.03 (2H, t), 3.61 (2H, d), 2.56 (2H, q), 2.45 (2H, q), 1.74 (2H, m), 1.19 (3H, t), 1.03 (3H, t), 0.97 (3H, t) |

Example 194

2-(3-(4,5-Diethyl-1,6-dihydro-6-oxopyrimidin-2-yl)-4-n-propoxyphenylaminoformyl)-2-acetamidoethyl acetate

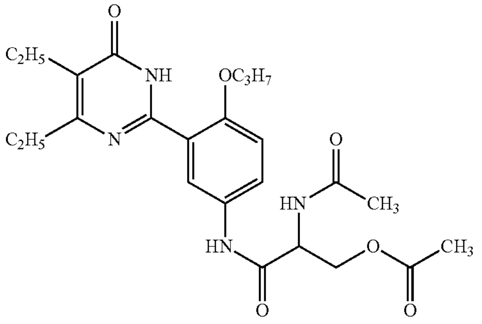

At room temperature, the compound (0.21 g, 0.5 mmol) of example 193 was dissolved in dichloromethane (10 ml), and added with pyridine (40 mg, 0.5 mmol) and acetic anhydride (51 mg, 0.5 mmol). 0.5 h later, TLC showed that the reaction was complete. The reaction mixture was washed with 1N hydrochloric acid (2 ml), water (10 ml) and saturated saline (10 ml) respectively. The organic layer was dried with anhydrous sodium sulfate, and concentrated. The residue was passed through a silica gel column to give the white title compound (175 mg, yield: 74%). $^1$H NMR ($CDCl_3$) δ: 9.49 (1H, br), 8.33 (1H, d), 7.89 (1H, dd), 6.97 (1H, d), 6.92 (1H, d), 5.11 (1H, m), 4.51 (1H, dd), 4.39 (1H, dd), 4.08 (2H, t), 2.60 (2H, q), 2.55 (2H, q), 2.12 (3H, s), 2.06 (3H, s), 1.92 (2H, m), 1.23 (3H, t), 1.12 (3H, t), 1.09 (3H, t)

Example 195

5,6-Diethyl-2-(5-(ethylamino)-2-n-propoxyphenyl) pyrimid-4(3H)-one

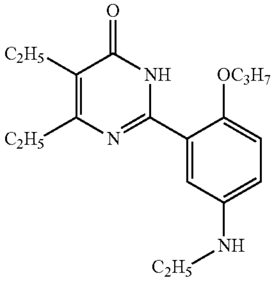

The compound (2.2 g, 7.3 mmol) of example 42 was dissolved in 50 ml of 80% acetonitrile aqueous solution, and added with 0.14 g of 5% Pd/C and 5 g of ammonium formate, followed by stirring at room temperature for 20 h under nitrogen atmosphere. The reaction mixture was filtered off Pd/C and distilled off the solvent. The residue was dissolved in $CH_2Cl_2$ (50 ml), washed with water (50 ml) and saturated saline (50 ml), dried with anhydrous $Na_2SO_4$, and concentrated to dryness to give a white solid crude, which was passed through a silica gel column (eluant: 10% petroleumether-ethyl acetate) to afford the title compound (1.9 g, yield: 79%). $^1H$ NMR ($CDCl_3$) δ: 8.38 (1H, d), 7.33 (1H, dd), 7.04 (1H, d), 4.19 (2H, t), 4.04 (2H, q), 2.66 (2H, q), 2.59 (2H, q), 2.01 (2H, m), 1.28 (3H, t), 1.19 (3H, t), 1.15 (3H, t), 1.06 (3H, t).

Examples 196~197

The compounds of examples 196 and 197 were prepared by reacting the compound of example 195 with propionyl chloride and ethyl oxalyl monochloride respectively in the same manner as that of example 50.

| Example | Structural Formula | Nomenclature and data of 1H-NMR(δ) |
|---|---|---|
| 196 | 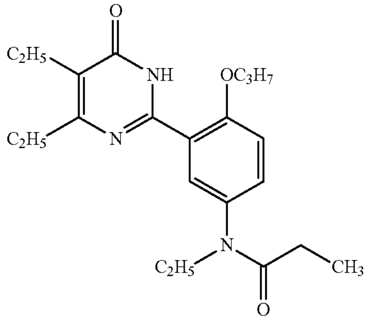 | N-ethyl-N-(3-(4,5-diethyl-1,6-dihydro-6-oxopyrimidin-2-yl)-4-n-propoxyphenyl)propionamide ($DMSO-d_6$) δ: 11.94 (1H, br), 7.55 (1H, d), 7.40 (1H, dd), 7.21 (1H, d), 4.06 (2H, t), 3.61 (2H, q), 2.55 (2H, q), 2.45 (2H, q), 1.96 (2H, q), 1.75 (2H, m), 1.17 (3H, t), 1.03 (3H, t), 0.99 (3H, t), 0.97 (3H, t), 0.90 (3H, t) |
| 197 | 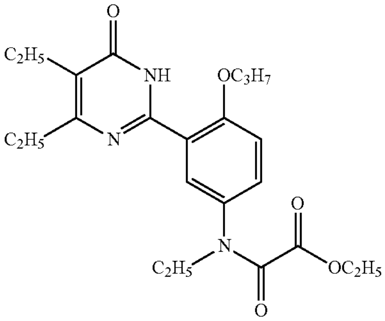 | ethyl (N-ethyl-N-(3-(4,5-diethyl-1,6-dihydro-6-oxopyrimidin-2-yl)-4-n-propoxyphenyl)aminoformylformate ($CDCl_3$) δ: 8.38 (1H, d), 7.33 (1H, dd), 7.04 (1H, d), 4.19 (2H, t), 4.04 (2H, q), 3.84 (2H, q), 2.66 (2H, q), 2.59 (2H, q), 2.01 (2H, m), 1.28 (3H, t), 1.19 (3H, t), 1.15 (3H, t), 1.14 (3H, t), 1.06 (3H, t) |

Examples 198

1,3-Diethyl-1-(3-(4,5-diethyl-1,6-dihydro-6-oxopyrimidin-2-yl)-4-n-propoxyphenyl)urea

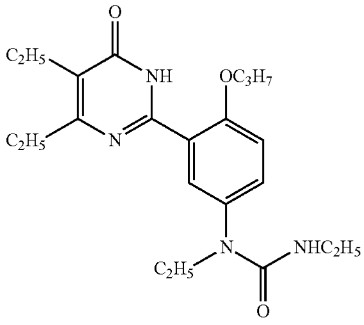

The compound (0.33 g, 1 mmol) of example 195 was dissolved in ethanol (10 ml), and added with ethyl isocyanate (0.8 g, 1.1 mmol). After refluxed for 1 h, the reaction mixture was concentrated to dryness. The resultant solid was recrystallized from ethyl acetate-petroleum ether to obtain the title compound (0.32 g, yield: 80%). $^1H$ NMR ($DMSO-d_6$) δ: 11.81 (1H, br), 7.58 (1H, d), 7.30 (1H, dd), 7.19 (1H, d), 5.65 (1H, t), 4.07 (2H, t), 3.55 (2H, q), 3.00 (2H, m), 2.56 (2H, q), 2.46 (2H, q), 1.77 (2H, m), 1.18 (3H, t), 1.04 (3H, t), 0.99 (3H, t), 0.98 (3H, t), 0.95 (3H, t).

Example 199

N-(3-(4,5-Diethyl-1,6-dihydro-6-oxopyrimidin-2-yl)-4-n-propoxyphenyl)piperidine-1-formamide

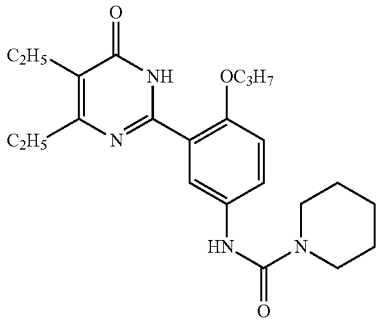

The compound (1 g, 3.3 mmol) of example 42 was dissolved in dichloromethane (10 ml), and added with N,N'-carbonyldiimidazole (589 mg, 3.63 mmol), followed by stirring at room temperature for 2 h. A precipitate was generated, and TLC showed that the reaction was complete. The reaction mixture was filtered, and the resultant white solid (1 g) was added into piperidine (10 ml), and heated to 80° C. to stir for 5 h. TLC showed that the reaction was complete. The reaction mixture was cooled down to room temperature, and added with dichloromethane. The organic layer was washed with water and saturated saline, dried with anhydrous sodium sulfate and concentrated to give an oily crude, which was passed through a column to obtain the title compound (300 mg, yield: 22%). $^1$H NMR ($CDCl_3$) δ: 8.08 (1H, d), 7.80 (1H, dd), 6.98 (1H, d), 6.49 (1H, br), 4.12 (2H, t), 3.46 (4H, t), 2.66 (2H, q), 2.58 (2H, q), 1.96 (2H, m), 1.64 (6H, m), 1.29 (3H, t), 1.14 (3H, t), 1.12 (3H, t).

Examples 200~203

According to the same manner as that of example 199, the compound of example 42 was first reacted with N,N'-carbonyldiimidazole to give an intermediate, which was then reacted with N-methylpiperazine, n-propylamine, cyclohexylamine and diethylamine respectively to provide the compounds of examples 200~203.

| Example | Structural Formula | Nomenclature and data of 1H-NMR(δ) |
|---|---|---|
| 200 | 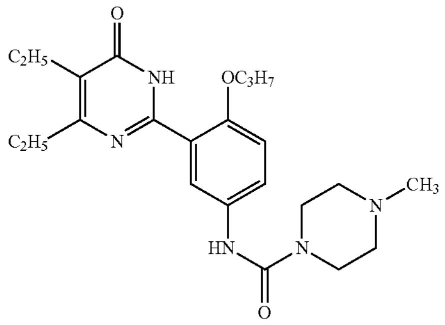 | N-(3-(4,5-diethyl-1,6-dihydro-6-oxopyrimidin-2-yl)-4-n-propoxyphenyl)-4-methylpiperazine-1-formamide (DMSO-$d_6$) δ: 11.76 (1H, br), 8.55 (1H, br), 7.83 (1H, d), 7.60 (1H, dd), 7.07 (1H, d), 4.01 (2H, t), 3.43 (4H, t), 2.56 (2H, q), 2.46 (2H, q), 2.32 (4H, t), 2.20 (3H, s), 1.74 (2H, m), 1.19 (3H, t), 1.03 (3H, t), 0.97 (3H, t) |
| 201 | 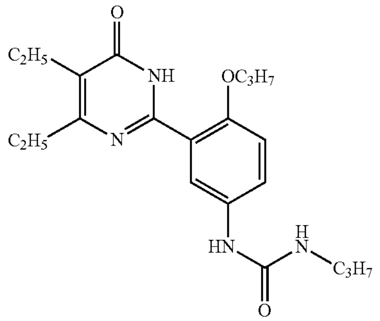 | 1-(3-(4,5-diethyl-1,6-dihydro-6-oxopyrimidin-2-yl)-4-n-propoxyphenyl)-3-propylurea (DMSO-$d_6$) δ: 11.71 (1H, br), 8.42 (1H, br), 7.79 (1H, d), 7.57 (1H, dd), 7.06 (1H, d), 6.03 (1H, t), 4.01 (2H, t), 3.03 (2H, t), 2.57 (2H, q), 2.46 (2H, q), 1.74 (2H, m), 1.43 (2H, m), 1.19 (3H, t), 1.04 (3H, t), 0.97 (3H, t), 0.87 (3H, t) |
| 202 | 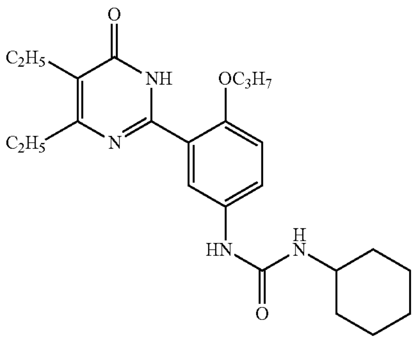 | 1-cyclohexyl-3-(3-(4,5-diethyl-1,6-dihydro-6-oxopyrimidin-2-yl)-4-n-propoxyphenyl)urea (DMSO-$d_6$) δ: 8.33 (1H, br), 7.77 (1H, d), 7.54 (1H, dd), 7.06 (1H, d), 5.96 (1H, d), 4.00 (2H, t), 3.44 (1H, m), 2.56 (2H, q), 2.45 (2H, q), 1.84-1.24 (12H, m), 1.19 (3H, t), 1.03 (3H, t), 0.96 (3H, t) |

-continued

| Example | Structural Formula | Nomenclature and data of 1H-NMR(δ) |
|---|---|---|
| 203 | 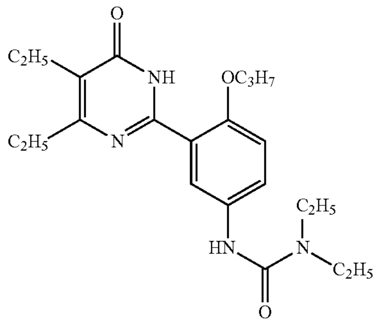 | 1,1-diethyl-3-(3-(4,5-diethyl-1,6-dihydro-6-oxopyrimidin-2-yl)-4-n-propoxyphenyl)urea ($CDCl_3$) δ: 8.13 (1H, d), 7.93 (1H, dd), 6.99 (1H, d), 6.42 (1H, br), 4.14 (2H, t), 3.40 (4H, q), 2.69 (2H, q), 2.58 (2H, q), 1.97 (2H, m), 1.30 (3H, t), 1.24 (6H, t), 1.15 (3H, t), 1.13 (3H, t) |

Example 204

1-(2-(Diethylamino)ethyl)-3-(3-(4,5-diethyl-1,6-dihydro-6-oxopyrimidin-2-yl)-4-n-propoxyphenyl) urea maleate

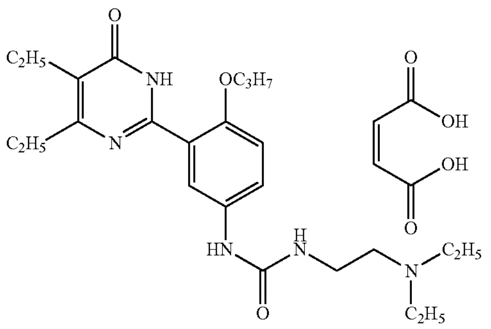

The compound (1 g, 3.3 mmol) of example 42 was dissolved in dichloromethane (10 ml), and added with N,N'-carbonyldiimidazole (589 mg, 3.63 mmol), followed by stirring at room temperature for 2 h to generate a solid. TLC showed that the reaction was complete. The reaction mixture was filtered, the resultant white solid (1 g) was added into N,N'-diethylethylenediamine (10 ml), and heated to 80° C. to stir for 5 h. TLC showed that the reaction was complete. The reaction mixture was cooled down to the room temperature, and added with dichlormethane. The organic layer was washed with water and saturated saline, dried with anhydrous sodium sulfate and concentrated to give an oily crude, which was passed through a column to obtain the title compound (300 mg) in alkaline form. The compound was dissolved in acetone (3 ml), added with maleic acid (79 mg, 0.677 mmol), and stirred for 10 h to generate a solid, which was filtered and dried to obtain the title compound (300 mg, yield: 16%). $^1$H NMR (DMSO-$d_6$) δ: 7.84 (1H, d), 7.56 (1H, dd), 7.09 (1H, d), 6.04 (2H, s), 4.01 (2H, t), 3.42 (2H, t), 3.17 (6H, m), 2.56 (2H, q), 2.45 (2H, q), 1.74 (2H, m), 1.20 (6H, t), 1.18 (3H, t), 1.03 (3H, t), 0.97 (3H, t).

Example 205

(4-Methylpiperazin-1-yl)(3-(4,5-diethyl-1,6-dihydro-6-oxopyrimidin-2-yl)-4-n-propoxybenzophenone

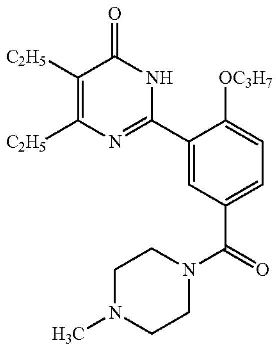

According to the same manner as that of example 89, the compound of example 58 was first reacted with thionyl chloride, and the resultant product was reacted with N-methylpiperazine to give the title compound. $^1$H NMR ($CDCl_3$) δ: 11.08 (1H, br), 8.58 (1H, d), 7.57 (1H, dd), 7.06 (1H, d), 4.19 (2H, t), 3.68 (4H, br), 2.65 (2H, q), 2.58 (2H, q), 2.45 (4H, br), 2.33 (3H, s), 2.00 (2H, m), 1.28 (3H, t), 1.14 (6H, t).

Example 206

5-Iodo-6-isopropyl-2-[2-n-propoxy-5-(4-methyl-1-piperazinylsulfonyl)phenyl]pyrimid-4(3H)-one

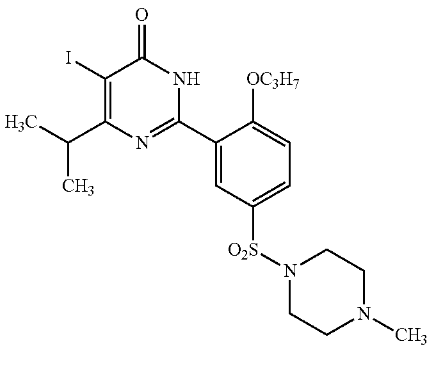

The compound (1.69 g, 3.9 mmol) of example 1 was added into methanol (15 ml), and added with silver nitrate (0.66 g, 3.9 mol), and then with $I_2$ grain (0.98 g, 3.9 mmol) under stirring. The reaction mixture was stirred at room temperature for 0.5 h, and TLC showed that the reaction was complete. The reaction mixture was filtered, and the filtrate was concentrated. The concentrate was washed with water, extracted with dichloromethane. The organic layer was washed with saturated saline, dried with anhydrous sodium sulfate, and concentrated. The residue was recrystallized from ethyl acetate to give a yellowish solid (1.52 g, yield: 70%). $^1$H NMR ($CDCl_3$) δ: 8.90 (1H, d), 7.89 (1H, dd), 7.16 (1H, d), 4.27 (2H, t), 3.46 (1H, m), 3.08 (4H, t), 2.49 (4H, t), 2.27 (3H, s), 2.03 (2H, m), 1.25 (6H, d), 1.16 (3H, t).

Example 207

5-Chloro-6-ethyl-2-[2-n-propoxy-5-(4-methyl-1-piperazinylsulfonyl)phenyl]pyrimid-4(3H)-one

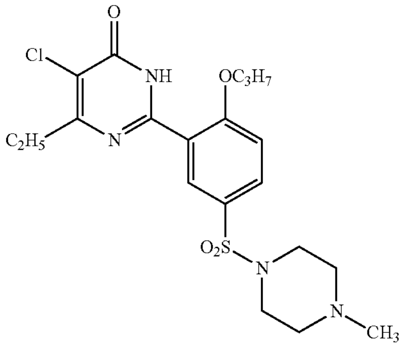

The compound (0.42 g, 1 mmol) of example 6 was dissolved in $CH_2Cl_2$ (20 ml), added with pyridine (0.3 ml), and fed with chlorine gas for about 2 min under ice-bath. The reaction mixture was washed with 1M $Na_2S_2O_3$ (20 ml), 1M HCl (20 ml) and saturated saline (40 ml) respectively. The organic phase was dried with anhydrous sodium sulfate, and concentrated to dryness under reduced pressure. The residue was recrystallized from acetonitrile-ethylether to give the title compound (0.41 g, yield: 90%). $^1$H NMR ($CDCl_3$) δ: 11.25 (1H, br), 8.85 (1H, d), 7.87 (1H, dd), 7.16 (1H, d), 4.27 (2H, t), 3.08 (4H, t), 2.85 (2H, q), 2.49 (4H, t), 2.27 (3H, s), 2.03 (2H, m), 1.29 (3H, t), 1.15 (3H, t).

Example 208

5,6-Diethyl-2-(2-n-propoxy-5-((tetrahydro-2,4,5-trihydroxy-6-(hydroxymethyl)-2H-pyran-3-ylamino)sulfonyl)phenyl]pyrimid-4(3H)-one

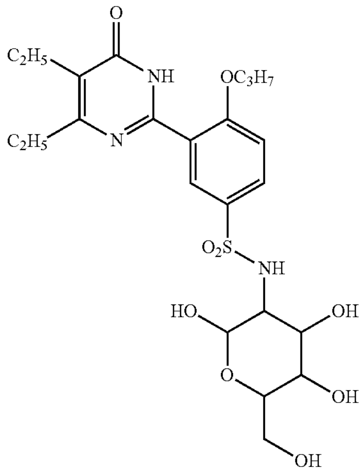

According to the same manner as that of example 10, the compound of preparation example 33 was first chlorosulfonated, and then reacted with aminoglucose to give the compound of example 208. $^1$H NMR ($CDCl_3$) 11.02 (1H, s), 8.52 (1H, s), 7.96 (1H, d), 7.12 (1H, d), 4.06 (2H, t), 3.52~3.84 (5H, m), 3.35 (1H, m), 3.15 (1H, m), 2.52 (2H, q), 2.49 (2H, q), 1.80 (2H, m), 1.24 (3H, t), 1.06 (3H, t), 0.84 (3H, t).

Example 209

According to the same manner as that of example 89, the compound of example 58 was first reacted with thionyl chloride, and the resultant product was reacted with citrulline, ornithine and aminosugar respectively to obtain the compounds of examples 209~211.

| Example | Structural Formula | Nomenclature and data of 1H-NMR(δ) |
|---|---|---|
| 209 | 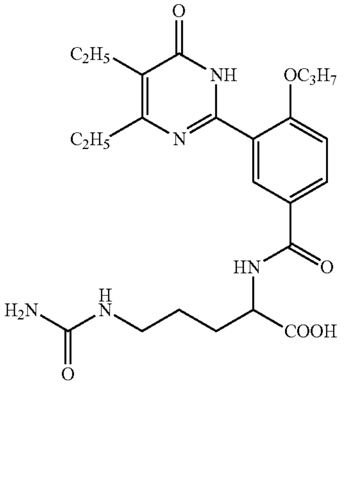 | 2-(3-(4,5-diethyl-1,6-dihydro-6-oxopyrimidin-2-yl)-4-n-propoxybenzamido)-5-ureavaleric acid (DMSO-$d_6$) δ: 8.19 (1H, d), 8.04 (1H, dd), 7.23 (1H, d), 4.34 (1H, m), 4.08 (2H, t), 2.97 (2H, m), 2.56 (2H, q), 2.44 (2H, q), 1.75 (4H, m), 1.45 (2H, m), 1.18 (3H, t), 1.04 (3H, t), 0.96 (3H, t) |

-continued

| Example | Structural Formula | Nomenclature and data of 1H-NMR(δ) |
|---|---|---|
| 210 | 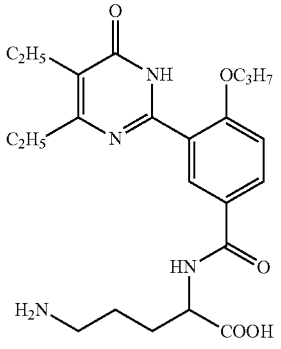 | 2-(3-(4,5-diethyl-1,6-dihydro-6-oxopyrimidin-2-yl)-4-n-propoxybenzamido)-5-aminovaleric acid (DMSO-$d_6$) δ: 8.14 (1H, d), 7.97 (1H, dd), 7.20 (1H, d), 4.07 (2H, t), 3.59 (1H, m), 3.28 (2H, t), 2.56 (2H, q), 2.46 (2H, q), 1.84 (2H, m), 1.74 (2H, m), 1.63 (2H, m), 1.17 (3H, t), 1.03 (3H, t), 0.95 (3H, t) |
| 211 | 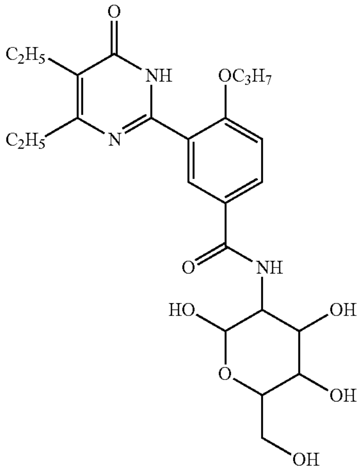 | 3-(3-(4,5-diethyl-1,6-dihydro-6-oxopyrimidin-2-yl)-N-(tetrahydro-2,4,5-trihydroxy-6-(hydroxymethyl)-2H-pyran-3-yl)-4-n-propoxybenzamide (DMSO-$d_6$) δ: 8.20 (1H, d), 8.05 (1H, m), 7.22 (1H, d), 4.08 (1H, t), 3.6~3.8 (5H, m), 3.50 (1H, dd), 3.19 (1H, t), 2.58 (2H, q), 2.47 (2H, q), 1.68 (2H, m), 1.19 (3H, t), 1.05 (3H, t), 0.95 (3H, t) |

Example 212~214

According to the same manner as that of example 89, the compound of example 170 was first reacted with thionyl chloride, and the resultant product was reacted with ammonia, N-methylpiperazine and diethylamine respectively to obtain the compounds of examples 212-214.

| Example | Structural Formula | Nomenclature and data of 1H-NMR(δ) |
|---|---|---|
| 212 | 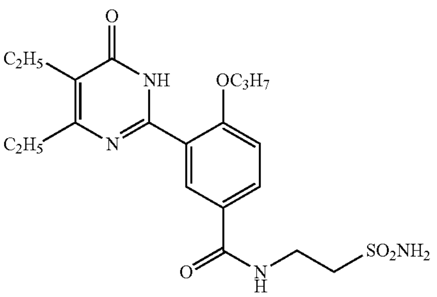 | 2-(3-(4,5-diethyl-1,6-dihydro-6-oxopyrimidin-2-yl)-4-n-propoxybenzamido)ethylsulphonamide (DMSO-$d_6$) δ: 8.13 (1H, d), 7.96 (1H, dd), 7.24 (1H, d), 4.08 (2H, t), 3.64 (2H, t), 3.24 (2H, t), 2.57 (2H, q), 2.46 (2H, q), 1.74 (2H, m), 1.19 (3H, t), 1.04 (3H, t), 0.96 (3H, t) |

-continued

| Example | Structural Formula | Nomenclature and data of 1H-NMR(δ) |
|---|---|---|
| 213 | 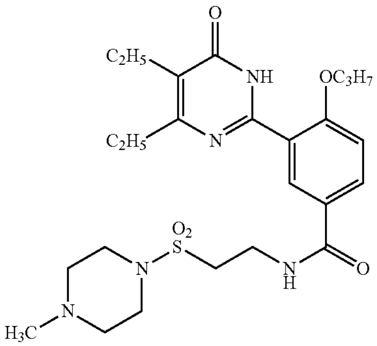 | 3-(4,5-diethyl-1,6-dihydro-6-oxopyrimidin-2-yl)-N-(4-methyl-1-piperazinylsulfonylethyl)-4-n-propoxybenzamide ($CDCl_3$) δ: 11.00 (1H, br), 8.84 (1H, d), 7.94 (1H, dd), 7.18 (1H, t), 7.05 (1H, d), 4.19 (2H, t), 3.97 (2H, q), 3.32 (4H, t), 3.19 (2H, t), 2.66 (2H, q), 2.57 (2H, q), 2.48 (4H, t), 2.31 (3H, s), 1.98 (2H, m), 1.29 (3H, t), 1.13 (6H, t) |
| 214 | 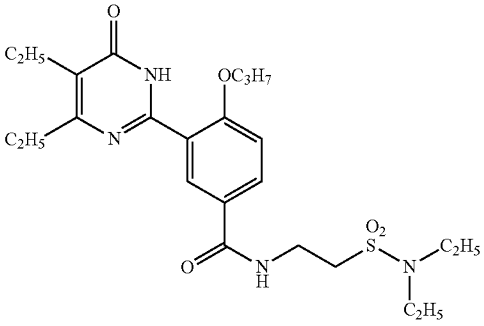 | 3-(4,5-diethyl-1,6-dihydro-6-oxopyrimidin-2-yl)-N-(N,N-diethylaminosulfonylethyl)-4-n-propoxybenzamide ($CDCl_3$) δ: 8.86 (1H, d), 7.95 (1H, dd), 7.05 (1H, d), 4.19 (2H, t), 3.94 (2H, m), 3.31 (4H, q), 3.19 (2H, t), 2.66 (2H, q), 2.57 (2H, q), 1.98 (2H, m), 1.29 (3H, t), 1.21 (6H, t), 1.13 (6H, t) |

Example 215~217

According to the same manner as that of example 89, the compound of example 169 was first reacted with thionyl chloride, and the resultant product was reacted with ammonia, N-methylpiperazine and diethylamine respectively to obtain the compounds of examples 215-217.

| Example | Structural Formula | Nomenclature and data of 1H-NMR(δ) |
|---|---|---|
| 215 | 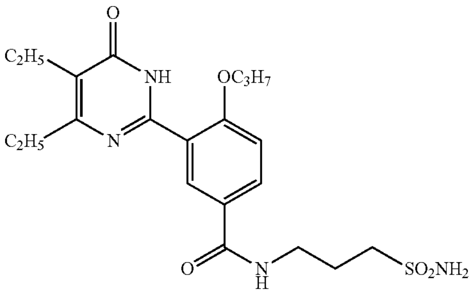 | 3-(3-(4,5-diethyl-1,6-dihydro-6-oxopyrimidin-2-yl)-4-n-propoxybenzamido)propylsulphonamide (DMSO-$d_6$) δ: 12.02 (1H, br), 8.58 (1H, t), 8.13 (1H, d), 7.98 (1H, dd), 7.23 (1H, d), 6.79 (2H, s), 4.07 (2H, t), 3.36 (2H, m), 3.01 (2H, t), 2.58 (2H, q), 2.47 (2H, q), 1.93 (2H, m), 1.74 (2H, m), 1.19 (3H, t), 1.04 (3H, t), 0.96(3H,t) |
| 216 | 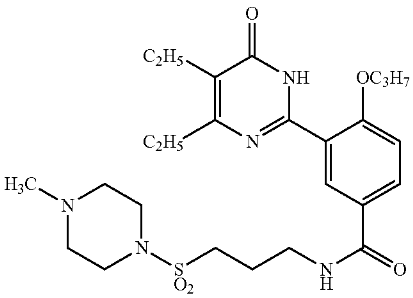 | 3-(4,5-diethyl-1,6-dihydro-6-oxopyrimidin-2-yl)-N-(4-methyl-1-piperazinylsulfonylpropyl)-4-n-propoxybenzamide ($CDCl_3$) δ: 10.97 (1H, br), 8.80 (1H, d), 7.97 (1H, dd), 7.05 (1H, d), 6.90 (1H, t), 4.18 (2H, t), 3.65 (2H, q), 3.30 (4H, t), 3.03 (2H, t), 2.67 (2H, q), 2.58 (2H, q), 2.48 (4H, t), 2.32 (3H, s), 2.20 (2H, m), 1.98 (2H, m), 1.27 (3H, t), 1.15 (3H, t), 1.14 (3H, t) |

-continued

| Example | Structural Formula | Nomenclature and data of 1H-NMR(δ) |
|---|---|---|
| 217 | 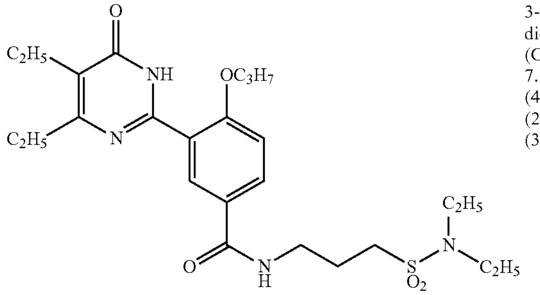 | 3-(4,5-diethyl-1,6-dihydro-6-oxopyrimidin-2-yl)-N-(N,N-diethylaminosulfonylethyl)-4-n-propoxybenzamide ($CDCl_3$) δ: 10.93 (1H, br), 8.78 (1H, d), 7.92 (1H, dd), 7.16 (1H, t), 6.99 (1H, d), 4.13 (2H, t), 3.62 (2H, q), 3.28 (4H, q), 3.04 (2H, t), 2.64 (2H, q), 2.56 (2H, q), 2.16 (2H, m), 1.93 (2H, m), 1.27 (3H, t), 1.18 (6H, t), 1.13 (3H, t), 1.10 (3H, t) |

Example 218

5,6-Diethyl-2-(5-(tetrahydro-3,4,5-trihydroxy-6-(hydroxymethyl)-2H-pyran-2-yl)-2-n-propoxyphenyl)pyrimid-4(3H)-one

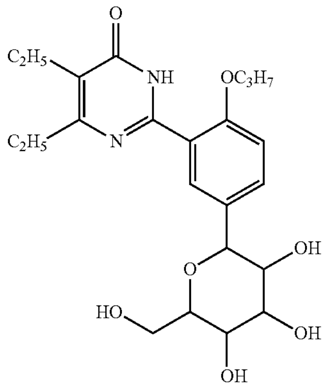

The compound (728 mg, 2 mmol) of preparation example 34 was dissolved in tetrahydrofuran (4 mL), and added slowly with a 1.6 mol/L n-BuLi solution (2.8 mL, 4.4 mmol) in n-hexane at −78° C., the dropping speed being controlled to keep the temperature below −70° C. 40 min later, gluconolactone protected by trimethylsilicane and dissolved in 4 mL of toluene was slowly added dropwise into the reaction system. The reaction temperature was kept below −70° C. for 1 h and then raised to −40° C. to stir for 30 min. A methanol solution (4 mL) of methanesulfonic acid (0.38 mL, 6.0 mmol) was slowly added dropwise into the reaction system. After the addition, the reaction mixture was slowly raised to room temperature and stirred for 8 h, added with saturated sodium bicarbonate to adjust to a PH of 8, and extracted with ethyl acetate. The organic phase was washed with saturated saline, dried with anhydrous sodium sulfate, and concentrated to dryness to give a yellow oil, which was passed through a silica gel column (petroleum ether:ethyl acetate=1:4) to obtain an intermediate (380 mg). The intermediate (380 mg, 0.8 mmol) was dissolved in 5 mL of acetonitrile, and added with triethylsilicane (0.4 mL, 2.3 mmol) and boron trifluoride diethyl ether (0.1 mL, 1.6 mmol) under ice-bath, followed by stirring under ice-bath for 40 min. The stirring continued at room temperature for another 3 h, and TLC showed that the reaction was complete. The reaction mixture was adjusted to a PH of 7 with saturated sodium bicarbonate solution, and extracted with ethyl acetate. The organic phase was washed with saturated saline, dried with anhydrous sodium sulfate, and concentrated to dryness. The residue was recrystallized from ethyl acetate-ethanol to obtain the title compound (300 mg, yield: 34%). $^1H$ NMR ($CDCl_3$) 8.60 (1H, s), 7.72 (1H, s), 7.53 (1H, d), 7.02 (1H, d), 4.03 (2H, t), 3.85 (3H, m), 3.66 (2H, m), 3.55 (1H, m), 3.23 (1H, d), 2.74 (2H, q), 2.58 (2H, q), 1.54 (2H, m), 1.24 (3H, t), 1.10 (3H, t), 1.05 (3H, t).

Example 219

5-Iodo-6-ethyl-2-[2-n-propoxy-5-(4-methyl-1-piperazinylsulfonyl)phenyl]pyrimid-4(3H)-one

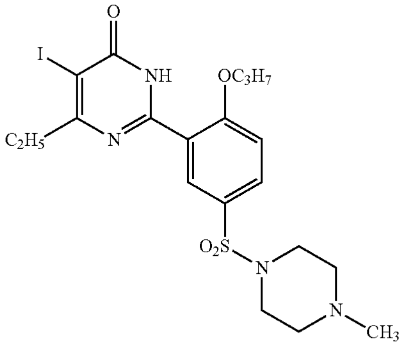

The compound of example 219 was prepared by reacting the compound of example 6 with $I_2$ in the same manner as that of example 206. $^1H$ NMR ($CDCl_3$) 11.12 (1H, br), 8.88 (1H, d), 7.88 (1H, dd), 7.16 (1H, d), 4.27 (2H, t), 3.10 (4H, t), 2.92 (2H, q), 2.52 (4H, t), 2.30 (3H, s), 2.03 (2H, m), 1.28 (3H, t), 1.16 (3H, t).

Example 220

5-Bromo-6-ethyl-2-[2-n-propoxy-5-(4-methyl-1-piperazinylsulfonyl)phenyl]pyrimid-4(3H)-one

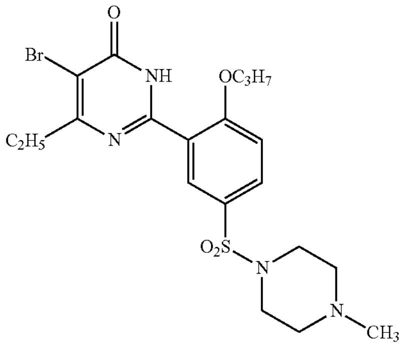

The compound of example 220 was prepared by reacting the compound of example 6 with liquid bromine in the same manner as that of preparation example 19. $^1$H NMR ($CDCl_3$) 11.20 (1H, br), 8.86 (1H, d), 7.88 (1H, dd), 7.16 (1H, d), 4.27 (2H, t), 3.09 (4H, t), 2.88 (2H, q), 2.50 (4H, t), 2.28 (3H, s), 2.03 (2H, m), 1.29 (3H, t), 1.15 (3H, t).

Example 221

5-Chloro-6-isopropyl-2-[2-n-propoxy-5-(4-methyl-1-piperazinylsulfonyl)phenyl]pyrimid-4(3H)-one

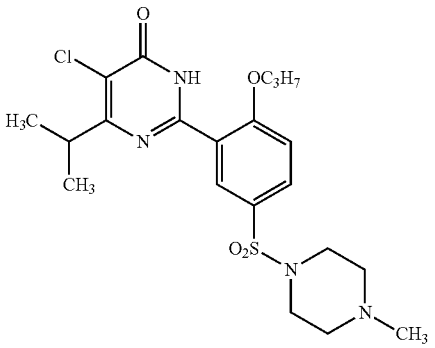

The compound of example 221 was prepared by reacting the compound of example 1 with chlorine gas in the same manner as that of example 207. $^1$H NMR ($CDCl_3$) 8.86 (1H, d), 7.88 (1H, dd), 7.16 (1H, d), 4.27 (2H, t), 3.49 (1H, m), 3.09 (4H, t), 2.50 (4H, t), 2.27 (3H, s), 2.03 (2H, m), 1.26 (6H, d), 1.16 (3H, t).

Example 222

Capsule

| Formula | |
|---|---|
| phenylpyrimidone compound(Example 46) | 20.0 g |
| starch | 80.0 g |
| lactose | 60.0 g |
| microcrystalline cellulose | 35.0 g |
| 10% ethanol solution of polyvinyl pyrrolidone | suitable amount |
| magnesium stearate | 0.5 g |
| total 1000 capsules | |

The said phenylpyrimidone compound and the adjuvants, i.e. starch, lactose and microcrystalline cellulose, were screened with a 80 mesh sieve, weighed according to the formula, granulated into suitable granules with a 16 mesh sieve using a 10% ethanol solution of polyvinyl pyrrolidone as the adhesive, dried at 65° C., sized with a 14 mesh sieve, and added with magnesium stearate to mix uniformly. Then, the content of the granules was measured, and the loading amount was calculated. A suitable amount of granules were put into the capsules, thereby to obtain the final product.

Example 223

Tablet (Wet Granulation)

| Formula | |
|---|---|
| phenylpyrimidone compound(Example 50) | 20.0 g |
| lactose | 120.0 g |
| microcrystalline cellulose | 40.0 g |
| 8% starch paste | suitable amount |
| sodium carboxymethyl starch | 10.0 g |
| magnesium stearate | 1.0 g |
| total 1000 tablets | |

The said phenylpyrimidone compound, microcrystalline cellulose, lactose and sodium carboxymethyl starch were screened with a 80 mesh sieve, mixed uniformly, prepared into a damp mass with a 8% starch paste, granulated with a 16 mesh sieve, dried, sized with a 14 mesh sieve, and added with magnesium stearate to mix uniformly. Then, the content of the granules was measured, and the weigh of the tablet was calculated. Tabletting was performed to obtain the final product.

Example 224

Tablet (Powder Compression)

| Formula | |
|---|---|
| phenylpyrimidone compound(Example 53) | 20.0 g |
| microcrystalline cellulose | 30.0 g |
| anhydrous lactose | 45.0 g |
| polyvinylpyrrolidone | 3.0 g |

| Formula | |
|---|---|
| silica gel | 0.2 g |
| magnesium stearate | 0.5 g |
| total 1000 tablets | |

The saided phenyl pyrimidone compound, microcrystalline cellulose, anhydrous lactose, polyvinylpyrrolidone and silica gel were mixed uniformly in a mixer, and then added with magnesium stearate to mix uniformly. Tabletting was performed to obtain the final product.

Measurement of Compounds' Activity

Results of Enzyme Inhibition Activity Test

The enzyme used for the enzyme inhibition activity test was obtained by suitably treating various tissues and separating the enzyme with FPLC, according to a method similar as those reported in the literatures (Thrombosis Res. 1991, 62, 31 and J. Biol. Chem. 1997, 272, 2714). More specifically, PDE5 and PDE3 were obtained from human blood platelet, and PDE6 was separated from bovine retina. Upon enzyme was separated out, the enzyme inhibition activity test would be carried out immediately. The said enzyme inhibition activity test was performed by directly detecting the scintillation proximity of AMP/GMP using TRKQ7100 and TRKQ7090 kits, which was generally as follows. In the presence of different concentrations of inhibitor and a small amount of substrate, 10 μl of buffer (50 mM Tris/HCl PH 7.5, 8.3 mM $MgCl_2$, 1.7 mM EGTA) was added, and then water was added to a final volume of 100 μl. The reaction was initiated with a fixed amount of enzyme, incubated at 30° C. for 30 min, and then quenched with 50 μl of yttrium silicate beads comprising zinc sulphate. After shaken for 20 min, the reaction mixture was put in dark and settled for 30 min, and then readed on a BECKMAN LS6500 MULTI-PURPOSE SCINTILLATION COUNTER. Finally, the 50% inhibitory ratio ($IC_{50}$) for enzyme of the compound according to the present invention was calculated based on the readings.

Results of PDE5 Inhibition Activity Test

According to the above-mentioned method, the inhibition activity for human blood platelet PDE5 of some compounds of formula I according to the present invention was measured, and the results are shown in the following table:

| Measured compound | PDE5 $IC_{50}$ (nM) | Measured compound | PDE5 $IC_{50}$ (nM) |
|---|---|---|---|
| Sildenafil | 3.94 | Example 29 | 4.52 |
| Example 31 | 1.36 | Example 32 | 2.02 |
| Example 43 | 3.72 | Example 46 | 1.09 |
| Example 49 | 1.86 | Example 50 | 1.24 |
| Example 51 | 1.23 | Example 52 | 1.46 |
| Example 53 | 0.57 | Example 54 | 1.21 |
| Example 55 | 0.92 | Example 57 | 1.19 |
| Example 59 | 0.57 | Example 60 | 2.04 |
| Example 61 | 1.93 | Example 63 | 1.24 |
| Example 67 | 1.61 | Example 68 | 0.53 |
| Example 76 | 1.99 | Example 87 | 3.29 |
| Example 89 | 1.98 | Example 98 | 2.77 |
| Example 102 | 4.61 | Example 107 | 0.92 |
| Example 108 | 0.54 | Example 110 | 2.85 |
| Example 114 | 0.83 | Example 116 | 0.93 |
| Example 117 | 0.66 | Example 118 | 0.76 |
| Example 119 | 6.31 | Example 123 | 0.49 |
| Example 124 | 0.13 | Example 125 | 0.19 |
| Example 126 | 1.79 | Example 133 | 1.13 |
| Example 135 | 1.01 | Example 138 | 0.47 |

| Measured compound | PDE5 $IC_{50}$ (nM) | Measured compound | PDE5 $IC_{50}$ (nM) |
|---|---|---|---|
| Example 139 | 0.61 | Example 140 | 0.57 |
| Example 145 | 0.47 | Example 146 | 0.93 |
| Example 149 | 1.80 | Example 150 | 0.52 |
| Example 151 | 0.54 | Example 154 | 0.40 |
| Example 155 | 0.54 | Example 163 | 7.92 |
| Example 164 | 0.46 | Example 166 | 0.33 |
| Example 169 | 0.11 | Example 174 | 0.45 |
| Example 179 | 0.23 | Example 186 | 0.34 |
| Example 204 | 0.88 | Example 205 | 1.93 |
| Example 208 | 3.69 | Example 209 | 0.64 |
| Example 210 | 6.23 | Example 211 | 0.90 |
| Example 212 | 0.79 | Example 213 | 2.80 |
| Example 214 | 1.80 | Example 215 | 0.88 |
| Example 216 | 0.83 | Example 217 | 2.12 |
| Example 218 | 8.63 | | |

According to the inhibition activity ($IC_{50}$) for PDE5 of the compounds in the above table, it can be seen that the compounds of formula I according to the present invention have a PDE 5 inhibition activity. It is more important that most of the compounds in the above table show a stronger PDE5 inhibition activity than Sildenafil, and thus have a smaller oral dose than Sildenafil and a reduced probability of causing side effects.

Results of PDE6 Inhibition Activity Test

Taking into account that the compounds according to the present invention can have the inhibition activity for PDE6 distributed in retina to cause visual disorder, the present inventors measured the inhibition activity for PDE6 in bovine retina of some compounds of formula I according to the present invention, and the results are shown in the following table:

| Measured compound | PDE6 $IC_{50}$ (nM) | PDE5 $IC_{50}$ (nM) | PDE6 $IC_{50}$/PDE5 $IC_{50}$ |
|---|---|---|---|
| Sildenafil | 40.2 | 3.94 | 10.2 |
| Example 29 | 130 | 4.52 | 28.8 |
| Example 31 | 52.8 | 1.36 | 38.8 |
| Example 32 | 40.6 | 2.02 | 20.1 |
| Example 43 | 42.8 | 3.72 | 11.5 |
| Example 46 | 642 | 1.09 | 589.0 |
| Example 49 | 619.6 | 1.86 | 10.5 |
| Example 50 | 114 | 1.24 | 91.9 |
| Example 51 | 34.8 | 1.23 | 28.3 |
| Example 52 | 52.6 | 1.46 | 36.0 |
| Example 53 | 36.8 | 0.57 | 66.2 |
| Example 54 | 13.2 | 1.21 | 10.9 |
| Example 55 | 20.1 | 0.93 | 21.8 |
| Example 57 | 8.19 | 1.19 | 6.9 |
| Example 59 | 7.88 | 0.57 | 13.7 |
| Example 60 | 8.19 | 2.04 | 4.0 |
| Example 61 | 29.1 | 1.93 | 15.1 |
| Example 63 | 33.4 | 1.24 | 26.9 |
| Example 67 | 26.9 | 1.61 | 16.7 |
| Example 68 | 16.4 | 0.53 | 31.0 |
| Example 76 | 25.2 | 1.99 | 12.7 |
| Example 89 | 11.7 | 1.98 | 5.88 |
| Example 98 | 10.4 | 2.77 | 3.77 |
| Example 102 | 24.6 | 4.61 | 5.33 |
| Example 107 | 6.42 | 0.92 | 22.64 |
| Example 108 | 5.73 | 0.54 | 6.99 |
| Example 110 | 22.2 | 2.85 | 7.80 |
| Example 114 | 18.7 | 0.83 | 10.53 |
| Example 116 | 22.9 | 0.93 | 24.5 |
| Example 117 | 10.4 | 0.66 | 15.6 |
| Example 123 | 13.3 | 0.49 | 27.3 |
| Example 124 | 3.76 | 0.13 | 28.6 |
| Example 125 | 2.71 | 0.19 | 14.6 |
| Example 126 | 54.9 | 1.79 | 30.7 |

-continued

| Measured compound | PDE6 $IC_{50}$ (nM) | PDE5 $IC_{50}$ (nM) | PDE6 $IC_{50}$/PDE5 $IC_{50}$ |
|---|---|---|---|
| Example 133 | 20.9 | 1.31 | 15.9 |
| Example 135 | 9.66 | 1.01 | 9.6 |
| Example 138 | 5.42 | 0.47 | 11.4 |
| Example 139 | 7.82 | 0.61 | 12.8 |
| Example 140 | 4.25 | 0.57 | 7.5 |
| Example 145 | 24.2 | 0.47 | 51.5 |
| Example 146 | 6.64 | 0.93 | 7.2 |
| Example 150 | 2.78 | 0.52 | 5.3 |
| Example 154 | 37.9 | 0.40 | 94.6 |
| Example 163 | 48.6 | 7.92 | 6.1 |
| Example 164 | 31.8 | 0.46 | 68.7 |
| Example 166 | 5.15 | 0.33 | 15.6 |
| Example 169 | 10.4 | 0.11 | 91.3 |
| Example 174 | 13.7 | 0.45 | 30.3 |
| Example 179 | 22.2 | 0.23 | 96 |
| Example 186 | 7.4 | 0.34 | 21.4 |
| Example 204 | 54.5 | 0.88 | 61.9 |
| Example 205 | 17.2 | 1.93 | 8.9 |

The selectivity for PDE6 and PDE5 of the compounds according to the present invention was determined as the ratio of $IC_{50}$ PDE6/$IC_{50}$ PDE5 in the present invention. It can be seen from the above results that the compounds of formula I according to the present invention have an excellent PDE5 selectivity, especially, most of the compounds obtained in the examples have a higher selectivity than Sildenafil. Accordingly, the compounds according to the present application have a reduced possibility of causing visual disorder, compared with Sildenafil.

The invention claimed is:

1. A compound of formula I, or a pharmaceutically acceptable salt or solvate thereof:

I

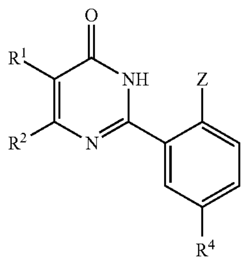

wherein, $R^1$ and $R^2$ are each independently H; $C_1$-$C_{10}$ alkyl; halogen; $OR^5$; $NR^6R^7$; $NHCOR^8$; aryl;

Z is $OR^3$;

$R^3$ is $C_1$-$C_6$ alkyl or $C_1$-$C_3$ alkyl substituted with $C_1$-$C_3$ alkoxy;

$R^4$ is $NO_2$; CN; $SO_2NR^6R^7$; $NR^9R^{10}$; $COR^{11}$; $OR^{12}$; or, $R^4$ is a 5- or 6-member heterocyclyl optionally substituted with one or more substituents selected from OH, $COOR^8$, $CONH_2$, $C_1$-$C_6$ alkyl, $C_1$-$C_4$ alkoxy, $C_3$-$C_6$ cycloalkyl, aryl, Het and $C_1$-$C_6$ alkyl substituted with OH; or, $R^4$ is a 5- or 6-member monosaccharide group optionally substituted with one or more substituents selected from $C_1$-$C_6$ alkyl, trimethylsilyl, benzyl and acetyl;

$R^5$ is H; $C_1$-$C_6$ alkyl; $C_1$-$C_4$ alkyl optionally substituted with OH, $C_1$-$C_4$ alkoxy or $NR^6R^7$; or aryl;

$R^6$ and $R^7$ are each independently H, OH, $C_1$-$C_6$ alkyl, $C_1$-$C_6$ alkoxy, $C_3$-$C_6$ alkenyl, $C_3$-$C_6$ cycloalkyl, adamantyl, $C_3$-$C_8$ lactamyl, aryl, Het, or $(CH_2CH_2O)_jH$ wherein j is 1~3; or $R^6$ and $R^7$ are each independently $C_1$-$C_6$ alkyl optionally substituted with OH, $C_1$-$C_4$ alkoxy, $SO_3H$, $SO_2NR^{13}R^{14}$, $SO_2R^{16}$, $PO(OH)_2$, $PO(OR^{16})_2$, $NR^{13}R^{14}$, aryl, Het or 4~8-member heterocyclyl; or $R^6$ and $R^7$ are each independently a 4~8-member heterocyclyl optionally substituted with one or more substituents selected from OH, $COOR^8$, $CONH_2$, $COR^{16}$, $SO_2R^{16}$, $C_1$-$C_6$ alkyl, $C_3$-$C_6$ cycloalkyl, aryl, Het and $C_1$-$C_6$ alkyl substituted with $C_1$-$C_4$ alkoxy or hydroxyl; or $R^6$ and $R^7$, together with the nitrogen atom to which they are attached, form a 4~8-member heterocyclyl optionally substituted with one or more substituents selected from OH, $COOR^8$, $CONH_2$, $COR^{16}$, $SO_2R^{16}$, $C_1$-$C_6$ alkyl, $(CH_2CH_2O)_jH$ wherein j is 1~3, $C_3$-$C_6$ cycloalkyl, aryl, Het, and $C_1$-$C_6$ alkyl substituted with $C_1$-$C_4$ alkoxy or hydroxyl or aryl; or $R^6$ and $R^7$, together with the nitrogen atom to which they are attached, form glucosylamino group, amino-acid residue, amino-acid ester residue or aminoamide residue, which are optionally substituted with one or more substituents selected from $C_1$-$C_6$ alkyl, $NR^{13}R^{14}$, $COR^{16}$, benzyl, benzyloxycarbonyl and t-butyloxycarbonyl;

$R^8$ is H, $C_1$-$C_6$ alkyl or aryl;

$R^9$ is H, $C_1$-$C_6$ alkyl or $SO_2R^{16}$;

$R^{10}$ is H; $C_1$-$C_6$ alkyl; $COR^{15}$; $SO_2R^{16}$;

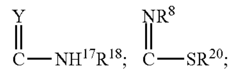

a 5- or 6-member monosaccharide group; or $R^{10}$ is a 5-member heterocyclyl optionally substituted with one or more substituents, wherein the heterocyclyl is dihydroimidazolyl substituted with hydroxyalkyl, or 1,2,4-triazolyl optionally substituted with $C_1$-$C_6$ alkyl, aryl or amino group; or when $R^9$ is H, $R^{10}$ is an amino-acid residue optionally substituted with one or more substituents selected from OH, $C_1$-$C_6$ alkyl, $C_1$-$C_4$ alkoxy, $COR^{16}$, benzyl, benzyloxycarbonyl and t-butyloxycarbonyl;

$R^{11}$ is H; OH; $C_1$-$C_6$ alkyl; aryl; Het; $NH(CH_2)_kNH_2$, $NH(CH_2)_kNHSO_2R^{16}$, or $NH(CH_2)_kNHCOR^{16}$, wherein k is 0~4; $C_1$-$C_3$ alkyl substituted with halogen, OH or $C_1$-$C_6$ alkoxy; or $(CH_2)_mNR^6R^7$, wherein m is 0~2; or, $R^{11}$ is an amino-acid residue or an aminoamide residue, which are optionally substituted with $C_1$-$C_4$ alkoxy;

$R^{12}$ is H, $COR^{19}$, $SO_2R^{16}$ or a 5- or 6-member monosaccharide group;

$R^{13}$ and $R^{14}$ are each independently H or $C_1$-$C_6$ alkyl; or, $R^{13}$ and $R^{14}$, together with the nitrogen atom to which they are attached, form a 4~8-member heterocyclyl optionally substituted with one or more substituents selected from OH and $C_1$-$C_6$ alkyl;

$R^{15}$ is H; $CF_3$; $C_1$-$C_6$ alkyl optionally substituted with halogen, OH, $C_1$-$C_6$ alkoxycarbonylamino, $NR^{13}R^{14}$, $NHSO_2R^{16}$, $NHCOR^{16}$, $SO_2NR^{13}R^{14}$, $SO_2R^{16}$, $PO(OH)_2$, $PO(OR^{16})_2$, aryl or Het; $(CH_2)_nCOOR^8$, or $(CH_2)_nCONHR^8$, wherein n is 0~6; $C_2$-$C_4$ alkenyl optionally substituted with $C_1$-$C_6$ alkyl, OH, $C_1$-$C_6$ alkoxy or $NR^{13}R^{14}$; $C_3$-$C_6$ cycloalkyl optionally substituted with $C_1$-$C_6$ alkyl or OH; $C_3$-$C_6$ cycloalkoxy optionally substituted with $C_1$-$C_6$ alkyl or OH; aryl; or Het;

$R^{16}$ is $C_1$-$C_6$ alkyl or aryl;

$R^{17}$ and $R^{18}$ are each independently H; $C_1$-$C_6$ alkyl optionally substituted with OH, $SO_3H$, $SO_2NR^{13}R^{14}$, $SO_2R^{16}$, $PO(OH)_2$, $PO(OR^{16})_2$, $NR^{13}R^{14}$, aryl, Het or 4~8-member heterocyclyl; $C_3$-$C_6$ cycloalkyl; or aryl optionally substituted with OH; or, $R^{17}$ and $R^{18}$, together with the nitrogen atom to which they are attached, form a 4~8-member heterocyclyl optionally substituted with one or more substituents selected from OH and $C_1$-$C_6$ alkyl;

$R^{19}$ is $C_1$-$C_6$ alkyl, aryl or $NHR^8$;

$R^{20}$ is $C_1$-$C_3$ alkyl;

halogen is F, Cl, Br or I;

Y is O, S or $NR^8$;

said 'aryl' is phenyl unsubstituted or substituted with one or more substituents selected from halogen, $C_1$-$C_3$ alkyl, and $C_1$-$C_3$ alkoxy;

said '5- or 6-member heterocyclyl', '4~8-member heterocycly', '5-member heterocyclyl" denote saturated or unsaturated heterocyclyl comprising one or more heteroatoms selected from N, S and O;

said 'Het' is a 5~6-member aromatic heterocyclyl comprising 1~4 heteroatoms selected from N, S and O, said 5~6-member aromatic heterocyclyl being optionally substituted with one or more substituents selected from halogen, $C_1$-$C_3$ alkyl, $C_1$-$C_3$ alkoxy, $CF_3$, CN and $NO_2$;

said 'amino-acid' is glycine, alanine, phenylalanine, serine, tryptophane, valine, leucine, isoleucine, t-leucine, tyrosine, lysine, histidine, methionine, arginine, threonine, aspartate, cysteine, proline, glutamic acid, asparagine, glutamine, ornithine or citrulline;

said '5- or 6-member monosaccharide' is ribose, deoxyribose, xylose, arabinose, glucose, mannose, galactose or fructose.

2. The compound or a pharmaceutically acceptable salt or solvate thereof according to claim 1, wherein, $R^1$ is H, F, Cl, Br, I, $NH_2$, OH, methyl, ethyl, propyl, isopropyl or acetamido;

$R^2$ is $NH_2$, Br, $OR^5$, ethyl, propyl, isopropyl, benzylamino, phenyl, benzyl, isobutyl, n-octyl or acetamido;

Z is $OR^3$;

$R^3$ is ethyl, propyl, n-butyl, n-hexyl or 3-methoxylpropyl;

$R^4$ is $NO_2$, $SO_2NR^6R^7$, $NR^9R^{10}$, $COR^{11}$, $OR^{12}$ or glucosyl; or $R^4$ is a 5- or 6-member heterocyclyl, wherein said 5- or 6-member heterocyclyl is thienyl, thiazolyl, 1,2,4-triazolyl, imidazolyl, pyrrolyl, oxadiazolyl, pyrimidinyl, morpholinyl, thiomorpholinyl, piperidyl, pyrrolidinyl or piperazinyl, and said 5- or 6-member heterocyclyl is optionally substituted with one or more substituents selected from OH, COOH, $CONH_2$, $C_1$-$C_6$ alkyl, $C_1$-$C_4$ alkoxy, $C_3$-$C_6$ cycloalkyl, aryl, Het and $C_1$-$C_6$ alkyl substituted with OH;

$R^5$ is H; $C_1$-$C_4$ alkyl optionally substituted with OH, $C_1$-$C_4$ alkoxy or $NR^6R^7$; or aryl;

$R^6$ and $R^7$ are each independently H, methyl, methoxyl, cyclopropyl, propenyl, isobutyl, t-butyl, adamantyl, cyclohexyl, caprolactamyl, 2-(1-methylpyrrol-2-yl) ethylamino, pyridylmethyl, thienylmethyl,

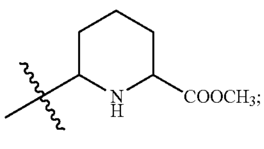 [SMILES: *C1CCCC(C(=O)OC)N1]

or $C_2$-$C_3$ alkyl optionally substituted with OH, $NR^{13}R^{14}$, $SO_3H$, $SO_2NR^{13}R^{14}$ or 5~6-member heterocyclyl, wherein said 5~6-member heterocyclyl is morpholinyl, thiomorpholinyl, piperidyl, pyrrolidinyl or piperazinyl, and said 5~-member heterocyclyl is optionally substituted with one or more substituents selected from OH, $COOR^8$, $CONH_2$, $COR^{16}$, $SO_2R^{16}$, $C_1$-$C_6$ alkyl and aryl; or $R^6$ and $R^7$, together with the nitrogen atom to which they are attached, form a 5~6-member heterocyclyl, wherein said 5~6-member heterocyclyl is morpholinyl, thiomorpholinyl, piperidyl, pyrrolidinyl or piperazinyl, and said 5~6-member heterocyclyl is optionally substituted with one or more substituents selected from OH, $COOR^8$, $CONH_2$, $COR^{16}$, $SO_2R^{16}$, $C_1$-$C_6$ alkyl, $(CH_2CH_2O)_jH$ wherein j is 1~2, dichlorophenyl, benzyl, pyridyl and aryl; or $NR^6R^7$ is glucosylamino group, amino-acid residue, amino-acid ester residue or amino-amide residue, which are optionally substituted with one or more substituents selected from $NR^{13}R^{14}$ and acetyl;

$R^8$ is H, methyl or ethyl;

$R^9$ is H, methyl or $SO_2R^{16}$;

$R^{10}$ is H, methyl, $COR^{15}$, $SO_2R^{16}$,

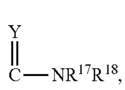, 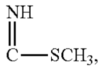, 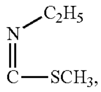, glucosyl or mannosyl; dihydroimidazolyl substituted with hydroxyethyl; or when $R^9$ is H, $R^{10}$ is an amino-acid residue optionally substituted with one or more selected from OH, t-butyloxycarbonyl, and acetyl;

$R^{11}$ is OH; pyrazolyl substituted with isopropyl; aminoamide residue; amino-ester residue;

$NR^6R^7$; $CH_2Br$ or $CH_2NR^6R^7$;

$R^{12}$ is H, $COR^{19}$, $SO_2R^{16}$, mannosyl or glucosyl;

$R^{13}$ and $R^{14}$ are each independently H or ethyl; or, $R^{13}$ and $R^{14}$, together with the nitrogen atom to which they are attached, form a 5~6-member heterocyclyl, wherein said 5~6-member heterocyclyl is morpholinyl, piperidyl, pyrrolidinyl or piperazinyl, and said 5~6-member heterocyclyl is optionally substituted with one or more substituents selected from OH and $C_1$-$C_6$ alkyl;

$R^{15}$ is H; methyl; ethyl; cyclohexyl; $CF_3$; $(CH_2)_nCOOR^8$, or $(CH_2)_nCONH_2$, wherein, n is 0 or 1; vinyl; propenyl; pyridyl; phenyl substituted with ethoxy; or thiazolyl substituted with isopropyl;

$R^{16}$ is methyl;

$R^{17}$ and $R^{18}$ are each independently H, ethyl or phenyl; or $R^{17}$ and $R^{18}$, together with the nitrogen atom to which they are attached, form a 4~8-member heterocyclyl, wherein said 4~8-member heterocyclyl is morpholinyl, piperidyl, pyrrolidinyl or piperazinyl, and said 4~8-member heterocyclyl is optionally substituted with one or more substituents selected from OH and $C_1$-$C_6$ alkyl; or when Y is NH, $R^{17}$ and C(Y)N form a dihydroimidazolyl;

$R^{19}$ is methyl or $NHC_2H_5$;

$R^{20}$ is methyl;

halogen is F, Cl, Br or I;

Y is O, S, NH or $NC_2H_5$;

said 'aryl' is phenyl unsubstituted or substituted with one or more substituents selected from halogen, $C_1$-$C_3$ alkyl, and $C_1$-$C_3$ alkoxy;

said 'Het' is a 5~6-member aromatic heterocyclyl comprising 1~4 heteroatoms selected from N, S and O, said 5~6-member aromatic heterocyclyl being optionally substituted with one or more substituents selected from halogen, $C_1$-$C_3$ alkyl, $C_1$-$C_3$ alkoxy, $CF_3$, CN and $NO_2$;

said 'amino-acid' is glycine, alanine, phenylalanine, serine, tryptophane, valine, leucine, isoleucine, t-leucine, tyrosine, lysine, histidine, methionine, arginine, threonine, aspartate, cysteine, proline, glutamic acid, asparagine, glutamine, ornithine or citrulline;

said '5- or 6-member monosaccharide' is glucose or mannose.

3. The compound or a pharmaceutically acceptable salt or solvate thereof according to claim 1, wherein, said phenylpyrimidone compound is selected from the group consisting of:

6-isopropyl-2-[2-n-propoxyl-5-(4-methyl-1-piperazinylsulfonyl)phenyl]pyrimid-4(3H)-one, 6-amino-2-[2-n-propoxyl-5-(4-methyl-1-piperazinylsulfonyl)phenyl]pyrimid-4(3H)-one, 6-hydroxy-2-[2-n-propoxyl-5-(4-methyl-1-piperazinylsulfonyl)phenyl]pyrimid-4(3H)-one, 5-acetamido-6-hydroxy-2-[2-n-propoxyl-5-(4-methyl-1-piperazinylsulfonyl)phenyl]pyrimid-4(3H)-one, 6-phenyl-2-[2-n-propoxyl-5-(4-methyl-1-piperazinylsulfonyl)phenyl]pyrimid-4(3H)-one, 6-ethyl-2-[2-n-propoxyl-5-(4-methyl-1-piperazinylsulfonyl)phenyl]pyrimid-4(3H)-one, 5-acetamido-6-ethyl-2-[2-n-propoxyl-5-(4-methyl-1-piperazinylsulfonyl)phenyl]pyrimid-4(3H)-one, 5-acetamido-6-amino-2-[2-n-propoxyl-5-(4-methyl-1-piperazinylsulfonyl)phenyl]pyrimid-4(3H)-one, 6-acetamido-2-[2-n-propoxyl-5-(4-methyl-1-piperazinylsulfonyl)phenyl]pyrimid-4(3H)-one, 5-bromo-6-isopropyl-2-[2-n-propoxyl-5-(4-methyl-1-piperazinylsulfonyl)phenyl]pyrimid-4(3H)-one, 6-isopropyl-2-[2-ethoxyl-5-(4-methyl-1-piperazinylsulfonyl)phenyl]pyrimid-4(3H)-one, 5-bromo-6-isopropyl-2-[2-ethoxyl-5-(4-methyl-1-piperazinylsulfonyl)phenyl]pyrimid-4(3H)-one, 5-chloro-6-isopropyl-2-[2-ethoxyl-5-(4-methyl-1-piperazinylsulfonyl)phenyl]pyrimid-4(3H)-one, 5-acetamido-6-isopropyl-2-[2-ethoxyl-5-(4-methyl-1-piperazinylsulfonyl)phenyl]pyrimid-4(3H)-one, 5-bromo-6-isopropyl-2-[2-n-butoxy-5-(4-methyl-1-piperazinylsulfonyl)phenyl]pyrimid-4(3H)-one, 5-bromo-6-n-octyl-2-[2-ethoxyl-5-(4-methyl-1-piperazinylsulfonyl)phenyl]pyrimid-4(3H)-one, 5-bromo-6-phenyl-2-[2-ethoxyl-5-(4-methyl-1-piperazinylsulfonyl)phenyl]pyrimid-4(3H)-one, 5-methyl-6-isopropyl-2-[2-n-propoxyl-5-(4-methyl-1-piperazinylsulfonyl)phenyl]pyrimid-4(3H)-one, 5-fluoro-6-ethyl-2-[2-n-propoxyl-5-(4-methyl-1-piperazinylsulfonyl)phenyl]pyrimid-4(3H)-one, 5-methyl-6-ethyl-2-[2-n-propoxyl-5-(4-methyl-1-piperazinylsulfonyl)phenyl]pyrimid-4(3H)-one, 5-hydroxy-6-isopropyl-2-[2-ethoxyl-5-(4-methyl-1-piperazinylsulfonyl)phenyl]pyrimid-4(3H)-one, 5-amino-6-isopropyl-2-[2-ethoxyl-5-(4-methyl-1-piperazinylsulfonyl)phenyl]pyrimid-4(3H)-one, 5-bromo-6-isopropyl-2-[2-n-hexyloxy-5-(4-methyl-1-piperazinylsulfonyl)phenyl]pyrimid-4(3H)-one, 5-bromo-6-isobutyl-2-[2-ethoxyl-5-(4-methyl-1-piperazinylsulfonyl)phenyl]pyrimid-4(3H)-one, 5-bromo-6-isopropyl-2-{2-n-propoxyl-5-[N-methyl-N-(2-hydroxyethyl)aminosulfonyl]phenyl}pyrimid-4(3H)-one, 5-bromo-6-isopropyl-2-{2-n-propoxyl-5-[N-(2-morpholinoethyl)aminosulfonyl]phenyl}pyrimid-4(3H)-one, 5-bromo-6-isopropyl-2-{2-n-propoxyl-5-[N-(3-morpholinopropyl)aminosulfonyl]phenyl}pyrimid-4(3H)-one, 5-bromo-6-isopropyl-2-{2-n-propoxyl-5-[N—(N',N'-diethylamino)ethylaminosulfonyl]phenyl}pyrimid-4(3H)-one, 5,6-diethyl-2-[2-n-propoxyl-5-(4-methyl-1-piperazinylsulfonyl)phenyl]pyrimid-4(3H)-one, 5,6-diethyl-2-{2-n-propoxyl-5-[N-methyl-N-(hydroxyethyl)aminosulfonyl]phenyl}pyrimid-4(3H)-one, 5,6-diethyl-2-{2-n-propoxyl-5-[N-(2-ethylaminoethyl)aminosulfonyl)phenyl}pyrimid-4(3H)-one, N-(3-(4,5-diethyl-1,6-dihydro-6-oxopyrimidin-2-yl)-4-n-propoxyphenylsulfonylproline, 2-(5-nitro-2-n-propoxyphenyl)-5-bromo-6-isopropylpyrimid-4(3H)-one, 2-(5-amino-2-n-propoxyphenyl)-5-bromo-6-isopropylpyrimid-4(3H)-one, 1-(3-(4-isopropyl-5-bromo-1,6-dihydro-6-oxopyrimidin-2-yl)-4-n-propoxyphenyl)-3-ethylthiourea, 1-[3-(4-isopropyl-5-bromo-1,6-dihydro-6-oxopyrimidin-2-yl)-4-n-propoxyphenyl]-3-ethyl-2-methylisothiourea, N-[3-(4-isopropyl-5-bromo-1,6-dihydro-6-oxopyrimidin-2-yl)-4-n-propoxyphenyl]-N',N"-triethylguanidine, N-[3-(4-isopropyl-5-bromo-1,6-dihydro-6-oxopyrimidin-2-yl)-4-n-propoxyphenyl]-N'-ethyl-piperidyl-1-formamidine, N-[3-(4-isopropyl-5-bromo-1,6-dihydro-6-oxopyrimidin-2-yl)-4-n-propoxyphenyl]-N'-ethyl-pyrrolyl-1-formamidine, 2-{2-[3-(4-isopropyl-5-bromo-1,6-dihydro-6-oxopyrimidin-2-yl)-4-n-propoxyphenyl]amino-4,5-dihydro-imidazol-1-yl}-ethanol, 2-(5-nitro-2-n-propoxyphenyl)-5,6-diethylpyrimid-4(3H)-one, 2-(5-amino-2-n-propoxyphenyl)-5,6-diethylpyrimid-4(3H)-one, 1-(3-(4,5-diethyl-1,6-dihydro-6-oxopyrimidin-2-yl)-4-n-propoxyphenyl)-3-ethylthiourea, 1-[3-(4,5-diethyl-1,6-dihydro-6-oxopyrimidin-2-yl)-4-n-propoxyphenyl]-3-ethyl-2-methylisothiourea, N-[3-(4,5-diethyl-1,6-dihydro-6-oxopyrimidin-2-yl)-4-n-propoxyphenyl]-N'-ethyl-piperidyl-1-formamidine, N-[3-(4,5-diethyl-1,6-dihydro-6-oxopyrimidin-2-yl)-4-n-propoxyphenyl]-N',N"-triethylguanidine, 2-{2-[3-(4,5-diethyl-1,6-dihydro-6-oxopyrimidin-2-yl)-4-n-propoxyphenyl]amino-4,5-dihydro-imidazol-1-yl}-ethanol, N-[3-(4,5-diethyl-1,6-dihydro-6-oxopyrimidin-2-yl)-4-n-propoxyphenyl]-N'-ethyl-pyrrolyl-1-formamide, N-[3-(4,5-diethyl-1,6-dihydro-6-oxopyrimidin-2-yl)-4-n-propoxyphenyl]-pyrrolyl-1-formamidine, 5-bromo-6-isopropyl-2-(2-n-propoxyl-5-mesylamidophenyl)pyrimid-4(3H)-one, 5,6-diethyl-2-(2-n-propoxyl-5-mesylamidophenyl)pyrimid-4(3H)-one, N-(3-(1,6-dihydro-4-isopropyl-5-bromo-6-oxopyrimidin-2-yl)-4-propoxyphenyl)acetamide, N-(3-(1,6-dihydro-4,5-diethyl-6-oxopyrimidin-2-yl)-4-propoxyphenyl)acetamide, N-(3-(1,6-dihydro-4,5-diethyl-6-oxopyrimidin-2-yl)-4-propoxyphenyl)propionamide, N-(3-(1,6-dihydro-4,5-diethyl-6-oxopyrimidin-2-yl)-4-propoxyphenyl)cyclohexamide, N-(3-(1,6-dihydro-4,5-diethyl-6-oxopyrimidin-2-yl)-4-propoxyphenyl)formamide, N-(3-(1,6-dihydro-4,5-diethyl-6-oxopyrimidin-2-yl)-4-propoxyphenyl)-1-t-butyloxycarbonyl-4-hydroxy-prolylamide,
4-n-propoxyl-3-(1,6-dihydro-4,5-diethyl-6-oxopyrimidin-2-yl)benzoic acid,
(morpholin-1-yl)(3-(4,5-diethyl-1,6-dihydro-6-oxopyrimidin-2-yl)-4-n-propoxyl)benzophenone,
(piperid-1-yl)(3-(4,5-diethyl-1,6-dihydro-6-oxopyrimidin-2-yl)-4-n-propoxyl)benzophenone,
(2-aminoformylpyrrol-1-yl)(3-(4,5-diethyl-1,6-dihydro-6-oxopyrimidin-2-yl)-4-n-propoxyl)benzophenone,
4-n-propoxyl-3-(1,6-dihydro-4-isopropyl-6-oxopyrimidin-2-yl)benzoic acid,
(morpholin-1-yl)(3-(4-isopropyl-5-bromo-1,6-dihydro-6-oxopyrimidin-2-yl)-4-n-propoxyl)benzophenone,
(piperid-1-yl)(3-(4-isopropyl-5-bromo-1,6-dihydro-6-oxopyrimidin-2-yl)-4-n-propoxyl)benzophenone,
(4-methyl-piperazin-1-yl)(3-(4-isopropyl-5-bromo-1,6-dihydro-6-oxopyrimidin-2-yl)-4-n-propoxyl)benzophenone,
2-(5-(N,N-dimethylamino-2-n-propoxyphenyl)-5,6-diethylpyrimid-4(3H)-one,
1-(3-(4,5-diethyl-1,6-dihydro-6-oxopyrimidin-2-yl)-4-n-propoxyphenyl)urea,
1-(3-(4,5-diethyl-1,6-dihydro-6-oxopyrimidin-2-yl)-4-n-propoxyphenyl)-3-ethylurea,
1-(3-(4-isopropyl-5-bromo-1,6-dihydro-6-oxopyrimidin-2-yl)-4-n-propoxyphenyl)-3-phenylthiourea,
1-(3-(4,5-diethyl-1,6-dihydro-6-oxopyrimidin-2-yl)-4-n-propoxyphenyl)-guanidine,
5-bromo-6-isopropyl-2-(5-(2-bromoacetyl)-2-n-propoxyphenyl)pyrimid-4(3H)-one,
5-bromo-6-isopropyl-2-(5-(2-morpholinylacetyl)-2-n-propoxyphenyl)pyrimid-4(3H)-one,
5-bromo-6-isopropyl-2-(5-(2-(4-methyl-piperazin-1-yl)acetyl)-2-n-propoxyphenyl)pyrimid-4(3H)-one,
5,6-diethyl-2-(5-(2-bromoacetyl)-2-n-propoxyphenyl)pyrimid-4(3H)-one,
5,6-diethyl-2-(5-(2-(4-methyl-piperazin-1-yl)acetyl)-2-n-propoxyphenyl)pyrimid-4(3H)-one,
5,6-diethyl-2-(5-(2-morpholinylacetyl)-2-n-propoxyphenyl)pyrimid-4(3H)-one,
5-bromo-6-isopropyl-2-(2-n-propoxyl-5-(tetrahydro-3,4,5-trihydroxy-6-(hydroxymethyl)-2H-pyran-2-ylamino)phenyl)pyrimid-4(3H)-one,
5-bromo-6-isopropyl-2-(2-n-propoxyl-5-(tetrahydro-3,4-dihydroxy-5-(1,2-dihydroxyethyl)fur-2-ylamino)phenyl)pyrimid-4(3H)-one,
5,6-diethyl-2-(2-n-propoxyl-5-(tetrahydro-3,4-dihydroxy-5-(1,2-dihydroxyethyl)fur-2-ylamino)phenyl)pyrimid-4(3H)-one,
5,6-diethyl-2-(2-n-propoxyl-5-(tetrahydro-3,4,5-trihydroxy-6-(hydroxymethyl)-2H-pyran-2-ylamino)phenyl)pyrimid-4(3H)-one,
2-(5-hydroxy-2-n-propoxyphenyl)-5,6-diethylpyrimid-4(3H)-one,
(3-(4,5-diethyl-1,6-dihydro-6-oxopyrimidin-2-yl)-4-n-propoxyphenyl)acetate,
(3-(4,5-diethyl-1,6-dihydro-6-oxopyrimidin-2-yl)-4-n-propoxyphenyl)ethylaminoformate,
5,6-diethyl-2-(2-n-propoxyl-5-(tetrahydro-3,4,5-trihydroxy-6-(hydroxymethyl)-2H-pyran-2-yloxy)phenyl)pyrimid-4(3H)-one,
(3-(4,5-diethyl-1,6-dihydro-6-oxopyrimidin-2-yl)-4-n-propoxyphenyl)mesylate,
2-(5-(2,5-dimethyl-1H-pyrrol-1-yl)-2-propoxyphenyl)-5,6-diethylpyrimid-4(3H)-one,
2,2'-(4-n-propoxyl-1,3-phenylene)bis(5,6-diethylpyrimid-4(3H)-one),
2-(5-(1,3,4-oxadiazol-2-yl)-2-propoxyphenyl)-5,6-diethylpyrimid-4(3H)-one,
ethyl 2-(3-(4,5-diethyl-1,6-dihydro-6-oxopyrimidin-2-yl)-4-n-propoxybenzamido)acetate,
3-(4,5-diethyl-1,6-dihydro-6-oxopyrimidin-2-yl)-N-(2-morpholinylethyl)-4-n-propoxybenzamide,
3-(4,5-diethyl-1,6-dihydro-6-oxopyrimidin-2-yl)-N,N-di(2-hydroxyethyl)-4-n-propoxybenzamide,
3-(4,5-diethyl-1,6-dihydro-6-oxopyrimidin-2-yl)-N-(2-caprolactam-3-yl)-4-n-propoxybenzamide,
(4-(2,3-dichlorophenyl)piperazin-1-yl)(3-(4,5-diethyl-1,6-dihydro-6-oxopyrimidin-2-yl)-4-n-propoxyl)benzophenone,
(3-isopropylpyrazol-1-yl)(3-(4,5-diethyl-1,6-dihydro-6-oxopyrimidin-2-yl)-4-n-propoxyl)benzophenone,
N-cyclohexyl-3-(4,5-diethyl-1,6-dihydro-6-oxopyrimidin-2-yl)-4-n-propoxybenzamide,
N-((pyrid-2-yl)methyl)-3-(4,5-diethyl-1,6-dihydro-6-oxopyrimidin-2-yl)-4-n-propoxybenzamide,
methyl 2-(3-(4,5-diethyl-1,6-dihydro-6-oxopyrimidin-2-yl)-4-n-propoxybenzamido)-3,3-dimethylbutyrate,
N-(3-(4,5-diethyl-1,6-dihydro-6-oxopyrimidin-2-yl)-4-n-propoxyphenyl)-2,2,2-trifluoroacetamide,
ethyl N-(3-(4,5-diethyl-1,6-dihydro-6-oxopyrimidin-2-yl)-4-n-propoxyphenyl)aminoformylformate,
N-(3-(4,5-diethyl-1,6-dihydro-6-oxopyrimidin-2-yl)-4-n-propoxyphenyl)acrylamide,
N-(3-(4,5-diethyl-1,6-dihydro-6-oxopyrimidin-2-yl)-4-n-propoxyphenyl)-2-crotonamide,
ethyl N-(3-(4,5-diethyl-1,6-dihydro-6-oxopyrimidin-2-yl)-4-n-propoxyphenyl)aminoformylacetate,
2-ethoxyl-N-(3-(4,5-diethyl-1,6-dihydro-6-oxopyrimidin-2-yl)-4-n-propoxyphenyl)benzamide,
N-(3-(4,5-diethyl-1,6-dihydro-6-oxopyrimidin-2-yl)-4-n-propoxyphenyl)nicotinamide,
N-(3-(4,5-diethyl-1,6-dihydro-6-oxopyrimidin-2-yl)-4-n-propoxyphenyl)-5-isopropylthiazolyl-2-formamide,
t-butyl 3-(N-(3-(4,5-diethyl-1,6-dihydro-6-oxopyrimidin-2-yl)-4-n-propoxyphenyl)aminoformyl)propylamino formate,
4-acetamido-N-(3-(4,5-diethyl-1,6-dihydro-6-oxopyrimidin-2-yl)-4-n-propoxyphenyl)butyramide,
1-acetyl-N-(3-(4,5-diethyl-1,6-dihydro-6-oxopyrimidin-2-yl)-4-n-propoxyphenyl)pyrrolidinyl-2-formamide,
2-acetamido-N-(3-(4,5-diethyl-1,6-dihydro-6-oxopyrimidin-2-yl)-4-n-propoxyphenyl)-3-methylbutyramide,
2-acetamido-N-(3-(4,5-diethyl-1,6-dihydro-6-oxopyrimidin-2-yl)-4-n-propoxyphenyl)-3-phenylpropionamide,
2-acetamido-N-(3-(4,5-diethyl-1,6-dihydro-6-oxopyrimidin-2-yl)-4-n-propoxyphenyl)propionamide,
2,6-diacetamido-N-(3-(4,5-diethyl-1,6-dihydro-6-oxopyrimidin-2-yl)-4-n-propoxyphenyl)hexanamide,
$N^1$-(3-(4,5-diethyl-1,6-dihydro-6-oxopyrimidin-2-yl)-4-n-propoxyphenyl)propanediamide,
$N^1$-(3-(4,5-diethyl-1,6-dihydro-6-oxopyrimidin-2-yl)-4-n-propoxyphenyl)oxalamide,
N-(aminoformylmethyl)-3-(4,5-diethyl-1,6-dihydro-6-oxopyrimidin-2-yl)-4-n-propoxybenzamide,
5,6-diethyl-2-{2-n-propoxyl-5-[(2-(1-methylpyrrol-2-yl)ethyl)aminosulfonyl]phenyl}pyrimid-4(3H)-one,
3-(4,5-diethyl-1,6-dihydro-6-oxopyrimidin-2-yl)-N-(2-(1-methylpyrrol-2-yl)ethyl)-4-n-propoxylbenzamide,
2-(N-(3-(4,5-diethyl-1,6-dihydro-6-oxopyrimidin-2-yl)-4-n-propoxyphenyl)sulfonyl)amino-5-ureapentanoic acid, 2-(N-(3-(4,5-diethyl-1,6-dihydro-6-oxopyrimidin-2-yl)-4-n-propoxyphenyl)sulfonyl)amino-5-aminopentanoic acid,
2-(N-(3-(4,5-diethyl-1,6-dihydro-6-oxopyrimidin-2-yl)-4-n-propoxyphenyl)sulfonyl)amino-3-methylbutyric acid,
2-(N-(3-(4,5-diethyl-1,6-dihydro-6-oxopyrimidin-2-yl)-4-n-propoxyphenyl)sulfonyl)aminopropanoic acid,
2-(N-(3-(4,5-diethyl-1,6-dihydro-6-oxopyrimidin-2-yl)-4-n-propoxyphenyl)sulfonyl)amino-3-hydroxypropanoic acid,
ethyl 2-(N-(3-(4,5-diethyl-1,6-dihydro-6-oxopyrimidin-2-yl)-4-n-propoxyphenyl)sulfonyl)aminopropionate,
3-(N-(3-(4,5-diethyl-1,6-dihydro-6-oxopyrimidin-2-yl)-4-n-propoxyphenyl)sulfonyl)aminopropylsulfonic acid,
2-(N-(3-(4,5-diethyl-1,6-dihydro-6-oxopyrimidin-2-yl)-4-n-propoxyphenyl)sulfonyl)aminoethylsulfonic acid,
2-(N-(3-(4,5-diethyl-1,6-dihydro-6-oxopyrimidin-2-yl)-4-n-propoxyphenyl)sulfonyl)amino-3-aminoformylpropanoic acid,
2-(N-(3-(4,5-diethyl-1,6-dihydro-6-oxopyrimidin-2-yl)-4-n-propoxyphenyl)sulfonyl)amino-3-indolepropionic acid,
2-(N-(3-(4,5-diethyl-1,6-dihydro-6-oxopyrimidin-2-yl)-4-n-propoxyphenyl)sulfonyl)aminoacetic acid,
2-(N-(3-(4,5-diethyl-1,6-dihydro-6-oxopyrimidin-2-yl)-4-n-propoxyphenyl)sulfonyl)amino-3,3-dimethylbutyric acid,
2-(N-(3-(4,5-diethyl-1,6-dihydro-6-oxopyrimidin-2-yl)-4-n-propoxyphenyl)sulfonyl)amino-4-aminoformylbutyric acid,
ethyl 2-(N-(3-(4,5-diethyl-1,6-dihydro-6-oxopyrimidin-2-yl)-4-n-propoxyphenyl)sulfonyl)amino-3-methylvalerate,
methyl 2-(3-(4,5-diethyl-1,6-dihydro-6-oxopyrimidin-2-yl)-4-n-propoxyphenylsulfonamido)-6-acetamidocaproate,
5,6-diethyl-2-(2-n-propoxyl-5-(4-hydroxyethyl-1-piperazinylsulfonyl)phenyl]pyrimid-4(3H)-one,
5,6-diethyl-2-(2-n-propoxyl-5-(3-hydroxypropylaminosulfonyl)phenyl]pyrimid-4(3H)-one,
5,6-diethyl-2-(2-n-propoxyl-5-(N-(2-morpholinylethyl)-N-(2-hydroxyethyl)aminosulfonyl)phenyl)pyrimid-4(3H)-one,
5,6-diethyl-2-(2-n-propoxyl-5-(N-methyl-N-(2-(pyrrolidin-1-yl)ethyl)aminosulfonyl)phenyl)pyrimid-4(3H)-one,
5,6-diethyl-2-(2-n-propoxyl-5-(2-(N,N-diethyl)aminoethylaminosulfonyl)phenyl]pyrimid-4(3H)-one maleate,
2-(3-(4,5-diethyl-1,6-dihydro-6-oxopyrimidin-2-yl)-4-n-propoxybenzamido)-3-phenylpropanoic acid,
methyl N-(3-(4,5-diethyl-1,6-dihydro-6-oxopyrimidin-2-yl)-4-n-propoxylbenzoylprolinate,
methyl 2-(3-(4,5-diethyl-1,6-dihydro-6-oxopyrimidin-2-yl)-4-n-propoxylbenzamido)-3-(4-hydroxyphenyl)propionate,
ethyl 2-3-(4,5-diethyl-1,6-dihydro-6-oxopyrimidin-2-yl)-4-n-propoxybenzamido)-3-(1H-indol-3-yl)propionate,
methyl 2-(3-(4,5-diethyl-1,6-dihydro-6-oxopyrimidin-2-yl)-4-n-propoxylbenzamido)-3-methylbutyrate,
methyl 2-(3-(4,5-diethyl-1,6-dihydro-6-oxopyrimidin-2-yl)-4-n-propoxylbenzamido)-3-(1H-imidazol-4-yl)propionate,
ethyl 2-3-(4,5-diethyl-1,6-dihydro-6-oxopyrimidin-2-yl)-4-n-propoxybenzamido)-3-methylvalerate,
2-(3-(4,5-diethyl-1,6-dihydro-6-oxopyrimidin-2-yl)-4-n-propoxylbenzamido)propionic acid,
2-(3-(4,5-diethyl-1,6-dihydro-6-oxopyrimidin-2-yl)-4-n-propoxybenzamido)-3-aminoformylpropionic acid,
2-(3-(4,5-diethyl-1,6-dihydro-6-oxopyrimidin-2-yl)-4-n-propoxybenzamido)-4-aminoformylbutyric acid,
2-(3-(4,5-diethyl-1,6-dihydro-6-oxopyrimidin-2-yl)-4-n-propoxybenzamido)-3-hydroxypropionic acid,
2-(3-(4,5-diethyl-1,6-dihydro-6-oxopyrimidin-2-yl)-4-n-propoxybenzamido)-5-guanidinopentanoic acid,
methyl 2-(3-(4,5-diethyl-1,6-dihydro-6-oxopyrimidin-2-yl)-4-n-propoxybenzamido)-3-phenylpropionate,
methyl 2-(3-(4,5-diethyl-1,6-dihydro-6-oxopyrimidin-2-yl)-4-n-propoxybenzamido)propionate,
methyl 2-(3-(4,5-diethyl-1,6-dihydro-6-oxopyrimidin-2-yl)-4-n-propoxybenzamido)-4-methylvalerate,
ethyl 2-(3-(4,5-diethyl-1,6-dihydro-6-oxopyrimidin-2-yl)-4-n-propoxybenzamido) propionate,
3-(4,5-diethyl-1,6-dihydro-6-oxopyrimidin-2-yl)-N-(1-(4-methylpiperazin-1-yl)-1-oxopropan-2-yl)-4-n-propoxybenzamide,
N-(1-aminoformylethyl)-3-(4,5-diethyl-1,6-dihydro-6-oxopyrimidin-2-yl)-4-n-propoxybenzamide,
3-(4,5-diethyl-1,6-dihydro-6-oxopyrimidin-2-yl)-4-n-propoxybenzamide,
3-(4,5-diethyl-1,6-dihydro-6-oxopyrimidin-2-yl)-4-n-propoxyl-N-(2-(thien-2-yl)ethyl)benzamide,
3-(4,5-diethyl-1,6-dihydro-6-oxopyrimidin-2-yl)-4-n-propoxyl-N-((fur-2-yl)methyl)benzamide,
N-t-butyl-3-(4,5-diethyl-1,6-dihydro-6-oxopyrimidin-2-yl)-4-n-propoxybenzamide,
3-(4,5-diethyl-1,6-dihydro-6-oxopyrimidin-2-yl)-N-isobutyl-4-n-propoxylbenzamide,
3-(4,5-diethyl-1,6-dihydro-6-oxopyrimidin-2-yl)-N-allyl-4-n-propoxylbenzamide,
(4-(pyrid-2-yl)piperazin-1-yl)(3-(4,5-diethyl-1,6-dihydro-6-oxopyrimidin-2-yl)-4-n-propoxylbenzophenone,
(4-(hydroxyethyloxylethyl)piperazin-1-yl)(3-(4,5-diethyl-1,6-dihydro-6-oxopyrimidin-2-yl)-4-n-propoxylbenzophenone,
(4-(hydroxyethyl)piperazin-1-yl)(3-(4,5-diethyl-1,6-dihydro-6-oxopyrimidin-2-yl)-4-n-propoxylbenzophenone,
3-(4,5-diethyl-1,6-dihydro-6-oxopyrimidin-2-yl)-N-(3-hydroxypropyl)-4-n-propoxylbenzamide,
3-(4,5-diethyl-1,6-dihydro-6-oxopyrimidin-2-yl)-N-(1-hydroxy-2-propyl)-4-n-propoxybenzamide,
N-ethyl-3-(4,5-diethyl-1,6-dihydro-6-oxopyrimidin-2-yl)-N-(2-hydroxyethyl)-4-n-propoxylbenzamide,
3-(4,5-diethyl-1,6-dihydro-6-oxopyrimidin-2-yl)-N-(2-diethylaminoethyl)-4-n-propoxylbenzamide,
3-(3-(4,5-diethyl-1,6-dihydro-6-oxopyrimidin-2-yl)-4-n-propoxybenzamido)propyl-1-sulfonic acid,
2-(3-(4,5-diethyl-1,6-dihydro-6-oxopyrimidin-2-yl)-4-n-propoxybenzamido)ethylsulfonic acid,
3-(4,5-diethyl-1,6-dihydro-6-oxopyrimidin-2-yl)-N-(2-hydroxyethyl)-N-methyl-4-n-propoxylbenzamide,
(4-benzylpiperazin-1-yl)(3-(4,5-diethyl-1,6-dihydro-6-oxopyrimidin-2-yl)-4-n-propoxylbenzophenone,
3-(4,5-diethyl-1,6-dihydro-6-oxopyrimidin-2-yl)-N-methyl-N-(2-(pyrrolidin-1-yl)ethyl)-4-n-propoxybenzamide,
methyl 5-(3-(4,5-diethyl-1,6-dihydro-6-oxopyrimidin-2-yl)-4-n-propoxybenzamido)piperidyl-2-formate,
3-(4,5-diethyl-1,6-dihydro-6-oxopyrimidin-2-yl)-N-methoxyl-N-methyl-4-n-propoxybenzamide, 5,6-diethyl-2-[2-(3-methoxyln-propoxyl)-5-(4-methyl-1-piperazinylsulfonyl)phenyl]pyrimid-4(3H)-one, 2-chloro-N-3-(4,5-diethyl-1,6-dihydro-6-oxopyrimidin-2-yl)-4-n-propoxyphenyl)acetamide, 2-(dimethylamino)-N-3-(4,5-diethyl-1,6-dihydro-6-oxopyrimidin-2-yl)-4-n-propoxyphenyl)acetamide, N-(3-(4,5-diethyl-1,6-dihydro-6-oxopyrimidin-2-yl)-4-n-propoxyphenyl)-2-(4-methylpiperazin-1-yl)acetamide, N-(3-(4,5-diethyl-1,6-dihydro-6-oxopyrimidin-2-yl)-4-n-propoxyphenyl)-2-morpholinyl)acetamide, N-(3-(4,5-diethyl-1,6-dihydro-6-oxopyrimidin-2-yl)-4-n-propoxyphenyl)-2-(piperid-1-yl)acetamide, dimethyl(3-(4,5-diethyl-1,6-dihydro-6-oxopyrimidin-2-yl)-4-n-propoxyphenylaminoformyl)methylphosphate, N-(3-(4,5-diethyl-1,6-dihydro-6-oxopyrimidin-2-yl)-4-n-propoxyphenyl)isobutyramide, N-(3-(4,5-diethyl-1,6-dihydro-6-oxopyrimidin-2-yl)-4-n-propoxyphenyl)-3-methylbutyramide, N-(3-(4,5-diethyl-1,6-dihydro-6-oxopyrimidin-2-yl)-4-n-propoxyphenyl)-2-phenylacetamide, N-(3-(4,5-diethyl-1,6-dihydro-6-oxopyrimidin-2-yl)-4-n-propoxyphenyl)benzamide, ethyl 3-(3-(4,5-diethyl-1,6-dihydro-6-oxopyrimidin-2-yl)-4-n-propoxyphenylaminoformyl)propionate, N-(3-(4,5-diethyl-1,6-dihydro-6-oxopyrimidin-2-yl)-4-n-propoxyphenyl)-5-oxopyrrolidinyl-2-formamide, 2-acetamido-N-3-(4,5-diethyl-1,6-dihydro-6-oxopyrimidin-2-yl)-4-n-propoxyphenyl)-4-methylpentanamide, N-(3-(4,5-diethyl-1,6-dihydro-6-oxopyrimidin-2-yl)-4-n-propoxyphenyl)-2-acetamido-3-(1H-indol-3-yl)propionamide, 2-acetamido-N-(3-(4,5-diethyl-1,6-dihydro-6-oxopyrimidin-2-yl)-4-n-propoxyphenyl)glutaramide, 2-acetamido-N-(3-(4,5-diethyl-1,6-dihydro-6-oxopyrimidin-2-yl)-4-n-propoxyphenyl)-3-hydroxybutyramide, 2-acetamido-N-(3-(4,5-diethyl-1,6-dihydro-6-oxopyrimidin-2-yl)-4-n-propoxyphenyl)-3-hydroxypropionamide, 2-(3-(4,5-diethyl-1,6-dihydro-6-oxopyrimidin-2-yl)-4-n-propoxyphenylaminoformyl)-2-acetamidoethyl acetate, 5,6-diethyl-2-(5-(ethylamino)-2-n-propoxyphenyl)pyrimid-4(3H)-one, N-ethyl-N-(3-(4,5-diethyl-1,6-dihydro-6-oxopyrimidin-2-yl)-4-n-propoxyphenyl)propionamide, ethyl (N-ethyl-N-(3-(4,5-diethyl-1,6-dihydro-6-oxopyrimidin-2-yl)-4-n-propoxyphenyl)aminoformylformate, 1,3-diethyl-1-(3-(4,5-diethyl-1,6-dihydro-6-oxopyrimidin-2-yl)-4-n-propoxyphenyl)urea, N-(3-(4,5-diethyl-1,6-dihydro-6-oxopyrimidin-2-yl)-4-n-propoxyphenyl)piperidyl-1-formamide, N-(3-(4,5-diethyl-1,6-dihydro-6-oxopyrimidin-2-yl)-4-n-propoxyphenyl)-4-methylpiperazinyl-1-formamide, 1-(3-(4,5-diethyl-1,6-dihydro-6-oxopyrimidin-2-yl)-4-n-propoxyphenyl)-3-propylurea, 1-cyclohexyl-3-(3-(4,5-diethyl-1,6-dihydro-6-oxopyrimidin-2-yl)-4-n-propoxyphenyl)urea, 1,1-diethyl-3-(3-(4,5-diethyl-1,6-dihydro-6-oxopyrimidin-2-yl)-4-n-propoxyphenyl)urea, 1-(2-(diethylamino)ethyl)-3-(3-(4,5-diethyl-1,6-dihydro-6-oxopyrimidin-2-yl)-4-n-propoxyphenyl)urea maleate, (4-methylpiperazin-1-yl)(3-(4,5-diethyl-1,6-dihydro-6-oxopyrimidin-2-yl)-4-n-propoxylbenzophenone, 5-iodo-6-isopropyl-2-[2-n-propoxyl-5-(4-methyl-1-piperazinylsulfonyl)phenyl]pyrimid-4(3H)-one, 5-chloro-6-ethyl-2-[2-n-propoxyl-5-(4-methyl-1-piperazinylsulfonyl)phenyl]pyrimid-4(3H)-one, 5,6-diethyl-2-(2-n-propoxyl-5-((tetrahydro-2,4,5-trihydroxy-6-(hydroxymethyl)-2H-pyran-3-ylamino)sulfonyl)phenyl]pyrimid-4(3H)-one, 2-(3-(4,5-diethyl-1,6-dihydro-6-oxopyrimidin-2-yl)-4-n-propoxybenzamido)-5-ureapentanoic acid, 2-(3-(4,5-diethyl-1,6-dihydro-6-oxopyrimidin-2-yl)-4-n-propoxybenzamido)-5-aminopentanoic acid, 3-(3-(4,5-diethyl-1,6-dihydro-6-oxopyrimidin-2-yl)-N-(tetrahydro-2,4,5-trihydroxy-6-(hydroxymethyl)-2H-pyran-3-yl)-4-n-propoxybenzamide, 2-(3-(4,5-diethyl-1,6-dihydro-6-oxopyrimidin-2-yl)-4-n-propoxybenzamido)ethylsulfamide, 3-(4,5-diethyl-1,6-dihydro-6-oxopyrimidin-2-yl)-N-(4-methyl-piperazin-1-ylsulfonylethyl)-4-n-propoxybenzamide, 3-(4,5-diethyl-1,6-dihydro-6-oxopyrimidin-2-yl)-N—(N,N-diethylaminosulfonylethyl)-4-n-propoxybenzamide, 3-(3-(4,5-diethyl-1,6-dihydro-6-oxopyrimidin-2-yl)-4-n-propoxybenzamido)propylsulfamide, 3-(4,5-diethyl-1,6-dihydro-6-oxopyrimidin-2-yl)-N-(4-methyl-piperazin-1-ylsulfonylpropyl)-4-n-propoxybenzamide, 3-(4,5-diethyl-1,6-dihydro-6-oxopyrimidin-2-yl)-N—(N,N-diethylaminosulfonylpropyl)-4-n-propoxybenzamide, 5,6-diethyl-2-(5-(tetrahydro-3,4,5-trihydroxy-6-(hydroxymethyl)-2H-pyran-2-yl)-2-n-propoxyphenyl)pyrimid-4(3H)-one, 5-iodo-6-ethyl-2-[2-n-propoxyl-5-(4-methyl-1-piperazinylsulfonyl)phenyl]pyrimid-4(3H)-one, 5-bromo-6-ethyl-2-[2-n-propoxyl-5-(4-methyl-1-piperazinylsulfonyl)phenyl]pyrimid-4(3H)-one, and 5-chloro-6-isopropyl-2-[2-n-propoxyl-5-(4-methyl-1-piperazinylsulfonyl)phenyl]pyrimid-4(3H)-one.

4. The compound or a pharmaceutically acceptable salt or solvate thereof according to claim 1, wherein, said phenylpyrimidone compound is selected from the group consisting of:

5,6-diethyl-2-[2-n-propoxyl-5-(4-methyl-1-piperazinylsulfonyl)phenyl]pyrimid-4(3H)-one, 5,6-diethyl-2-{2-n-propoxyl-5-[N-(2-morpholinylethyl)aminosulfonyl)phenyl}pyrimid-4(3H)-one, N-(3-(4,5-diethyl-1,6-dihydro-6-oxopyrimidin-2-yl)-4-n-propoxyphenylsulfonylproline, 1-(3-(4,5-diethyl-1,6-dihydro-6-oxopyrimidin-2-yl)-4-n-propoxyphenyl)-3-ethylthiourea, N-[3-(4,5-diethyl-1,6-dihydro-6-oxopyrimidin-2-yl)-4-n-propoxyphenyl]-N',N"-triethyl guanidine, N-[3-(4,5-diethyl-1,6-dihydro-6-oxopyrimidin-2-yl)-4-n-propoxyphenyl]-pyrrolyl-1-formamide, 5-bromo-6-isopropyl-2-(2-n-propoxyl-5-mesylamidophenyl)pyrimid-4(3H)-one, 5,6-diethyl-2-(2-n-propoxyl-5-mesylamidophenyl)pyrimid-4(3H)-one, N-(3-(1,6-dihydro-4-isopropyl-5-bromo-6-oxopyrimidin-2-yl)-4-propoxyphenyl)acetamide, N-(3-(1,6-dihydro-4,5-diethyl-6-oxopyrimidin-2-yl)-4-propoxyphenyl)acetamide, N-(3-(1,6-dihydro-4,5-diethyl-6-oxopyrimidin-2-yl)-4-propoxyphenyl)propionamide, N-(3-(1,6-dihydro-4,5-diethyl-6-oxopyrimidin-2-yl)-4-propoxyphenyl)cyclohexamide, N-(3-(1,6-dihydro-4,5-diethyl-6-oxopyrimidin-2-yl)-4-propoxyphenyl)-1-t-butyloxycarbonyl-4-hydroxy-prolylamide, (morpholin-1-yl)(3-(4,5-diethyl-1,6-dihydro-6-oxopyrimidin-2-yl)-4-n-propoxyl)benzophenone,
(piperid-1-yl)(3-(4,5-diethyl-1,6-dihydro-6-oxopyrimidin-2-yl)-4-n-propoxyl)benzophenone,
(2-aminoformylpyrrol-1-yl)(3-(4,5-diethyl-1,6-dihydro-6-oxopyrimidin-2-yl)-4-n-propoxyl)benzophenone,
(morpholin-1-yl)(3-(4-isopropyl-5-bromo-1,6-dihydro-6-oxopyrimidin-2-yl)-4-n-propoxyl)benzophenone,
1-(3-(4,5-diethyl-1,6-dihydro-6-oxopyrimidin-2-yl)-4-n-propoxyphenyl)urea,
1-(3-(4,5-diethyl-1,6-dihydro-6-oxopyrimidin-2-yl)-4-n-propoxyphenyl)-3-ethylurea,
5,6-diethyl-2-(5-(2-morpholinylacetyl)-2-n-propoxyphenyl)pyrimid-4(3H)-one,
2,2'-(4-n-propoxyl-1,3-phenylenyl)bis(5,6-diethylpyrimid-4(3H)-one),
ethyl 2-(3-(4,5-diethyl-1,6-dihydro-6-oxopyrimidin-2-yl)-4-n-propoxybenzamido)acetate,
N-(3-(4,5-diethyl-1,6-dihydro-6-oxopyrimidin-2-yl)-4-n-propoxyphenyl)-2,2,2-trifluoroacetamide,
ethyl N-(3-(4,5-diethyl-1,6-dihydro-6-oxopyrimidin-2-yl)-4-n-propoxyphenyl)aminoformylacetate,
4-acetamido-N-(3-(4,5-diethyl-1,6-dihydro-6-oxopyrimidin-2-yl)-4-n-propoxyphenyl)butyramide,
1-acetyl-N-(3-(4,5-diethyl-1,6-dihydro-6-oxopyrimidin-2-yl)-4-n-propoxyphenyl)pyrrolidinyl-2-formamide,
2-acetamido-N-(3-(4,5-diethyl-1,6-dihydro-6-oxopyrimidin-2-yl)-4-n-propoxyphenyl)-3-phenylpropionamide,
$N^1$-(3-(4,5-diethyl-1,6-dihydro-6-oxopyrimidin-2-yl)-4-n-propoxyphenyl)oxalamide,
5,6-diethyl-2-{2-n-propoxyl-5-[(2-(1-methylpyrrol-2-yl)ethyl)aminosulfonyl]phenyl}pyrimid-4(3H)-one,
3-(4,5-diethyl-1,6-dihydro-6-oxopyrimidin-2-yl)-N-(2-(1-methylpyrrol-2-yl)ethyl)-4-n-propoxylbenzamide,
2-(N-(3-(4,5-diethyl-1,6-dihydro-6-oxopyrimidin-2-yl)-4-n-propoxyphenyl)sulfonyl)amino-5-ureapentanoic acid,
2-(N-(3-(4,5-diethyl-1,6-dihydro-6-oxopyrimidin-2-yl)-4-n-propoxyphenyl)sulfonyl)amino-5-aminopentanoic acid,
ethyl 2-(N-(3-(4,5-diethyl-1,6-dihydro-6-oxopyrimidin-2-yl)-4-n-propoxyphenyl)sulfonyl)aminopropionate,
3-(N-(3-(4,5-diethyl-1,6-dihydro-6-oxopyrimidin-2-yl)-4-n-propoxyphenyl)sulfonyl)aminopropylsulfonic acid,
2-(N-(3-(4,5-diethyl-1,6-dihydro-6-oxopyrimidin-2-yl)-4-n-propoxyphenyl)sulfonyl)aminoethylsulfonic acid,
2-(N-(3-(4,5-diethyl-1,6-dihydro-6-oxopyrimidin-2-yl)-4-n-propoxyphenyl)sulfonyl)amino-3-aminoformylpropanoic acid,
5,6-diethyl-2-(2-n-propoxyl-5-(4-hydroxyethyl-1-piperazinylsulfonyl)phenyl]pyrimid-4(3H)-one,
5,6-diethyl-2-(2-n-propoxyl-5-(N-(2-morpholinylethyl)-N-(2-hydroxyethyl)aminosulfonyl)phenyl)pyrimid-4(3H)-one,
2-(3-(4,5-diethyl-1,6-dihydro-6-oxopyrimidin-2-yl)-4-n-propoxybenzamido)-3-phenylpropanoic acid,
methyl N-(3-(4,5-diethyl-1,6-dihydro-6-oxopyrimidin-2-yl)-4-n-propoxylbenzoylprolinate,
methyl 2-(3-(4,5-diethyl-1,6-dihydro-6-oxopyrimidin-2-yl)-4-n-propoxylbenzamido)-3-(4-hydroxyphenyl)propionate,
2-(3-(4,5-diethyl-1,6-dihydro-6-oxopyrimidin-2-yl)-4-n-propoxylbenzamido)propanoic acid,
2-(3-(4,5-diethyl-1,6-dihydro-6-oxopyrimidin-2-yl)-4-n-propoxybenzamido)-3-aminoformylpropanoic acid,
2-(3-(4,5-diethyl-1,6-dihydro-6-oxopyrimidin-2-yl)-4-n-propoxybenzamido)-5-guanidinopentanoic acid,
methyl 2-(3-(4,5-diethyl-1,6-dihydro-6-oxopyrimidin-2-yl)-4-n-propoxybenzamido)-3-phenylpropanoic acid,
methyl 2-(3-(4,5-diethyl-1,6-dihydro-6-oxopyrimidin-2-yl)-4-n-propoxybenzamido)propanoic acid,
3-(4,5-diethyl-1,6-dihydro-6-oxopyrimidin-2-yl)-N-(1-(4-methylpiperazin-1-yl)-1-oxopropan-2-yl)-4-n-propoxybenzamide,
N-(1-aminoformylethyl)-3-(4,5-diethyl-1,6-dihydro-6-oxopyrimidin-2-yl)-4-n-propoxybenzamide,
(4-(hydroxyethyoxylethyl)piperazin-1-yl)(3-(4,5-diethyl-1,6-dihydro-6-oxopyrimidin-2-yl)-4-n-propoxylbenzophenone,
(4-(hydroxyethyl)piperazin-1-yl)(3-(4,5-diethyl-1,6-dihydro-6-oxopyrimidin-2-yl)-4-n-propoxylbenzophenone,
3-(4,5-diethyl-1,6-dihydro-6-oxopyrimidin-2-yl)-N-(1-hydroxy-2-propyl)-4-n-propoxybenzamide,
3-(3-(4,5-diethyl-1,6-dihydro-6-oxopyrimidin-2-yl)-4-n-propoxybenzamido)propyl-1-sulfonic acid,
methyl 5-(3-(4,5-diethyl-1,6-dihydro-6-oxopyrimidin-2-yl)-4-n-propoxybenzamido)piperidinyl-2-formate,
N-(3-(4,5-diethyl-1,6-dihydro-6-oxopyrimidin-2-yl)-4-n-propoxyphenyl)-2-(4-methylpiperazin-1-yl)acetamide,
N-(3-(4,5-diethyl-1,6-dihydro-6-oxopyrimidin-2-yl)-4-n-propoxyphenyl)benzamide,
1-(2-(diethylamino)ethyl)-3-(3-(4,5-diethyl-1,6-dihydro-6-oxopyrimidin-2-yl)-4-n-propoxyphenyl)urea maleate, (4-methylpiperazin-1-yl)(3-(4,5-diethyl-1,6-dihydro-6-oxopyrimidin-2-yl)-4-n-propoxylbenzophenone,
5,6-diethyl-2-(2-n-propoxyl-5-((tetrahydro-2,4,5-trihydroxy-6-(hydroxymethyl)-2H-pyran-3-ylamino)sulfonyl)phenyl]pyrimid-4(3H)-one,
2-(3-(4,5-diethyl-1,6-dihydro-6-oxopyrimidin-2-yl)-4-n-propoxybenzamido)-5-ureapentanoic acid,
2-(3-(4,5-diethyl-1,6-dihydro-6-oxopyrimidin-2-yl)-4-n-propoxybenzamido)-5-aminopentanoic acid,
3-(3-(4,5-diethyl-1,6-dihydro-6-oxopyrimidin-2-yl)-N-(tetrahydro-2,4,5-trihydroxy-6-(hydroxymethyl)-2H-pyran-3-yl)-4-n-propoxybenzamide,
2-(3-(4,5-diethyl-1,6-dihydro-6-oxopyrimidin-2-yl)-4-n-propoxybenzamido)ethylsulfamide,
3-(4,5-diethyl-1,6-dihydro-6-oxopyrimidin-2-yl)-N-(4-methyl-piperazin-1-ylsulfonylethyl)-4-n-propoxybenzamide,
3-(4,5-diethyl-1,6-dihydro-6-oxopyrimidin-2-yl)-N—(N,N-diethylaminosulfonylethyl)-4-n-propoxybenzamide,
3-(3-(4,5-diethyl-1,6-dihydro-6-oxopyrimidin-2-yl)-4-n-propoxybenzamido)propylsulfamide,
3-(4,5-diethyl-1,6-dihydro-6-oxopyrimidin-2-yl)-N-(4-methyl-piperazin-1-ylsulfonylpropyl)-4-n-propoxybenzamide,
3-(4,5-diethyl-1,6-dihydro-6-oxopyrimidin-2-yl)-N—(N,N-diethylaminosulfonylpropyl)-4-n-propoxybenzamide, and
5,6-diethyl-2-(5-(tetrahydro-3,4,5-trihydroxy-6-(hydroxymethyl)-2H-pyran-2-yl)-2-n-propoxyphenyl)pyrimid-4(3H)-one.

5. The compound or a pharmaceutically acceptable salt or solvate thereof according to claim 1, wherein, said phenylpyrimidone compound is selected from the group consisting of:
5,6-diethyl-2-[2-n-propoxyl-5-(4-methyl-1-piperazinylsulfonyl)phenyl]pyrimid-4(3H)-one,
5,6-diethyl-2-{2-n-propoxyl-5-[N-(2-morpholinylethyl)aminosulfonyl)phenyl}pyrimid-4(3H)-one, N-(3-(4,5-diethyl-1,6-dihydro-6-oxopyrimidin-2-yl)-4-n-propoxyphenylsulfonylproline, 1-(3-(4,5-diethyl-1,6-dihydro-6-oxopyrimidin-2-yl)-4-n-propoxyphenyl)-3-ethylthiourea, N-[3-(4,5-diethyl-1,6-dihydro-6-oxopyrimidin-2-yl)-4-n-propoxyphenyl]-N',N"-triethylguanidine, N-[3-(4,5-diethyl-1,6-dihydro-6-oxopyrimidin-2-yl)-4-n-propoxyphenyl]-pyrrolyl-1-formamide, 5-bromo-6-isopropyl-2-(2-n-propoxyl-5-mesylamidophenyl)pyrimid-4(3H)-one, 5,6-diethyl-2-(2-n-propoxyl-5-mesylamidophenyl)pyrimid-4(3H)-one, N-(3-(1,6-dihydro-4-isopropyl-5-bromo-6-oxopyrimidin-2-yl)-4-propoxyphenyl)acetamide, N-(3-(1,6-dihydro-4,5-diethyl-6-oxopyrimidin-2-yl)-4-propoxyphenyl)acetamide, N-(3-(1,6-dihydro-4,5-diethyl-6-oxopyrimidin-2-yl)-4-propoxyphenyl)propionamide, N-(3-(1,6-dihydro-4,5-diethyl-6-oxopyrimidin-2-yl)-4-propoxyphenyl)cyclohexamide, N-(3-(1,6-dihydro-4,5-diethyl-6-oxopyrimidin-2-yl)-4-propoxyphenyl)-1-t-butyloxycarbonyl-4-hydroxy-prolylamide, (morpholin-1-yl)(3-(4,5-diethyl-1,6-dihydro-6-oxopyrimidin-2-yl)-4-n-propoxyl)benzophenone, (piperid-1-yl)(3-(4,5-diethyl-1,6-dihydro-6-oxopyrimidin-2-yl)-4-n-propoxyl)benzophenone, (2-aminoformylpyrrol-1-yl)(3-(4,5-diethyl-1,6-dihydro-6-oxopyrimidin-2-yl)-4-n-propoxyl)benzophenone, (morpholin-1-yl)(3-(4-isopropyl-5-bromo-1,6-dihydro-6-oxopyrimidin-2-yl)-4-n-propoxyl)benzophenone, 1-(3-(4,5-diethyl-1,6-dihydro-6-oxopyrimidin-2-yl)-4-n-propoxyphenyl)urea, 1-(3-(4,5-diethyl-1,6-dihydro-6-oxopyrimidin-2-yl)-4-n-propoxyphenyl)-3-ethylurea, 5,6-diethyl-2-(5-(2-morpholinylacetyl)-2-n-propoxyphenyl)pyrimid-4(3H)-one, 2,2'-(4-n-propoxyl-1,3-phenylenyl)bis(5,6-diethylpyrimid-4(3H)-one), ethyl2-(3-(4,5-diethyl-1,6-dihydro-6-oxopyrimidin-2-yl)-4-n-propoxybenzamido)acetate, N-(3-(4,5-diethyl-1,6-dihydro-6-oxopyrimidin-2-yl)-4-n-propoxyphenyl)-2,2,2-trifluoroacetamide, ethyl N-(3-(4,5-diethyl-1,6-dihydro-6-oxopyrimidin-2-yl)-4-n-propoxyphenyl)aminoformylacetate, 4-acetamido-N-(3-(4,5-diethyl-1,6-dihydro-6-oxopyrimidin-2-yl)-4-n-propoxyphenyl)butyramide, 1-acetyl-N-(3-(4,5-diethyl-1,6-dihydro-6-oxopyrimidin-2-yl)-4-n-propoxyphenyl)pyrrolidinyl-2-formamide, 2-acetamido-N-(3-(4,5-diethyl-1,6-dihydro-6-oxopyrimidin-2-yl)-4-n-propoxyphenyl)-3-phenylpropionamide, N1-(3-(4,5-diethyl-1,6-dihydro-6-oxopyrimidin-2-yl)-4-n-propoxyphenyl)oxalamide, 5,6-diethyl-2-{2-n-propoxyl-5-[(2-(1-methylpyrrol-2-yl)ethyl)aminosulfonyl]phenyl}pyrimid-4(3H)-one, 3-(4,5-diethyl-1,6-dihydro-6-oxopyrimidin-2-yl)-N-(2-(1-methylpyrrol-2-yl)ethyl)-4-n-propoxylbenzamide, 2-(N-(3-(4,5-diethyl-1,6-dihydro-6-oxopyrimidin-2-yl)-4-n-propoxyphenyl)sulfonyl)amino-5-ureapentanoic acid, 2-(N-(3-(4,5-diethyl-1,6-dihydro-6-oxopyrimidin-2-yl)-4-n-propoxyphenyl)sulfonyl)amino-5-aminopentanoic acid, ethyl 2-(N-(3-(4,5-diethyl-1,6-dihydro-6-oxopyrimidin-2-yl)-4-n-propoxyphenyl)sulfonyl)aminopropionate, 3-(N-(3-(4,5-diethyl-1,6-dihydro-6-oxopyrimidin-2-yl)-4-n-propoxyphenyl)sulfonyl)aminopropylsulfonic acid, 2-(N-(3-(4,5-diethyl-1,6-dihydro-6-oxopyrimidin-2-yl)-4-n-propoxyphenyl)sulfonyl)aminoethyl sulfonic acid, 2-(N-(3-(4,5-diethyl-1,6-dihydro-6-oxopyrimidin-2-yl)-4-n-propoxyphenyl)sulfonyl)amino-3-aminoformylpropanoic acid, 5,6-diethyl-2-(2-n-propoxyl-5-(4-hydroxyethyl-1-piperazinylsulfonyl)phenyl]pyrimid-4(3H)-one, 5,6-diethyl-2-(2-n-propoxyl-5-(N-(2-morpholinylethyl)-N-(2-hydroxyethyl)aminosulfonyl)phenyl)pyrimid-4(3H)-one, 2-(3-(4,5-diethyl-1,6-dihydro-6-oxopyrimidin-2-yl)-4-n-propoxybenzamido)-3-phenylpropanoic acid, methyl N-(3-(4,5-diethyl-1,6-dihydro-6-oxopyrimidin-2-yl)-4-n-propoxylbenzoylprolinate, methyl 2-(3-(4,5-diethyl-1,6-dihydro-6-oxopyrimidin-2-yl)-4-n-propoxylbenzamido)-3-(4-hydroxyphenyl)propionate, 2-(3-(4,5-diethyl-1,6-dihydro-6-oxopyrimidin-2-yl)-4-n-propoxylbenzamido)propanoic acid, 2-(3-(4,5-diethyl-1,6-dihydro-6-oxopyrimidin-2-yl)-4-n-propoxybenzamido)-3-aminoformylpropanoic acid, 2-(3-(4,5-diethyl-1,6-dihydro-6-oxopyrimidin-2-yl)-4-n-propoxybenzamido)-5-guanidinopentanoic acid, methyl 2-(3-(4,5-diethyl-1,6-dihydro-6-oxopyrimidin-2-yl)-4-n-propoxybenzamido)-3-phenylpropanoic acid, methyl 2-(3-(4,5-diethyl-1,6-dihydro-6-oxopyrimidin-2-yl)-4-n-propoxybenzamido)propanoic acid, 3-(4,5-diethyl-1,6-dihydro-6-oxopyrimidin-2-yl)-N-(1-(4-methylpiperazin-1-yl)-1-oxopropan-2-yl)-4-n-propoxybenzamide, N-(1-aminoformylethyl)-3-(4,5-diethyl-1,6-dihydro-6-oxopyrimidin-2-yl)-4-n-propoxybenzamide, (4-(hydroxyethyoxylethyl)piperazin-1-yl)(3-(4,5-diethyl-1,6-dihydro-6-oxopyrimidin-2-yl)-4-n-propoxylbenzophenone, (4-(hydroxyethyl)piperazin-1-yl)(3-(4,5-diethyl-1,6-dihydro-6-oxopyrimidin-2-yl)-4-n-propoxylbenzophenone, 3-(4,5-diethyl-1,6-dihydro-6-oxopyrimidin-2-yl)-N-(1-hydroxy-2-propyl)-4-n-propoxybenzamide, 3-(3-(4,5-diethyl-1,6-dihydro-6-oxopyrimidin-2-yl)-4-n-propoxybenzamido)propyl-1-sulfonic acid, methyl 5-(3-(4,5-diethyl-1,6-dihydro-6-oxopyrimidin-2-yl)-4-n-propoxybenzamido)piperidinyl-2-formate, N-(3-(4,5-diethyl-1,6-dihydro-6-oxopyrimidin-2-yl)-4-n-propoxyphenyl)-2-(4-methylpiperazin-1-yl)acetamide, N-(3-(4,5-diethyl-1,6-dihydro-6-oxopyrimidin-2-yl)-4-n-propoxyphenyl)benzamide, 1-(2-(diethylamino)ethyl)-3-(3-(4,5-diethyl-1,6-dihydro-6-oxopyrimidin-2-yl)-4-n-propoxyphenyl)urea maleate, (4-methylpiperazin-1-yl)(3-(4,5-diethyl-1,6-dihydro-6-oxopyrimidin-2-yl)-4-n-propoxylbenzophenone, 5,6-diethyl-2-(2-n-propoxyl-5-((tetrahydro-2,4,5-trihydroxy-6-(hydroxymethyl)-2H-pyran-3-ylamino)sulfonyl)phenyl]pyrimid-4(3H)-one, 2-(3-(4,5-diethyl-1,6-dihydro-6-oxopyrimidin-2-yl)-4-n-propoxybenzamido)-5-ureapentanoic acid, 2-(3-(4,5-diethyl-1,6-dihydro-6-oxopyrimidin-2-yl)-4-n-propoxybenzamido)-5-aminopentanoic acid, 3-(3-(4,5-diethyl-1,6-dihydro-6-oxopyrimidin-2-yl)-N-(tetrahydro-2,4,5-trihydroxy-6-(hydroxymethyl)-2H-pyran-3-yl)-4-n-propoxybenzamide, 2-(3-(4,5-diethyl-1,6-dihydro-6-oxopyrimidin-2-yl)-4-n-propoxybenzamido)ethylsulfamide, 3-(4,5-diethyl-1,6-dihydro-6-oxopyrimidin-2-yl)-N-(4-methyl-piperazin-1-ylsulfonylethyl)-4-n-propoxybenzamide, 3-(4,5-diethyl-1,6-dihydro-6-oxopyrimidin-2-yl)-N—(N,N-diethylaminosulfonylethyl)-4-n-propoxybenzamide, 3-(3-(4,5-diethyl-1,6-dihydro-6-oxopyrimidin-2-yl)-4-n-propoxybenzamido)propylsulfamide, 3-(4,5-diethyl-1,6-dihydro-6-oxopyrimidin-2-yl)-N-(4-methyl-piperazin-1-ylsulfonylpropyl)-4-n-propoxybenzamide, 3-(4,5-diethyl-1,6-dihydro-6-oxopyrimidin-2-yl)-N—(N,N-diethylaminosulfonylpropyl)-4-n-propoxybenzamide, and 5,6-diethyl-2-(5-(tetrahydro-3,4,5-trihydroxy-6-(hydroxymethyl)-2H-pyran-2-yl)-2-n-propoxyphenyl)pyrimid-4(3H)-one.

6. The compound or a pharmaceutically acceptable salt or solvate thereof according to claim 2, wherein, said phenylpyrimidone compound is selected from the group consisting of:

5,6-diethyl-2-[2-n-propoxyl-5-(4-methyl-1-piperazinylsulfonyl)phenyl]pyrimid-4(3H)-one, 5,6-diethyl-2-{2-n-propoxyl-5-[N-(2-morpholinylethyl)aminosulfonyl)phenyl}pyrimid-4(3H)-one, N-(3-(4,5-diethyl-1,6-dihydro-6-oxopyrimidin-2-yl)-4-n-propoxyphenylsulfonylproline, 1-(3-(4,5-diethyl-1,6-dihydro-6-oxopyrimidin-2-yl)-4-n-propoxyphenyl)-3-ethylthiourea, N-[3-(4,5-diethyl-1,6-dihydro-6-oxopyrimidin-2-yl)-4-n-propoxyphenyl]-N',N"-triethyl guanidine, N-[3-(4,5-diethyl-1,6-dihydro-6-oxopyrimidin-2-yl)-4-n-propoxyphenyl]-pyrrolyl-1-formamide, 5-bromo-6-isopropyl-2-(2-n-propoxyl-5-mesylamidophenyl)pyrimid-4(3H)-one, 5,6-diethyl-2-(2-n-propoxyl-5-mesylamidophenyl)pyrimid-4(3H)-one, N-(3-(1,6-dihydro-4-isopropyl-5-bromo-6-oxopyrimidin-2-yl)-4-propoxyphenyl)acetamide, N-(3-(1,6-dihydro-4,5-diethyl-6-oxopyrimidin-2-yl)-4-propoxyphenyl)acetamide, N-(3-(1,6-dihydro-4,5-diethyl-6-oxopyrimidin-2-yl)-4-propoxyphenyl)propionamide, N-(3-(1,6-dihydro-4,5-diethyl-6-oxopyrimidin-2-yl)-4-propoxyphenyl)cyclohexamide, N-(3-(1,6-dihydro-4,5-diethyl-6-oxopyrimidin-2-yl)-4-propoxyphenyl)-1-t-butyloxycarbonyl-4-hydroxy-prolylamide, (morpholin-1-yl)(3-(4,5-diethyl-1,6-dihydro-6-oxopyrimidin-2-yl)-4-n-propoxyl)benzophenone, (piperid-1-yl)(3-(4,5-diethyl-1,6-dihydro-6-oxopyrimidin-2-yl)-4-n-propoxyl)benzophenone, (2-aminoformylpyrrol-1-yl)(3-(4,5-diethyl-1,6-dihydro-6-oxopyrimidin-2-yl)-4-n-propoxyl)benzophenone, (morpholin-1-yl)(3-(4-isopropyl-5-bromo-1,6-dihydro-6-oxopyrimidin-2-yl)-4-n-propoxyl)benzophenone, 1-(3-(4,5-diethyl-1,6-dihydro-6-oxopyrimidin-2-yl)-4-n-propoxyphenyl)urea, 1-(3-(4,5-diethyl-1,6-dihydro-6-oxopyrimidin-2-yl)-4-n-propoxyphenyl)-3-ethylurea, 5,6-diethyl-2-(5-(2-morpholinylacetyl)-2-n-propoxyphenyl)pyrimid-4(3H)-one, 2,2'-(4-n-propoxyl-1,3-phenylenyl)bis(5,6-diethylpyrimid-4(3H)-one), ethyl 2-(3-(4,5-diethyl-1,6-dihydro-6-oxopyrimidin-2-yl)-4-n-propoxybenzamido)acetate, N-(3-(4,5-diethyl-1,6-dihydro-6-oxopyrimidin-2-yl)-4-n-propoxyphenyl)-2,2,2-trifluoroacetamide, ethyl N-(3-(4,5-diethyl-1,6-dihydro-6-oxopyrimidin-2-yl)-4-n-propoxyphenyl)aminoformylacetate, 4-acetamido-N-(3-(4,5-diethyl-1,6-dihydro-6-oxopyrimidin-2-yl)-4-n-propoxyphenyl)butyramide, 1-acetyl-N-(3-(4,5-diethyl-1,6-dihydro-6-oxopyrimidin-2-yl)-4-n-propoxyphenyl)pyrrolidinyl-2-formamide, 2-acetamido-N-(3-(4,5-diethyl-1,6-dihydro-6-oxopyrimidin-2-yl)-4-n-propoxyphenyl)-3-phenylpropionamide, N1-(3-(4,5-diethyl-1,6-dihydro-6-oxopyrimidin-2-yl)-4-n-propoxyphenyl)oxalamide, 5,6-diethyl-2-{2-n-propoxyl-5-[(2-(1-methylpyrrol-2-yl)ethyl)aminosulfonyl]phenyl}pyrimid-4(3H)-one, 3-(4,5-diethyl-1,6-dihydro-6-oxopyrimidin-2-yl)-N-(2-(1-methylpyrrol-2-yl)ethyl)-4-n-propoxylbenzamide, 2-(N-(3-(4,5-diethyl-1,6-dihydro-6-oxopyrimidin-2-yl)-4-n-propoxyphenyl)sulfonyl)amino-5-ureapentanoic acid, 2-(N-(3-(4,5-diethyl-1,6-dihydro-6-oxopyrimidin-2-yl)-4-n-propoxyphenyl)sulfonyl)amino-5-aminopentanoic acid, ethyl 2-(N-(3-(4,5-diethyl-1,6-dihydro-6-oxopyrimidin-2-yl)-4-n-propoxyphenyl)sulfonyl)aminopropionate, 3-(N-(3-(4,5-diethyl-1,6-dihydro-6-oxopyrimidin-2-yl)-4-n-propoxyphenyl)sulfonyl)aminopropylsulfonic acid, 2-(N-(3-(4,5-diethyl-1,6-dihydro-6-oxopyrimidin-2-yl)-4-n-propoxyphenyl)sulfonyl)aminoethyl sulfonic acid, 2-(N-(3-(4,5-diethyl-1,6-dihydro-6-oxopyrimidin-2-yl)-4-n-propoxyphenyl)sulfonyl)amino-3-aminoformylpropanoic acid, 5,6-diethyl-2-(2-n-propoxyl-5-(4-hydroxyethyl-1-piperazinylsulfonyl)phenyl]pyrimid-4(3H)-one, 5,6-diethyl-2-(2-n-propoxyl-5-(N-(2-morpholinylethyl)-N-(2-hydroxyethyl)aminosulfonyl)phenyl)pyrimid-4(3H)-one, 2-(3-(4,5-diethyl-1,6-dihydro-6-oxopyrimidin-2-yl)-4-n-propoxybenzamido)-3-phenylpropanoic acid, methyl N-(3-(4,5-diethyl-1,6-dihydro-6-oxopyrimidin-2-yl)-4-n-propoxylbenzoylprolinate, methyl 2-(3-(4,5-diethyl-1,6-dihydro-6-oxopyrimidin-2-yl)-4-n-propoxylbenzamido)-3-(4-hydroxyphenyl)propionate, 2-(3-(4,5-diethyl-1,6-dihydro-6-oxopyrimidin-2-yl)-4-n-propoxylbenzamido)propanoic acid, 2-(3-(4,5-diethyl-1,6-dihydro-6-oxopyrimidin-2-yl)-4-n-propoxybenzamido)-3-aminoformylpropanoic acid, 2-(3-(4,5-diethyl-1,6-dihydro-6-oxopyrimidin-2-yl)-4-n-propoxybenzamido)-5-guanidinopentanoic acid, methyl 2-(3-(4,5-diethyl-1,6-dihydro-6-oxopyrimidin-2-yl)-4-n-propoxybenzamido)-3-phenylpropanoic acid, methyl 2-(3-(4,5-diethyl-1,6-dihydro-6-oxopyrimidin-2-yl)-4-n-propoxybenzamido)propanoic acid, 3-(4,5-diethyl-1,6-dihydro-6-oxopyrimidin-2-yl)-N-(1-(4-methylpiperazin-1-yl)-1-oxopropan-2-yl)-4-n-propoxybenzamide, N-(1-aminoformylethyl)-3-(4,5-diethyl-1,6-dihydro-6-oxopyrimidin-2-yl)-4-n-propoxybenzamide, (4-(hydroxyethyoxylethyl)piperazin-1-yl)(3-(4,5-diethyl-1,6-dihydro-6-oxopyrimidin-2-yl)-4-n-propoxylbenzophenone, (4-(hydroxyethyl)piperazin-1-yl)(3-(4,5-diethyl-1,6-dihydro-6-oxopyrimidin-2-yl)-4-n-propoxylbenzophenone, 3-(4,5-diethyl-1,6-dihydro-6-oxopyrimidin-2-yl)-N-(1-hydroxy-2-propyl)-4-n-propoxybenzamide, 3-(3-(4,5-diethyl-1,6-dihydro-6-oxopyrimidin-2-yl)-4-n-propoxybenzamido)propyl-1-sulfonic acid, methyl 5-(3-(4,5-diethyl-1,6-dihydro-6-oxopyrimidin-2-yl)-4-n-propoxybenzamido)piperidinyl-2-formate, N-(3-(4,5-diethyl-1,6-dihydro-6-oxopyrimidin-2-yl)-4-n-propoxyphenyl)-2-(4-methylpiperazin-1-yl)acetamide, N-(3-(4,5-diethyl-1,6-dihydro-6-oxopyrimidin-2-yl)-4-n-propoxyphenyl)benzamide, 1-(2-(diethylamino)ethyl)-3-(3-(4,5-diethyl-1,6-dihydro-6-oxopyrimidin-2-yl)-4-n-propoxyphenyl)urea maleate, (4-methylpiperazin-1-yl)(3-(4,5-diethyl-1,6-dihydro-6-oxopyrimidin-2-yl)-4-n-propoxylbenzophenone, 5,6-diethyl-2-(2-n-propoxyl-5-((tetrahydro-2,4,5-trihydroxy-6-(hydroxymethyl)-2H-pyran-3-ylamino)sulfonyl)phenyl]pyrimid-4(3H)-one, 2-(3-(4,5-diethyl-1,6-dihydro-6-oxopyrimidin-2-yl)-4-n-propoxybenzamido)-5-ureapentanoic acid, 2-(3-(4,5-diethyl-1,6-dihydro-6-oxopyrimidin-2-yl)-4-n-propoxybenzamido)-5-aminopentanoic acid, 3-(3-(4,5-diethyl-1,6-dihydro-6-oxopyrimidin-2-yl)-N-(tetrahydro-2,4,5-trihydroxy-6-(hydroxymethyl)-2H-pyran-3-yl)-4-n-propoxybenzamide, 2-(3-(4,5-diethyl-1,6-dihydro-6-oxopyrimidin-2-yl)-4-n-propoxybenzamido)ethylsulfamide, 3-(4,5-diethyl-1,6-dihydro-6-oxopyrimidin-2-yl)-N-(4-methyl-piperazin-1-ylsulfonylethyl)-4-n-propoxybenzamide, 3-(4,5-diethyl-1,6-dihydro-6-oxopyrimidin-2-yl)-N—(N,N-diethylaminosulfonylethyl)-4-n-propoxybenzamide, 3-(3-(4,5-diethyl-1,6-dihydro-6-oxopyrimidin-2-yl)-4-n-propoxybenzamido)propylsulfamide, 3-(4,5-diethyl-1,6-dihydro-6-oxopyrimidin-2-yl)-N-(4-methyl-piperazin-1-ylsulfonylpropyl)-4-n-propoxybenzamide, 3-(4,5-diethyl-1,6-dihydro-6-oxopyrimidin-2-yl)-N—(N,N-diethylaminosulfonylpropyl)-4-n-propoxybenzamide, and 5,6-diethyl-2-(5-(tetrahydro-3,4,5-trihydroxy-6-(hydroxymethyl)-2H-pyran-2-yl)-2-n-propoxyphenyl)pyrimid-4(3H)-one.

7. The compound or a pharmaceutically acceptable salt or solvate thereof according to claim 3, wherein, said phenylpyrimidone compound is selected from the group consisting of:

5,6-diethyl-2-[2-n-propoxyl-5-(4-methyl-1-piperazinylsulfonyl)phenyl]pyrimid-4(3H)-one, 5,6-diethyl-2-{2-n-propoxyl-5-[N-(2-morpholinylethyl)aminosulfonyl)phenyl}pyrimid-4(3H)-one, N-(3-(4,5-diethyl-1,6-dihydro-6-oxopyrimidin-2-yl)-4-n-propoxyphenylsulfonylproline, 1-(3-(4,5-diethyl-1,6-dihydro-6-oxopyrimidin-2-yl)-4-n-propoxyphenyl)-3-ethylthiourea, N-[3-(4,5-diethyl-1,6-dihydro-6-oxopyrimidin-2-yl)-4-n-propoxyphenyl]-N',N"-triethyl guanidine, N-[3-(4,5-diethyl-1,6-dihydro-6-oxopyrimidin-2-yl)-4-n-propoxyphenyl]-pyrrolyl-1-formamide, 5-bromo-6-isopropyl-2-(2-n-propoxyl-5-mesylamidophenyl)pyrimid-4(3H)-one, 5,6-diethyl-2-(2-n-propoxyl-5-mesylamidophenyl)pyrimid-4(3H)-one, N-(3-(1,6-dihydro-4-isopropyl-5-bromo-6-oxopyrimidin-2-yl)-4-propoxyphenyl)acetamide, N-(3-(1,6-dihydro-4,5-diethyl-6-oxopyrimidin-2-yl)-4-propoxyphenyl)acetamide, N-(3-(1,6-dihydro-4,5-diethyl-6-oxopyrimidin-2-yl)-4-propoxyphenyl)propionamide, N-(3-(1,6-dihydro-4,5-diethyl-6-oxopyrimidin-2-yl)-4-propoxyphenyl)cyclohexamide, N-(3-(1,6-dihydro-4,5-diethyl-6-oxopyrimidin-2-yl)-4-propoxyphenyl)-1-t-butyloxycarbonyl-4-hydroxy-prolylamide, (morpholin-1-yl)(3-(4,5-diethyl-1,6-dihydro-6-oxopyrimidin-2-yl)-4-n-propoxyl)benzophenone, (piperid-1-yl)(3-(4,5-diethyl-1,6-dihydro-6-oxopyrimidin-2-yl)-4-n-propoxyl)benzophenone, (2-aminoformylpyrrol-1-yl)(3-(4,5-diethyl-1,6-dihydro-6-oxopyrimidin-2-yl)-4-n-propoxyl)benzophenone, (morpholin-1-yl)(3-(4-isopropyl-5-bromo-1,6-dihydro-6-oxopyrimidin-2-yl)-4-n-propoxyl)benzophenone, 1-(3-(4,5-diethyl-1,6-dihydro-6-oxopyrimidin-2-yl)-4-n-propoxyphenyl)urea, 1-(3-(4,5-diethyl-1,6-dihydro-6-oxopyrimidin-2-yl)-4-n-propoxyphenyl)-3-ethylurea, 5,6-diethyl-2-(5-(2-morpholinylacetyl)-2-n-propoxyphenyl)pyrimid-4(3H)-one, 2,2'-(4-n-propoxyl-1,3-phenylenyl)bis(5,6-diethylpyrimid-4(3H)-one), ethyl 2-(3-(4,5-diethyl-1,6-dihydro-6-oxopyrimidin-2-yl)-4-n-propoxybenzamido)acetate, N-(3-(4,5-diethyl-1,6-dihydro-6-oxopyrimidin-2-yl)-4-n-propoxyphenyl)-2,2,2-trifluoroacetamide, ethyl N-(3-(4,5-diethyl-1,6-dihydro-6-oxopyrimidin-2-yl)-4-n-propoxyphenyl)aminoformylacetate, 4-acetamido-N-(3-(4,5-diethyl-1,6-dihydro-6-oxopyrimidin-2-yl)-4-n-propoxyphenyl)butyramide, 1-acetyl-N-(3-(4,5-diethyl-1,6-dihydro-6-oxopyrimidin-2-yl)-4-n-propoxyphenyl)pyrrolidinyl-2-formamide, 2-acetamido-N-(3-(4,5-diethyl-1,6-dihydro-6-oxopyrimidin-2-yl)-4-n-propoxyphenyl)-3-phenylpropionamide, N1-(3-(4,5-diethyl-1,6-dihydro-6-oxopyrimidin-2-yl)-4-n-propoxyphenyl)oxalamide, 5,6-diethyl-2-{2-n-propoxyl-5-[(2-(1-methylpyrrol-2-yl)ethyl)aminosulfonyl]phenyl}pyrimid-4(3H)-one, 3-(4,5-diethyl-1,6-dihydro-6-oxopyrimidin-2-yl)-N-(2-(1-methylpyrrol-2-yl)ethyl)-4-n-propoxylbenzamide, 2-(N-(3-(4,5-diethyl-1,6-dihydro-6-oxopyrimidin-2-yl)-4-n-propoxyphenyl)sulfonyl)amino-5-ureapentanoic acid, 2-(N-(3-(4,5-diethyl-1,6-dihydro-6-oxopyrimidin-2-yl)-4-n-propoxyphenyl)sulfonyl)amino-5-aminopentanoic acid, ethyl 2-(N-(3-(4,5-diethyl-1,6-dihydro-6-oxopyrimidin-2-yl)-4-n-propoxyphenyl)sulfonyl)aminopropionate, 3-(N-(3-(4,5-diethyl-1,6-dihydro-6-oxopyrimidin-2-yl)-4-n-propoxyphenyl)sulfonyl)aminopropylsulfonic acid, 2-(N-(3-(4,5-diethyl-1,6-dihydro-6-oxopyrimidin-2-yl)-4-n-propoxyphenyl)sulfonyl)aminoethyl sulfonic acid, 2-(N-(3-(4,5-diethyl-1,6-dihydro-6-oxopyrimidin-2-yl)-4-n-propoxyphenyl)sulfonyl)amino-3-aminoformylpropanoic acid, 5,6-diethyl-2-(2-n-propoxyl-5-(4-hydroxyethyl-1-piperazinylsulfonyl)phenyl]pyrimid-4(3H)-one, 5,6-diethyl-2-(2-n-propoxyl-5-(N-(2-morpholinylethyl)-N-(2-hydroxyethyl)aminosulfonyl)phenyl)pyrimid-4(3H)-one, 2-(3-(4,5-diethyl-1,6-dihydro-6-oxopyrimidin-2-yl)-4-n-propoxybenzamido)-3-phenylpropanoic acid, methyl N-(3-(4,5-diethyl-1,6-dihydro-6-oxopyrimidin-2-yl)-4-n-propoxylbenzoylprolinate, methyl 2-(3-(4,5-diethyl-1,6-dihydro-6-oxopyrimidin-2-yl)-4-n-propoxylbenzamido)-3-(4-hydroxyphenyl)propionate, 2-(3-(4,5-diethyl-1,6-dihydro-6-oxopyrimidin-2-yl)-4-n-propoxylbenzamido)propanoic acid, 2-(3-(4,5-diethyl-1,6-dihydro-6-oxopyrimidin-2-yl)-4-n-propoxybenzamido)-3-aminoformylpropanoic acid, 2-(3-(4,5-diethyl-1,6-dihydro-6-oxopyrimidin-2-yl)-4-n-propoxybenzamido)-5-guanidinopentanoic acid, methyl 2-(3-(4,5-diethyl-1,6-dihydro-6-oxopyrimidin-2-yl)-4-n-propoxybenzamido)-3-phenylpropanoic acid, methyl 2-(3-(4,5-diethyl-1,6-dihydro-6-oxopyrimidin-2-yl)-4-n-propoxybenzamido)propanoic acid, 3-(4,5-diethyl-1,6-dihydro-6-oxopyrimidin-2-yl)-N-(1-(4-methylpiperazin-1-yl)-1-oxopropan-2-yl)-4-n-propoxybenzamide, N-(1-aminoformylethyl)-3-(4,5-diethyl-1,6-dihydro-6-oxopyrimidin-2-yl)-4-n-propoxybenzamide, (4-(hydroxyethyoxylethyl)piperazin-1-yl)(3-(4,5-diethyl-1,6-dihydro-6-oxopyrimidin-2-yl)-4-n-propoxylbenzophenone, (4-(hydroxyethyl)piperazin-1-yl)(3-(4,5-diethyl-1,6-dihydro-6-oxopyrimidin-2-yl)-4-n-propoxylbenzophenone, 3-(4,5-diethyl-1,6-dihydro-6-oxopyrimidin-2-yl)-N-(1-hydroxy-2-propyl)-4-n-propoxybenzamide, 3-(3-(4,5-diethyl-1,6-dihydro-6-oxopyrimidin-2-yl)-4-n-propoxybenzamido)propyl-1-sulfonic acid, methyl 5-(3-(4,5-diethyl-1,6-dihydro-6-oxopyrimidin-2-yl)-4-n-propoxybenzamido)piperidinyl-2-formate, N-(3-(4,5-diethyl-1,6-dihydro-6-oxopyrimidin-2-yl)-4-n-propoxyphenyl)-2-(4-methylpiperazin-1-yl)acetamide, N-(3-(4,5-diethyl-1,6-dihydro-6-oxopyrimidin-2-yl)-4-n-propoxyphenyl)benzamide, 1-(2-(diethylamino)ethyl)-3-(3-(4,5-diethyl-1,6-dihydro-6-oxopyrimidin-2-yl)-4-n-propoxyphenyl)urea maleate, (4-methylpiperazin-1-yl)(3-(4,5-diethyl-1,6-dihydro-6-oxopyrimidin-2-yl)-4-n-propoxylbenzophenone, 5,6-diethyl-2-(2-n-propoxyl-5-((tetrahydro-2,4,5-trihydroxy-6-(hydroxymethyl)-2H-pyran-3-ylamino)sulfonyl)phenyl]pyrimid-4(3H)-one, 2-(3-(4,5-diethyl-1,6-dihydro-6-oxopyrimidin-2-yl)-4-n-propoxybenzamido)-5-ureapentanoic acid, 2-(3-(4,5-diethyl-1,6-dihydro-6-oxopyrimidin-2-yl)-4-n-propoxybenzamido)-5-aminopentanoic acid, 3-(3-(4,5-diethyl-1,6-dihydro-6-oxopyrimidin-2-yl)-N-(tetrahydro-2,4,5-trihydroxy-6-(hydroxymethyl)-2H-pyran-3-yl)-4-n-propoxybenzamide, 2-(3-(4,5-diethyl-1,6-dihydro-6-oxopyrimidin-2-yl)-4-n-propoxybenzamido)ethylsulfamide, 3-(4,5-diethyl-1,6-dihydro-6-oxopyrimidin-2-yl)-N-(4-methyl-piperazin-1-ylsulfonylethyl)-4-n-propoxybenzamide, 3-(4,5-diethyl-1,6-dihydro-6-oxopyrimidin-2-yl)-N—(N,N-diethylaminosulfonylethyl)-4-n-propoxybenzamide, 3-(3-(4,5-diethyl-1,6-dihydro-6-oxopyrimidin-2-yl)-4-n-propoxybenzamido)propylsulfamide, 3-(4,5-diethyl-1,6-dihydro-6-oxopyrimidin-2-yl)-N-(4-methyl-piperazin-1-ylsulfonylpropyl)-4-n-propoxybenzamide, 3-(4,5-diethyl-1,6-dihydro-6-oxopyrimidin-2-yl)-N—(N,N-diethylaminosulfonylpropyl)-4-n-propoxybenzamide, and 5,6-diethyl-2-(5-(tetrahydro-3,4,5-trihydroxy-6-(hydroxymethyl)-2H-pyran-2-yl)-2-n-propoxyphenyl)pyrimid-4(3H)-one.

8. A pharmaceutical composition having PDE5 inhibition activity comprising an therapeutically effective dose of one or more compounds selected from the group consisting of the compounds or a pharmaceutically acceptable salt or solvate thereof according to claim 1, and one or more pharmaceutically acceptable auxiliaries.

9. The pharmaceutical composition having PDE5 inhibition activity according to claim 8, wherein, the dose of said compound or the pharmaceutically acceptable salt or solvate thereof is 1-500 mg per day.

10. A process of preparing the compound of formula I, a pharmaceutically acceptable salt or solvate thereof according to claim 1, wherein, the process is any one of the following methods:

when Z is $OR^3$, the compound of formula I can be prepared by the following methods:

(1) when $R^4$ is OH, $SO_2NR^6R^7$, $COR^{11}$, unsubstituted or substituted $C_2$-$C_4$ alkyl, unsubstituted or substituted $C_2$-$C_4$ alkenyl, or, unsubstituted or substituted 5~7-member heterocyclyl, the compound of formula I is prepared by cyclizing the compound of formula II with the compound of formula III in the presence of a base, wherein $R^1$, $R^2$, $R^3$, $R^6$, $R^7$, $R^{11}$ and said 5~7-member heterocyclyl are defined the same as those in claim 1;

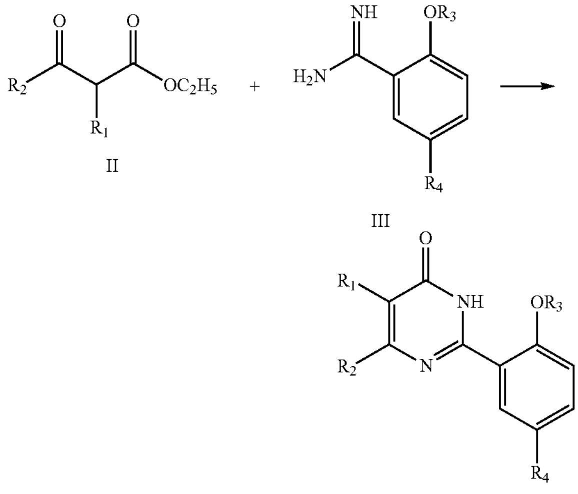

II

III

I or, (2) the compound of formula I is prepared from the compound of formula Ia, the compound of formula Ie or other compounds of formula I, wherein $R^1$, $R^2$, $R^3$, $R^5$, $R^6$, $R^7$, $R^8$, $R^9$, $R^{10}$, $R^{12}$, $R^{15}$, $R^{16}$, $R^{17}$, $R^{18}$, $R^{19}$ and $R^{20}$ are defined the same as those in claim 1; wherein, 1) when $R^4$ is $SO_2NR^6R^7$, the compound of formula Ib is prepared from the compound of formula Ia through chlorosulfonating followed by reacting with $R^6R^7NH$ in the presence of a base;

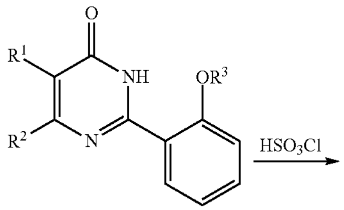

Ia

-continued

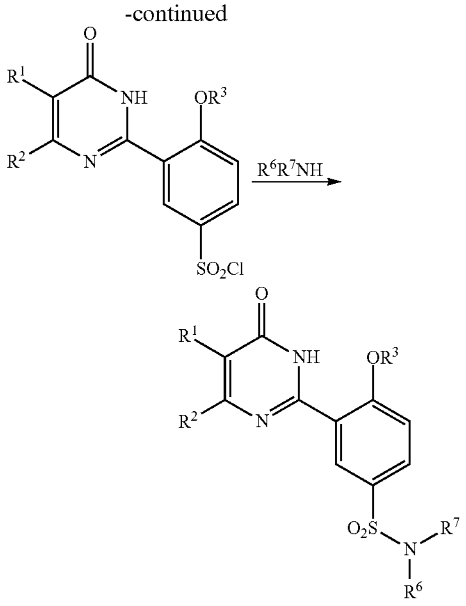

Ib or, 2) when $R^4$ is $NO_2$, the compound of formula Ic is prepared by nitrating the compound of formula Ia;

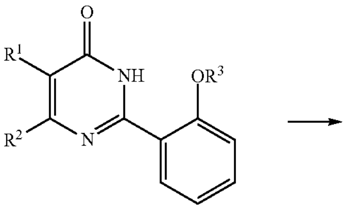

Ia

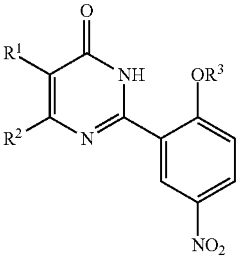

Ic or, 3) when $R^4$ is $NH_2$, the compound of formula Id is prepared by reducing the compound of formula Ic

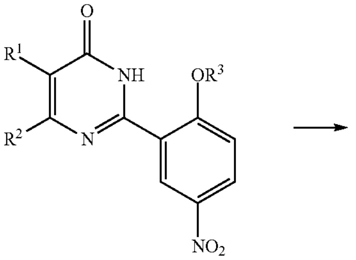

Ic

-continued

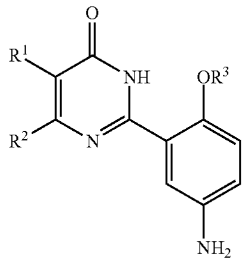

Id or, 4) when $R^4$ is CN, the compound of formula If is prepared from the compound of formula Ie by nucleophilic substitution with cyanide;

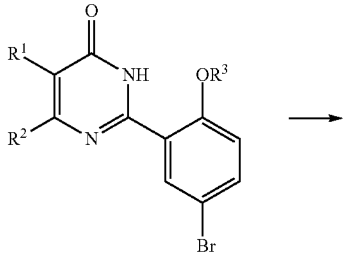

Ie

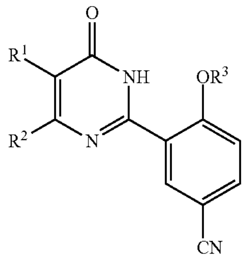

If or, 5) when $R^4$ is COOH, the compound of formula Ig is prepared from the compound of formula If by hydrolysis;

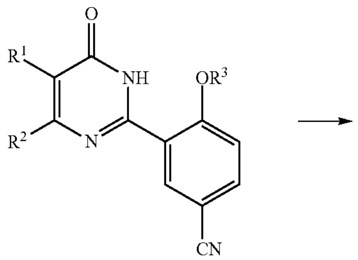

If

-continued

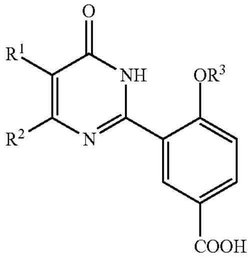

Ig or, 6) when $R^4$ is $NR^9R^{10}$, the compound of formula I is prepared from the compound of formula Id wherein $R^4$ is $NH_2$, wherein, 1> when $R^9$ and $R^{10}$ are simultaneouly methyl, the compound of formula I is prepared through N-methylation by using a methylating agent;

2> when $R^9$ is H and $R^{10}$ is $SO_2R^{16}$, the compound of formula I is prepared from the compound of formula Id through sulfonylation in the presence of a base;

3> when $R^9$ is H and $R^{10}$ is $COR^{15}$, the compound of formula I is prepared by reacting the compound of formula Id with an acyl chloride derivative of an organic acid, which is obtained by reacting the organic acid with oxalyl chloride or thionyl chloride; or by condensing the compound of formula Id with an organic acid;

4> when $R^9$ is H, $R^{10}$ is $C(Y)NR^{17}R^{18}$, and Y is O or S, the compound of formula I is prepared by the addition reaction of the compound of formula Id with the compound of formula $Y{=}C{=}NR^{17}R^{18}$;

5> when $R^9$ is H, $R^{10}$ is a 5- or 6-member monosaccharide group, the compound of formula I is prepared by reacting the compound of formula Id with a 5- or 6-member monosaccharide having no protecting group in the presence of a trace amount of an organic acid as a catalyst;

6> when $R^9$ is H, $R^{10}$ is

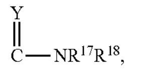

and Y is $NR^8$, the compound of formula I is prepared by nucleophilic substitution from the compound of formula Ih with a compound of formula $R^{17}NHR^{18}$, wherein the compound of formula Ih is prepared by the addition reaction of the compound of formula Ii with iodomethane, and the compound of formula II is prepared by the addition reaction of the compound of formula Id with $R^8SCN$;

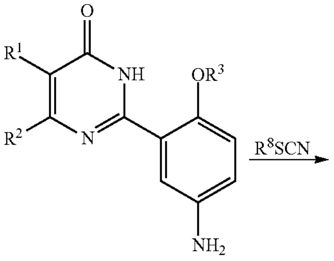

Id

-continued

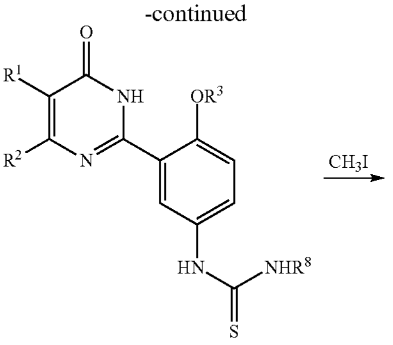

Ii

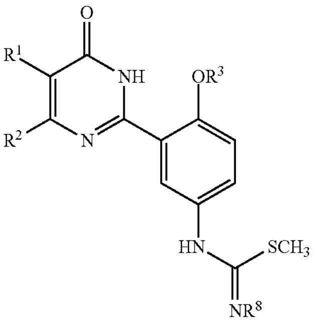

Ih

7> when $R^9$ is H and $R^{10}$ is an amino-acid residue substituted with acetyl, condensing the compound of formula Id with a N-Boc protected amino-acid in the presence of a coupling agent and an activator to give an intermediate, followed by deprotecting Boc group in trifluoroacetic acid, and finally reacting with acetic anhydride in pyridine to give the compound of formula I;

or, 7) when $R^4$ is $COR^{11}$ and $R^{11}$ is $NR^6R^7$, the compound of formula I is prepared by condensing the compound of formula Ig with $R^6R^7NH$; or by transforming the compound of formula Ig into an corresponding acyl chloride derivative, followed by reacting with $R^6R^7NH$;

or, 8) when $R^4$ is $COR^{11}$ and $R^{11}$ is $CH_2NR^6R^7$, the compound of formula I is prepared by condensing the compound of formula Ij with $R^6R^7NH$, wherein the compound of formula Ij is prepared by bromizing the compound of formula Ik, and the compound of formula Ik is prepared by reacting the compound of formula Ia with vinyl n-butyl ether in the presence of an metal catalyst, followed by hydrolysis; or the compound of formula Ij can also be prepared by Friedel-Crafts reaction of the compound of formula Ia with bromoacetyl bromide;

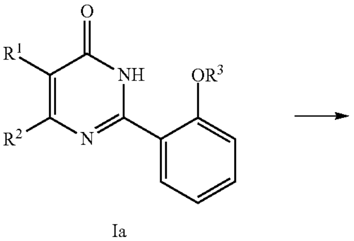

Ia

-continued

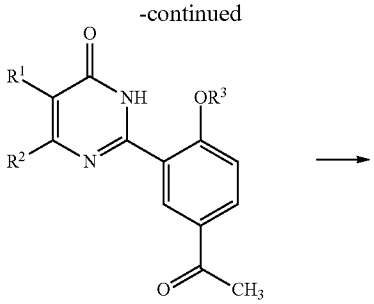

Ik

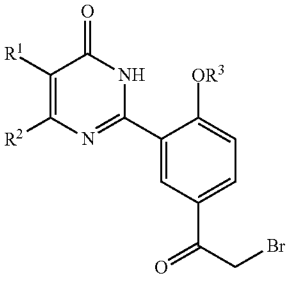

Ij or, 9) when $R^4$ is $OR^{12}$, the compound of formula I is prepared from the compound of formula Il, wherein, 1> when $R^{12}$ is $COR^{19}$ and $R^{19}$ is $C_1$-$C_6$ alkyl or aryl, the compound of formula I is prepared by esterifing the compound of formula Il wherein $R^4$ is OH;

2> when $R^{12}$ is $COR^{19}$ and $R^{19}$ is $NHR^8$, the compound of formula I is prepared by addition reaction of $R^8NCO$ with the compound of formula Il wherein $R^4$ is OH;

3> when $R^{12}$ is $SO_2R^{16}$, the compound of formula I is prepared by sulfonylation of the compound of formula Il wherein $R^4$ is OH;

4> when $R^{12}$ is a 5- or 6-member monosaccharide group, the compound of formula In is prepared by firstly condensing the compound of formula Il with a hydroxyl-protected 5- or 6-member monosaccharide activated with trichloroacetonitrile to give the compound of formula Im, followed by hydrolysis and deprotection;

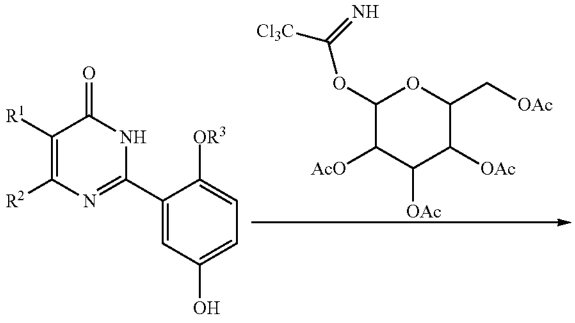

Il

-continued

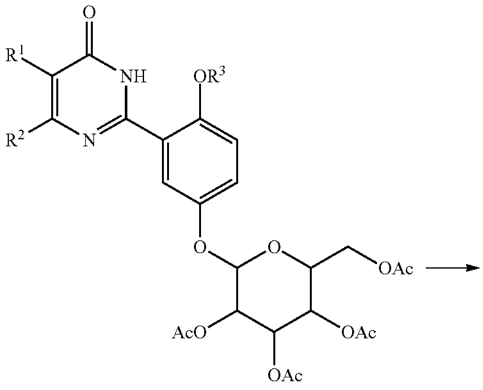

Im

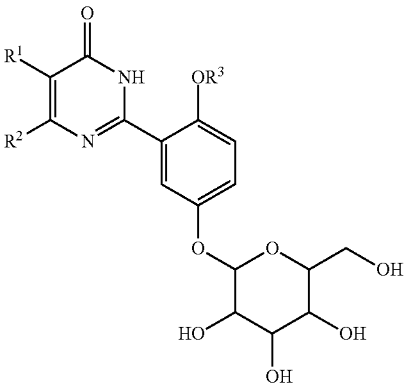

In or 10) when $R^4$ is pyrrolyl, the compound of formula Io is prepared by condensing 2,5-hexanedione with the compound of formula Id where $R^4$ is $NH_2$;

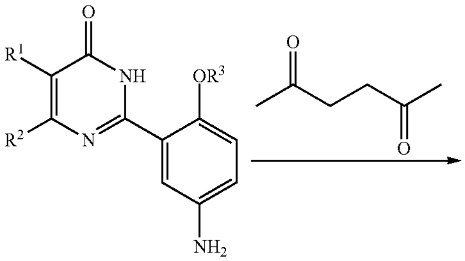

Id

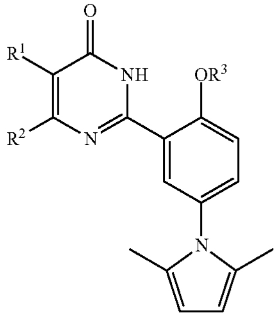

Io or, 11) when $R^4$ is a glycoside, the compound of formula I is prepared by firstly reacting the compound of formula Ie where $R^4$ is Br with n-BuLi, then reacting with a protected glucolactone, followed by reducing by using a reducing agent;

or, (3) the compound of formula I is prepared by converting other compounds of formula I where $R^1$ is a different substituent, wherein $R^2$, $R^3$ and $R^4$ are defined the same as claim 1; wherein, 1) when $R^1$ is a halogen, the compound of formula Iq is prepared by halogenating the compound of formula Ip where $R^1$ is H in the presence of an organic base;

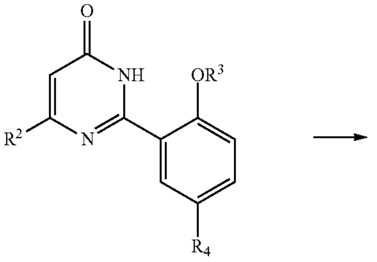

Ip

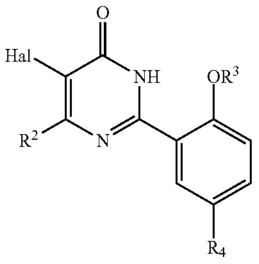

Iq or, 2) when $R^1$ is $NH_2$, the compound of formula Is is prepared by hydrolyzing the compound of formula Ir wherein $R^1$ is acetamido

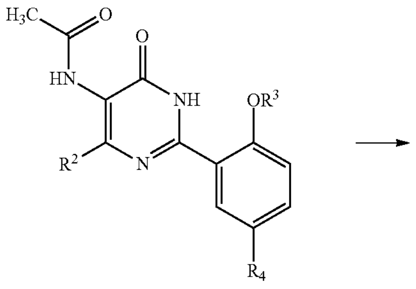

Ir

-continued

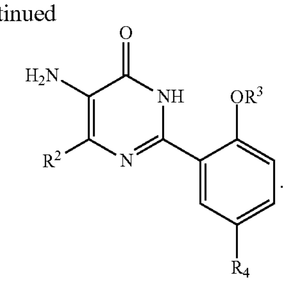

Is

11. The process of preparing a compound of formula I, a pharmaceutically acceptable salts or solvates salt or solvate thereof according to claim 1, wherein, the process is any one of the following methods:

when Z is $NR^3R^{10}$, the compound of formula I is prepared by nitration, reduction and N-substitution, with reference to a similar method with that for preparing the compound of formula I wherein $R^4$ is $NR^9R^{10}$ as said in claim 6;

or, when Z is $COR^{11}$, $NHCOR^{15}$ or $OCOR^{15}$, the compound of formula I is prepared, with reference to the method of claim 6 for preparing the compound of formula I wherein $R^4$ is $COR^{11}$, $NHCOR^{15}$ or $OCOR^{15}$.

12. A method of inhibiting PDE5 in a human patient in need thereof comprising administering the compound of formula I or a pharmaceutically acceptable salt or solvate thereof according to claim 1.

13. A method of treating one or more male erectile dysfunction, benign prostatic hyperplasia, female sexual dysfunction, premature delivery, menorrhalgia, bladder outlet obstruction, incontinence, instable and variant Prinzmetal angina pectoris, hypertension, pulmonary hypertension, congestive heart failure, renal failure, atherosclerosis, apoplexy, peripheral vascular disease, Raynaud's diseases, inflammation diseases, bronchitis, chronicity asthma, allergic asthma, allergic coryza, glaucoma or diseases characterized by enterocinesia dysfunction.

14. The method according to claim 13, further comprising administering to the patient the compound of formula I or the pharmaceutically acceptable salt or solvate thereof in combination with one or more of a selective 5-HT reuptake inhibitor, an α-receptor blockade, an antihypertensive drug, propionyl-L-carnitine, testosterone undecanoate and Tianeptine.

* * * * *

UNITED STATES PATENT AND TRADEMARK OFFICE

CERTIFICATE OF CORRECTION

PATENT NO. : 8,871,777 B2
APPLICATION NO. : 13/139156
DATED : October 28, 2014
INVENTOR(S) : Zheng Liu et al.

It is certified that error appears in the above-identified patent and that said Letters Patent is hereby corrected as shown below:

delete title page, and insert new title page (attached)

Claims in claim 8, at column 181, line 66, change “an therapeutically” to --a therapeutically-- in claim 8, at column 182, line 1, change “compounds” to --compound-- in claim 10, at column 185, line 19, change “simultaneouly” to --simultaneously-- in claim 10, at column 187, line 37, change “esterifing” to --esterifying-- please delete claim 11, at column 190, line 18 renumber claims 12-14, as claims 11-13 respectively in claim 13, at column 190, line 38, please insert after “one or more” the following text --selected from a group consisting of-- in claim 13, at column 190, line 47, please insert after “enterocinesia dysfunction” the following text --in a subject in need thereof comprising administering the compound of formula I or a pharmaceutically acceptable salt or solvate thereof according to claim 1-- in claim 14, at column 190, line 52, insert after “one or more” the following text --selected from a group consisting--

Signed and Sealed this
Fifteenth Day of December, 2015

Michelle K. Lee
*Director of the United States Patent and Trademark Office*

(12) United States Patent
Liu et al.

(10) Patent No.: US 8,871,777 B2
(45) Date of Patent: Oct. 28, 2014

(54) PHENYLPYRIMIDONE COMPOUNDS, THE PHARMACEUTICAL COMPOSITIONS, PREPARATION METHODS AND USES THEREOF

(75) Inventors: Zheng Liu, Shanghai (CN); Jianfeng Li, Shanghai (CN); Xiaofun Yang, Shanghai (CN); Zhen Wang, Shanghai (CN); Haifeng Zhang, Shanghai (CN); Yi Zhu, Shandong (CN); Guanghui Han, Shanghai (CN); Qing Jin, Shanghai (CN); Jingkang Shen, Shanghai (CN); Weiliang Zhu, Shanghai (CN); Hualiang Jiang, Shanghai (CN); Jingshan Shen, Shanghai (CN)

(73) Assignees: Topharman Shanghai Co., Ltd., Shanghai (CN); Shanghai Institute of Materia Medica, Chinese Academy of Sciences, Shanghai (CN); Topharman Shandong Co., Ltd., Shandong (CN)

(*) Notice: Subject to any disclaimer, the term of this patent is extended or adjusted under 35 U.S.C. 154(b) by 212 days.

(21) Appl. No.: 13/139,156

(22) PCT Filed: Dec. 10, 2009

(86) PCT No.: PCT/CN2009/001418

§ 371 (c)(1),
(2), (4) Date: Aug. 24, 2011

(87) PCT Pub. No.: WO2010/066111

PCT Pub. Date: Jun. 17, 2010

(65) Prior Publication Data

US 2011/0301104 A1 Dec. 8, 2011

(30) Foreign Application Priority Data

Dec. 10, 2008 (CN) .......... 2008 1 0204358

(51) Int. Cl.

| | |
|---|---|
| *A01N 43/54* | (2006.01) |
| *A61K 31/505* | (2006.01) |
| *C07D 239/02* | (2006.01) |
| *C07D 401/12* | (2006.01) |
| *C07D 417/12* | (2006.01) |
| *C07D 409/12* | (2006.01) |
| *C07D 239/36* | (2006.01) |
| *C07D 405/12* | (2006.01) |
| *C07D 403/12* | (2006.01) |
| *C07H 15/26* | (2006.01) |

(52) U.S. Cl.
CPC ....... *A61K 31/505* (2013.01); *C07D 401/12* (2013.01); *C07D 417/12* (2013.01); *C07D 409/12* (2013.01); *C07D 239/36* (2013.01); *C07D 405/12* (2013.01); *C07D 403/12* (2013.01); *C07H 15/26* (2013.01)
USPC .......... 514/269; 544/319

(58) Field of Classification Search
None
See application file for complete search history.

(56) References Cited

U.S. PATENT DOCUMENTS 4,031,093 A * 6/1977 Juby et al. ........ 544/319

FOREIGN PATENT DOCUMENTS

| | | | |
|---|---|---|---|
| CA | 2550677 | A1 | 9/2004 |
| CN | 1240171 | A | 3/2000 |
| EP | 1069844 | A1 | 2/2000 |
| EP | 2030974 | A1 | 3/2009 |
| GB | 1561451 | A | 2/1979 |
| WO | 9428902 | A1 | 12/1994 |
| WO | 9849166 | A1 | 11/1998 |
| WO | 9954333 | A1 | 10/1999 |
| WO | 0187888 | A1 | 11/2001 |
| WO | 03020724 | A1 | 3/2003 |
| WO | 2004096810 | A1 | 11/2004 |
| WO | 2004101567 | A1 | 11/2004 |
| WO | 2004108726 | A1 | 12/2004 |
| WO | 2005012303 | A1 | 2/2005 |
| WO | 2005080752 | A1 | 9/2005 |
| WO | 2006126081 | A2 | 11/2006 |
| WO | 2006126083 | A1 | 11/2006 |
| WO | 2007002125 | A1 | 1/2007 |
| WO | 2007020521 | A1 | 2/2007 |
| WO | 2007056955 | A1 | 5/2007 |

OTHER PUBLICATIONS

Bretschneider, et. al., Monatshefte fuer Chemie (1950), 81, 372-3.*
Hai-Jun Chen et al. "Rational Design and Synthesis of 2,2-Bisheterocycle Tandem Derivatives as Non-Nucleoside Hepatitis B Virus Inhibitors" ChemMedChem, Sep. 15, 2008, pp. 1316-1321, vol. 3, No. 9, Wiley-VCH Verlag GmbH & Co., KGaA, Weinheim. Published online on Jul. 28, 2008.
Supplementary European Search Report, Application No. 09830011 filed Oct. 31, 2012.
European Search Report of European Publication No. 2383262 (Application No. 09831458.4 filed Dec. 10, 2009).

* cited by examiner

*Primary Examiner* — Jeffrey H Murray
(74) *Attorney, Agent, or Firm* — Baker & Hostetler LLP

(57) ABSTRACT

The present invention relates to a class of phenylpyrimidone compounds, the pharmaceutical composition, the preparation method and the use thereof. More specifically, the present invention relates to a type of phenylpyrimidone compounds of the following formula I, the pharmaceutically acceptable salts or solvates thereof and to the pharmaceutical compositions as well as the preparation method of the compounds. The compounds of formula I according to the present invention can effectively inhibit type V phosphodiesterase (PDE5), and thus can be used for the treatment of various vascular disorders, such as male erectile dysfunction, pulmonary hypertension and the like.

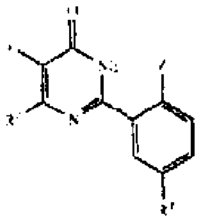

13 Claims, No Drawings